(12) United States Patent
Dress et al.

(10) Patent No.: US 7,468,375 B2
(45) Date of Patent: Dec. 23, 2008

(54) INHIBITORS OF THE HIV INTEGRASE ENZYME

(75) Inventors: Klaus Ruprecht Dress, San Diego, CA (US); Qiyue Hu, Carlsbad, CA (US); Ted William Johnson, San Diego, CA (US); Michael Bruno Plewe, San Diego, CA (US); Steven Paul Tanis, Carlsbad, CA (US); Hai Wang, San Diego, CA (US); Anle Yang, San Diego, CA (US); Chunfeng Yin, San Diego, CA (US); Junhu Zhang, San Diego, CA (US)

(73) Assignee: Pfizer Inc., New York, NY (US)

( * ) Notice: Subject to any disclaimer, the term of this patent is extended or adjusted under 35 U.S.C. 154(b) by 470 days.

(21) Appl. No.: 11/115,003

(22) Filed: Apr. 25, 2005

(65) Prior Publication Data

US 2005/0277662 A1    Dec. 15, 2005

Related U.S. Application Data

(60) Provisional application No. 60/565,705, filed on Apr. 26, 2004, provisional application No. 60/660,502, filed on Mar. 9, 2005.

(51) Int. Cl.
C07D 471/02 (2006.01)
A61K 31/4745 (2006.01)

(52) U.S. Cl. .......................... 514/300; 546/113
(58) Field of Classification Search .......... None
See application file for complete search history.

(56) References Cited

U.S. PATENT DOCUMENTS

| | | | |
|---|---|---|---|
| 4,371,536 A | 2/1983 | Braestrup et al. | |
| 5,010,077 A | 4/1991 | Braestrup et al. | |
| 5,616,609 A | 4/1997 | Ikekawa et al. | |
| 5,726,203 A | 3/1998 | Li et al. | |
| 6,057,297 A | 5/2000 | Politi et al. | |
| 6,075,021 A | 6/2000 | Evanno et al. | |
| 6,395,743 B1 | 5/2002 | Heimbuch et al. | |
| 6,403,347 B1 | 6/2002 | Bills et al. | |
| 7,001,912 B2 | 2/2006 | Kuki et al. | |
| 7,135,482 B2 | 11/2006 | Hu et al. | |
| 7,138,408 B2 | 11/2006 | Kuki et al. | |
| 2002/0123527 A1 | 9/2002 | Walker et al. | |

FOREIGN PATENT DOCUMENTS

| EP | 0 030 254 B1 | 10/1984 |
|---|---|---|
| EP | 1 086 101 B1 | 3/2001 |
| EP | 1 209 158 A1 | 5/2002 |
| EP | 1 375 486 A1 | 1/2004 |
| GB | 2 209 032 A | 4/1989 |
| GB | 2 271 566 A | 4/1994 |
| GB | 2 306 476 A | 5/1997 |
| GB | 2 327 674 A | 2/1999 |
| JP | 2003/119137 | 4/2003 |
| JP | 2003/171381 | 6/2003 |
| WO | WO 98/18473 A1 | 5/1998 |
| WO | WO 00/68235 | 11/2000 |
| WO | WO 01/09114 A1 | 2/2001 |
| WO | WO 02/02516 A2 | 1/2002 |
| WO | WO 02/070491 A1 | 9/2002 |
| WO | WO 03/033496 A1 | 4/2003 |
| WO | WO 03/035076 A1 | 5/2003 |
| WO | WO 03/047564 | 6/2003 |
| WO | WO 03/049690 A2 | 6/2003 |
| WO | WO 03/062204 A1 | 7/2003 |
| WO | WO 03/077850 A2 | 9/2003 |
| WO | WO 03/082881 A2 | 10/2003 |
| WO | WO 03/086319 A2 | 10/2003 |
| WO | WO 2004/035076 A1 | 4/2004 |
| WO | WO 2004/039803 A2 | 5/2004 |
| WO | WO 2004/067531 A1 | 8/2004 |
| WO | WO 2005/103003 | 11/2005 |
| WO | WO 2005/103051 | 11/2005 |
| WO | WO 2005/103051 A1 | 11/2005 |
| WO | WO 2006/027694 | 3/2006 |

OTHER PUBLICATIONS

Abdel-Magid, A.F., et al., "Reductive Amination of Aldehydes and Ketones by Using Sodium Triacetoxyborohydride," *Tetrahedron Letters*, 1990, p. 5595-5598, vol. 31, No. 39.
Abdel-Magid, et al., "Reductive Amination of Aldehydes and Ketones with Sodium Triacetoxyborohydride. Studies on Direct and Indirect Reductive Amination Procedures," *Journal of Organic Chemistry*, 1996, p. 3849-3862, vol. 61.
Bagshawe, K., "Antibody-Directed Enzyme Prodrug Therapy: A Review," *Drug Development Research*, 1995, p. 220-230, vol. 34.
Barbier, C., et al., "Preparation of Lavendamycin Analogues," *Heterocycles*, 2000, p. 37-48, vol. 53, No. 1.
Bertolini, et al., "A New Rational Hypothesis for the Pharmacophore of the Active Metabolite of Leflunomide, a Potent Immonsuppresive Drug," *Journal of Medicinal Chemistry*, 1997, p. 2011-2016, vol. 40.

(Continued)

Primary Examiner—Zinna N Davis
(74) Attorney, Agent, or Firm—Steve T. Zelson; Christian M. Smolizza

(57) ABSTRACT

The present invention is directed to compounds of formula (I), and pharmaceutically acceptable salts and solvates thereof, their synthesis, and their use as modulators or inhibitors of the human immunodeficiency virus ("HIV") integrase enzyme.

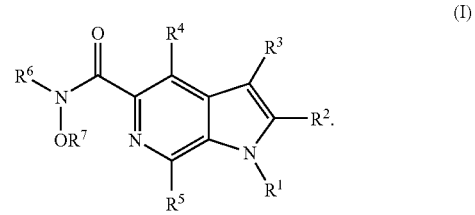

(I)

20 Claims, No Drawings

OTHER PUBLICATIONS

Biere, H., et al., "Ein einfacher Zugang zum Pyrrolo[1,2-c]pyrimidin und Pyrrolo[3,2-c]pyridin-System," *Liebigs Ann. Chem.*, 1987, p. 491-497 (English Abstract Enclosed).

Bodor, "Novel Approaches to the Design of Safer Drugs: Soft Drugs and Site-Specific Chemical Delivery Systems," *Advances in Drug Research*, 1984, p. 255-331, vol. 13.

Butler, S.L., et al., "A quantitative assay for HIV DNA integration in vivo," *Nature Medicine*, May 2001, 631-634, vol. 7, No. 5.

Cain, M., et al., "Biomimetic Approach to Potential Benzodiazepine Agonists and Antagonists," *Heterocycles*, 1982, p. 1003-1007, vol. 19, No. 6.

Campbell, K.N., et al., "The Preparation of unsymmetrical Secondary Aliphatic Amines," *J. Am. Chem. Soc.*, 1944, p. 82-84, vol. 66.

Chen, B.K., et al., "Distinct modes of human immunodeficiency virus type 1 proviral latency revealed by superinfection of nonproductively infected cell lines with recombinant luciferase-encoding viruses," *Journal of Virology*, 1994, p. 654-660, vol. 68, No. 2.

Chen, J.C-H., et al., "Crystal structure of the HIV-1 integrase catalytic core and C-terminal domains: A model for viral DNA binding," *PNAS*, 2000, p. 8233-8238, vol. 97, No. 15.

Coker, J.N., et al., "The Cyanomethylation of Indole," *Journal of Organic Chemistry*, 1963, p. 589-590, vol. 28.

Dear, G.J., et al., "Mass directed peak selection, an efficient method of drug metabolite identification using directly coupled liquid chromatography—mass spectrometry—nuclear magnetic resonance spectroscopy," *Journal of Chromatography B*, 2000, p. 281-293, vol. 748.

Dekhane, M., et al., "A Practical Synthesis of 1h-Pyrrlo[2,3-c]Pyridine-5-Carboxylic Acid Derivatives From Pyrrole-2-Carboxaldehydes," *Tetrahedron*, 1993, p. 8139-8146, vol. 49, No. 36.

Dekhane, M., et al., "A New Efficient Synthesis of Ethyl β-Carboline-3-Carboxylate (β-CCE) and Methyl 4-Methyl-β-Carboline-3-Carboxylate (4-Methyl-β-CCM) Starting from Indole-2-Carboxaldehyde," *Tetrahedron*, 1994, p. 6299-6306, vol. 50, No. 21.

Dodd, R.H., et al., "The Oxidation of Aromatic Aldehydes to Carboxylic Acids Using Hydrogen Peroxide in Formic Acid," *Synthesis*, 1993, p. 295-297.

Dodd, R.H., et al., "Synthesis and Pharmacological Activity of a Pyrido [3',3':5,4]Pyrrolo[1,2-c]-[1,4] Benzodiazepine-3, 10-Dione, A New Benzodiazepine-β-Carboline Type Hybrid Molecule," *Heterocycles*, 1989, p. 1101-1113, vol. 28, No. 2.

Doisy, X., et al., "Synthesis and Benzodiazepine Receptor (ω Receptor) Affinities of 3-Substituted Derivatives of Pyrrolo[2,3-c]pyridine-5-Carboxylate, a Novel Class of $\omega_1$ Selective Ligands," *Bioorganic Medicinal Chemistry*, 1999, p. 921-932, vol. 7.

Doyle, T.W., et al., "Nuclear Analogs of β-lactam Antibiotics. I. Synthesis of O-2-isocephams," *Can. J. Chem.*, 1977, p. 468-483, vol. 55.

Eberle, M.K., "Contribution to the Chemistry of Indole About the 5-(1-Indolyl)-2-pentanone System," *Journal of Organic Chemistry*, 1976, p. 633-636, vol. 41, No. 4.

Erofeev, Y.V., et al., "Introduction of 3-Indolylmethyl Residues in Nitroacetic Acid Esters," *Khim. Get. Soed.*, 1978, p. 780.

Gilchrist, T.L., et al., "Synthesis of Fused Pyridines under Neutral Conditions," *J.C.S. Chem. Comm.*, 1979, p. 627-628.

Goldgur, Y., et al., "Structure of the HIV-1 integrase catalytic domain complexed with an inhibitor: A platform for antiviral drug design," *PNAS*, Nov. 1999, p. 13040-13043, vol. 96, No. 23.

Grobler, J., et al., "Diketo Acid Inhibitor Mechanism and HIV-1 Integrase: Implications for Metal Binding in the Active Site of Phosphotransferase Enzymes," *PNAS*, 2002, p. 6661-6666, vol. 99, No. 10.

Guzman, F., et al., "Biomimetic Approach to Potential Benzodiazepine Receptor Agonists and Antagonists," *Journal of Medicinal Chemistry*, 1984, p. 564-570, vol. 27.

Hansen, M. S., et al., "Integration complexes derived from HIV vectors for rapid assays in vitro," *Nature Biotechnology*, Jun. 1999, p. 578-582, vol. 17, No. 6.

Hazuda, D., et al., "Discovery and Analysis of Inhibitors of the Human Immunodeficiency Integrase," *Drug Design and Discovery*, 1997, p. 17-24, vol. 15.

Henn, L., et al., "Formation of Indoles, Isoquinolines, and Other Fused Pyridines from Azidocrylates," *J. Chem. Soc. Perkin Trans.*, 1984, p. 2189-2196, vol. 1.

Ho, B., et al. "Inhibitors of Monoamine Oxidase: Influence of Methyl Substitution on the Inhibitory Activiy of beta-Carbolines," *J. Pharm. Sci.*, 1968, p. 269-274, vol. 57, No. 2.

Ho, B., et al., "Inhibitors of Monoamine Oxidase III: 9-Substituted beta-Carbolines," *J.Pharm Sci.*, 1969, p. 219-221, vol. 58, No. 2.

Hughes, D., "Progress in the Mitsunobu Reaction. A Review," *Org. Prep. Proced. Int.*, 1996, p. 127-164, vol. 28, No. 2.

Jenkins, T.M., et al., "A Soluble Active Mutant of HIV-1 Integrase," *Journal of Biological Chemistry*, 1996, p. 7712-7718, vol. 271, No. 13.

Kantlehner, W., et al., "Umsetzungen von *tert*-Butoxy,$N,N,N^1,N_1$-tetramethylmethandiamin mit NH- und CH-aciden Verbingdungen," *Liebigs Ann. Chem.*, 1980, p. 344-357 (English Abstract Enclosed).

Kelley, J.L., et al., "Attempted Inhibition of Histidine Decarboxylase with β-Alkyl Analogues of Histidine," *Journal of Medicinal Chemistry*, 1977, p. 721-723, vol. 20, No. 5.

Kozikowski, A. P., et al., "Use of N,N-Dimethyl(Methylene)Ammonium Chloride in the Functionalization of Indoles," *Heterocycles*, 1980, p. 55-58, vol. 14, No. 1.

Kreher, R. P., et al., "Cyclisierende Kondensation von 1H-Pyrrol-3,4-dicarbaldehyden mit 1,2-bifunktionellen Verbindungen [1]," *Chemiker-Zeitung*, 1984, p. 275-277, vol. 108, No. 9 (English Abstract Enclosed).

Krutosikova, A., et al., "Condensed O-, N-Heterocycles by the Transformation of Azidoacrylates," *Monatsh. Chem.*, 1992, p. 807-815, vol. 123.

Lane, C. F., "Sodium Cyanoborohydride—A Highly Selective Reducing Agent for Organic Functional Groups," *Synthesis*, 1975, p. 135-146.

Lee, J.G., et al., "Aromatization of Cyclohexenes and Cyclohexadienes With Selenium Dioxide-Trimethylsilyl Polyphosphate," *Tetrahedron Letters*, 1992, p. 6363-6366, vol. 33, No. 42.

Lewin, S.R., et al., "Use of Real-Time PCR and Molecular Beacons to Detect Virus Replication in Human Immunodeficiency Virus Type 1-Infected Individuals on Prolonged Effective Antiretroviral Therapy," *Journal of Virology*, Jul. 1999, p. 6099-6103, vol. 73, No. 7.

Lyttle, D.A., et al., "The Chemistry of Nitroacetic Acid and its Esters. I. The Alkylation of Alkylnitroacetates with Gramine," *J. Am. Chem. Soc.*, 1947, p. 2118-2119, vol. 69.

Mataka, S., et al., "Condensation Reaction of 3,4-Dibenzoyl-1-methyl-2,5-diphenylpyrrole and —1-phenylpyrazole with Methylamine Derivatives Affording Pyrrolo [3,4-c]pyridine and 2*H*-Pyrazolo[3,4-c]- and [4,3-c]pyridines," *J. Heterocyclic. Chem.*, 1981, p. 1073-1075, vol. 18.

Mehta, A., et al., "Ortho-Directed Lithiation Studies of 3-Carboxybeta-carbolines," *J. Org. Chem.*, 1993, p. 7587-7590, vol. 58.

Molina, P., et al., "An Efficient Iminophosphorane-Mediated Synthesis of Thieno[3,2-c]pyridine, Thieno[2,3-c]pyridine and Furo[3,2-c]-pyridine Derivatives," *Synthesis*, 1987, p. 45-48.

Molina, P., et al., "Pyrido Annelation Reaction by a Tandem Aza Wittig/Electro-cyclic Ring-Closure Strategy: Preparation of Pyrazolo [4,3-c]- and Pyrazolo[3,4-c]pyridine Derivatives," *Tetrahedron*, 1991, p. 6737-6746, vol. 47, No. 33.

Neef, G., et al., "Synthesis of 4-Substituted β-Carbolines," *Heterocycles*, 1983, p. 1295-1313, vol. 20, No. 7.

Pais, G.C.G., et al., "Structure Activity of 3-Aryl-1,3-diketo-Containing Compounds as HIV-1 Integrase Inhibitors," *Journal of Medicinal Chemistry*, 2002, p. 3184-3194, vol. 45.

Prokopov, A.A., et al., "Synthesis of 6-Azaindole," *Khim. Geterotsikl, Soedin.*, 1977, p. 919.

Prox, A., et al., "Rapid Structure Elucidation of Drug Metabolites by Use of Stable Isotopes," *Xenobiotica.*, 1973, p. 103-112, vol. 3, No. 2.

Rousseau, J.F., et al., "Synthesis of 3-Deaza-β-hydroxyhistidine Derivatives and Their Use for the Preparation of Substituted Pyrrolo[2,3-c]pyridine-5-carboxylates via the Pictet-Spengler Reaction," *Journal of Organic Chemistry*, 1998, 2731-2737, vol. 63.

Sandrin, J., et al., "Pictet-Spengler Condensations in Refluxing Benzene," *Heterocycles*, 1976, p. 1101-1104, vol. 4 no. 6.

Sakamoto, T., et al., "Condensed Heteroaromatic ring Systems. XXI. Synthesis of Pyrrolo[2,3-d]pyrimidines and Pyrrolo[3,2-d]pyrimidines," *Chem. Pharm. Sci.*, 1993, p. 81-86, vol. 41, No. 1.

Sayasith, K., et al., "Targeting HIV-1 Integrase," *Expert Opinion Ther. Targets*, 2001, p. 443-464, vol. 5, No. 4.

Schlecker, W., et al., "Synthesis of 4-arylpyridines and Substituted beta-Carbolines," *Tetrahedron*, 1995, p. 9531-9542, vol. 51, No. 35.

Settimj, G., et al, "β-/carbolines as Agonistic or Antagonistic Benzodiazepine Receptor Ligands. 1. Synthesis of some 5-, 6- and 7-Amino Derivatives of 3-Methoxycarbonyl-β-carboline (β-CCM) and of 3-ethoxycarbonyl-β-Carboline (β-CCE,)" *J. Heterocycl. Chem.*, 1988, p. 1391-1397, vol. 25.

Shafiee, A., et al., "Synthesis of 2-Aryl-6-carbethoxythiazolo[4,5-c]pyridine and 7-Chloro-2-phenylthiazolo[5,4-c]pyridine [1]," *J. Heterocyclic Chem.*, 1986, p. 1171-1173, vol. 23.

Shan, D., et al., "Prodrug Strategies Based on Intramolecular Cyclization Reactions," *Journal of Pharmaceutical Science*, 1997, p. 765-767, vol. 86, No. 7.

Singh, S.K., et al., "Ethyl α-Amino-β,β-Diethoxypropionate, a Useful Synthon for the Preparation of 3,4-Fused Pyridine-6-Carboxylates from Aromatic Aldehydes," *Heterocycles*, 1997, p. 379-391, vol. 44, No. 1.

Snyder, H.R., et al., "The Synthesis of the 2-Amino-3-(3-indolyl)-butyric Acids(β-Methyltryptophans)," J. Am. Chem. Soc., 1957, p. 2217-2221, vol. 79.

Soerens, D., et al., "Study of the Pictet-Spengler Reaction in Aprotic Media: Synthesis of the β-Galactosidase Inhibitor, Pyridindolol," *Journal of Organic Chemistry*, 1979, p. 535-545, vol. 44, No. 4.

Spraul, M., et al., "Liquid chromatography coupled with high-field proton NMR for profiling human urine for endogenous compounds and drug metabolites," *Journal of Pharmaceutical & Biomedical Analysis*, 1992, p. 601-605, vol. 10, No. 8.

Still, W.C., et al., "Rapid Chromatographic Technique for Preparative Separations with Moderate Resolution," *Journal of Organic Chemistry*, 1978, p. 2923-2925, vol. 43, No. 14.

Sundberg, R.J., et al., "Syntheses with N-Protected 2-Lithioindoles," *Journal of Organic Chemistry*, 1973, p. 3324-3330, vol. 38, No. 19.

Terwilliger, E.F., et al., "Construction and use of a replication-competent human immunodeficiency virus (HIV-1) that expresses the chloramphenicol acetyltransferase enzyme," *PNAS*, 1989, p. 3857-3861, vol. 86.

Trout, G., et al., "Synthesis of Some Histidine Analogs and Their Effect on the Growth of a Histidine-Requiring Mutant of *Leuconostoc mesenteroides*," *Journal of Medicinal Chemistry*, 1972, p. 1259-1261, vol. 15, No. 12.

Wai, J.S., et al., "4-Aryl-2,4-dioxobutanoic Acid Inhibitors of HIV-1 Integrase and Viral Replication in Cells," *Journal of Medicinal Chemistry*, 2000, p. 4923-4926, vol. 43, No. 26.

Weislow, O.S., et al., "New Soluble-Formazan Assay for HIV-1 Cytopathic Effects: Application to High-Flux Screening of Synthetic and Natural Products for AIDS-Antiviral Activity," *J. Natl. Cancer Inst.*, 1989, p. 577-586, vol. 81, No. 8.

Young, S.D., "Inhibition of HIV-1 integrase by small molecules: The potential for a new class of AIDS chemotherapeutics," *Curr. Opin. Drug Disc. & Development*, 2001, p. 402-410, vol. 4, No. 4.

Young, S., et al., "L-870, 810: A Potent Antiviral HIV Integrase Inhibitor with Potential Clinical Utility," *Poster presented at International AIDS Conference*, Barcelona, (Jul. 7-12, 2002).

Knight, D., et al., "On The diverse Outcomes Of Base-Induced Cyclisations Of 2-Alkynylphenylhydroxamic Acids," *Tetrahedron Letters*, 2002, 9187-9189, vol. 43.

Little, S., et al., "Anitretroviral Effect Of L-000870810, A Novel HIV-1 Integrase Inhibitor, In HIV-1 Infected Patients," 12th Conference On Retroviruses And Opportunistic Infections, Feb. 2005, Abstract 161.

Quandil, A., et al., "Synthesis And Pharmacological Evaluation Of Substituted Naphth[2,3-*de*]isoquinolines (Dinapsoline Analogues) As $D_1$ and $D_2$ Dopamine Receptor Ligands," *Bioorganic & Medicimal Chemistry*, 2003, 1451-1464, vol. 11.

INHIBITORS OF THE HIV INTEGRASE ENZYME

This application claims priority under 35 U.S.C. § 119(e) to U.S. Patent Application No. 60/565,705, filed Apr. 26, 2004, and U.S. Patent Application No. 60/660,502, filed Mar. 9, 2005, both of which are hereby incorporated by reference in their entirety.

FIELD

The present invention is directed to compounds, and pharmaceutically acceptable salts and solvates thereof, their synthesis, and their use as modulators or inhibitors of the human immunodeficiency virus ("HIV") integrase enzyme. The compounds of the present invention are useful for modulating (e.g. inhibiting) an enzyme activity of HIV integrase enzyme and for treating diseases or conditions mediated by HIV, such as for example, acquired immunodeficiency syndrome ("AIDS"), and AIDS related complex ("ARC").

BACKGROUND

The retrovirus designated "human immunodeficiency virus" or "HIV" is the etiological agent of a complex disease that progressively destroys the immune system. The disease is known as acquired immune deficiency syndrome or AIDS. AIDS and other HIV-caused diseases are difficult to treat due to the ability of HIV to rapidly replicate, mutate and acquire resistance to drugs. In order to slow the proliferation of the virus after infection, treatment of AIDS and other HIV-caused diseases has focused on inhibiting HIV replication.

Since HIV is a retrovirus, and thus, encodes a positive-sense RNA strand, its mechanism of replication is based on the conversion of viral RNA to viral DNA, and subsequent insertion of the viral DNA into the host cell genome. HIV replication relies on three constitutive HIV encoded enzymes: reverse transcriptase (RT), protease and integrase.

Upon infection with HIV, the retroviral core particles bind to specific cellular receptors and gain entry into the host cell cytoplasm. Once inside the cytoplasm, viral RT catalyzes the reverse transcription of viral ssRNA to form viral RNA-DNA hybrids. The RNA strand from the hybrid is then partially degraded and a second DNA strand is synthesized resulting in viral dsDNA. Integrase, aided by viral and cellular proteins, then transports the viral dsDNA into the host cell nucleus as a component of the pre-integration complex (PIC). In addition, integrase provides the permanent insertion, i.e., integration, of the viral dsDNA to the host cell genome, which, in turn, provides viral access to the host cellular machinery for gene expression. Following integration, transcription and translation produce viral precursor proteins.

A key step in HIV replication, insertion of the viral dsDNA into the host cell genome, is believed to be mediated by integrase in at least three, and possibly, four, steps: (1) assembly of proviral DNA; (2) 3'-end processing causing assembly of the PIC; (3) 3'-end joining or DNA strand transfer, i.e., integration; and (4) gap filling, a repair function. See, e.g., Goldgur, Y. et al., *PNAS* 96(23): 13040-13043 (November 1999); Sayasith, K. et al., *Expert Opin. Ther. Targets* 5(4): 443-464 (2001); Young, S. D., *Curr. Opin. Drug Disc. & Devel.* 4(4): 402-410 (2001); Wai, J. S. et al., *J. Med. Chem.* 43(26): 4923-4926 (2000); Debyser, Z. et al., *Assays for the Evaluation of HIV-1 Integrase Inhibitors*, from *Methods in Molecular Biology* 160: 139-155, Schein, C. H. (ed.), Humana Press Inc., Totowa, N.J. (2001); and Hazuda, D. et al., *Drug Design and Disc.* 13:17-24 (1997).

Currently, AIDS and other HIV-caused disease are treated with an "HIV cocktail" containing multiple drugs including RT and protease inhibitors. However, numerous side effects and the rapid emergence of drug resistance limit the ability of the RT and protease inhibitors to safely and effectively treat AIDS and other HIV-caused diseases. In view of the shortcomings of RT and protease inhibitors, there is a need for another mechanism through which HIV replication can be inhibited. Integration, and thus integrase, a virally encoded enzyme with no mammalian counterpart, is a logical alternative. See, e.g., Wai, J. S. et al., *J. Med. Chem.* 43:4923-4926 (2000); Grobler, J. et al., *PNAS* 99: 6661-6666 (2002); Pais, G. C. G. et al., *J. Med. Chem.* 45: 3184-3194 (2002); Young, S. D., *Curr. Opin. Drug Disc. & Devel.* 4(4): 402-410 (2001); Godwin, C. G. et al., *J. Med. Chem.* 45: 3184-3194 (2002); Young, S. D. et al., "L-870, 810: Discovery of a Potent HIV Integrase Inhibitor with Potential Clinical Utility," Poster presented at the XIV International AIDS Conference, Barcelona (Jul. 7-12, 2002); and WO 02/070491.

It has been suggested that for an integrase inhibitor to function, it should inhibit the strand transfer integrase function. See, e.g., Young, S. D., *Curr. Opin. Drug Disc. & Devel.* 4(4): 402-410 (2001). Thus, there is a need for HIV inhibitors, specifically, integrase inhibitors, and, more specifically, strand transfer inhibitors, to treat AIDS and other HIV-caused diseases. The inventive agents disclosed herein are novel, potent and selective HIV-integrase inhibitors, and, more specifically, strand transfer inhibitors, with high antiviral activity.

SUMMARY

The present invention provides compounds of formula (I),

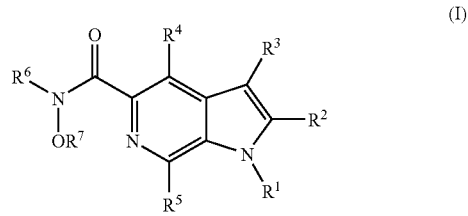

(I)

wherein:

$R^1$ is hydrogen, $C_1$-$C_8$ alkyl, $C_2$-$C_8$ alkenyl, or $C_1$-$C_8$ heteroalkyl, wherein said $C_1$-$C_8$ alkyl, $C_2$-$C_8$ alkenyl, or $C_1$-$C_8$ heteroalkyl groups may be optionally substituted with at least one substituent independently selected from:

halo, —$OR^{12a}$, —$N(R^{12a}R^{12b})$, —$C(O)N(R^{12a})_2$, —$NR^{12a}C(O)N(R^{12a}R^{12b})$, —$NR^{12a}C(O)R^{12a}$, —$NR^{12a}C(NR^{12a})N(R^{12a}R^{12b})$, —$SR^{12a}$, —$S(O)R^{12a}$, —$S(O)_2R^{12a}$, —$S(O)_2N(R^{12a}R^{12b})_2$, $C_1$-$C_8$ alkyl, $C_6$-$C_{14}$ aryl, $C_3$-$C_8$ cycloalkyl, and $C_2$-$C_9$ heteroaryl, wherein said $C_1$-$C_8$ alkyl, $C_6$-$C_{14}$ aryl, $C_3$-$C_8$ cycloalkyl, and $C_2$-$C_9$ heteroaryl groups are optionally substituted with at least one substituent independently selected from halo, —$C(R^{12a}R^{12b}R^{12c})$, —OH, and $C_1$-$C_8$ alkoxy;

$R^2$ is hydrogen;

$R^3$ is —$(CR^8R^9)_xNR^{10}R^{11}$ or $C_1$-$C_8$ heteroalkyl, wherein said $C_1$-$C_8$ heteroalkyl is substituted with $R^{24}$;

$R^4$ is hydrogen, halo, $C_1$-$C_8$ alkyl, —$OR^{12a}$, —$NR^{12a}R^{12b}$, $C_1$-$C_8$ heteroalkyl, $C_2$-$C_8$ alkenyl, or $C_2$-$C_8$ alkynyl, wherein said $C_2$-$C_8$ alkenyl or $C_2$-$C_8$ alkynyl are optionally substituted with at least one $R^{26}$;

$R^5$ is hydrogen;

$R^6$ is hydrogen, $C_1$-$C_8$ alkyl, $C_1$-$C_8$ heteroalkyl, or $C_2$-$C_8$ alkenyl, wherein said $C_2$-$C_8$ alkenyl is optionally substituted with at least one —$OR^{12a}$ group;

$R^7$ is hydrogen, $C_1$-$C_8$ heteroalkyl, $C_6$-$C_{14}$ aryl, $C_2$-$C_8$ alkenyl, or $C_1$-$C_8$ alkyl, wherein said $C_1$-$C_8$ alkyl is optionally substituted with at least one $C_3$-$C_8$ cycloalkyl or $C_6$-$C_{14}$ aryl group;

each $R^8$ and $R^9$, which may be the same or different, are independently selected from hydrogen and $C_1$-$C_8$ alkyl;

$R^{10}$ and $R^{11}$, together with the nitrogen atom to which they are attached, form a $C_2$-$C_9$ cycloheteroalkyl group optionally substituted with at least one $C_1$-$C_8$ alkyl;

each $R^{12a}$, $R^{12b}$, and $R^{12c}$, which may be the same or different, is independently selected from hydrogen and $C_1$-$C_8$ alkyl;

$R^{24}$ is $C_3$-$C_8$ cycloalkyl, $C_1$-$C_8$ heteroalkyl, $C_2$-$C_9$ cycloheteroalkyl, or $C_2$-$C_9$ heteroaryl, each of which is optionally substituted with at least one substituent independently selected from $C_1$-$C_8$ alkyl, $C_6$-$C_{14}$ aryl, $C_2$-$C_9$ heteroaryl, —$CF_3$, and —$OR^{12a}$;

each $R^{26}$ is independently selected from —$OR^{12a}$, halo, $C_6$-$C_{14}$ aryl, $C_2$-$C_9$ heteroaryl, $C_1$-$C_8$ heteroalkyl, $C_3$-$C_8$ cycloalkyl, $C_2$-$C_9$ cycloheteroalkyl, and —$C(R^{12a}R^{12b}R^{12c})$;

t is an integer from 1 to 3; and pharmaceutically acceptable salts and solvates thereof.

In another aspect are afforded compounds of formula (I), wherein:

$R^1$ is hydrogen, $C_1$-$C_8$ alkyl, $C_2$-$C_8$ alkenyl, or $C_1$-$C_8$ heteroalkyl, wherein said $C_1$-$C_8$ alkyl, $C_2$-$C_8$ alkenyl, or $C_1$-$C_8$ heteroalkyl groups may be optionally substituted with at least one substituent independently selected from:

halo, —$OR^{12a}$, —$N(R^{12a}R^{12b})$, —$C(O)N(R^{12a})_2$, —$NR^{12a}C(O)N(R^{12a}R^{12b})$, —$NR^{12a}C(O)R^{12a}$, —$NR^{12a}C(NR^{12a})N(R^{12a}R^{12b})$, —$SR^{12a}$, —$S(O)R^{12a}$, —$S(O)_2R^{12a}$, —$S(O)_2N(R^{12a}R^{12b})_2$, $C_1$-$C_8$ alkyl, $C_6$-$C_{14}$ aryl, $C_3$-$C_8$ cycloalkyl, and $C_2$-$C_9$ heteroaryl, wherein said $C_1$-$C_8$ alkyl, $C_6$-$C_{14}$ aryl, $C_3$-$C_8$ cycloalkyl, and $C_2$-$C_9$ heteroaryl groups are optionally substituted with at least one substituent independently selected from halo, —$C(R^{12a}R^{12b}R^{12c})$, —H, and $C_1$-$C_8$ alkoxy;

$R^2$ is hydrogen;

$R^3$ is —$(CR^8R^9)_tNR^{10}R^{11}$;

$R^4$ is hydrogen, halo, $C_1$-$C_8$ alkyl, —$OR^{12a}$, —$NR^{12a}R^{12b}$, $C_1$-$C_8$ heteroalkyl, $C_2$-$C_8$ alkenyl, or $C_2$-$C_6$ alkynyl, wherein said $C_2$-$C_8$ alkenyl or $C_2$-$C_8$ alkynyl are optionally substituted with at least one $R^{26}$;

$R^5$ is hydrogen;

$R^6$ is hydrogen, $C_1$-$C_8$ alkyl, $C_1$-$C_8$ heteroalkyl, or $C_2$-$C_8$ alkenyl, wherein said $C_2$-$C_8$ alkenyl is optionally substituted with at least one —$OR^{12a}$ group;

$R^7$ is hydrogen, $C_1$-$C_8$ heteroalkyl, $C_6$-$C_{14}$ aryl, $C_2$-$C_8$ alkenyl, or $C_1$-$C_8$ alkyl, wherein said $C_1$-$C_8$ alkyl is optionally substituted with at least one $C_3$-$C_8$ cycloalkyl or $C_6$-$C_{14}$ aryl group;

each $R^8$ and $R^9$, which may be the same or different, are independently selected from hydrogen and $C_1$-$C_8$ alkyl;

$R^{10}$ and $R^{11}$, together with the nitrogen atom to which they are attached, form a $C_2$-$C_9$ cycloheteroalkyl group optionally substituted with at least one $C_1$-$C_8$ alkyl;

each $R^{12a}$, $R^{12b}$, and $R^{12c}$, which may be the same or different, is independently selected from hydrogen and $C_1$-$C_8$ alkyl;

each $R^{26}$ is independently selected from —$OR^{12a}$, halo, $C_6$-$C_{14}$ aryl, $C_2$-$C_9$ heteroaryl, $C_1$-$C_8$ heteroalkyl, $C_3$-$C_8$ cycloalkyl, $C_2$-$C_9$ cycloheteroalkyl, and —$C(R^{12a}R^{12b}R^{12c})$;

t is an integer from 1 to 3; and pharmaceutically acceptable salts and solvates thereof.

In yet another aspect are compounds of formula (I), wherein:

$R^1$ is $C_1$-$C_8$ alkyl substituted with $C_6$-$C_{14}$ aryl, $C_3$-$C_8$ cycloalkyl, or $C_2$-$C_9$ heteroaryl, wherein said $C_6$-$C_{14}$ aryl, $C_3$-$C_8$ cycloalkyl, and $C_2$-$C_9$ heteroaryl groups are optionally substituted with at least one substituent independently selected from halo, —$C(R^{12a}R^{12b}R^{12c})$, —H, and $C_1$-$C_8$ alkoxy;

$R^2$ is hydrogen;

$R^3$ is —$(CR^8R^9)_tNR^{10}R^{11}$;

$R^4$ is hydrogen, halo, $C_1$-$C_8$ alkyl, —$OR^{12a}$, —$NR^{12a}R^{12b}$, $C_1$-$C_8$ heteroalkyl, $C_2$-$C_8$ alkenyl, or $C_2$-$C_8$ alkynyl, wherein said $C_2$-$C_8$ alkenyl or $C_2$-$C_8$ alkynyl are optionally substituted with at least one $R^{26}$;

$R^5$ is hydrogen;

$R^6$ is hydrogen, $C_1$-$C_8$ alkyl, $C_1$-$C_8$ heteroalkyl, or $C_2$-$C_8$ alkenyl, wherein said $C_2$-$C_8$ alkenyl is optionally substituted with at least one —$OR^{12a}$ group;

$R^7$ is hydrogen, $C_1$-$C_8$ heteroalkyl, $C_6$-$C_{14}$ aryl, $C_2$-$C_8$ alkenyl, or $C_1$-$C_8$ alkyl, wherein said $C_1$-$C_8$ alkyl is optionally substituted with at least one $C_3$-$C_8$ cycloalkyl or $C_6$-$C_{14}$ aryl group;

$R^8$ and $R^9$ are hydrogen;

$R^{10}$ and $R^{11}$, together with the nitrogen atom to which they are attached, form a $C_2$-$C_9$ cycloheteroalkyl group optionally substituted with at least one $C_1$-$C_8$ alkyl;

each $R^{12a}$, $R^{12b}$, and $R^{12c}$, which may be the same or different, is independently selected from hydrogen and $C_1$-$C_8$ alkyl;

each $R^{26}$ is independently selected from —$OR^{12a}$, halo, $C_6$-$C_{14}$ aryl, $C_2$-$C_9$ heteroaryl, $C_1$-$C_8$ heteroalkyl, $C_3$-$C_8$ cycloalkyl, $C_2$-$C_9$ cycloheteroalkyl, and —$C(R^{12a}R^{12b}R^{12c})$;

t is an integer from 1 to 3; and pharmaceutically acceptable salts and solvates thereof.

Also provided are compounds of formula (I), wherein:

$R^1$ is $C_1$-$C_8$ alkyl substituted with $C_6$-$C_{14}$ aryl, wherein said $C_6$-$C_{14}$ aryl is optionally substituted with at least one substituent independently selected from halo, —$C(R^{12a}R^{12b}R^{12c})$, —H, and $C_1$-$C_8$ alkoxy;

$R^2$ is hydrogen;

$R^3$ is —$(CH_2)_tNR^{10}R^{11}$;

$R^4$ is hydrogen or $C_2$-$C_8$ alkenyl, wherein said $C_2$-$C_8$ alkenyl is optionally substituted with at least one $R^{26}$;

$R^5$ is hydrogen;

$R^6$ is hydrogen or $C_1$-$C_8$ alkyl;

$R^7$ is hydrogen, $C_1$-$C_8$ heteroalkyl, $C_6$-$C_{14}$ aryl, $C_2$-$C_8$ alkenyl, or C, —$C_8$ alkyl, wherein said $C_1$-$C_8$ alkyl is optionally substituted with at least one $C_3$-$C_8$ cycloalkyl or $C_6$-$C_{14}$ aryl group;

$R^{10}$ and $R^{11}$, together with the nitrogen atom to which they are attached, form a $C_2$-$C_9$ cycloheteroalkyl group optionally substituted with at least one $C_1$-$C_8$ alkyl;

each $R^{12a}$, $R^{12b}$, and $R^{12c}$, which may be the same or different, is independently selected from hydrogen and $C_1$-$C_8$ alkyl;

each $R^{26}$ is independently selected from —$OR^{12a}$, halo, $C_6$-$C_{14}$ aryl, $C_2$-$C_9$ heteroaryl, $C_1$-$C_8$ heteroalkyl, $C_3$-$C_8$ cycloalkyl, $C_2$-$C_9$ cycloheteroalkyl, and —$C(R^{12a}R^{12b}R^{12c})$;

t is an integer from 1 to 3; and pharmaceutically acceptable salts and solvates thereof.

The present invention also provides compounds of formula (I), wherein:

$R^1$ is $C_1$-$C_8$ alkyl substituted with $C_6$-$C_{14}$ aryl, wherein said $C_6$-$C_{14}$ aryl is optionally substituted with at least one halo;

R² is hydrogen;
R³ is —(CH₂)ₜNR¹⁰R¹¹;
R⁴ is hydrogen or C₂-C₈ alkenyl, wherein said C₂-C₈ alkenyl is optionally substituted with at least one R²⁶;
R⁵ is hydrogen;
R⁶ is hydrogen or —CH₃;
R⁷ is hydrogen, C₁-C₈ heteroalkyl, C₆-C₁₄ aryl, C₂-C₈ alkenyl, or C₁-C₈ alkyl, wherein said C₁-C₈ alkyl is optionally substituted with at least one C₃-C₈ cycloalkyl or C₆-C₁₄ aryl group;
R¹⁰ and R¹¹, together with the nitrogen atom to which they are attached, form a C₂-C₉ cycloheteroalkyl group optionally substituted with at least one C₁-C₈ alkyl;
t is an integer from 1 to 3; and
pharmaceutically acceptable salts and solvates thereof.
Also provided are compounds of formula (I), wherein:
R¹ is C₁-C₈ alkyl substituted with C₆-C₁₄ aryl, wherein said C₆-C₁₄ aryl is substituted with at least one fluorine;
R² is hydrogen;
R³ is —(CH₂)NR¹⁰R¹¹;
R⁴ is hydrogen;
R⁵ is hydrogen;
R⁶ is hydrogen or —CH₃;
R⁷ is hydrogen, —CH₃, phenyl, allyl, or benzyl;
R¹⁰ and R¹¹, together with the nitrogen atom to which they are attached, form a C₂-C₉ cycloheteroalkyl group optionally substituted with at least one C₁-C₈ alkyl; and
pharmaceutically acceptable salts and solvates thereof.
Additionally, the present invention affords compounds of formula (I), wherein:
R¹ is benzyl substituted with at least one fluorine;
R² is hydrogen;
R³ is —(CH₂)NR¹⁰R¹¹;
R⁴ is hydrogen;
R⁵ is hydrogen;
R⁶ is hydrogen or —CH₃;
R⁷ is hydrogen, —CH₃, phenyl, allyl, or benzyl;
R¹⁰ and R¹¹, together with the nitrogen atom to which they are attached, form a C₂-C₉ cycloheteroalkyl group optionally substituted with at least one C₁-C₈ alkyl; and
pharmaceutically acceptable salts and solvates thereof.
Further provided are compounds of formula (i), wherein:
R¹ is 2-fluorobenzyl, 3-fluorobenzyl, 4-fluorobenzyl, 2,3-difluorobenzyl, 2,4-difluorobenzyl, or 3,4-difluorobenzyl;
R² is hydrogen;
R³ is —(CH₂)NR¹⁰R¹¹;
R⁴ is hydrogen;
R⁵ is hydrogen;
R⁶ is hydrogen or —CH₃;
R⁷ is hydrogen, —CH₃, phenyl, allyl, or benzyl;
R¹⁰ and R¹¹, together with the nitrogen atom to which they are attached, form a C₂-C₉ cycloheteroalkyl group optionally substituted with at least one C₁-C₈ alkyl; and
pharmaceutically acceptable salts and solvates thereof.
Also afforded are compounds of formula (I), wherein:
R¹ is 2-fluorobenzyl, 3-fluorobenzyl, 4-fluorobenzyl, 2,3-difluorobenzyl, 2,4-difluorobenzyl, or 3,4-difluorobenzyl;
R² is hydrogen;
R³ is —(CH₂)NR¹⁰R¹¹;
R⁴ is hydrogen;
R⁵ is hydrogen;
R⁶ is hydrogen or —CH₃;
R⁷ is hydrogen, —CH₃, phenyl, allyl, or benzyl;
R¹⁰ and R¹¹, together with the nitrogen atom to which they are attached, form a C₂-C₉ cycloheteroalkyl group optionally substituted with at least one C₁-C₈ alkyl; and
pharmaceutically acceptable salts and solvates thereof.

Further afforded in the present invention are any of the above compounds of formula (I), wherein R¹⁰ and R¹¹, together with the nitrogen atom to which they are attached, form a C₂-C₉ cycloheteroalkyl group comprising 4 carbon atoms and a nitrogen atom.

Also provided are any of the above compounds of formula (I), wherein R¹⁰ and R¹¹, together with the nitrogen atom to which they are attached, form a C₂-C₉ cycloheteroalkyl group comprising 4 carbon atoms and 2 nitrogen atoms.

Also provided are any of the above compounds of formula (I), wherein R¹⁰ and R¹¹, together with the nitrogen atom to which they are attached, form a C₂-C₉ cycloheteroalkyl group comprising 4 carbon atoms, a nitrogen atom, and an oxygen atom, provided that said nitrogen atom and said oxygen atom are not bonded to each other.

Further provided are any of the above compounds of formula (I), wherein R¹⁰ and R¹¹, together with the nitrogen atom to which they are attached, form a C₂-C₉ cycloheteroalkyl group comprising 4 carbon atoms, a nitrogen atom, and a sulfur atom.

In yet another aspect of the present invention are any of the above compounds of formula (I), wherein R¹⁰ and R¹¹, together with the nitrogen atom to which they are attached, form a C₂-C₉ cycloheteroalkyl group comprising 4 carbon atoms, a nitrogen atom, and an oxidized sulfur atom.

Another aspect is any of the above compounds of formula (I), wherein R¹⁰ and R¹¹, together with the nitrogen atom to which they are attached, form a C₂-C₉ cycloheteroalkyl group comprising three carbon atoms and three nitrogen atoms.

Also provided are any of the above compounds of formula (I), wherein R¹⁰ and R¹¹, together with the nitrogen atom to which, they are attached, form a C₂-C₉ cycloheteroalkyl group selected from:

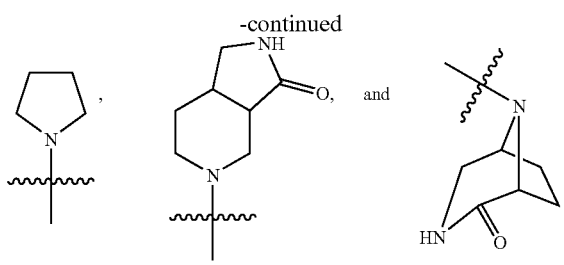

In a further aspect are any of the above compounds of formula (I), wherein $R^6$ is hydrogen; or wherein $R^6$ is —$CH_3$; or wherein $R^7$ is hydrogen; or wherein $R^7$ is —$CH_3$, phenyl, allyl, or benzyl; or wherein $R^6$ and $R^7$ are hydrogen; or wherein $R^6$ is hydrogen and $R^7$ is —$CH_3$, phenyl, allyl, or benzyl; or wherein $R^6$ is —$CH_3$ and $R^7$ is hydrogen.

Also provided are compounds selected from 1-(2,4-difluorobenzyl)-N-hydroxy-3-(morpholin-4-ylmethyl)-1H-pyrrolo[2,3-c]pyridine-5-carboxamide; 1-(2,4-difluorobenzyl)-N-hydroxy-3-[(4-methylpiperazin-1-yl)methyl]-1H-pyrrolo[2,3-c]pyridine-5-carboxamide; 1-(2,4-difluorobenzyl)-N-hydroxy-3-(piperidin-1-ylmethyl)-1H-pyrrolo[2,3-c]pyridine-5-carboxamide; 1-(2,4-difluorobenzyl)-N-hydroxy-N-methyl-3-(morpholin-4-ylmethyl)-1H-pyrrolo[2,3-c]pyridine-5-carboxamide; 1-(2,4-difluorobenzyl)-3-[(1,1-dioxidothiomorpholin-4-yl)methyl]-N-hydroxy-1H-pyrrolo[2,3-c]pyridine-5-carboxamide; 1-(4-fluorobenzyl)-N-hydroxy-N-methyl-3-[(4-methylpiperazin-1-yl)methyl]-1H-pyrrolo[2,3-c]pyridine-5-carboxamide; 1-(4-fluorobenzyl)-N-hydroxy-3-[(3-oxopiperazin-1-yl) methyl]-1H-pyrrolo[2,3-c]pyridine-5-carboxamide; 1-(2,4-difluorobenzyl)-N-hydroxy-N-methyl-3-[(4-methylpiperazin-1-yl)methyl]-1H-pyrrolo[2,3-c]pyridine-5-carboxamide; 1-(4-fluorobenzyl)-N-hydroxy-N-methyl-3-[(2-methyl-3-oxopiperazin-1-yl)methyl]-1H-pyrrolo[2,3-c]pyridine-5-carboxamide; 1-(4-fluorobenzyl)-N-hydroxy-N-methyl-3-{[(1R,5S)-2-oxo-3,8-diazabicyclo[3.2.1]oct-8-yl]methyl}-1H-pyrrolo[2,3-c]pyridine-5-carboxamide; rac 1-(2,4-difluorobenzyl)-N-hydroxy-3-{[(3aR*,7aS*)-3-oxooctahydro-5H-pyrrolo[3,4-c]pyridin-5-yl]methyl}-1H-pyrrolo[2,3-c]pyridine-5-carboxamide; 1-(2,4-difluorobenzyl)-N-methoxy-3-[(4-methylpiperazin-1-yl)methyl]-1H-pyrrolo[2,3-c]pyridine-5-carboxamide; rac 1-(2,4-difluorobenzyl)-N-methoxy-3-{[(3aR*,7aS*)-3-oxooctahydro-5H-pyrrolo[3,4-c]pyridin-5-yl]methyl}-1H-pyrrolo[2,3-c]pyridine-5-carboxamide; rac 1-(2,4-difluorobenzyl)-N-hydroxy-N-methyl-3-{[(3aR*,7aS*)-3-oxooctahydro-5H-pyrrolo[3,4-c]pyridin-5-yl]methyl}-1H-pyrrolo[2,3-c]pyridine-5-carboxamide; N-(benzyloxy)-1-(4-fluorobenzyl)-3-[(3-oxopiperazin-1-yl)methyl]-1H-pyrrolo[2,3-c]pyridine-5-carboxamide; N-(allyloxy)-1-(4-fluorobenzyl)-3-[(3-oxopiperazin-1-yl) methyl]-1H-pyrrolo[2,3-c]pyridine-5-carboxamide; and 1-(4-fluorobenzyl)-3-[(3-oxopiperazin-1-yl)methyl]-N-phenoxy-1H-pyrrolo[2,3-c]pyridine-5-carboxamide; 1-(2,4-difluorobenzyl)-N-hydroxy-3-[(2-methylpyrrolidin-1-yl)methyl]-1H-pyrrolo[2,3-c]pyridine-5-carboxamide; 1-(2,4-Difluorobenzyl)-N-hydroxy-3-(4-methylpiperazin-1-yl)-1H-pyrrolo[2,3-c]pyridine-5-carboxamide; 1-(2,4-difluorobenzyl)-N-hydroxy-3-{[(3aR*,7aS*)-1-oxooctahydro-5H-pyrrolo[3,4-c]pyridin-5-yl]methyl}-1H-pyrrolo[2,3-c]pyridine-5-carboxamide; 1-(2,4-Difluorobenzyl)-N-methoxy-3-{[(3aR*,7aS*)-1-oxooctahydro-5H-pyrrolo[3,4-c]pyridin-5-yl]methyl}-1H-pyrrolo[2,3-c]pyridine-5-carboxamide; 1-(2,4-difluorobenzyl)-N-hydroxy-N-methyl-3-{[(3aR*,7aS*)-1-oxooctahydro-5H-pyrrolo[3,4-c]pyridin-5-yl]methyl}-1H-pyrrolo[2,3-c]pyridine-5-carboxamide; 1-(2,4-Difluorobenzyl)-N-hydroxy-N-methyl-3-{[(3aS,7aS*)-1-oxooctahydro-5H-pyrrolo[3,4-c]pyridin-5-yl]methyl}-1H-pyrrolo[2,3-c]pyridine-5-carboxamide; 1-(2,4-Difluorobenzyl)-N-hydroxy-N-methyl-3-{{[(3aR,7aR*)-1-oxooctahydro-5H-pyrrolo[3,4-c]pyridin-5-yl]methyl}-1H-pyrrolo[2,3-c]pyridine-5-carboxamide; and 1-(4-fluorobenzyl)-N-hydroxy-N-methyl-3-[(3-oxopiperazin-1-yl)methyl]-1H-pyrrolo[2,3-c]pyridine-5-carboxamide; or pharmaceutically acceptable salts or solvates thereof.

In yet another aspect of the present invention are compounds of formula (I), wherein:

$R^1$ is hydrogen, $C_1$-$C_8$ alkyl, $C_2$-$C_8$ alkenyl, or $C_1$-$C_8$ heteroalkyl, wherein said $C_1$-$C_8$ alkyl, $C_2$-$C_8$ alkenyl, or $C_1$-$C_8$ heteroalkyl groups may be optionally substituted with at least one substituent independently selected from:

halo, —$OR^{12a}$, —$N(R^{12a}R^{12b})$, —$C(O)N(R^{12a})_2$, —$NR^{12a}C(O)N(R^{12a}R^{12b})$, —$NR^{12a}C(O)R^{12a}$, —$NR^{12a}C(NR^{12a})N(R^{12a}R^{12b})$, —$SR^{12}$, —$S(O)R^{12a}$, —$S(O)_2R^{12a}$, —$S(O)_2N(R^{12a}R^{12b})_2$, $C_1$-$C_8$ alkyl, $C_6$-$C_{14}$ aryl, $C_3$-$C_8$ cycloalkyl, and $C_2$-$C_9$ heteroaryl, wherein said $C_1$-$C_8$ alkyl, $C_6$-$C_{14}$ aryl, $C_3$-$C_8$ cycloalkyl, and $C_2$-$C_9$ heteroaryl groups are optionally substituted with at least one substituent independently selected from halo, —$C(R^{12a}R^{12b}R^{12}C)$, —OH, and $C_1$-$C_8$ alkoxy;

$R^2$ is hydrogen;

$R^3$ is $C_1$-$C_8$ heteroalkyl substituted with $R^{24}$;

$R^4$ is hydrogen, halo, $C_1$-$C_8$ alkyl, —$OR^{12a}$, —$NR^{12a}R^{12b}$, $C_1$-$C_8$ heteroalkyl, $C_2$-$C_8$ alkenyl, or $C_2$-$C_8$ alkynyl, wherein said $C_2$-$C_8$ alkenyl or $C_2$-$C_8$ alkynyl are optionally substituted with at least one $R^{26}$;

$R^5$ is hydrogen;

$R^6$ is hydrogen, $C_1$-$C_8$ alkyl, $C_1$-$C_8$ heteroalkyl, or $C_2$-$C_8$ alkenyl, wherein said $C_2$-$C_8$ alkenyl is optionally substituted with at least one —$OR^{12a}$ group;

$R^7$ is hydrogen, $C_1$-$C_8$ heteroalkyl, $C_6$-$C_{14}$ aryl, $C_2$-$C_8$ alkenyl, or $C_1$-$C_8$ alkyl, wherein said $C_1$-$C_8$ alkyl is optionally substituted with at least one $C_3$-$C_8$ cycloalkyl or $C_6$-$C_{14}$ aryl group;

each $R^{12a}$, $R^{12b}$, and $R^{12c}$, which may be the same or different, is independently selected from hydrogen and $C_1$-$C_8$ alkyl;

$R^{24}$ is $C_3$-$C_8$ cycloalkyl, $C_1$-$C_8$ heteroalkyl, $C_2$-$C_9$ cycloheteroalkyl, or $C_2$-$C_9$ heteroaryl, each of which is optionally substituted with at least one substituent independently selected from $C_1$-$C_8$ alkyl, $C_6$-$C_{14}$ aryl, $C_2$-$C_9$ heteroaryl, —$CF_3$, and —$OR^{12a}$;

each $R^{26}$ is independently selected from —$OR^{12a}$, halo, $C_6$-$C_{14}$ aryl, $C_2$-$C_9$ heteroaryl, $C_1$-$C_8$ heteroalkyl, $C_3$-$C_8$ cycloalkyl, $C_2$-$C_9$ cycloheteroalkyl, and —$C(R^{12a}R^{12b}R^{12c})$; and pharmaceutically acceptable salts and solvates thereof.

Further provided are compounds of formula (I), wherein:

$R^1$ is $C_1$-$C_8$ alkyl optionally substituted with at least one $C_6$-$C_{14}$ aryl, and wherein said $C_6$-$C_{14}$ is optionally substituted with at least one substituent independently selected from halo, —$C(R^{12a}R^{12b}R^{12c})$, —OH, and $C_1$-$C_8$ alkoxy;

$R^2$ is hydrogen;

$R^3$ is $C_1$-$C_8$ heteroalkyl substituted with $R^{24}$;

$R^4$ is hydrogen, halo, $C_1$-$C_8$ alkyl, —$OR^{12a}$, —$NR^{12a}R^{12b}$, $C_1$-$C_8$ heteroalkyl, $C_2$-$C_6$ alkenyl, or $C_2$-$C_8$ alkynyl, wherein said $C_2$-$C_8$ alkenyl or $C_2$-$C_8$ alkynyl are optionally substituted with at least one $R^{26}$;

$R^5$ is hydrogen;

$R^6$ is hydrogen, $C_1$-$C_8$ alkyl, $C_1$-$C_8$ heteroalkyl, or $C_2$-$C_8$ alkenyl, wherein said $C_2$-$C_8$ alkenyl is optionally substituted with at least one —$OR^{12a}$ group;

$R^7$ is hydrogen, $C_1$-$C_8$ heteroalkyl, $C_6$-$C_{14}$ aryl, $C_2$-$C_8$ alkenyl, or $C_1$-$C_8$ alkyl, wherein said $C_1$-$C_8$ alkyl is optionally substituted with at least one $C_3$-$C_8$ cycloalkyl or $C_6$-$C_{14}$ aryl group;

each $R^{12a}$, $R^{12b}$, and $R^{12c}$, which may be the same or different, is independently selected from hydrogen and $C_1$-$C_8$ alkyl;

$R^{24}$ is $C_3$-$C_8$ cycloalkyl, $C_1$-$C_8$ heteroalkyl, $C_2$-$C_9$ cycloheteroalkyl, or $C_2$-$C_9$ heteroaryl, each of which is optionally substituted with at least one substituent independently selected from $C_1$-$C_8$ alkyl, $C_6$-$C_{14}$ aryl, $C_2$-$C_9$ heteroaryl, —$CF_3$, and —$OR^{12a}$;

each $R^{26}$ is independently selected from —$OR^{12a}$, halo, $C_6$-$C_{14}$ aryl, $C_2$-$C_9$ heteroaryl, $C_1$-$C_8$ heteroalkyl, $C_3$-$C_8$ cycloalkyl, $C_2$-$C_9$ cycloheteroalkyl, and —$C(R^{12a}R^{12b}R^{12c})$; and pharmaceutically acceptable salts and solvates thereof.

Another aspect of the present invention provides compounds of formula (I), wherein:

$R^1$ is $C_1$-$C_8$ alkyl substituted with $C_6$-$C_{14}$ aryl, wherein said $C_6$-$C_{14}$ aryl is optionally substituted with at least one substituent independently selected from halo, —$C(R^{12a}R^{12b}R^{12c})$, —OH, and $C_1$-$C_8$ alkoxy;

$R^2$ is hydrogen;

$R^3$ is $C_1$-$C_8$ heteroalkyl substituted with $R^{24}$;

$R^4$ is hydrogen, halo, $C_1$-$C_8$ alkyl, —$OR^{12a}$, —$NR^{12a}R^{12b}$, $C_1$-$C_8$ heteroalkyl, $C_2$-$C_8$ alkenyl, or $C_2$-$C_8$ alkynyl, wherein said $C_2$-$C_8$ alkenyl or $C_2$-$C_8$ alkynyl are optionally substituted with at least one $R^{26}$;

$R^5$ is hydrogen;

$R^6$ is hydrogen, $C_1$-$C_8$ alkyl, or $C_1$-$C_8$ heteroalkyl;

$R^7$ is hydrogen, $C_1$-$C_8$ heteroalkyl, $C_6$-$C_{14}$ aryl, $C_2$-$C_8$ alkenyl, or $C_1$-$C_8$ alkyl, wherein said $C_1$-$C_8$ alkyl is optionally substituted with at least one $C_3$-$C_8$ cycloalkyl or $C_6$-$C_{14}$ aryl group;

each $R^{12a}$, $R^{12b}$, and $R^{12c}$, which may be the same or different, is independently selected from hydrogen and $C_1$-$C_8$ alkyl;

$R^{24}$ is $C_3$-$C_8$ cycloalkyl, $C_1$-$C_8$ heteroalkyl, $C_2$-$C_9$ cycloheteroalkyl, or $C_2$-$C_9$ heteroaryl, each of which is optionally substituted with at least one substituent independently chosen from $C_1$-$C_8$ alkyl, $C_6$-$C_{14}$ aryl, $C_2$-$C_9$ heteroaryl, —$CF_3$, and —$OR^{12a}$;

each $R^{26}$ is independently selected from —$OR^{12a}$, halo, $C_6$-$C_{14}$ aryl, $C_2$-$C_9$ heteroaryl, $C_1$-$C_8$ heteroalkyl, $C_3$-$C_8$ cycloalkyl, $C_2$-$C_9$ cycloheteroalkyl, and —$C(R^{12a}R^{12b}R^{12c})$; and pharmaceutically acceptable salts and solvates thereof.

In yet another aspect are afforded compounds of formula (I), wherein:

$R^1$ is $C_1$-$C_8$ alkyl substituted with $C_6$-$C_{14}$ aryl, wherein said $C_6$-$C_{14}$ aryl is optionally substituted with at least one halo;

$R^2$ is hydrogen;

$R^3$ is $C_1$-$C_8$ heteroalkyl substituted with $R^{24}$;

$R^4$ is hydrogen, halo, $C_1$-$C_8$ alkyl, —$OR^{12a}$, —$NR^{12a}R^{12b}$, $C_1$-$C_8$ heteroalkyl, $C_2$-$C_8$ alkenyl, or $C_2$-$C_8$ alkynyl, wherein said $C_2$-$C_8$ alkenyl or $C_2$-$C_8$ alkynyl are optionally substituted with at least one $R^{26}$;

$R^5$ is hydrogen;

$R^6$ is hydrogen, $C_1$-$C_8$ alkyl, or $C_1$-$C_8$ heteroalkyl;

$R^7$ is hydrogen, $C_1$-$C_8$ heteroalkyl, $C_6$-$C_{14}$ aryl, $C_2$-$C_8$ alkenyl, or $C_1$-$C_8$ alkyl, wherein said $C_1$-$C_8$ alkyl is optionally substituted with at least one $C_3$-$C_8$ cycloalkyl or $C_6$-$C_{14}$ aryl group;

each $R^{12a}$, $R^{12b}$, and $R^{12c}$, which may be the same or different, is independently selected from hydrogen and $C_1$-$C_8$ alkyl;

$R^{24}$ is $C_3$-$C_8$ cycloalkyl, $C_1$-$C_8$ heteroalkyl, $C_2$-$C_9$ cycloheteroalkyl, or $C_2$-$C_9$ heteroaryl, each of which is optionally substituted with at least one substituent independently selected from $C_1$-$C_8$ alkyl, $C_6$-$C_{14}$ aryl, $C_2$-$C_9$ heteroaryl, —$CF_3$, and —$OR^{12a}$;

each $R^{26}$ is independently selected from —$OR^{12a}$, halo, $C_6$-$C_{14}$ aryl, $C_2$-$C_9$ heteroaryl, $C_1$-$C_8$ heteroalkyl, $C_3$-$C_8$ cycloalkyl, $C_2$-$C_9$ cycloheteroalkyl, and —$C(R^{12a}R^{12b}R^{12c})$; and pharmaceutically acceptable salts and solvates thereof.

In still another aspect of the present invention are provided compounds of formula (I), wherein:

$R^1$ is $C_1$-$C_8$ alkyl substituted with $C_6$-$C_{14}$ aryl, wherein said $C_6$-$C_{14}$ aryl is optionally substituted with at least one halo;

$R^2$ is hydrogen;

$R^3$ is $C_1$-$C_8$ heteroalkyl substituted with $R^{24}$;

$R^4$ is hydrogen or $C_2$-$C_8$ alkenyl, wherein said $C_2$-$C_8$ alkenyl is optionally substituted with at least one $R^{26}$;

$R^5$ is hydrogen;

$R^6$ is hydrogen or —$CH_3$;

$R^7$ is hydrogen, $C_1$-$C_8$ heteroalkyl, $C_6$-$C_{14}$ aryl, $C_2$-$C_8$ alkenyl, or $C_1$-$C_8$ alkyl, wherein said $C_1$-$C_8$ alkyl is optionally substituted with at least one $C_3$-$C_8$ cycloalkyl or $C_6$-$C_{14}$ aryl group;

each $R^{12a}$, $R^{12b}$, and $R^{12c}$, which may be the same or different, is independently selected from hydrogen and $C_1$-$C_8$ alkyl;

$R^{24}$ is $C_3$-$C_8$ cycloalkyl, $C_1$-$C_8$ heteroalkyl, $C_2$-$C_9$ cycloheteroalkyl, or $C_2$-$C_9$ heteroaryl, each of which is optionally substituted with at least one substituent independently selected from $C_1$-$C_8$ alkyl, $C_6$-$C_{14}$ aryl, $C_2$-$C_9$ heteroaryl, —$CF_3$, and —$OR^{12a}$;

each $R^{26}$ is independently selected from —$OR^{12a}$, halo, $C_6$-$C_{14}$ aryl, $C_2$-$C_9$ heteroaryl, $C_1$-$C_8$ heteroalkyl, $C_3$-$C_8$ cycloalkyl, $C_2$-$C_9$ cycloheteroalkyl, and —$C(R^{12a}R^{12b}R^{12c})$; and pharmaceutically acceptable salts and solvates thereof.

Further provided are compounds of formula (I), wherein:

$R^1$ is $C_1$-$C_8$ alkyl substituted with $C_6$-$C_{14}$ aryl, wherein said $C_6$-$C_{14}$ aryl is optionally substituted with at least one halo;

$R^2$ is hydrogen;

$R^3$ is $C_1$-$C_8$ heteroalkyl substituted with $R^{24}$;

$R^4$ is hydrogen;

$R^5$ is hydrogen;

$R^6$ is hydrogen, $C_1$-$C_8$ alkyl, or $C_1$-$C_8$ heteroalkyl;

$R^7$ is hydrogen, —$CH_3$, phenyl, allyl, or benzyl;

each $R^{12a}$ is independently selected from hydrogen and $C_1$-$C_8$ alkyl;

$R^{24}$ is $C_2$-$C_9$ heteroaryl, which is optionally substituted with at least one substituent independently chosen from $C_1$-$C_8$ alkyl, $C_6$-$C_{14}$ aryl, $C_2$-$C_9$ heteroaryl, —$CF_3$, and —$OR^{12a}$; and pharmaceutically acceptable salts and solvates thereof.

The present invention also affords compounds of formula (I), wherein:

$R^1$ is $C_1$-$C_8$ alkyl substituted with $C_6$-$C_{14}$ aryl, wherein said $C_6$-$C_{14}$ aryl is optionally substituted with at least one fluorine;

$R^2$ is hydrogen;

$R^3$ is $C_1$-$C_8$ heteroalkyl substituted with $R^{24}$;

$R^4$ is hydrogen;

$R^5$ is hydrogen;

$R^6$ is hydrogen, $C_1$-$C_8$ alkyl, or $C_1$-$C_8$ heteroalkyl;
$R^7$ is hydrogen, —$CH_3$, phenyl, allyl, or benzyl;
each $R^{12a}$ is independently selected from hydrogen and $C_1$-$C_8$ alkyl;
$R^{24}$ is $C_3$-$C_8$ cycloalkyl, $C_2$-$C_9$ cycloheteroalkyl or $C_2$-$C_9$ heteroaryl, each of which is optionally substituted with at least one substituent independently chosen from $C_1$-$C_8$ alkyl, $C_6$-$C_{14}$ aryl, $C_2$-$C_9$ heteroaryl, —$CF_3$, and —$OR^{12a}$; and
pharmaceutically acceptable salts and solvates thereof.

Also provided are compounds of formula (I), wherein:
$R^1$ is benzyl substituted with at least one fluorine;
$R^2$ is hydrogen;
$R^3$ is $C_1$-$C_8$ heteroalkyl substituted with $R^{24}$;
$R^4$ is hydrogen;
$R^5$ is hydrogen;
$R^6$ is hydrogen, $C_1$-$C_8$ alkyl, or $C_1$-$C_8$ heteroalkyl;
$R^7$ is hydrogen, —$CH_3$, phenyl, allyl, or benzyl;
each $R^{12a}$ is independently selected from hydrogen and $C_1$-$C_8$ alkyl;
$R^{24}$ is $C_3$-$C_8$ cycloalkyl, $C_2$-$C_9$ cycloheteroalkyl or $C_2$-$C_9$ heteroaryl, each of which is optionally substituted with at least one substituent independently chosen from $C_1$-$C_8$ alkyl, $C_6$-$C_{14}$ aryl, $C_2$-$C_9$ heteroaryl, —$CF_3$, and —$OR^{12a}$; and
pharmaceutically acceptable salts and solvates thereof.

The present invention further provides compounds of formula (I), wherein:
$R^1$ is 2-fluorobenzyl, 3-fluorobenzyl, 4-fluorobenzyl, 2,3-difluorobenzyl, 2,4-difluorobenzyl, or 3,4-difluorobenzyl;
$R^2$ is hydrogen;
$R^3$ is $C_1$-$C_8$ heteroalkyl substituted with $R^{24}$;
$R^4$ is hydrogen;
$R^5$ is hydrogen;
$R^6$ is hydrogen, $C_1$-$C_8$ alkyl, or $C_1$-$C_8$ heteroalkyl;
$R^7$ is hydrogen, —$CH_3$, phenyl, allyl, or benzyl;
each $R^{12a}$ is independently selected from hydrogen and $C_1$-$C_8$ alkyl;
$R^{24}$ is $C_3$-$C_8$ cycloalkyl, $C_2$-$C_9$ cycloheteroalkyl or $C_2$-$C_9$ heteroaryl, each of which is optionally substituted with at least one substituent independently chosen from $C_1$-$C_8$ alkyl, $C_6$-$C_{14}$ aryl, $C_2$-$C_9$ heteroaryl, —$CF_3$, and —$OR^{12a}$; and
pharmaceutically acceptable salts and solvates thereof.

The present invention further provides compounds of formula (I), wherein:
$R^1$ is hydrogen, $C_1$-$C_8$ alkyl, $C_2$-$C_8$ alkenyl, or $C_1$-$C_8$ heteroalkyl, wherein said $C_1$-$C_8$ alkyl, $C_2$-$C_8$ alkenyl, or $C_1$-$C_8$ heteroalkyl groups may be optionally substituted with at least one substituent independently selected from:
halo, —$OR^{12a}$, —$N(R^{12a}R^{12b})$, —$C(O)N(R^{12a})_2$, —$NR^{12a}C(O)N(R^{12a}R^{12b})$, —$NR^{12a}C(O)R^{12a}$, —$NR^{12a}C(NR^{12a})N(R^{12a}R^{12b})$, —$SR^{12a}$, —$S(O)R^{12a}$, —$S(O)_2R^{12a}$, —$S(O)_2N(R^{12a}R^{12b})_2$, $C_1$-$C_8$ alkyl, $C_6$-$C_{14}$ aryl, $C_3$-$C_8$ cycloalkyl, and $C_2$-$C_9$ heteroaryl, wherein said $C_1$-$C_8$ alkyl, $C_6$-$C_{14}$ aryl, $C_3$-$C_8$ cycloalkyl, and $C_2$-$C_9$ heteroaryl groups are optionally substituted with at least one substituent independently selected from halo, —$C(R^{12a}R^{12b}R^{12}C)$, —OH, and $C_1$-$C_8$ alkoxy;
$R^2$ is hydrogen;
$R^3$ is $C_1$-$C_8$ heteroalkyl substituted with $R^{24}$;
$R^4$ is hydrogen;
$R^5$ is hydrogen;
$R^6$ is hydrogen;
$R^7$ is hydrogen, —$CH_3$, phenyl, allyl, or benzyl;
each $R^{12a}$ is independently selected from hydrogen and $C_1$-$C_8$ alkyl;

$R^{24}$ is $C_3$-$C_8$ cycloalkyl optionally substituted with at least one substituent independently chosen from $C_1$-$C_8$ alkyl, $C_6$-$C_{14}$ aryl, $C_2$-$C_9$ heteroaryl, —$CF_3$, and —$OR^{12a}$; and
pharmaceutically acceptable salts and solvates thereof.

The present invention further provides compounds of formula (I), wherein:
$R^1$ is hydrogen, $C_1$-$C_8$ alkyl, $C_2$-$C_8$ alkenyl, or $C_1$-$C_8$ heteroalkyl, wherein said $C_1$-$C_8$ alkyl, $C_2$-$C_8$ alkenyl, or $C_1$-$C_8$ heteroalkyl groups may be optionally substituted with at least one substituent independently selected from:
halo, —$OR^{12a}$, —$N(R^{12a}R^{12b})$, —$C(O)N(R^{12a})_2$, —$NR^{12a}C(O)N(R^{12a}R^{12b})$, —$NR^{12a}C(O)R^{12a}$, —$NR^{12a}C(NR^{12a})N(R^{12a}R^{12b})$, —$SR^{12a}$, —$S(O)R^{12a}$, —$S(O)_2R^{12a}$, —$S(O)_2N(R^{12a}R^{12b})_2$, $C_1$-$C_8$ alkyl, $C_6$-$C_{14}$ aryl, $C_3$-$C_8$ cycloalkyl, and $C_2$-$C_9$ heteroaryl, wherein said $C_1$-$C_8$ alkyl, $C_6$-$C_{14}$ aryl, $C_3$-$C_8$ cycloalkyl, and $C_2$-$C_9$ heteroaryl groups are optionally substituted with at least one substituent independently selected from halo, —$C(R^{12a}R^{12b}R^{12c})$, —OH, and $C_1$-$C_8$ alkoxy;
$R^2$ is hydrogen;
$R^3$ is $C_1$-$C_8$ heteroalkyl substituted with $R^{24}$;
$R^4$ is hydrogen;
$R^5$ is hydrogen;
$R^6$ is hydrogen;
$R^7$ is hydrogen, —$CH_3$, phenyl, allyl, or benzyl;
each $R^{12a}$ is independently selected from hydrogen and $C_1$-$C_8$ alkyl;
$R^{24}$ is $C_2$-$C_9$ cycloheteroalkyl optionally substituted with at least one substituent independently chosen from $C_1$-$C_8$ alkyl, $C_6$-$C_{14}$ aryl, $C_2$-$C_9$ heteroaryl, —$CF_3$, and —$OR^{12a}$; and
pharmaceutically acceptable salts and solvates thereof.

The present invention further provides compounds of formula (I), wherein:
$R^1$ is hydrogen, $C_1$-$C_8$ alkyl, $C_2$-$C_8$ alkenyl, or $C_1$-$C_8$ heteroalkyl, wherein said C, —CB alkyl, $C_2$-$C_8$ alkenyl, or $C_1$-$C_8$ heteroalkyl groups may be optionally substituted with at least one substituent independently selected from:
halo, —$OR^{12a}$, —$N(R^{12a}R^{12b})$, —$C(O)N(R^{12a})_2$, —$NR^{12a}C(O)N(R^{12a}R^{12b})$, —$NR^{12a}C(O)R^{12a}$, —$NR^{12a}C(NR^{12a})N(R^{12a}R^{12b})$, —$SR^{12a}$, —$S(O)R^{12a}$, —$S(O)_2R^{12a}$, —$S(O)_2N(R^{12a}R^{12b})_2$, $C_1$-$C_8$ alkyl, $C_6$-$C_{14}$ aryl, $C_3$-$C_8$ cycloalkyl, and $C_2$-$C_9$ heteroaryl, wherein said $C_1$-$C_8$ alkyl, $C_6$-$C_{14}$ aryl, $C_3$-$C_8$ cycloalkyl, and $C_2$-$C_9$ heteroaryl groups are optionally substituted with at least one substituent independently selected from halo, —$C(R^{12a}R^{12b}R^{12}C)$, —OH, and $C_1$-$C_8$ alkoxy;
$R^2$ is hydrogen;
$R^3$ is $C_1$-$C_8$ heteroalkyl substituted with $R^{24}$;
$R^4$ is hydrogen;
$R^5$ is hydrogen;
$R^5$ is hydrogen;
$R^7$ is hydrogen, —$CH_3$, phenyl, allyl, or benzyl;
each $R^{12a}$ is independently selected from hydrogen and $C_1$-$C_8$ alkyl;
$R^{24}$ is $C_2$-$C_9$ heteroaryl optionally substituted with at least one substituent independently chosen from $C_1$-$C_8$ alkyl, $C_6$-$C_{14}$ aryl, $C_2$-$C_9$ heteroaryl, —$CF_3$, and —$OR^{12a}$; and
pharmaceutically acceptable salts and solvates thereof.

The present invention further provides compounds of formula (I), wherein:
$R^1$ is $C_1$-$C_8$ alkyl substituted with $C_6$-$C_{14}$ aryl, wherein said $C_6$-$C_{14}$ aryl is optionally substituted with at least one halo;
$R^2$ is hydrogen;
$R^3$ is $C_1$-$C_8$ heteroalkyl substituted with $R^{24}$;
$R^4$ is hydrogen;
$R^5$ is hydrogen;

R[6] is hydrogen;
R[7] is hydrogen, —CH₃, phenyl, allyl, or benzyl;
each R[12a] is independently selected from hydrogen and C₁-C₈ alkyl;
R[24] is C₃-C₈ cycloalkyl optionally substituted with at least one substituent independently chosen from C₁-C₈ alkyl, C₆-C₁₄ aryl, C₂-C₉ heteroaryl, —CF₃, and —OR[12a]; and
pharmaceutically acceptable salts and solvates thereof.

The present invention further provides compounds of formula (I), wherein:
R[1] is C₁-C₈ alkyl substituted with C₆-C₁₄ aryl, wherein said C₆-C₁₄ aryl is optionally substituted with at least one halo;
R[2] is hydrogen;
R[3] is C₁-C₈ heteroalkyl substituted with R[24];
R[4] is hydrogen;
R[5] is hydrogen;
R[6] is hydrogen;
R[7] is hydrogen, —CH₃, phenyl, allyl, or benzyl;
each R[12a] is independently selected from hydrogen and C₁-C₈ alkyl;
R[24] is C₂-C₉ cycloheteroalkyl optionally substituted with at least one substituent independently chosen from C₁-C₈ alkyl, C₆-C₁₄ aryl, C₂-C₉ heteroaryl, —CF₃, and —OR[12a]; and
pharmaceutically acceptable salts and solvates thereof.

The present invention further provides compounds of formula (I), wherein:
R[1] is C₁-C₈ alkyl substituted with C₆-C₁₄ aryl, wherein said C₆-C₁₄ aryl is optionally substituted with at least one halo;
R[2] is hydrogen;
R[3] is C₁-C₈ heteroalkyl substituted with R[24];
R[4] is hydrogen;
R[5] is hydrogen;
R[6] is hydrogen;
R[7] is hydrogen, —CH₃, phenyl, allyl, or benzyl;
each R[12a] is independently selected from hydrogen and C₁-C₈ alkyl;
R[24] is C₂-C₉ heteroaryl optionally substituted with at least one substituent independently chosen from C₁-C₈ alkyl, C₆-C₁₄ aryl, C₂-C₉ heteroaryl, —CF₃, and —OR[12a]; and
pharmaceutically acceptable salts and solvates thereof.

In still a further aspect of the present invention are compounds selected from 1-(2,4-difluorobenzyl)-N-hydroxy-3-{[methyl(pyridin-3-ylmethyl)amino]methyl}-1H-pyrrolo[2,3-c]pyridine-5-carboxamide; 1-(2,4-difluorobenzyl)-N-hydroxy-3-[(pyridin-3-ylamino)methyl]-1H-pyrrolo[2,3-c]pyridine-5-carboxamide; 1-(2,4-difluorobenzyl)-N-hydroxy-3-{[(2-pyridin-2-ylethyl)amino]methyl}-1H-pyrrolo[2,3-c]pyridine-5-carboxamide; 1-(2,4-difluorobenzyl)-N-hydroxy-3-{[methyl(2-pyridin-2-ylethyl)amino]methyl}-1H-pyrrolo[2,3-c]pyridine-5-carboxamide; 1-(2,4-difluorobenzyl)-N-hydroxy-3-({[(5-methylpyrazin-2-yl)methyl]amino}methyl)-1H-pyrrolo[2,3-c]pyridine-5-carboxamide; 1-(2,4-difluorobenzyl)-N-hydroxy-3-({[2-(1H-indol-3-yl)ethyl]amino}methyl)-1H-pyrrolo[2,3-c]pyridine-5-carboxamide; 1-(2,4-difluorobenzyl)-N-hydroxy-3-({[(1S)-2-hydroxy-1-(1H-indol-3-ylmethyl)ethyl]amino}methyl)-1H-pyrrolo[2,3-c]pyridine-5-carboxamide; 1-(2,4-difluorobenzyl)-N-hydroxy-3-[({[6-(trifluoromethyl)pyridin-3-yl]methyl}amino)methyl]-1H-pyrrolo[2,3-c]pyridine-5-carboxamide; 1-(2,4-difluorobenzyl)-N-hydroxy-3-[(2-methoxypyridin-3-yl)amino]methyl}-1H-pyrrolo[2,3-c]pyridine-5-carboxamide; 1-(2,4-difluorobenzyl)-N-hydroxy-3-({methyl[(1-phenyl-1H-pyrazol-4-yl)methyl]amino}methyl)-1H-pyrrolo[2,3-c]pyridine-5-carboxamide; 1-(2,4-difluorobenzyl)-N-hydroxy-3-({[2-(5-methyl-4H-1,2,4-triazol-3-yl)ethyl]amino}methyl)-1H-pyrrolo[2,3-c]pyridine-5-carboxamide; 1-(2,4-difluorobenzyl)-3-{[(1,1-dioxidotetrahydrothien-3-yl)amino]methyl}-N-hydroxy-1H-pyrrolo[2,3-c]pyridine-5-carboxamide; 3-{[(cyclopropylmethyl)(propyl)amino]methyl}-1-(2,4-difluorobenzyl)-N-hydroxy-1H-pyrrolo[2,3-c]pyridine-5-carboxamide; 3-{[(1R,2R,4S)-bicyclo[2.2.1]hept-2-ylamino]methyl}-1-(2,4-difluorobenzyl)-N-hydroxy-1H-pyrrolo[2,3-c]pyridine-5-carboxamide; rac 1-(2,4-difluorobenzyl)-N-hydroxy-3-({[(1 S*,2R*)-2-phenylcyclopropyl]amino}methyl)-1H-pyrrolo[2,3-c]pyridine-5-carboxamide; 3-({[(1R)-1-cyclohexylethyl]amino}methyl)-1-(2,4-difluorobenzyl)-N-hydroxy-1H-pyrrolo[2,3-c]pyridine-5-carboxamide; 3-({[1-cyclopropyl-3-(cyclopropylamino)-3-oxopropyl]amino}methyl)-1-(2,4-difluorobenzyl)-N-hydroxy-1H-pyrrolo[2,3-c]pyridine-5-carboxamide; 1-(2,4-difluorobenzyl)-N-hydroxy-3-({[2-(1-methylpyrrolidin-2-yl)ethyl]amino}methyl)-1H-pyrrolo[2,3-c]pyridine-5-carboxamide; 1-(2,4-difluorobenzyl)-N-hydroxy-3-({[3-(4-methylpiperazin-1-yl)propyl]amino}methyl)-1H-pyrrolo[2,3-c]pyridine-5-carboxamide; 1-(2,4-difluorobenzyl)-N-hydroxy-3-{[(2-morpholin-4-ylethyl)amino]methyl}-1H-pyrrolo[2,3-c]pyridine-5-carboxamide; 1-(2,4-difluorobenzyl)-N-hydroxy-3-{[(2-pyrrolidin-1-ylethyl)amino]methyl}-1H-pyrrolo[2,3-c]pyridine-5-carboxamide; 1-(2,4-difluorobenzyl)-N-hydroxy-3-{[(tetrahydrofuran-2-ylmethyl)amino]methyl}-1H-pyrrolo[2,3-c]pyridine-5-carboxamide; 1-(2,4-difluorobenzyl)-3-({[(1-ethylpyrrolidin-2-yl)methyl]amino}methyl)-N-hydroxy-1H-pyrrolo[2,3-c]pyridine-5-carboxamide; 1-(2,4-difluorobenzyl)-N-hydroxy-3-({[3-(2-oxopyrrolidin-1-yl)propyl]amino}methyl)-1H-pyrrolo[2,3-c]pyridine-5-carboxamide; 1-(2,4-difluorobenzyl)-N-hydroxy-3-{[(1-methylpiperidin-4-yl)amino]methyl}-1H-pyrrolo[2,3-c]pyridine-5-carboxamide; 1-(2,4-difluorobenzyl)-N-hydroxy-3-[(tetrahydro-2H-pyran-4-ylamino)methyl]-1H-pyrrolo[2,3-c]pyridine-5-carboxamide; 1-(2,4-difluorobenzyl)-N-hydroxy-3-{[(tetrahydro-1H-pyrrolizin-7a(5H)-ylmethyl)amino]methyl}-1H-pyrrolo[2,3-c]pyridine-5-carboxamide; 1-(2,4-difluorobenzyl)-3-({[4-(difluoromethoxy)benzyl]amino}methyl)-N-hydroxy-1H-pyrrolo[2,3-c]pyridine-5-carboxamide; 1-(2,4-difluorobenzyl)-N-hydroxy-3-({[2-(tetrahydro-2H-pyran-4-yl)ethyl]amino}methyl)-1H-pyrrolo[2,3-c]pyridine-5-carboxamide; 1-(2,4-difluorobenzyl)-N-hydroxy-3-{[(6-methyl-3,4-dihydro-2H-chromen-4-yl)amino]methyl}-1H-pyrrolo[2,3-c]pyridine-5-carboxamide; 1-(2,4-difluorobenzyl)-N-hydroxy-3-{[(1,4,5,6-tetrahydrocyclopenta[c]pyrazol-3-ylmethyl)amino]methyl}-1H-pyrrolo[2,3-c]pyridine-5-carboxamide; 1-(2,4-difluorobenzyl)-3-({[(1-ethylpyrrolidin-2-yl)methyl]amino}methyl)-N-methoxy-1H-pyrrolo[2,3-c]pyridine-5-carboxamide; 1-(4-fluorobenzyl)-N,4-dihydroxy-1H-pyrrolo[2,3-c]pyridine-5-carboxamide; 1-(4-fluorobenzyl)-4-hydroxy-N-methoxy-1H-pyrrolo[2,3-c]pyridine-5-carboxamide; 1-(4-fluorobenzyl)-N-hydroxy-4-methoxy-N-methyl-1H-pyrrolo[2,3-c]pyridine-5-carboxamide; 1-(4-fluorobenzyl)-N-hydroxy-N-propyl-1H-pyrrolo[2,3-c]pyridine-5-carboxamide; 1-(2,4-Difluorobenzyl)-N-hydroxy-3-[(2-methoxyethoxy)methyl]-1H-pyrrolo[2,3-c]pyridine-5-carboxamide; 1-(2,4-Difluorobenzyl)-N-hydroxy-3-{[2-(2-methoxyethoxy)ethoxy]methyl}-1H-pyrrolo[2,3-c]pyridine-5-carboxamide; 1-(2,4-Difluorobenzyl)-3-({[(4R)-2,2-dimethyl-1,3-dioxolan-4-yl]methoxy}methyl)-N-hydroxy-1H-pyrrolo[2,3-c]pyridine-5-carboxamide; 1-(4-Fluorobenzyl)-N-hydroxy-4-(3-hydroxypropyl)-1H-pyrrolo[2,3-c]pyridine-5-carboxamide; 4-Ethyl-1-(4-fluoro-benzyl)-1H-pyrrolo[2,3-c]pyridine-5- carboxylic acid hydroxyamide; 1-(2,4-Difluorobenzyl)-N-hydroxy-3-{[(pyridin-2-ylmethyl)amino]methyl}-1H-pyrrolo[2,3-c]pyridine-5-carboxamide; 1-(2,4-Difluorobenzyl)-N-hydroxy-3-({[(1S,2R)-2-phenylcyclopropyl]amino}methyl)-1H-pyrrolo[2,3-c]pyridine-5-carboxamidel; and 3-({[(4S)-2,2-dimethyl-1,3-dioxolan-4-yl]methoxy}methyl)-1-(4-fluorobenzyl)-N-hydroxy-1H-pyrrolo[2,3-c]pyridine-5-carboxamide; or pharmaceutically acceptable salts or solvates thereof.

In still a further aspect of the present invention are compounds of formula (II),

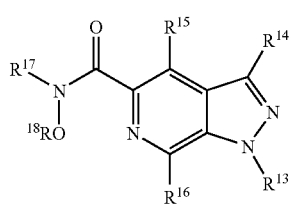

(II)

wherein:

$R^{13}$ is hydrogen, $C_1$-$C_8$ alkyl, $C_2$-$C_8$ alkenyl, or $C_1$-$C_8$ heteroalkyl, wherein said $C_1$-$C_8$ alkyl, $C_2$-$C_8$ alkenyl, or $C_1$-$C_8$ heteroalkyl groups may be optionally substituted with at least one substituent independently selected from:

halo, —$OR^{23a}$, —$N(R^{23a}R^{23b})$, —$C(O)N(R^{23a}R^{23b})$, —$NR^{23a}C(O)N(R^{23a}R^{23b})$, —$NR^{23a}C(O)R^{23a}$, —$NR^{23a}C(NR^{23a})N(R^{23a}R^{23b})$, —$SR^{23a}$, —$S(O)R^{23a}$, —$S(O)_2R^{23a}$, —$S(O)_2N(R^{23a}R^{23b})$, $C_1$-$C_8$ alkyl, $C_6$-$C_{14}$ aryl, $C_3$-$C_8$ cycloalkyl, and $C_2$-$C_9$ heteroaryl, wherein said $C_1$-$C_8$ alkyl, $C_6$-$C_{14}$ aryl, $C_3$-$C_8$ cycloalkyl, and $C_2$-$C_9$ heteroaryl groups are optionally substituted with at least one substituent independently selected from halo, —$C(R^{23a}R^{23b}R^{23c})$, —OH, and $C_1$-$C_8$ alkoxy;

$R^{14}$ is hydrogen, —$(CR^{19}R^{20})_tNR^{21}R^{22}$, or $C_1$-$C_8$ heteroalkyl, wherein said $C_1$-$C_8$ heteroalkyl is substituted with $R^{25}$;

$R^{15}$ is hydrogen, halo, $C_1$-$C_8$ alkyl, —$OR^{23a}$, —$NR^{23a}R^{23b}$, $C_1$-$C_8$ heteroalkyl, $C_2$-$C_8$ alkenyl, or $C_2$-$C_8$ alkynyl, wherein said $C_2$-$C_8$ alkenyl or $C_2$-$C_8$ alkynyl are optionally substituted with at least one $R^{27}$;

$R^{16}$ is hydrogen;

$R^{17}$ is hydrogen, $C_1$-$C_8$ alkyl, $C_1$-$C_8$ heteroalkyl, or $C_2$-$C_8$ alkenyl, wherein said $C_2$-$C_8$ alkenyl is optionally substituted with at least one —$OR^{23a}$ group;

$R^{18}$ is hydrogen, $C_1$-$C_8$ heteroalkyl, $C_6$-$C_{14}$ aryl, $C_2$-$C_8$ alkenyl, or $C_1$-$C_8$ alkyl, wherein said $C_1$-$C_8$ alkyl is optionally substituted with at least one $C_3$-$C_8$ cycloalkyl or $C_6$-$C_{14}$ aryl group;

each $R^{19}$ and $R^{20}$, which may be the same or different, are independently selected from hydrogen and $C_1$-$C_8$ alkyl;

$R^{21}$ and $R^{22}$, together with the nitrogen atom to which they are attached, form a $C_2$-$C_9$ cycloheteroalkyl group optionally substituted with at least one $C_1$-$C_8$ alkyl;

each $R^{23a}$, $R^{23b}$, and $R^{23c}$, which may be the same or different, is independently selected from hydrogen and $C_1$-$C_8$ alkyl;

$R^{25}$ is $C_3$-$C_8$ cycloalkyl, $C_2$-$C_9$ cycloheteroalkyl, or $C_2$-$C_9$ heteroaryl, each of which is optionally substituted with at least one substituent independently selected from $C_1$-$C_8$ alkyl, $C_6$-$C_{14}$ aryl, $C_2$-$C_9$ heteroaryl, —$CF_3$, and —$OR^{23a}$;

each $R^{27}$ is independently selected from —$OR^{23a}$, halo, $C_6$-$C_{14}$ aryl, $C_2$-$C_9$ heteroaryl, $C_1$-$C_8$ heteroalkyl, $C_3$-$C_8$ cycloalkyl, $C_2$-$C_9$ cycloheteroalkyl, and —$C(R^{23a}R^{23b}R^{23c})$;

t is an integer from 1 to 3; and pharmaceutically acceptable salts and solvates thereof.

Also provided are compounds of formula (II), wherein:

$R^{13}$ is hydrogen, $C_1$-$C_8$ alkyl, $C_2$-$C_8$ alkenyl, or $C_1$-$C_8$ heteroalkyl, wherein said $C_1$-$C_8$ alkyl, $C_2$-$C_8$ alkenyl, or $C_1$-$C_8$ heteroalkyl groups may be optionally substituted with at least one substituent independently selected from:

halo, —$OR^{23a}$, —$N(R^{23a}R^{23b})$, —$C(O)N(R^{23a}R^{23b})$, —$NR^{23a}C(O)N(R^{12a}R^{23b})$, —$NR^{23a}C(O)R^{23a}$, —$NR^{23a}C(NR^{23a})N(R^{23a}R^{23b})$, —$SR^{23a}$, —$S(O)R^{23a}$, —$S(°)_2R^{23a}$, —$S(O)_2N(R^{23a}R^{23b})$, $C_1$-$C_8$ alkyl, $C_6$-$C_{14}$ aryl, $C_3$-$C_8$ cycloalkyl, and $C_2$-$C_9$ heteroaryl, wherein said $C_1$-$C_8$ alkyl, $C_6$-$C_{14}$ aryl, $C_3$-$C_8$ cycloalkyl, and $C_2$-$C_9$ heteroaryl groups are optionally substituted with at least one substituent independently selected from halo, —$C(R^{23a}R^{23b}R^{23c})$, —OH, and $C_1$-$C_8$ alkoxy;

$R^{14}$ is hydrogen;

$R^{15}$ is hydrogen, halo, $C_1$-$C_8$ alkyl, —$OR^{23a}$, —$NR^{23a}R^{23b}$, $C_1$-$C_8$ heteroalkyl, $C_2$-$C_8$ alkenyl, or $C_2$-$C_8$ alkynyl, wherein said $C_2$-$C_8$ alkenyl or $C_2$-$C_8$ alkynyl are optionally substituted with at least one $R^{27}$;

$R^{16}$ is hydrogen;

$R^{17}$ is hydrogen, $C_1$-$C_8$ alkyl, $C_1$-$C_8$ heteroalkyl, or $C_2$-$C_8$ alkenyl, wherein said $C_2$-$C_8$ alkenyl is optionally substituted with at least one —$OR^{23a}$ group;

$R^{18}$ is hydrogen, $C_1$-$C_8$ heteroalkyl, $C_6$-$C_{14}$ aryl, $C_2$-$C_8$ alkenyl, or $C_1$-$C_8$ alkyl, wherein said $C_1$-$C_8$ alkyl is optionally substituted with at least one $C_3$-$C_8$ cycloalkyl or $C_6$-$C_{14}$ aryl group;

each $R^{23a}$, $R^{23b}$, and $R^{23c}$, which may be the same or different, is independently selected from hydrogen and $C_1$-$C_8$ alkyl;

each $R^{27}$ is independently selected from —$OR^{23a}$, halo, $C_6$-$C_{14}$ aryl, $C_2$-$C_9$ heteroaryl, $C_1$-$C_8$ heteroalkyl, $C_3$-$C_8$ cycloalkyl, $C_2$-$C_9$ cycloheteroalkyl, and —$C(R^{23a}R^{23b}R^{23c})$; and pharmaceutically acceptable salts and solvates thereof.

Also provided are compounds of formula (II), wherein:

$R^{13}$ is hydrogen, $C_1$-$C_8$ alkyl, $C_2$-$C_8$ alkenyl, or $C_1$-$C_8$ heteroalkyl, wherein said $C_1$-$C_8$ alkyl, $C_2$-$C_8$ alkenyl, or $C_1$-$C_8$ heteroalkyl groups may be optionally substituted with at least one substituent independently selected from:

halo, —$OR^{23a}$—$N(R^{23a}R^{23b})$, —$C(O)N(R^{23a}R^{23b})$, —$NR^{23a}C(O)N(R^{23a}R^{23b})$, —$NR^{23a}C(O)R^{23a}$, —$NR^{23a}C(NR^{23a})N(R^{23a}R^{23b})$, —$SR^{23a}$, —$S(O)R^{23a}$, —$S(O)_2R^{23a}$, —$S(O)_2N(R^{23a}R^{23b})$, $C_1$-$C_8$ alkyl, $C_6$-$C_{14}$ aryl, $C_3$-$C_8$ cycloalkyl, and $C_2$-$C_9$ heteroaryl, wherein said $C_1$-$C_8$ alkyl, $C_6$-$C_{14}$ aryl, $C_3$-$C_8$ cycloalkyl, and $C_2$-$C_9$ heteroaryl groups are optionally substituted with at least one substituent independently selected from halo, —$C(R^{23a}R^{23b}R^{23c})$, —OH, and $C_1$-$C_8$ alkoxy;

$R^{14}$ is —$(CR^{19}R^{20})_tNR^{21}R^{22}$;

$R^{15}$ is hydrogen, halo, $C_1$-$C_8$ alkyl, —$OR^{23a}$, —$NR^{23a}R^{23b}$, $C_1$-$C_8$ heteroalkyl, $C_2$-$C_6$ alkenyl, or $C_2$-$C_8$ alkynyl, wherein said $C_2$-$C_8$ alkenyl or $C_2$-$C_8$ alkynyl are optionally substituted with at least one $R^{27}$;

$R^{16}$ is hydrogen;

$R^{17}$ is hydrogen, $C_1$-$C_8$ alkyl, $C_1$-$C_8$ heteroalkyl, or $C_2$-$C_8$ alkenyl, wherein said $C_2$-$C_8$ alkenyl is optionally substituted with at least one —$OR^{23a}$ group;

$R^{18}$ is hydrogen, $C_1$-$C_8$ heteroalkyl, $C_6$-$C_{14}$ aryl, $C_2$-$C_8$ alkenyl, or $C_1$-$C_8$ alkyl, wherein said $C_1$-$C_8$ alkyl is optionally substituted with at least one $C_3$-$C_8$ cycloalkyl or $C_6$-$C_{14}$ aryl group;

each $R^{19}$ and $R^{20}$, which may be the same or different, are independently selected from hydrogen and $C_1$-$C_8$ alkyl;

$R^{21}$ and $R^{22}$, together with the nitrogen atom to which they are attached, form a $C_2$-$C_9$ cycloheteroalkyl group optionally substituted with at least one $C_1$-$C_8$ alkyl;

each $R^{23a}$, $R^{23b}$, and $R^{23c}$, which may be the same or different, is independently selected from hydrogen and $C_1$-$C_8$ alkyl;

each $R^{27}$ is independently selected from —$OR^{23a}$, halo, $C_6$-$C_{14}$ aryl, $C_2$-$C_9$ heteroaryl, $C_1$-$C_8$ heteroalkyl, $C_3$-$C_8$ cycloalkyl, $C_2$-$C_9$ cycloheteroalkyl, and —$C(R^{23a}R^{23b}R^{23c})$;

t is an integer from 1 to 3; and pharmaceutically acceptable salts and solvates thereof.

Also provided are compounds of formula (II), wherein:

$R^{13}$ is hydrogen, $C_1$-$C_8$ alkyl, $C_2$-$C_8$ alkenyl, or $C_1$-$C_8$ heteroalkyl, wherein said $C_1$-$C_8$ alkyl, $C_2$-$C_8$ alkenyl, or $C_1$-$C_8$ heteroalkyl groups may be optionally substituted with at least one substituent independently selected from:

halo, —$OR^{23a}$, —$N(R^{23a}R^{23b})$, —$C(O)N(R^{23a}R^{23b})$, —$NR^{23a}C(O)N(R^{23a}R^{23b})$, —$NR^{23a}C(O)R^{12a}$, —$NR^{23a}C(NR^{23a})N(R^{23a}R^{23b})$, —$SR^{23a}$, —$S(O)R^{23a}$, —$S(O)_2R^{23a}$, —$S(O)_2N(R^{23a}R^{23b})$, $C_1$-$C_3$ alkyl, $C_6$-$C_{14}$ aryl, $C_3$-$C_8$ cycloalkyl, and $C_2$-$C_9$ heteroaryl, wherein said $C_1$-$C_8$ alkyl, $C_6$-$C_{14}$ aryl, $C_3$-$C_8$ cycloalkyl, and $C_2$-$C_9$ heteroaryl groups are optionally substituted with at least one substituent independently selected from halo, —$C(R^{23a}R^{23b}R^{23c})$, —OH, and $C_1$-$C_8$ alkoxy;

$R^{14}$ is $C_1$-$C_8$ heteroalkyl substituted with $R^{25}$;

$R^{15}$ is hydrogen, halo, $C_1$-$C_8$ alkyl, —$OR^{23a}$, —$NR^{23a}R^{23b}$, $C_1$-$C_8$ heteroalkyl, $C_2$-$C_6$ alkenyl, or $C_2$-$C_8$ alkynyl, wherein said $C_2$-$C_8$ alkenyl or $C_2$-$C_8$ alkynyl are optionally substituted with at least one $R^{27}$;

$R^{16}$ is hydrogen;

$R^{17}$ is hydrogen, $C_1$-$C_8$ alkyl, $C_1$-$C_8$ heteroalkyl, or $C_2$-$C_8$ alkenyl, wherein said $C_2$-$C_8$ alkenyl is optionally substituted with at least one —$OR^{23a}$ group;

$R^{18}$ is hydrogen, $C_1$-$C_8$ heteroalkyl, $C_6$-$C_{14}$ aryl, $C_2$-$C_8$ alkenyl, or $C_1$-$C_8$ alkyl, wherein said $C_1$-$C_8$ alkyl is optionally substituted with at least one $C_3$-$C_8$ cycloalkyl or $C_6$-$C_{14}$ aryl group;

each $R^{23a}$, $R^{23b}$, and $R^{23c}$, which may be the same or different, is independently selected from hydrogen and $C_1$-$C_8$ alkyl;

$R^{25}$ is $C_3$-$C_8$ cycloalkyl, $C_2$-$C_9$ cycloheteroalkyl, or $C_2$-$C_9$ heteroaryl, each of which is optionally substituted with at least one substituent independently selected from $C_1$-$C_8$ alkyl, $C_6$-$C_{14}$ aryl, $C_2$-$C_9$ heteroaryl, —$CF_3$, and —$OR^{23a}$;

each $R^{27}$ is independently selected from —$OR^{23a}$, halo, $C_6$-$C_{14}$ aryl, $C_2$-$C_9$ heteroaryl, $C_1$-$C_8$ heteroalkyl, $C_3$-$C_8$ cycloalkyl, $C_2$-$C_9$ cycloheteroalkyl, and —$C(R^{23a}R^{23b}R^{23c})$; and pharmaceutically acceptable salts and solvates thereof.

Also provided are compounds of formula (II), wherein:

$R^{13}$ is $C_1$-$C_8$ alkyl substituted with $C_6$-$C_{14}$ aryl, and wherein said $C_6$-$C_{14}$ aryl is optionally substituted with at least one substituent independently selected from halo, —$C(R^{23a}R^{23b}R^{23c})$, —OH, and $C_1$-$C_8$ alkoxy;

$R^4$ is hydrogen, —$(CR^9R^{20})_tNR^{23a}R^{23b}$, or $C_1$-$C_8$ heteroalkyl, wherein said $C_1$-$C_8$ heteroalkyl is substituted with $R^{25}$;

$R^{15}$ is hydrogen, halo, $C_1$-$C_8$ alkyl, —$OR^{23a}$, —$NR^{23a}R^{23b}$, $C_1$-$C_8$ heteroalkyl, $C_2$-$C_8$ alkenyl, or $C_2$-$C_8$ alkynyl, wherein said $C_2$-$C_8$ alkenyl or $C_2$-$C_8$ alkynyl are optionally substituted with at least one $R^{27}$;

$R^{16}$ is hydrogen;

$R^{17}$ is hydrogen, $C_1$-$C_8$ alkyl, $C_1$-$C_8$ heteroalkyl, or $C_2$-$C_8$ alkenyl, wherein said $C_2$-$C_8$ alkenyl is optionally substituted with at least one —$OR^{23a}$ group;

$R^{18}$ is hydrogen, $C_1$-$C_8$ heteroalkyl, $C_6$-$C_{14}$ aryl, $C_2$-$C_8$ alkenyl, or $C_1$-$C_8$ alkyl, wherein said $C_1$-$C_8$ alkyl is optionally substituted with at least one $C_3$-$C_8$ cycloalkyl or $C_6$-$C_{14}$ aryl group;

each $R^{19}$ and $R^{20}$, which may be the same or different, are independently selected from hydrogen and $C_1$-$C_8$ alkyl;

$R^{21}$ and $R^{22}$, together with the nitrogen atom to which they are attached, form a $C_2$-$C_9$ cycloheteroalkyl group optionally substituted with at least one $C_1$-$C_8$ alkyl;

each $R^{23a}$, $R^{23b}$, and $R^{23c}$, which may be the same or different, is independently selected from hydrogen and $C_1$-$C_8$ alkyl;

$R^{25}$ is $C_3$-$C_8$ cycloalkyl, $C_2$-$C_9$ cycloheteroalkyl, or $C_2$-$C_9$ heteroaryl, each of which is optionally substituted with at least one substituent independently selected from $C_1$-$C_8$ alkyl, $C_6$-$C_{14}$ aryl, $C_2$-$C_9$ heteroaryl, —$CF_3$, and —$OR^{23a}$;

each $R^{27}$ is independently selected from —$OR^{23a}$, halo, $C_6$-$C_{14}$ aryl, $C_2$-$C_9$ heteroaryl, $C_1$-$C_8$ heteroalkyl, $C_3$-$C_8$ cycloalkyl, $C_2$-$C_9$ cycloheteroalkyl, and —$C(R^{23a}R^{23b}R^{23c})$;

t is an integer from 1 to 3; and pharmaceutically acceptable salts and solvates thereof.

Also provided are compounds of formula (II), wherein:

$R^{13}$ is $C_1$-$C_8$ alkyl substituted with $C_6$-$C_{14}$ aryl, and wherein said $C_6$-$C_{14}$ aryl is optionally substituted with at least one halo;

$R^{14}$ is hydrogen, —$(CR^9R^{20})_tNR^{21}R^{22}$, or $C_1$-$C_8$ heteroalkyl, wherein said $C_1$-$C_8$ heteroalkyl is substituted with $R^{25}$;

$R^{15}$ is hydrogen, halo, $C_1$-$C_8$ alkyl —$OR^{23a}$, —$NR^{23a}R^{23b}$, $C_1$-$C_8$ heteroalkyl, $C_2$-$C_8$ alkenyl, or $C_2$-$C_8$ alkynyl, wherein said $C_2$-$C_8$ alkenyl or $C_2$-$C_8$ alkynyl are optionally substituted with at least one $R^{27}$;

$R^{16}$ is hydrogen;

$R^{17}$ is hydrogen, $C_1$-$C_8$ alkyl, $C_1$-$C_8$ heteroalkyl, or $C_2$-$C_8$ alkenyl, wherein said $C_2$-$C_8$ alkenyl is optionally substituted with at least one —$OR^{23a}$ group;

$R^{18}$ is hydrogen, $C_1$-$C_8$ heteroalkyl, $C_6$-$C_{14}$ aryl, $C_2$-$C_8$ alkenyl, or $C_1$-$C_8$ alkyl, wherein said $C_1$-$C_8$ alkyl is optionally substituted with at least one $C_3$-$C_8$ cycloalkyl or $C_6$-$C_{14}$ aryl group;

each $R^{19}$ and $R^{20}$, which may be the same or different, are independently selected from hydrogen and $C_1$-$C_8$ alkyl;

$R^{21}$ and $R^{22}$, together with the nitrogen atom to which they are attached, form a $C_2$-$C_9$ cycloheteroalkyl group optionally substituted with at least one $C_1$-$C_8$ alkyl;

each $R^{23a}$, $R^{23b}$, and $R^{23c}$, which may be the same or different, is independently selected from hydrogen and $C_1$-$C_8$ alkyl;

$R^{25}$ is $C_3$-$C_8$ cycloalkyl, $C_2$-$C_9$ cycloheteroalkyl, or $C_2$-$C_9$ heteroaryl, each of which is optionally substituted with at least one substituent independently selected from $C_1$-$C_8$ alkyl, $C_6$-$C_{14}$ aryl, $C_2$-$C_9$ heteroaryl, —$CF_3$, and —$OR^{23a}$;

each $R^{27}$ is independently selected from —$OR^{23a}$, halo, $C_6$-$C_{14}$ aryl, $C_2$-$C_9$ heteroaryl, $C_1$-$C_8$ heteroalkyl, $C_3$-$C_8$ cycloalkyl, $C_2$-$C_9$ cycloheteroalkyl, and —$C(R^{23a}R^{23b}R^{23c})$;

t is an integer from 1 to 3; and pharmaceutically acceptable salts and solvates thereof.

Also provided are compounds of formula (II), wherein:

$R^{13}$ is $C_1$-$C_8$ alkyl substituted with $C_6$-$C_{14}$ aryl, and wherein said $C_6$-$C_{14}$ aryl is optionally substituted with at least one fluorine;

$R^{14}$ is hydrogen, —$(CR^{19}R^{20})NR^{21}R^{22}$, or $C_1$-$C_8$ heteroalkyl, wherein said $C_1$-$C_8$ heteroalkyl is substituted with $R^{25}$;

$R^{15}$ is hydrogen, halo, $C_1$-$C_8$ alkyl —$OR^{23a}$, —$NR^{23a}R^{23b}$, $C_1$-$C_8$ heteroalkyl, $C_2$-$C_8$ alkenyl, or $C_2$-$C_8$ alkynyl, wherein said $C_2$-$C_8$ alkenyl or $C_2$-$C_8$ alkynyl are optionally substituted with at least one $R^{27}$;

$R^{16}$ is hydrogen;

$R^{17}$ is hydrogen, $C_1$-$C_8$ alkyl, $C_1$-$C_8$ heteroalkyl, or $C_2$-$C_8$ alkenyl, wherein said $C_2$-$C_8$ alkenyl is optionally substituted with at least one —$OR^{23a}$ group;

$R^{18}$ is hydrogen, $C_1$-$C_8$ heteroalkyl, $C_6$-$C_{14}$ aryl, $C_2$-$C_8$ alkenyl, or $C_1$-$C_8$ alkyl, wherein said $C_1$-$C_8$ alkyl is optionally substituted with at least one $C_3$-$C_8$ cycloalkyl or $C_6$-$C_{14}$ aryl group;

each $R^{19}$ and $R^{20}$, which may be the same or different, are independently selected from hydrogen and $C_1$-$C_8$ alkyl;

$R^{21}$ and $R^{22}$, together with the nitrogen atom to which they are attached, form a $C_2$-$C_9$ cycloheteroalkyl group optionally substituted with at least one $C_1$-$C_8$ alkyl;

each $R^{23a}$, $R^{23b}$, and $R^{23c}$, which may be the same or different, is independently selected from hydrogen and $C_1$-$C_8$ alkyl;

$R^{25}$ is $C_3$-$C_8$ cycloalkyl, $C_2$-$C_9$ cycloheteroalkyl, or $C_2$-$C_9$ heteroaryl, each of which is optionally substituted with at least one substituent independently selected from $C_1$-$C_8$ alkyl, $C_6$-$C_{14}$ aryl, $C_2$-$C_9$ heteroaryl, —$CF_3$, and —$OR^{23a}$;

each $R^{27}$ is independently selected from —$OR^{23a}$, halo, $C_6$-$C_{14}$ aryl, $C_2$-$C_9$ heteroaryl, $C_1$-$C_8$ heteroalkyl, $C_3$-$C_8$ cycloalkyl, $C_2$-$C_9$ cycloheteroalkyl, and —$C(R^{23a}R^{23b}R^{23c})$;

t is an integer from 1 to 3; and pharmaceutically acceptable salts and solvates thereof.

Also provided are compounds of formula (II), wherein:

$R^{13}$ is $C_1$-$C_8$ alkyl substituted with $C_6$-$C_{14}$ aryl, and wherein said $C_6$-$C_{14}$ aryl is optionally substituted with at least one fluorine;

$R^{14}$ is hydrogen;

$R^{15}$ is hydrogen, halo, $C_1$-$C_8$ alkyl, —$NR^{23a}R^{23b}$, $C_1$-$C_8$ heteroalkyl, $C_2$-$C_8$ alkenyl, or $C_2$-$C_8$ alkynyl, wherein said $C_2$-$C_8$ alkenyl or $C_2$-$C_8$ alkynyl are optionally substituted with at least one $R^{27}$;

$R^{16}$ is hydrogen;

$R^{17}$ is hydrogen, $C_1$-$C_8$ alkyl, $C_1$-$C_8$ heteroalkyl, or $C_2$-$C_8$ alkenyl, wherein said $C_2$-$C_8$ alkenyl is optionally substituted with at least one —$OR^{23a}$ group;

$R^{18}$ is hydrogen, $C_1$-$C_8$ heteroalkyl, $C_6$-$C_{14}$ aryl, $C_2$-$C_8$ alkenyl, or $C_1$-$C_8$ alkyl, wherein said $C_1$-$C_8$ alkyl is optionally substituted with at least one $C_3$-$C_8$ cycloalkyl or $C_6$-$C_{14}$ aryl group;

each $R^{23a}$, $R^{23b}$, and $R^{23c}$, which may be the same or different, is independently selected from hydrogen and $C_1$-$C_8$ alkyl;

each $R^{27}$ is independently selected from —$OR^{23a}$, halo, $C_6$-$C_{14}$ aryl, $C_2$-$C_9$ heteroaryl, $C_1$-$C_8$ heteroalkyl, $C_3$-$C_8$ cycloalkyl, $C_2$-$C_9$ cycloheteroalkyl, and —$C(R^{23a}R^{23b}R^{23c})$; and pharmaceutically acceptable salts and solvates thereof.

Also provided are compounds of formula (II), wherein:

$R^{13}$ is $C_1$-$C_8$ alkyl substituted with $C_6$-$C_{14}$ aryl, and wherein said $C_6$-$C_{14}$ aryl is optionally substituted with at least one fluorine;

$R^{14}$ is —$(CR^{19}R^{20})_t NR^{21}R^{22}$;

$R^{15}$ is hydrogen, halo, $C_1$-$C_8$ alkyl, —$OR^{23a}$, —$NR^{23a}R^{23b}$, $C_1$-$C_8$ heteroalkyl, $C_2$-$C_8$ alkenyl, or $C_2$-$C_8$ alkynyl, wherein said $C_2$-$C_8$ alkenyl or $C_2$-$C_8$ alkynyl are optionally substituted with at least one $R^{27}$;

$R^{16}$ is hydrogen;

$R^{17}$ is hydrogen, $C_1$-$C_8$ alkyl, $C_1$-$C_8$ heteroalkyl, or $C_2$-$C_8$ alkenyl, wherein said $C_2$-$C_8$ alkenyl is optionally substituted with at least one —$OR^{23a}$ group;

$R^{18}$ is hydrogen, $C_1$-$C_8$ heteroalkyl, $C_6$-$C_{14}$ aryl, $C_2$-$C_8$ alkenyl, or $C_1$-$C_8$ alkyl, wherein said $C_1$-$C_8$ alkyl is optionally substituted with at least one $C_3$-$C_8$ cycloalkyl or $C_6$-$C_{14}$ aryl group;

each $R^{19}$ and $R^{20}$, which may be the same or different, are independently selected from hydrogen and $C_1$-$C_8$ alkyl;

$R^{21}$ and $R^{22}$, together with the nitrogen atom to which they are attached, form a $C_2$-$C_9$ cycloheteroalkyl group optionally substituted with at least one $C_1$-$C_8$ alkyl;

each $R^{23a}$, $R^{23b}$, and $R^{23c}$, which may be the same or different, is independently selected from hydrogen and $C_1$-$C_8$ alkyl;

each $R^{27}$ is independently selected from —$OR^{23a}$, halo, $C_6$-$C_{14}$ aryl, $C_2$-$C_9$ heteroaryl, $C_1$-$C_8$ heteroalkyl, $C_3$-$C_8$ cycloalkyl, $C_2$-$C_9$ cycloheteroalkyl, and —$C(R^{23a}R^{23b}R^{23c})$;

t is an integer from 1 to 3; and pharmaceutically acceptable salts and solvates thereof.

Also provided are compounds of formula (II), wherein:

$R^{13}$ is $C_1$-$C_8$ alkyl substituted with $C_6$-$C_{14}$ aryl, and wherein said $C_6$-$C_{14}$ aryl is optionally substituted with at least one fluorine;

$R^{14}$ is $C_1$-$C_8$ heteroalkyl, wherein said $C_1$-$C_8$ heteroalkyl is substituted with $R^{25}$;

$R^{15}$ is hydrogen, halo, $C_1$-$C_8$ alkyl, —$OR^{23a}$, —$NR^{23a}R^{23b}$, $C_1$-$C_8$ heteroalkyl, $C_2$-$C_8$ alkenyl, or $C_2$-$C_8$ alkynyl, wherein said $C_2$-$C_8$ alkenyl or $C_2$-$C_8$ alkynyl are optionally substituted with at least one $R^{27}$;

$R^{16}$ is hydrogen;

$R^{17}$ is hydrogen, $C_1$-$C_8$ alkyl, $C_1$-$C_8$ heteroalkyl, or $C_2$-$C_8$ alkenyl, wherein said $C_2$-$C_8$ alkenyl is optionally substituted with at least one —$OR^{23a}$ group;

$R^{18}$ is hydrogen, $C_1$-$C_8$ heteroalkyl, $C_6$-$C_{14}$ aryl, $C_2$-$C_8$ alkenyl, or $C_1$-$C_8$ alkyl, wherein said $C_1$-$C_8$ alkyl is optionally substituted with at least one $C_3$-$C_8$ cycloalkyl or $C_6$-$C_{14}$ aryl group;

each $R^{23a}$, $R^{23b}$, and $R^{23c}$, which may be the same or different, is independently selected from hydrogen and $C_1$-$C_8$ alkyl;

$R^{25}$ is $C_3$-$C_8$ cycloalkyl, $C_2$-$C_9$ cycloheteroalkyl, or $C_2$-$C_9$ heteroaryl, each of which is optionally substituted with at least one substituent independently selected from $C_1$-$C_8$ alkyl, $C_6$-$C_{14}$ aryl, $C_2$-$C_9$ heteroaryl, —$CF_3$, and —$OR^{23a}$;

each $R^{27}$ is independently selected from —$OR^{23a}$, halo, $C_6$-$C_{14}$ aryl, $C_2$-$C_9$ heteroaryl, $C_1$-$C_8$ heteroalkyl, $C_3$-$C_8$ cycloalkyl, $C_2$-$C_9$ cycloheteroalkyl, and —$C(R^{23a}R^{23b}R^{23c})$; and pharmaceutically acceptable salts and solvates thereof.

In a further aspect are provided any of the above compounds of formula (II), wherein $R^{18}$ is hydrogen, —$CH_3$, phenyl, allyl, or benzyl.

In a further aspect are provided any of the above compounds of formula (II), wherein $R^{17}$ is hydrogen, or $R^{17}$ is $C_1$-$C_8$ alkyl, or $R^{17}$ is $C_1$-$C_8$ heteroalkyl, or $R^{17}$ and $R^{18}$ are hydrogen; or wherein $R^{17}$ is hydrogen and $R^{18}$ is $C_1$-$C_8$ alkyl; or wherein $R^{17}$ is $C_1$-$C_8$ alkyl and $R^{18}$ is hydrogen.

In yet another aspect of the present invention are afforded any of the above compounds of formula (II), wherein $R^{21}$ and $R^{22}$, together with the nitrogen atom to which they are attached, form a $C_2$-$C_9$ cycloheteroalkyl group comprising 4 carbon atoms and a nitrogen atom; or wherein $R^{21}$ and $R^{22}$, together with the nitrogen atom to which they are attached, form a $C_2$-$C_9$ cycloheteroalkyl group comprising 4 carbon atoms and 2 nitrogen atoms; or wherein $R^{21}$ and $R^{22}$, together with the nitrogen atom to which they are attached, form a $C_2$-$C_9$ cycloheteroalkyl group comprising 4 carbon atoms, a nitrogen atom, and an oxygen atom, provided that said nitrogen atom and said oxygen atom are not bonded to each other;

or wherein $R^{21}$ and $R^{22}$, together with the nitrogen atom to which they are attached, form a $C_2$-$C_9$ cycloheteroalkyl group comprising 4 carbon atoms, a nitrogen atom, and a sulfur atom; or wherein $R^{21}$ and $R^{22}$, together with the nitrogen atom to which they are attached, form a $C_2$-$C_9$ cycloheteroalkyl group comprising 4 carbon atoms, a nitrogen atom, and an oxidized sulfur atom; or wherein $R^{21}$ and $R^{22}$, together with the nitrogen atom to which they are attached, form a $C_2$-$C_9$ cycloheteroalkyl group comprising three carbon atoms and three nitrogen atoms; or wherein $R^{21}$ and $R^{22}$, together with the nitrogen atom to which they are attached, form a $C_2$-$C_9$ cycloheteroalkyl group selected from:

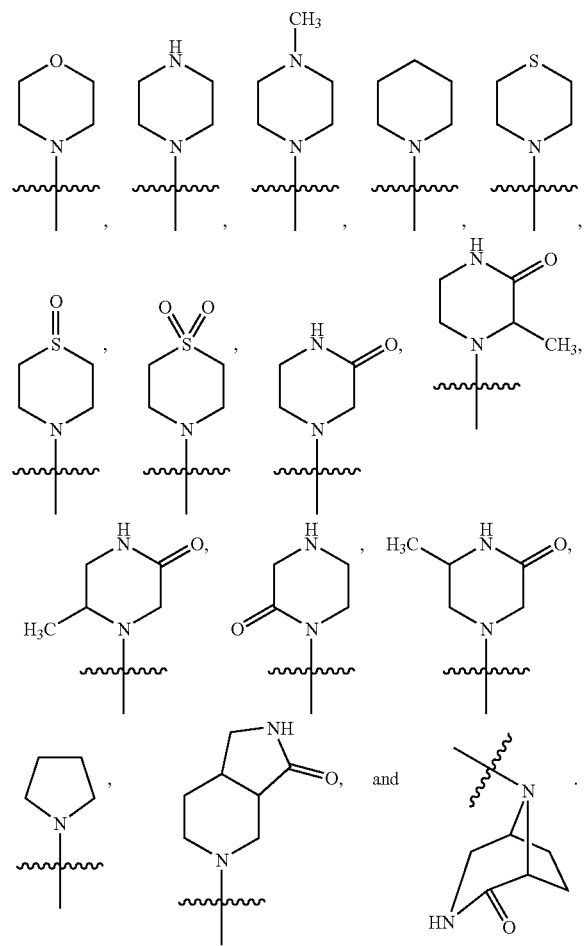

In a further aspect of the present invention, are compounds of formula (II) selected from 1-(4-fluorobenzyl)-N-hydroxy-1H-pyrazolo[3,4-c]pyridine-5-carboxamide; 1-(4-fluorobenzyl)-N-hydroxy-N-methyl-1H-pyrazolo[3,4-c]pyridine-5-carboxamide; and pharmaceutically acceptable salts and solvates thereof.

An additional aspect of the present invention affords compounds selected from 1-(2,4-difluorobenzyl)-N-hydroxy-3-{[(2-hydroxyethyl)amino]methyl}-1H-pyrrolo[2,3-c]pyridine-5-carboxamide; 1-(2,4-difluorobenzyl)-3-({[3-(dimethylamino)propyl]amino}methyl)-N-hydroxy-1H-pyrrolo[2,3-c]pyridine-5-carboxamide; 3-{[(2-amino-2-oxoethyl)amino]methyl}-1-(2,4-difluorobenzyl)-N-hydroxy-1H-pyrrolo[2,3-c]pyridine-5-carboxamide; 1-(2,4-difluorobenzyl)-N-methoxy-4-(methoxymethyl)-1H-pyrrolo[2,3-c]pyridine-5-carboxamide; 3-(4-fluorobenzyl)-N-hydroxy-3H-imidazo[4,5-c]pyridine-6-carboxamide; 3-(4-fluorobenzyl)-N-hydroxy-N-methyl-3H-imidazo[4,5-c]pyridine-6-carboxamide; 3-(2,3-difluorobenzyl)-N-hydroxy-3H-imidazo[4,5-c]pyridine-6-carboxamide; 3-(2-cyclohexylethyl)-N-hydroxy-3H-imidazo[4,5-c]pyridine-6-carboxamide; 1-(2-cyclohexylethyl)-N-hydroxy-1H-pyrrolo[2,3-c]pyridine-5-carboxamide; 1-(4-fluorobenzyl)-N-hydroxy-N-isopropyl-1H-pyrrolo[2,3-c]pyridine-5-carboxamide; 1-(4-fluorobenzyl)-N-hydroxy-N-isobutyl-1H-pyrrolo[2,3-c]pyridine-5-carboxamide; 1-(4-fluorobenzyl)-N-hydroxy-N-(3-hydroxypropyl)-1H-pyrrolo[2,3-c]pyridine-5-carboxamide; 1-(4-fluorobenzyl)-3-[(4-fluorophenyl)(hydroxy)methyl]-N-hydroxy-1H-pyrrolo[3,2-c]pyridine-6-carboxamide; 1,3-bis(4-fluorobenzyl)-N-hydroxy-1H-pyrrolo[3,2-c]pyridine-6-carboxamide; 1-(2,4-difluorobenzyl)-N-hydroxy-3-{[(2-hydroxy-1-methylethyl)amino]methyl}-1H-pyrrolo[2,3-c]pyridine-5-carboxamide; 1-(2,4-difluorobenzyl)-N-hydroxy-3-({[2-(2-hydroxyethoxy)ethyl]amino}methyl)-1H-pyrrolo[2,3-c]pyridine-5-carboxamide; 1-(2,4-difluorobenzyl)-N-hydroxy-3-({[(1R)-2-hydroxy-1-phenylethyl]amino}methyl)-1H-pyrrolo[2,3-c]pyridine-5-carboxamide; 1-(2,4-difluorobenzyl)-3-({[3-(dimethylamino)-2,2-dimethylpropyl]amino}methyl)-N-hydroxy-1H-pyrrolo[2,3-c]pyridine-5-carboxamide; 1-(2,4-difluorobenzyl)-N-hydroxy-3-{[(2-hydroxypropyl)amino]methyl}-1H-pyrrolo[2,3-c]pyridine-5-carboxamide; 1-(2,4-difluorobenzyl)-3-{[ethyl(2-hydroxyethyl)amino]methyl}-N-hydroxy-1H-pyrrolo[2,3-c]pyridine-5-carboxamide; 1-(2,4-difluorobenzyl)-3-{[(4-fluorobenzyl)amino]methyl}-N-hydroxy-1H-pyrrolo[2,3-c]pyridine-5-carboxamide; 1-(2,4-difluorobenzyl)-N-hydroxy-3-{[(1-phenylethyl)amino]methyl}-1H-pyrrolo[2,3-c]pyridine-5-carboxamide; 1-(2,4-difluorobenzyl)-3-({[2-(dimethylamino)ethyl]amino}methyl)-N-hydroxy-1H-pyrrolo[2,3-c]pyridine-5-carboxamide; 1-(2,4-difluorobenzyl)-N-hydroxy-3-({[1-(hydroxymethyl)-2-methylpropyl]amino}methyl)-1H-pyrrolo[2,3-c]pyridine-5-carboxamide; 1-(2,4-difluorobenzyl)-N-hydroxy-3-{[(3-methylbenzyl)amino]methyl}-1H-pyrrolo[2,3-c]pyridine-5-carboxamide; 1-(2,4-difluorobenzyl)-3-{[(1-ethylpropyl)amino]methyl}-N-hydroxy-1H-pyrrolo[2,3-c]pyridine-5-carboxamide; 1-(2,4-difluorobenzyl)-N-hydroxy-3-{[(3-isopropoxypropyl)amino]methyl}-1H-pyrrolo[2,3-c]pyridine-5-carboxamide; 1-(2,4-difluorobenzyl)-N-hydroxy-3-{[(2-hydroxy-2-phenylethyl)amino]methyl}-1H-pyrrolo[2,3-c]pyridine-5-carboxamide; 1-(2,4-difluorobenzyl)-3-({[2-(4-fluorophenyl)ethyl]amino}methyl)-N-hydroxy-1H-pyrrolo[2,3-c]pyridine-5-carboxamide; 1-(2,4-difluorobenzyl)-N-hydroxy-3-{[(2-hydroxy-1-methyl-2phenylethyl)amino]methyl}-1H-pyrrolo[2,3-c]pyridine-5-carboxamide; 1-(2,4-difluorobenzyl)-N-hydroxy-3-({[(1S)-1-(hydroxymethyl)-2,2-dimethylpropyl]amino}methyl)-1H-pyrrolo[2,3-c]pyridine-5-carboxamide; 1-(2,4-difluorobenzyl)-N-hydroxy-3-({methyl[2-(methylsulfonyl)ethyl]aminomethyl)-1H-pyrrolo[2,3-c]pyridine-5-carboxamide; 1-(2,4-difluorobenzyl)-N-hydroxy-3-[(phenylthio)methyl]-1H-pyrrolo[2,3-c]pyridine-5-carboxamide; 3-[(benzylthio)methyl]-1-(2,4-difluorobenzyl)-N-hydroxy-1H-pyrrolo[2,3-c]pyridine-5-carboxamide; 1-(2,4-difluorobenzyl)-N-hydroxy-3-[(phenylsulfonyl)methyl]-1H-pyrrolo[2,3-c]pyridine-5-carboxamide; 1-(2,4-difluorobenzyl)-N-hydroxy-3-[(phenylsulfinyl)methyl]-1H-pyrrolo[2,3-c]pyridine-5-carboxamide; 1,3-Bis(4-fluorobenzyl)-N-hydroxy-1H-pyrrolo[3,2-c]pyridine-6-carboxamide; 4-[(E)-2-Ethoxyvinyl]-1-(4-fluorobenzyl)-N-hydroxy-1H-pyrrolo[2,3-c]pyridine-5-carboxamide; 1-(4-Fluorobenzyl)-N-hydroxy-4-vinyl-1H-pyrrolo[2,3-c]pyridine-5-carboxamide;

3-({[(1S)-1-Benzyl-2-hydroxyethyl]amino}methyl)-1-(2,4-difluorobenzyl)-N-hydroxy-1H-pyrrolo[2,3-c]pyridine-5-carboxamide; Ethyl (1R,5S)-3-[({1-(2,4-difluorobenzyl)-5-[(hydroxyamino)carbonyl]-1H-pyrrolo[2,3-c]pyridin-3-yl}methyl)amino]-8-azabicyclo[3.2.1]octane-8-carboxylate; 1-(2,4-Difluorobenzyl)-N-methoxyl-4-(methoxymethyl)-1H-pyrrolo[2,3-c]pyridine-5-carboxamide; 1-(2,4-Difluorobenzyl)-3-({[(2R)-2,3-dihydroxypropyl]oxy}methyl)-N-hydroxy-1H-pyrrolo[2,3-c]pyridine-5-carboxamide; 1-(2,4-Difluorobenzyl)-3-({[(2S)-2,3-dihydroxypropyl]oxy}methyl)-N-hydroxy-1H-pyrrolo[2,3-c]pyridine-5-carboxamide; 1-(4-Fluorobenzyl)-N-hydroxy-3-[(2-methoxyethoxy)methyl]-N-methyl-1H-pyrrolo[2,3-c]pyridine-5-carboxamide; 1-(4-Fluorobenzyl)-N-methoxy-3-[(2-methoxyethoxy)methyl]-1H-pyrrolo[2,3-c]pyridine-5-carboxamide; 3-({[(4R)-2,2-Dimethyl-1,3-dioxolan-4-yl]methoxy}methyl)-1-(4-fluorobenzyl)-N-hydroxy-N-methyl-1H-pyrrolo[2,3-c]pyridine-5-carboxamide; N-ethoxy-1-(4-fluorobenzyl)-3-{[(2-hydroxyethyl)(propyl)amino]methyl}-1H-pyrrolo[2,3-c]pyridine-5-carboxamide; 3-{[[3-(Dimethylamino)propyl](methyl)amino]methyl}-N-ethoxy-1-(4-fluorobenzyl)-1H-pyrrolo[2,3-c]pyridine-5-carboxamide; 1-(4-Fluorobenzyl)-N-hydroxy-N-methyl-3-{[2-(2-oxopyrrolidin-1-yl)ethoxy]methyl}-1H-pyrrolo[2,3-c]pyridine-5-carboxamide; 1-(4-Fluorobenzyl)-N-hydroxy-N-methyl-3-[(tetrahydro-2H-pyran-4-yloxy)methyl]-1H-pyrrolo[2,3-c]pyridine-5-carboxamide; 1-(4-Fluorobenzyl)-N-hydroxy-N-methyl-3-([(1R)-1-phenylethoxy]methyl}-1H-pyrrolo[2,3-c]pyridine-5-carboxamide; 3-[(2-ethoxyethoxy)methyl]-1-(4-fluorobenzyl)-N-hydroxy-N-methyl-1H-pyrrolo[2,3-c]pyridine-5-carboxamide; 3-[(2-Ethoxyethoxy)methyl]-1-(4-fluorobenzyl)-N-methoxy-1H-pyrrolo[2,3-c]pyridine-5-carboxamide; 1-(4-Fluorobenzyl)-N-hydroxy-3-(methoxymethyl)-N-methyl-1H-pyrrolo[2,3-c]pyridine-5-carboxamide; and 1-(2,4-Difluorobenzyl)-N-hydroxy-3-[(2-methoxyethoxy)methyl]-N-methyl-1H-pyrrolo[2,3-c]pyridine-5-carboxamide; or pharmaceutically acceptable salts or solvates thereof.

In a further aspect are provided pharmaceutical compositions, comprising a therapeutically effective amount of at least one of any of the compounds herein, or a pharmaceutically acceptable salt or solvate thereof, and a pharmaceutically acceptable carrier or diluent.

Further provided are methods of inhibiting HIV replication in a mammal, comprising administering to said mammal an HIV-inhibiting amount of at least one of any of the compounds herein, or a pharmaceutically acceptable salt or solvate thereof.

Also afforded herein are methods of inhibiting HIV replication in a cell, comprising contacting said cell with an HIV-inhibiting amount of at least one of any of the compounds herein, or a pharmaceutically acceptable salt or solvate thereof.

Still further are provided methods of inhibiting HIV integrase enzyme activity, comprising contacting said integrase enzyme with a HIV integrase-inhibiting amount of at least one of any of the compounds herein, or a pharmaceutically acceptable salt or solvate thereof.

In yet another aspect of the present invention are afforded methods of treating acquired immune deficiency syndrome in a mammal, comprising administering to said mammal a therapeutically effective amount of at least one of any of the compounds herein, or a pharmaceutically acceptable salt or solvate thereof.

Further provided are methods of inhibiting HIV replication in a mammal, wherein said HIV is resistant to at least one HIV protease inhibitor, said method comprising administering to said mammal a therapeutically effective amount of at least one of any of the compounds herein, or a pharmaceutically acceptable salt or solvate thereof.

Also afforded herein are methods of inhibiting HIV replication in a mammal, wherein said HIV is resistant to at least one HIV reverse transcriptase inhibitor, said methods comprising administering to said mammal a therapeutically effective amount of at least one of any of the compounds herein, or a pharmaceutically acceptable salt or solvate thereof.

Further provided herein are methods of inhibiting HIV replication in mammal, comprising administering to said mammal a therapeutically effective amount of at least one of any of the compounds herein, or a pharmaceutically acceptable salt or solvate thereof, and at least one other anti-HIV agent.

Also provided are methods of reducing HIV viral load in a mammal infected with HIV, comprising administering to said mammal a therapeutically effective amount of at least one of any of the compounds herein, or a pharmaceutically acceptable salt or solvate thereof.

Further provided are uses of compounds herein, or a pharmaceutically acceptable salt or solvate thereof, in the manufacture of a medicament for the treatment of acquired immune deficiency syndrome (AIDS) or AIDS-related complex in an HIV-infected mammal, such as a human.

As used herein, the terms "comprising" and "including" are used in their open, non-limiting sense.

As used herein, the term "HIV" means Human Immunodeficiency Virus. The term "HIV integrase," as used herein, means the Human Immunodeficiency Virus integrase enzyme.

The term "$C_1$-$C_8$ alkyl," as used herein, means saturated monovalent hydrocarbon radicals having straight or branched moieties and containing from 1 to 8 carbon atoms. Examples of such groups include, but are not limited to, methyl, ethyl, propyl, iso-propyl, n-butyl, iso-butyl, and tert-butyl.

The term "$C_1$-$C_8$ heteroalkyl" refers to a straight- or branched-chain alkyl group having a total of from 2 to 12 atoms in the chain, including from 1 to 8 carbon atoms, and one or more atoms of which is a heteroatom selected from S, O, and N, with the proviso that said chain may not contain two adjacent O atoms or two adjacent S atoms, and with the proviso that no heteroatom may be attached directly to the five-membered ring at the $R^3$ position in the compounds of formula (I), directly to the five-membered ring at the $R^{14}$ position in the compounds of formula (II), or directly to the five-membered ring in any other compounds of the present invention. The S atoms in said chains may be optionally oxidized with one or two oxygen atoms, to afford sulfoxides and sulfones, respectively. Furthermore, the $C_1$-$C_8$ heteroalkyl groups in the compounds of the present invention can contain an oxo group at any carbon or heteroatom that will result in a stable compound, with the proviso that no carbonyl (C=O) group may be attached directly to the 1H-pyrrolo[2,3-c]pyridine core at the $R^3$ position in the compounds of formula (I), directly to the 1H-pyrazolo[3,4-c]pyridine core at the $R^{14}$ position in the compounds of formula (II), or directly to the five-membered ring of the core in any other compound of the present invention. Exemplary $C_1$-$C_8$ heteroalkyl groups include, but are not limited to, alcohols, alkyl ethers, primary, secondary, and tertiary alkyl amines, amides, ketones, esters, alkyl sulfides, and alkyl sulfones.

The term "$C_2$-$C_8$ alkenyl", as used herein, means an alkyl moiety comprising 2 to 8 carbons having at least one carbon-carbon double bond. The carbon-carbon double bond in such a group may be anywhere along the 2 to 8 carbon chain that will result in a stable compound. Such groups include both the E and Z isomers of said alkenyl moiety. Examples of such groups include, but are not limited to, ethenyl, propenyl, butenyl, allyl, and pentenyl. The term "allyl," as used herein, means a —$CH_2CH$=$CH_2$ group.

As used herein, the term "$C_2$-$C_8$ alkynyl" means an alkyl moiety comprising from 2 to 8 carbon atoms and having at least one carbon-carbon triple bond. The carbon-carbon triple bond in such a group may be anywhere along the 2 to 8 carbon chain that will result in a stable compound. Examples of such groups include, but are not limited to, ethyne, propyne, 1-butyne, 2-butyne, 1-pentyne, 2-pentyne, 1-hexyne, 2-hexyne, and 3-hexyne.

The term "$C_3$-$C_8$ cycloalkyl group" means a saturated, monocyclic, fused, or spiro, polycyclic ring structure having a total of from 3 to 8 carbon ring atoms. Examples of such groups include, but are not limited to, cyclopropyl, cyclobutyl, cyclopentyl, cyclopentenyl, cyclohexyl, cycloheptyl, and adamantyl.

The term "$C_6$-$C_{14}$ aryl", as used herein, means a group derived from an aromatic hydrocarbon containing from 6 to 14 carbon atoms. Examples of such groups include, but are not limited to, phenyl or naphthyl. The terms "Ph" and "phenyl," as used herein, mean a —$C_6H_5$ group. The term "benzyl," as used herein, means a —$CH_2C_6H_5$ group.

The term "$C_2$-$C_9$ heteroaryl," as used herein, means an aromatic heterocyclic group having a total of from 5 to 10 atoms in its ring, and containing from 2 to 9 carbon atoms and from one to four heteroatoms each independently selected from O, S and N, and with the proviso that the ring of said group does not contain two adjacent O atoms or two adjacent S atoms. The heterocyclic groups include benzo-fused ring systems. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The $C_2$-$C_9$ heteroaryl groups may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached).

The term "$C_2$-$C_9$ cycloheteroalkyl," as used herein, means a non-aromatic, monocyclic, bicyclic, tricyclic, or tetracyclic group having a total of from 4 to 10 atoms in its ring system, and containing from 2 to 9 carbon atoms and from one to four heteroatoms each independently selected from O, S and N, and with the proviso that the ring of said group does not contain two adjacent O atoms or two adjacent S atoms. Furthermore, such $C_2$-$C_9$ cycloheteroalkyl groups may contain an oxo substituent at any available atom that will result in a stable compound. For example, such a group may contain an oxo atom at an available carbon or nitrogen atom. Such a group may contain more than one oxo substituent if chemically feasible. In addition, it is to be understood that when such a $C_2$-$C_9$ cycloheteroalkyl group contains a sulfur atom, said sulfur atom may be oxidized with one or two oxygen atoms to afford either a sulfoxide or sulfone. An example of a 4 membered heterocyclic group is azetidinyl (derived from azetidine). An example of a 5 membered heterocyclic group is thiazolyl and an example of a 10 membered heterocyclic group is quinolinyl. Further examples of such $C_2$-$C_9$ cycloheteroalkyl groups include, but are not limited to, pyrrolidinyl, tetrahydrofuranyl, dihydrofuranyl, tetrahydrofuranyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl.

The term "$C_1$-$C_8$ alkoxy", as used herein, means an O-alkyl group wherein said alkyl group contains from 1 to 8 carbon atoms and is straight, branched, or cyclic. Examples of such groups include, but are not limited to, methoxy, ethoxy, n-propyloxy, iso-propyloxy, n-butoxy, iso-butoxy, tert-butoxy, cyclopentyloxy, and cyclohexyloxy.

The terms "halogen" and "halo," as used herein, mean fluorine, chlorine, bromine or iodine.

The term "substituted," means that the specified group or moiety bears one or more substituents. The term "unsubstituted," means that the specified group bears no substituents. The term "optionally substituted" means that the specified group is unsubstituted or substituted by one or more substituents. It is to be understood that in the compounds of the present invention when a group is said to be "unsubstituted," or is "substituted" with fewer groups than would fill the valencies of all the atoms in the compound, the remaining valencies on such a group are filled by hydrogen. For example, if a $C_6$ aryl group, also called "phenyl" herein, is substituted with one additional substituent, one of ordinary skill in the art would understand that such a group has 4 open positions left on carbon atoms of the $C_6$ aryl ring (6 initial positions, minus one to which the remainder of the compound of the present invention is bonded, minus an additional substituent, to leave 4). In such cases, the remaining 4 carbon atoms are each bound to one hydrogen atom to fill their valencies. Similarly, if a $C_6$ aryl group in the present compounds is said to be "disubstituted," one of ordinary skill in the art would understand it to mean that the $C_6$ aryl has 3 carbon atoms remaining that are unsubstituted. Those three unsubstituted carbon atoms are each bound to one hydrogen atom to fill their valencies.

The term "solvate," as used herein, means a pharmaceutically acceptable solvate form of a compound of the present invention that retains the biological effectiveness of such compound. Examples of solvates include, but are not limited to, compounds of the invention in combination with water, isopropanol, ethanol, methanol, dimethylsulfoxide (DMSO), ethyl acetate, acetic acid, ethanolamine, or mixtures thereof. It is specifically contemplated that in the present invention one solvent molecule can be associated with one molecule of the compounds of the present invention, such as a hydrate. Furthermore, it is specifically contemplated that in the present invention, more than one solvent molecule may be associated with one molecule of the compounds of the present invention, such as a dihydrate. Additionally, it is specifically contemplated that in the present invention less than one solvent molecule may be associated with one molecule of the compounds of the present invention, such as a hemihydrate. Furthermore, solvates of the present invention are contemplated as solvates of compounds of the present invention that retain the biological effectiveness of the non-hydrate form of the compounds.

The term "pharmaceutically acceptable salt," as used herein, means a salt of a compound of the present invention that retains the biological effectiveness of the free acids and bases of the specified derivative and that is not biologically or otherwise undesirable.

The term "pharmaceutically acceptable formulation," as used herein, means a combination of a compound of the invention, or a pharmaceutically acceptable salt or solvate thereof, and a carrier, diluent, and/or excipients that are compatible with a compound of the present invention, and is not deleterious to the recipient thereof. Pharmaceutical formulations can be prepared by procedures known to those of ordinary skill in the art. For example, the compounds of the present invention can be formulated with common excipients, diluents, or carriers, and formed into tablets, capsules, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as povidone, sodium starch glycolate, sodium carboxymethylcellulose, agar agar, calcium carbonate, and sodium bicarbonate; agents for retarding dissolution such as paraffin; resorption accelerators such as quaternary ammonium compounds; surfacelactive agents such as cetyl alcohol, glycerol monostearate; adsorptive carriers such as kaolin and bentonite; and lubricants such as talc, calcium and magnesium stearate and solid polyethylene glycols. Final pharmaceutical forms may be pills, tablets, powders, lozenges, saches, cachets, or sterile packaged powders, and the like, depending on the type of excipient used. Additionally, it is specifically contemplated that pharmaceutically acceptable formulations of the present invention can contain more than one active ingredient. For example, such formulations may contain more than one compound according to the present invention. Alternatively, such formulations may contain one or more compounds of the present invention and one or more additional anti-HIV agents.

The term "inhibiting HIV replication" means inhibiting human immunodeficiency virus (HIV) replication in a cell. Such a cell may be present in vitro, or it may be present in vivo, such as in a mammal, such as a human. Such inhibition may be accomplished by administering a compound of the present invention, or a pharmaceutically acceptable salt or solvate thereof, to the cell, such as in a mammal, in an HIV-inhibiting amount. The quantification of inhibition of HIV replication in a cell, such as in a mammal, can be measured using methods known to those of ordinary skill in the art. For example, an amount of a compound of the invention may be administered to a mammal, either alone or as part of a pharmaceutically acceptable formulation. Blood samples may then be withdrawn from the mammal and the amount of HIV virus in the sample may be quantified using methods known to those of ordinary skill in the art. A reduction in the amount of HIV virus in the sample compared to the amount found in the blood before administration of a compound of the invention would represent inhibition of the replication of HIV virus in the mammal. The administration of a compound of the invention to the cell, such as in a mammal, may be in the form of single dose or a series of doses. In the case of more than one dose, the doses may be administered in one day or they may be administered over more than one day.

An "HIV-inhibiting agent" means a compound of the present invention or a pharmaceutically acceptable salt or solvate thereof.

The term "anti-HIV agent," as used herein, means a compound or combination of compounds capable of inhibiting the replication of HIV in a cell, such as a cell in a mammal. Such compounds may inhibit the replication of HIV through any mechanism known to those of ordinary skill in the art.

The terms "human immunodeficiency virus-inhibiting amount" and "HIV-inhibiting amount," as used herein, refer to the amount of a compound of the present invention, or a pharmaceutically acceptable salt of solvate thereof, required to inhibit replication of the human immunodeficiency virus (HIV) in vivo, such as in a mammal, or in vitro. The amount of such compounds required to cause such inhibition can be determined without undue experimentation using methods described herein and those known to those of ordinary skill in the art.

The term "inhibiting HIV integrase enzyme activity," as used herein, means decreasing the activity or functioning of the HIV integrase enzyme either in vitro or in vivo, such as in a mammal, such as a human, by contacting the enzyme with a compound of the present invention.

The term, "HIV integrase enzyme-inhibiting amount," as used herein, refers to the amount of a compound of the present invention, or a pharmaceutically acceptable salt or solvate thereof, required to decrease the activity of the HIV integrase enzyme either in vivo, such as in a mammal, or in vitro. Such inhibition may take place by the compound of the present invention binding directly to the HIV integrase enzyme. In addition, the activity of the HIV integrase enzyme may be decreased in the presence of a compound of the present invention when such direct binding between the enzyme and the compound does not take place. Furthermore, such inhibition may be competitive, non-competitive, or uncompetitive. Such inhibition may be determined using in vitro or in vivo systems, or a combination of both, using methods known to those of ordinary skill in the art.

The term "therapeutically effective amount," as used herein, means an amount of a compound of the present invention, or a pharmaceutically acceptable salt or solvate thereof, that, when administered to a mammal in need of such treatment, is sufficient to effect treatment, as defined herein. Thus, a therapeutically effective amount of a compound of the present invention, or a pharmaceutically acceptable salt or solvate thereof, is a quantity sufficient to modulate or inhibit the activity of the HIV integrase enzyme such that a disease condition that is mediated by activity of the HIV integrase enzyme is reduced or alleviated.

The terms "treat", "treating", and "treatment" refer to any treatment of an HIV integrase mediated disease or condition in a mammal, particularly a human, and include: (i) preventing the disease or condition from occurring in a subject which may be predisposed to the condition, such that the treatment constitutes prophylactic treatment for the pathologic condition; (ii) modulating or inhibiting the disease or condition, i.e., arresting its development; (iii) relieving the disease or condition, i.e., causing regression of the disease or condition; or (iv) relieving and/or alleviating the disease or condition or the symptoms resulting from the disease or condition, e.g., relieving an inflammatory response without addressing the underlying disease or condition.

The terms "resistant," "resistance," and "resistant HIV," as used herein, refer to HIV virus demonstrating a reduction in sensitivity to a particular drug. A mammal infected with HIV that is resistant to a particular anti-HIV agent or combination of agents usually manifests an increase in HIV viral load despite continued administration of the agent or agents. Resistance may be either genotypic, meaning that a mutation in the HIV genetic make-up has occurred, or phenotypic, meaning that resistance is discovered by successfully growing laboratory cultures of HIV virus in the presence of an anti-HIV agent or a combination of such agents.

The terms "protease inhibitor" and "HIV protease inhibitor," as used herein, refer to compounds or combinations of compounds that interfere with the proper functioning of the HIV protease enzyme that is responsible for cleaving long strands of viral protein into the separate proteins making up the viral core.

The terms "reverse transcriptase inhibitor" and "HIV reverse transcriptase inhibitor," as used herein, refer to compounds or combinations of compounds that interfere with the proper functioning of the HIV reverse transcriptase enzyme that is responsible for converting single-stranded HIV viral RNA into HIV viral DNA.

The terms "fusion inhibitor" and "HIV fusion inhibitor," as used herein, refer to compounds or combinations of compounds that bind to the gp41 envelope protein on the surface of CD4 cells and thereby block the structural changes necessary for the virus to fuse with the cell.

The terms "integrase inhibitor" and "HIV integrase inhibitor," as used herein, refer to a compound or combination of compounds that interfere with the proper functioning of the HIV integrase enzyme that is responsible for inserting the genes of HIV into the DNA of a host cell.

The term "CCR5 antagonist," as used herein, refer to compounds or combinations of compounds that block the infection of certain cell types by HIV through the perturbation of CCR5 co-receptor activity.

The terms "viral load" and "HIV viral load," as used herein, mean the amount of HIV in the circulating blood of a mammal, such as a human. The amount of HIV virus in the blood of mammal can be determined by measuring the quantity of HIV RNA in the blood using methods known to those of ordinary skill in the art.

The term, "compound of the present invention" refers to any of the above-mentioned compounds, as well as those in the Examples that follow, and include those generically described or those described as species. The term also refers to pharmaceutically acceptable salts or solvates of these compounds.

DETAILED DESCRIPTION

The compounds of the present invention are useful for modulating or inhibiting HIV integrase enzyme. More particularly, the compounds of the present invention are useful as modulators or inhibitors of HIV integrase activity, and thus are useful for the prevention and/or treatment of HIV mediated diseases or conditions (e.g., AIDS, and ARC), alone or in combination with other known antiviral agents.

In accordance with a convention used in the art, the symbol

is used in structural formulas herein to depict the bond that is the point of attachment of the moiety or substituent to the core or backbone structure. In accordance with another convention, in some structural formulae herein the carbon atoms and their bound hydrogen atoms are not explicitly depicted, e.g.,

represents a methyl group,

represents an ethyl group,

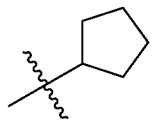

represents a cyclopentyl group, etc.

The term "stereoisomers" refers to compounds that have identical chemical constitution, but differ with regard to the arrangement of their atoms or groups in space. In particular, the term "enantiomers" refers to two stereoisomers of a compound that are non-superimposable mirror images of one another. The terms "racemic" or "racemic mixture," as used herein, refer to a 1:1 mixture of enantiomners of a particular compound. The term "diastereomers", on the other hand, refers to the relationship between a pair of stereoisomers that comprise two or more asymmetric centers and are not mirror images of one another.

The compounds of the present invention may have asymmetric carbon atoms. The carbon-carbon bonds of the compounds of the present invention may be depicted herein using a solid line (—), a solid wedge (—◀), or a dotted wedge (⋯⋯).

The use of a solid line to depict bonds from asymmetric carbon atoms is meant to indicate that all possible stereoisomers at that carbon atom are included. The use of either a solid or dotted wedge to depict bonds from asymmetric carbon atoms is meant to indicate that only the stereoisomer shown is meant to be included. It is possible that compounds of the invention may contain more than one asymmetric carbon atom. In those compounds, the use of a solid line to depict bonds from asymmetric carbon atoms is meant to indicate that all possible stereoisomers are meant to be included. The use of a solid line to depict bonds from one or more asymmetric carbon atoms in a compound of the invention and the use of a solid or dotted wedge to depict bonds from other asymmetric carbon atoms in the same compound is meant to indicate that a mixture of diastereomers is present.

If a derivative used in the method of the invention is a base, a desired salt may be prepared by any suitable method known to the art, including treatment of the free base with an inorganic acid, such as hydrochloric acid; hydrobromic acid; sulfuric acid; nitric acid; phosphoric acid; and the like, or with an organic acid, such as acetic acid; maleic acid; succinic acid; mandelic acid; fumaric acid; malonic acid; pyruvic acid; oxalic acid; glycolic acid; salicylic acid; pyranosidyl acid, such as glucuronic acid or galacturonic acid; alpha-hydroxy acid, such as citric acid or tartaric acid; amino acid, such as aspartic acid or glutamic acid; aromatic acid, such as benzoic acid or cinnamic acid; sulfonic acid, such as p-toluenesulfonic acid or ethanesulfonic acid; and the like.

If a derivative used in the method of the invention is an acid, a desired salt may be prepared by any suitable method known to the art, including treatment of the free acid with an inorganic or organic base, such as an amine (primary, secondary, or tertiary); an alkali metal or alkaline earth metal hydroxide; or the like. Examples of suitable salts include organic salts derived from amino acids such as glycine and arginine; ammonia; primary, secondary, and tertiary amines; and cyclic amines, such as piperidine, morpholine, and piperazine; as well as inorganic salts derived from sodium, calcium, potassium, magnesium, manganese, iron, copper, zinc, aluminum, and lithium.

A "solvate" is intended to mean a pharmaceutically acceptable solvate form of a specified compound that retains the biological effectiveness of such compound. Examples of solvates include, but are not limited to, compounds of the invention in combination with water, isopropanol, ethanol, methanol, dimethylsulfoxide (DMSO), ethyl acetate, acetic acid, ethanolamine, or mixtures thereof.

A "pharmaceutically acceptable salt" is intended to mean a salt that retains the biological effectiveness of the free acids and bases of the specified derivative, containing pharmacologically acceptable anions, and is not biologically or otherwise undesirable. Examples of pharmaceutically acceptable salts include, but are not limited to, acetate, acrylate, benzenesulfonate, benzoate (such as chlorobenzoate, methylbenzoate, dinitrobenzoate, hydroxybenzoate, and methoxybenzoate), bicarbonate, bisulfate, bisulfite, bitartrate, borate, bromide, butyne-1,4-dioate, calcium edetate, camsylate, carbonate, chloride, caproate, caprylate, clavulanate, citrate, decanoate, dihydrochloride, dihydrogenphosphate, edetate, edislyate, estolate, esylate, ethylsuccinate, formate, fumarate, gluceptate, gluconate, glutamate, glycollate, glycollylarsanilate, heptanoate, hexyne-1,6-dioate, hexylresorcinate, hydrabamine, hydrobromide, hydrochloride, γ-hydroxybutyrate, iodide, isobutyrate, isothionate, lactate, lactobionate, laurate, malate, maleate, malonate, mandelate, mesylate, metaphosphate, methane-sulfonate, methylsulfate, monohydrogenphosphate, mucate, napsylate, naphthalene-1-sulfonate, naphthalene-2-sulfonate, nitrate, oleate, oxalate, pamoate (embonate), palmitate, pantothenate, phenylacetates, phenylbutyrate, phenylpropionate, phthalate, phospate/diphosphate, polygalacturonate, propanesulfonate, propionate, propiolate, pyrophosphate, pyrosulfate, salicylate, stearate, subacetate, suberate, succinate, sulfate, sulfonate, sulfite, tannate, tartrate, teoclate, tosylate, triethiodode, and valerate salts.

The compounds of the present invention that are basic in nature are capable of forming a wide variety of different salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention can be prepared by treating the base compound with a substantially equivalent amount of the selected mineral or organic acid in an aqueous solvent medium or in a suitable organic solvent, such as methanol or ethanol. Upon evaporation of the solvent, the desired solid salt is obtained. The desired acid salt can also be precipitated from a solution of the free base in an organic solvent by adding an appropriate mineral or organic acid to the solution.

Those compounds of the present invention that are acidic in nature are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of the present invention. Such non-toxic base salts include those derived from such pharmacologically acceptable cations as sodium, potassium calcium and magnesium, etc. These salts can be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds, agents and salts may exist in different crystal or polymorphic forms, all of which are intended to be within the scope of the present invention and specified formulas.

The compounds of the present invention may be formulated into pharmaceutical compositions as described below in any pharmaceutical form recognizable to the skilled artisan as being suitable. Pharmaceutical compositions of the invention comprise a therapeutically effective amount of at least one compound of the present invention and an inert, pharmaceutically acceptable carrier or diluent.

To treat or prevent diseases or conditions mediated by HIV, a pharmaceutical composition of the invention is administered in a suitable formulation prepared by combining a therapeutically effective amount (i.e., an HIV Integrase modulating, regulating, or inhibiting amount effective to achieve therapeutic efficacy) of at least one compound of the present invention (as an active ingredient) with one or more pharmaceutically suitable carriers, which may be selected, for example, from diluents, excipients and auxiliaries that facilitate processing of the active compounds into the final pharmaceutical preparations.

The pharmaceutical carriers employed may be either solid or liquid. Exemplary solid carriers are lactose, sucrose, talc, gelatin, agar, pectin, acacia, magnesium stearate, stearic acid and the like. Exemplary liquid carriers are syrup, peanut oil, olive oil, water and the like. Similarly, the inventive compositions may include time-delay or time-release material known in the art, such as glyceryl monostearate or glyceryl distearate alone or with a wax, ethylcellulose, hydroxypropylmethylcellulose, methylmethacrylate or the like. Further additives or excipients may be added to achieve the desired formulation properties. For example, a bioavailability enhancer, such as Labrasol®, Gelucire® or the like, or formulator, such as CMC (carboxy-methylcellulose), PG (propyleneglycol), or PEG (polyethyleneglycol), may be added. Gelucire®, a semi-solid vehicle that protects active ingredients from light, moisture and oxidation, may be added, e.g., when preparing a capsule formulation.

If a solid carrier is used, the preparation can be tableted, placed in a hard gelatin capsule in powder or pellet form, or formed into a troche or lozenge. The amount of solid carrier may vary, but generally will be from about 25 mg to about 1 g. If a liquid carrier is used, the preparation may be in the form of syrup, emulsion, soft gelatin capsule, sterile injectable solution or suspension in an ampoule or vial or non-aqueous liquid suspension. If a semi-solid carrier is used, the preparation may be in the form of hard and soft gelatin capsule formulations. The inventive compositions are prepared in unit-dosage form appropriate for the mode of administration, e.g., parenteral or oral administration.

To obtain a stable water-soluble dose form, a pharmaceutically acceptable salt of a compound of the present invention may be dissolved in an aqueous solution of an organic or inorganic acid, such as 0.3 M solution of succinic acid or citric acid. If a soluble salt form is not available, the agent may be dissolved in a suitable cosolvent or combinations of cosolvents. Examples of suitable cosolvents include alcohol, propylene glycol, polyethylene glycol 300, polysorbate 80, glycerin and the like in concentrations ranging from 0-60% of the total volume. In an exemplary embodiment, a compound of Formula I is dissolved in DMSO and diluted with water. The composition may also be in the form of a solution of a salt form of the active ingredient in an appropriate aqueous vehicle such as water or isotonic saline or dextrose solution.

Proper formulation is dependent upon the route of administration selected. For injection, the agents of the compounds of the present invention may be formulated into aqueous solutions, preferably in physiologically compatible buffers such as Hanks solution, Ringer's solution, or physiological saline buffer. For transmucosal administration, penetrants appropriate to the barrier to be permeated are used in the formulation. Such penetrants are generally known in the art.

For oral administration, the compounds can be formulated by combining the active compounds with pharmaceutically acceptable carriers known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethylcellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agents.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration intranasally or by inhalation, the compounds for use according to the present invention may be conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator and the like may be formulated containing a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Alternatively, the active ingredient may be in powder form for constitution with a suitable vehicle, e.g., sterile pyrogen-free water, before use.

In addition to the formulations described above, the compounds of the present invention may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt. A pharmaceutical carrier for hydrophobic compounds is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD: 5W) contains VPD diluted 1:1 with a 5% dextrose in water solution. This co-solvent system dissolves hydrophobic compounds well, and itself produces low toxicity upon systemic administration. The proportions of a co-solvent system may be suitably varied without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity due to the toxic nature of DMSO. Additionally, the compounds may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. These carriers and excipients may provide marked improvement in the bioavailability of poorly soluble drugs. Examples of such carriers or excipients include calcium carbonate, calcium phosphate, sugars, starches, cellulose derivatives, gelatin, and polymers such as polyethylene glycols. Furthermore, additives or excipients such as Gelucire®, Capryol®, Labrafil®, Labrasol®, Lauroglycol®, Plurol®, Peceol® Transcutol® and the like may be used. Further, the pharmaceutical composition may be incorporated into a skin patch for delivery of the drug directly onto the skin.

It will be appreciated that the actual dosages of the agents of this invention will vary according to the particular agent being used, the particular composition formulated, the mode of administration, and the particular site, host, and disease being treated. Those skilled in the art using conventional dosage-determination tests in view of the experimental data for a given compound may ascertain optimal dosages for a given set of conditions. For oral administration, an exemplary daily dose generally employed will be from about 0.001 to about 1000 mg/kg of body weight, with courses of treatment repeated at appropriate intervals.

Furthermore, the pharmaceutically acceptable formulations of the present invention may contain a compound of the present invention, or a pharmaceutically acceptable salt or solvae thereof, in an amount of about 10 mg to about 2000 mg, or from about 10 mg to about 1500 mg, or from about 10 mg to about 1000 mg, or from about 10 mg to about 750 mg, or from about 10 mg to about 500 mg, or from about 25 mg to about 500 mg, or from about 50 to about 500 mg, or from about 100 mg to about 500 mg.

Additionally, the pharmaceutically acceptable formulations of the present invention may contain a compound of the present invention, or a pharmaceutically acceptable salt or solvate thereof, in an amount from about 0.5 w/w % to about 95 w/w %, or from about 1 w/w % to about 95 w/w %, or from about 1 w/w % to about 75 w/w %, or from about 5 w/w % to about 75 w/w %, or from about 10 w/w % to about 75 w/w %, or from about 10 w/w % to about 50 w/w %.

The compounds of the present invention, or a pharmaceutically acceptable salt or solvate thereof, may be administered to a mammal suffering from infection with HIV, such as a human, either alone or as part of a pharmaceutically acceptable formulation, once a day, twice a day, or three times a day.

Those of ordinary skill in the art will understand that with respect to the compounds of the present invention, the particular pharmaceutical formulation, the dosage, and the number of doses given per day to a mammal requiring such treatment, are all choices within the knowledge of one of ordinary skill in the art and can be determined without undue experimentation. For example, see "Guidelines for the Use of Antiretroviral Agents in HIV-1 Infected Adults and Adolescents," United States Department of Health and Human Services, available at http://www.aidsinfo.nih.gov/guidelines/ as of Apr. 16, 2004.

The compounds of the present invention may be administered in combination with an additional agent or agents for the treatment of a mammal, such as a human, that is suffering from an infection with the HIV virus, AIDS, AIDS-related complex (ARC), or any other disease or condition which is related to infection with the HIV virus. The agents that may be used in combination with the compounds of the present invention include, but are not limited to, those useful as HIV protease inhibitors, HIV reverse transcriptase inhibitors, non-nucleoside HIV reverse transcriptase inhibitors, inhibitors of HIV integrase, CCR5 inhibitors, HIV fusion inhibitors, compounds useful as immunomodulators, compounds that inhibit the HIV virus by an unknown mechanism, compounds useful for the treatment of herpes viruses, compounds useful as anti-infectives, and others as described below.

Compounds useful as HIV protease inhibitors that may be used in combination with the compounds of the present invention include, but are not limited to, 141 W94 (amprenavir), CGP-73547, CGP-61755, DMP-450, nelfinavir, ritonavir, saquinavir (invirase), lopinavir, TMC-126, atazanavir, palinavir, GS-3333, KN I-413, KNI-272, LG-71350, CGP-61755, PD 173606, PD 177298, PD 178390, PD 178392, U-140690, ABT-378, DMP-450, AG-1776, MK-944, VX-478, indinavir, tipranavir, TMC-114, DPC-681, DPC-684, fosamprenavir calcium (Lexiva), benzenesulfonamide derivatives disclosed in WO 03053435, R-944, Ro-03-34649, VX-385, GS-224338, OPT-TL3, PL-100, SM-309515, AG-148, DG-35-VIII, DMP-850, GW-5950x, KNI-1039, L-756423, LB-71262, LP-130, RS-344, SE-063, UIC-94-003, Vb-19038, A-77003, BMS-182193, BMS-186318, SM-309515, JE-2147, GS-9005.

Compounds useful as inhibitors of the HIV reverse transcriptase enzyme that may be used in combination with the compounds of the present invention include, but are not limited to, abacavir, FTC, GS-840, lamivudine, adefovir dipivoxil, beta-fluoro-ddA, zalcitabine, didanosine, stavudine, zidovudine, tenofovir, amdoxovir, SPD-754, SPD-756, racivir, reverset (DPC-817), MIV-210 (FLG), beta-L-Fd4C (ACH-126443), MIV-310 (alovudine, FLT), dOTC, DAPD, entecavir, GS-7340, emtricitabine, alovudine.

Compounds useful as non-nucleoside inhibitors of the HIV reverse transcriptase enzyme that may be used in combination with the compounds of the present invention include, but are not limited to, efavirenz, HBY-097, nevirapine, TMC-120 (dapivirine), TMC-125, etravirine, delavirdine, DPC-083, DPC-961, TMC-120, capravirine, GW-678248, GW-695634, calanolide, and tricyclic pyrimidinone derivatives as disclosed in WO 03062238.

Compounds useful as CCR5 inhibitors that may be used in combination with the compounds of the present invention include, but are not limited to, TAK-779, SC-351125, SCH-D, UK-427857, PRO-140, and GW-873140 (Ono-4128, AK-602).

Compounds useful as inhibitors of HIV integrase enzyme that may be used in combination with the compounds of the present invention include, but are not limited to, GW-810781, 1,5-naphthyridine-3-carboxamide derivatives disclosed in WO 03062204, compounds disclosed in WO 03047564, compounds disclosed in WO 03049690, and 5-hydroxypyrimidine-4-carboxamide derivatives disclosed in WO 03035076.

Fusion inhibitors for the treatment of HIV that may be used in combination with the compounds of the present invention include, but are not limited to enfuvirtide (T-20), T-1249, AMD-3100, and fused tricyclic compounds disclosed in JP 2003171381.

Other compounds that are useful inhibitors of HIV that may be used in combination with the compounds of the present invention include, but are not limited to, Soluble CD4, TNX-355, PRO-542, BMS-806, tenofovir disoproxil fumarate, and compounds disclosed in JP 2003119137.

Compounds useful in the treatment or management of infection from viruses other than HIV that may be used in combination with the compounds of the present invention include, but are not limited to, acyclovir, fomivirsen, penciclovir, HPMPC, oxetanocin G, AL-721, cidofovir, cytomegalovirus immune globin, cytovene, fomivganciclovir, famciclovir, foscarnet sodium, Isis 2922, KNI-272, valacyclovir, virazole ribavirin, valganciclovir, ME-609, PCL-016

Compounds that act as immunomodulators and may be used in combination with the compounds of the present invention include, but are not limited to, AD-439, AD-519, Alpha Interferon, AS-101, bropirimine, acemannan, CL246, 738, EL10, FP-21399, gamma interferon, granulocyte macrophage colony stimulating factor, IL-2, immune globulin intravenous, IMREG-1, IMREG-2, imuthiol diethyl dithio carbamate, alpha-2 interferon, methionine-enkephalin, MTP-PE, granulocyte colony stimulating sactor, remune, rCD4, recombinant soluble human CD4, interferon alfa-2, SK&F106528, soluble T4 yhymopentin, tumor necrosis factor (TNF), tucaresol, recombinant human interferon beta, and interferon alfa n-3.

Anti-infectives that may be used in combination with the compounds of the present invention include, but are not limited to, atovaquone, azithromycin, clarithromycin, trimethoprim, trovafloxacin, pyrimethamine, daunorubicin, clindamycin with primaquine, fluconazole, pastill, ornidyl, eflornithine pentamidine, rifabutin, spiramycin, intraconazole-R51211, trimetrexate, daunorubicin, recombinant human erythropoietin, recombinant human growth hormone, megestrol acetate, testerone, and total enteral nutrition.

Antifungals that may be used in combination with the compounds of the present invention include, but are not limited to, anidulafungin, C31G, caspofungin, DB-289, fluconzaole, itraconazole, ketoconazole, micafungin, posaconazole, and voriconazole.

Other compounds that may be used in combination with the compounds of the present invention include, but are not limited to, acmannan, ansamycin, LM 427, AR177, BMS-232623, BMS-234475, C1-1012, curdlan sulfate, dextran sulfate, STOCRINE EL10, hypericin, lobucavir, novapren, peptide T octabpeptide sequence, trisodium phosphonoformate, probucol, and RBC-CD4.

In addition, the compounds of the present invention may be used in combination with anti-proliferative agents for the treatment of conditions such as Kaposi's sarcoma. Such agents include, but are not limited to, inhibitors of metallomatrix proteases, A-007, bevacizumab, BMS-275291, halofuginone, interleukin-12, rituximab, paclitaxel, porfimer sodium, rebimastat, and COL-3.

The particular choice of an additional agent or agents will depend on a number of factors that include, but are not limited to, the condition of the mammal being treated, the particular condition or conditions being treated, the identity of the compound or compounds of the present invention and the additional agent or agents, and the identity of any additional compounds that are being used to treat the mammal. The particular choice of the compound or compounds of the invention and the additional agent or agents is within the knowledge of one of ordinary skill in the art and can be made without undue experimentation.

The compounds of the present invention may be administered in combination with any of the above additional agents for the treatment of a mammal, such as a human, that is suffering from an infection with the HIV virus, AIDS, AIDS-related complex (ARC), or any other disease or condition which is related to infection with the HIV virus. Such a combination may be administered to a mammal such that a compound or compounds of the present invention are present in the same formulation as the additional agents described above. Alternatively, such a combination may be administered to a mammal suffering from infection with the HIV virus such that the compound or compounds of the present invention are present in a formulation that is separate from the formulation in which the additional agent is found. If the compound or compounds of the present invention are administered separately from the additional agent, such administration may take place concomitantly or sequentially with an appropriate period of time in between. The choice of whether to include the compound or compounds of the present invention in the same formulation as the additional agent or agents is within the knowledge of one of ordinary skill in the art.

Additionally, the compounds of the present invention may be administered to a mammal, such as a human, in combination with an additional agent that has the effect of increasing the exposure of the mammal to a compound of the invention. The term "exposure," as used herein, refers to the concentration of a compound of the invention in the plasma of a mammal as measured over a period of time. The exposure of a mammal to a particular compound can be measured by administering a compound of the invention to a mammal in an appropriate form, withdrawing plasma samples at predetermined times, and measuring the amount of a compound of the invention in the plasma using an appropriate analytical technique, such as liquid chromatography or liquid chromatography/mass spectroscopy. The amount of a compound of the invention present in the plasma at a certain time is determined and the concentration and time data from all the samples are plotted to afford a curve. The area under this curve is calculated and affords the exposure of the mammal to the compound. The terms "exposure," "area under the curve," and "area under the concentration/time curve" are intended to have the same meaning and may be used interchangeably throughout.

Among the agents that may be used to increase the exposure of a mammal to a compound of the present invention are those that can as inhibitors of at least one isoform of the cytochrome P450 (CYP450) enzymes. The isoforms of CYP450 that may be beneficially inhibited include, but are not limited to, CYP1A2, CYP2d6, CYP2C$_9$, CYP2C$_{19}$ and CYP3A4. Suitable agents that may be used to inhibit CYP 3A4 include, but are not limited to, ritonavir and delavirdine.

Such a combination may be administered to a mammal such that a compound or compounds of the present invention are present in the same formulation as the additional agents described above. Alternatively, such a combination may be administered such that the compound or compounds of the present invention are present in a formulation that is separate from the formulation in which the additional agent is found. If the compound or compounds of the present invention are administered separately from the additional agent, such administration may take place concomitantly or sequentially with an appropriate period of time in between. The choice of whether to include the compound or compounds of the present invention in the same formulation as the additional agent or agents is within the knowledge of one of ordinary skill in the art.

Several different assay formats are available to measure integrase-mediated integration of viral DNA into target (or host) DNA and thus, identify compounds that modulate (e.g., inhibit) integrase activity. In general, for example, ligand-binding assays may be used to determine interaction with an enzyme of interest. When binding is of interest, a labeled enzyme may be used, wherein the label is a fluorescer, radioisotope, or the like, which registers a quantifiable change upon binding to the enzyme. Alternatively, the skilled artisan may employ an antibody for binding to the enzyme, wherein the antibody is labeled allowing for amplification of the signal. Thus, binding may be determined through direct measurement of ligand binding to an enzyme. In addition, binding may be determined by competitive displacement of a ligand bound to an enzyme, wherein the ligand is labeled with a detectable label. When inhibitory activity is of interest, an intact organism or cell may be studied, and the change in an organismic or cellular function in response to the binding of the inhibitory compound may be measured. Alternatively, cellular response can be determined microscopically by monitoring viral induced syncytium-formation (HIV-1 syncytium-formation assays), for example. Thus, there are various in vitro and in vivo assays useful for measuring HIV integrase inhibitory activity. See, e.g., Lewin, S. R. et al., *Journal of Virology* 73(7): 6099-6103 (July 1999); Hansen, M. S. et al., *Nature Biotechnology* 17(6): 578-582 (June 1999); and Butler, S. L. et al., *Nature Medicine* 7(5): 631-634 (May 2001).

Exemplary specific assay formats used to measure integrase-mediated integration include, but are not limited to, ELISA, DELFIA® (PerkinElmer Life Sciences Inc. (Boston, Mass.)) and ORIGEN®(IGEN International, Inc. (Gaithersburg, Md.)) technologies. In addition, gel-based integration (detecting integration by measuring product formation with SDS-PAGE) and scintillation proximity assay (SPA) disintegration assays that use a single unit of double stranded-DNA (ds-DNA) may be used to monitor integrase activity.

In one embodiment of the invention, the preferred assay is an integrase strand-transfer SPA (stINTSPA) which uses SPA to specifically measure the strand-transfer mechanism of integrase in a homogenous assay scalable for miniaturization to allow high-throughput screening. The assay focuses on strand transfer and not on DNA binding and/or 3' processing. This sensitive and reproducible assay is capable of distinguishing non-specific interactions from true enzymatic function by forming 3' processed viral DNA/integrase complexes before the addition of target DNA. Such a formation creates a bias toward compound modulators (e.g., inhibitors) of strand-transfer and not toward compounds that inhibit integrase 3' processing or prevent the association of integrase with viral DNA. This bias renders the assay more specific than known assays. In addition, the homogenous nature of the assay reduces the number of steps required to run the assay since the wash steps of a heterogenous assay are not required.

The integrase strand-transfer SPA format consists of 2 DNA components that model viral DNA and target DNA. The model viral DNA (also known as donor DNA) is biotinylated ds-DNA preprocessed at the 3' end to provide a CA nucleotide base overhang at the 5' end of the duplex. The target DNA (also known as host DNA) is a random nucleotide sequence of ds-DNA generally containing [$^3$H]-thymidine nucleotides on both strands, preferably, at the 3' ends, to enable detection of the integrase strand-transfer reaction that occurs on both strands of target ds-DNA.

Integrase (created recombinantly or synthetically and preferably, purified) is pre-complexed to the viral DNA bound to a surface, such as for example, streptavidin-coated SPA beads. Generally, the integrase is pre-complexed in a batch process by combining and incubating diluted viral DNA with integrase and then removing unbound integrase. The preferred molar ratio of viral DNA:integrase is about 1:about 5. The integrase/viral DNA incubation is optional, however, the incubation does provide for an increased specificity index with an integrase/viral DNA incubation time of about 15 to about 30 minutes at room temperature or at about 37° C. The preferred incubation is at about room temperature for about 15 minutes.

The reaction is initiated by adding target DNA, in the absence or presence of a potential integrase modulator compound, to the integrase/viral DNA beads (for example) and allowed to run for about 20 to about 50 minutes (depending on the type of assay container employed), at about room temperature or about 37° C., preferably, at about 37° C. The assay is terminated by adding stop buffer to the integrase reaction mixture. Components of the stop buffer, added sequentially or at one time, function to terminate enzymatic activity, dissociate integrase/DNA complexes, separate non-integrated DNA strands (denaturation agent), and, optionally, float the SPA beads to the surface of the reaction mixture to be closer in range to the detectors of, for example, a plate-based scintillation counter, to measure the level of integrated viral DNA which is quantified as light emitted (radiolabeled signal) from the SPA beads. The inclusion of an additional component in the stop buffer, such as for example CsCl or functionally equivalent compound, is optionally, and preferably, used with a plate-based scintillation counter, for example, with detectors positioned above the assay wells, such as for example a TopCount® counter (PerkinElmer Life Sciences Inc. (Boston, Mass.)). CsCl would not be employed when PMT readings are taken from the bottom of the plate, such as for example when a MicroBeta® counter (PerkinElmer Life Sciences Inc. (Boston, Mass.)) is used.

The specificity of the reaction can be determined from the ratio of the signal generated from the target DNA reaction with the viral DNA/integrase compared to the signal generated from the di-deoxy viral DNA/integrase. High concentrations (e.g., $\geqq 50$ nM) of target DNA may increase the d/dd DNA ratio along with an increased concentration of integrase in the integrase/viral DNA sample.

The results can be used to evaluate the integrase modulatory, such as for example inhibitory, activity of test compounds. For example, the skilled artisan may employ a high-throughput screening method to test combinatorial compound libraries or synthetic compounds. The percent inhibition of the compound may be calculated using an equation such as for example (1−((CPM sample−CPM min)/(CPM max−CPM min)))*100. The min value is the assay signal in the presence of a known modulator, such as for example an inhibitor, at a concentration about 100-fold higher than the $IC_{50}$ for that compound. The min signal approximates the true background for the assay. The max value is the assay signal obtained for the integrase-mediated activity in the absence of compound. In addition, the $IC_{50}$ values of synthetic and purified combinatorial compounds may be determined whereby compounds are prepared at about 10 or 100-fold higher concentrations than desired for testing in assays, followed by dilution of the compounds to generate an 8-point titration curve with ½-log dilution intervals, for example. The compound sample is then transferred to an assay well, for example. Further dilutions, such as for example, a 10-fold dilution, are optional. The percentage inhibition for an inhibitory compound, for example, may then be determined as above with values applied to a nonlinear regression, sigmoidal dose response equation (variable slope) using GraphPad Prism curve fitting software (GraphPad Software, Inc., San Diego, Calif.) or functionally equivalent software.

The stINTSPA assay conditions are preferably optimized for ratios of integrase, viral DNA and target DNA to generate a large and specific assay signal. A specific assay signal is defined as a signal distinguishing true strand-transfer catalytic events from complex formation of integrase and DNA that does not yield product. In other integrase assays, a large non-specific component (background) often contributes to the total assay signal unless the buffer conditions are rigorously optimized and counter-tested using a modified viral DNA oligonucleotide. The non-specific background is due to formation of integrase/viral DNA/target DNA complexes that are highly stable independent of a productive strand-transfer mechanism.

The preferred stINTSPA distinguishes complex formation from productive strand-transfer reactions by using a modified viral DNA oligonucleotide containing a di-deoxy nucleoside at the 3' end as a control. This modified control DNA can be incorporated into integrase/viral DNA/target DNA complexes, but cannot serve as a substrate for strand-transfer. Thus, a distinct window between productive and non-productive strand-transfer reactions can be observed. Further, reactions with di-deoxy viral DNA beads give an assay signal closely matched to the true background of the assay using the preferred optimization conditions of the assay. The true background of the assay is defined as a reaction with all assay components (viral DNA and [$^3$H]-target DNA) in the absence of integrase.

Assay buffers used in the integrase assay generally contain at least one reducing agent, such as for example 2-mercaptoethanol or DTT, wherein DTT as a fresh powder is preferred; at least one divalent cation, such as for example $Mg^{++}$, $Mn^{++}$, or $Zn^{++}$, preferably, $Mg^{++}$; at least one emulsifier/dispersing agent, such as for example octoxynol (also known as IGEPAL-CA or NP-40) or CHAPS; NaCl or functionally equivalent compound; DMSO or functionally equivalent compound; and at least one buffer, such as for example MOPS. Key buffer characteristics are the absence of PEG; inclusion of a high concentration of a detergent, such as for example about 1 to about 5 mM CHAPS and/or about 0.02 to about 0.15% IGEPAL-CA or functionally equivalent compound(s) at least capable of reducing non-specific sticking to the SPA beads and assay wells and, possibly, enhancing the specificity index; inclusion of a high concentration of DMSO (about 1 to about 12%); and inclusion of modest levels of NaCl ($\leqq 50$ mM) and $MgCl_2$ (about 3 to about 10 mM) or functionally equivalent compounds capable of reducing the dd-DNA background. The assay buffers may optionally contain a preservative, such as for example $NaN_3$, to reduce fungal and bacterial contaminants during storage.

The stop buffer preferably contains EDTA or functionally equivalent compound capable of terminating enzymatic activity, a denaturation agent comprising, for example, NaOH or guanidine hydrochloride, and, optionally, CsCl or functionally equivalent compound capable of assisting in floating the SPA beads to the top of the assay container for scintillation detection at the top of the reservoir and, possibly, minimizing compound interference. An example of an integrase strand-transfer SPA is set forth in Example 13.

Alternatively, the level of activity of the modulatory compounds may be determined in an antiviral assay, such as for example an assay that quantitatively measures the production of viral antigens (e.g., HIV-1 p24) or the activities of viral enzymes (e.g., HIV-1 reverse transcriptase) as indicators of virus replication, or that measures viral replication by monitoring the expression of an exogenous reporter gene introduced into the viral genome (HIV-1 reporter virus assays) (Chen, B. K. et al., *J. Virol.* 68(2): 654-660 (1994); Terwilliger, E. F. et al., *PNAS* 86:3857-3861 (1989)). A preferred method of measuring antiviral activity of a potential modulator compound employs an HIV-1 cell protection assay, wherein virus replication is measured indirectly by monitoring viral induced host-cell cytopathic effects using, for example, dye reduction methods.

In one embodiment, the compounds of the present invention include those having an $EC_{50}$ value against HIV integrase of at least $10^{-5}$ M (or at least 10 µM) when measured with an HIV cell protection assay. In another embodiment are compounds of the present invention with an $EC_{50}$ value against HIV integrase of at least $10^{-5}$ M when measured with an HIV cell protection assay. In yet another embodiment, the compounds of the present invention have an $EC_{50}$ against HIV integrase of at least 0.1 UM when measured with an HIV cell protection assay.

The inventive agents may be prepared using the reaction routes and synthesis schemes as described below, employing the techniques available in the art using starting materials that are readily available. The preparation of certain embodiments of the present invention is described in detail in the following examples, but those of ordinary skill in the art will recognize that the preparations described may be readily adapted to prepare other embodiments of the present invention. For example, the synthesis of non-exemplified compounds according to the invention may be performed by modifications apparent to those skilled in the art, e.g., by appropriately protecting interfering groups, by changing to other suitable reagents known in the art, or by making routine modifications of reaction conditions. Alternatively, other reactions disclosed herein or known in the art will be recognized as having adaptability for preparing other compounds of the invention.

General Procedures

The compounds of the present invention can be prepared directly from compound 1-1 (preferably a methyl or ethyl ester) and a substituted or unsubstituted hydroxylamine in the presence of a base, such as, for example, sodium hydroxide or sodium alkoxide in methanol or ethanol (Hauser, C. R. et al., *Org. Synth. Coll. Vol.* 2, p. 67, John Wiley, New York (1943)). Alternatively, the compound 1-1 can be saponified to the free acid 1-2 using lithium hydroxide or sodium hydroxide in methanol/water mixtures and heating the mixture to 100° C. in a SmithCreator® microwave for 1 to 5 min. Compound 1-2 can be coupled with a substituted or unsubstituted hydroxylamine using a coupling reagent. Typical coupling reagents and conditions can be used, such as, for example, O-(azabenzotriazole-1-yl)-1,1,3,3-tetramethyl uronium hexafluorophosphate (HATU), N-(3-dimethylaminopropyl)-N'-ethylcarbodiimide (EDC) in DMF at ambient temperature, or many others that are familiar to those skilled in the art. Other suitable methods are described, for example, in M. B. Smith, J. March, *Advanced Organic Chemistry*, 5th edition, John Whiley & Sons, p. 508-511 (2001). The use of the preferred conditions described in this scheme would allow for parallel preparation or combinatorial libraries of such hydroxamates 1-3.

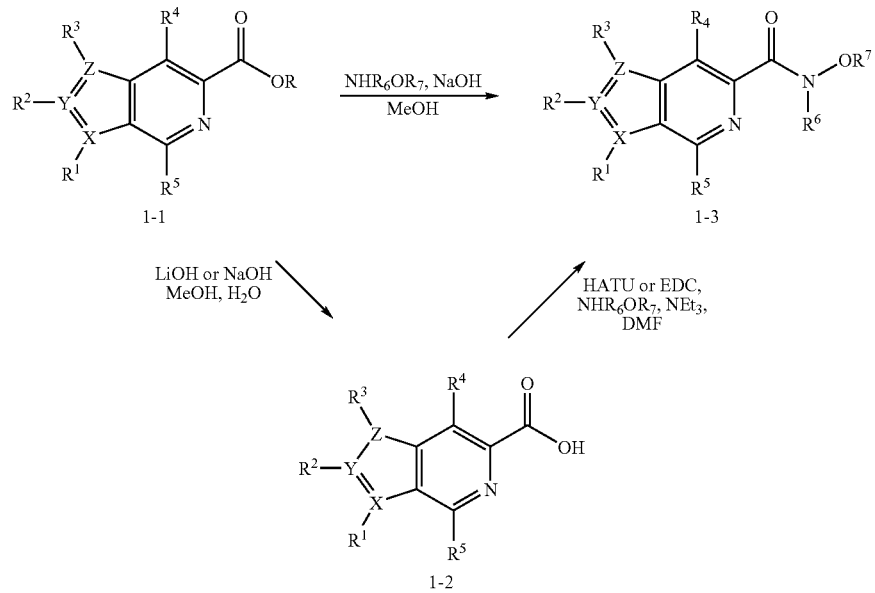

Scheme 1

Preparation of Intermediates and Starting Materials

The precursors of type 1-1 with X=N, Y=C, Z=C (Compound 2-7) can be prepared from an arylsulfonyl or alkylsulfonyl protected pyrrole compound 2-2 formed from pyrrole compound 2-1 and an arylsulfonylchloride or an alkylsulfonylchloride in the presence of a base, such as, for example, triethylamine, using methods decribed, for example, in T. W. Greene, Protective Groups in Organic Chemistry, 3$^{rd}$ edition, John Wiley & Sons, pp. 615-617 (1999). Reductive amination with a suitable substituted glycine ester compound 2-3 and a reducing agent, such as, for example, $NaBH_3CN$ or $NaBH(OAc)_3$ (Abdel-Magid, A. F. et al., *Tetrahedron Lett.*, 31, 5595-5598 (1990)) can provide the amine compound 2-4. Additional methods for reductive amination exist and are reviewed in C. F. Lane, *Synthesis*, p. 135 (1975). Titanium tetrachloride mediated cyclization (Dekhane, M. et al., *Tetrahedron*, 49, pp. 8139-8146 (1993); and Singh, S. K., *Heterocycles*, 44, pp. 379-391 (1997)) in a solvent, such as, for example, benzene or toluene, at the boiling temperature of the solvent can provide the arylsulfonyl or alkylsulfonyl protected precursor compound 2-5, which can be converted to the desired unprotected indole compound 2-6 using sodium alkoxide in alcohol (M. Dekhane, P. Potier, R. H. Dodd, *Tetrahedron*, 49, 8139-8146 (1993)). Alkylation of compound 2-6 with an alkylhalide in a polar solvent such as DMF or DMSO using sodium hydride as base (Eberle, M. K., *J. Org. Chem.* 41, pp. 633-636 (1976); Sundberg, R. J. et al., *J. Org. Chem.* 38, pp. 3324-3330 (1973)) can provide the desired precursor compound 2-7.

Scheme 2

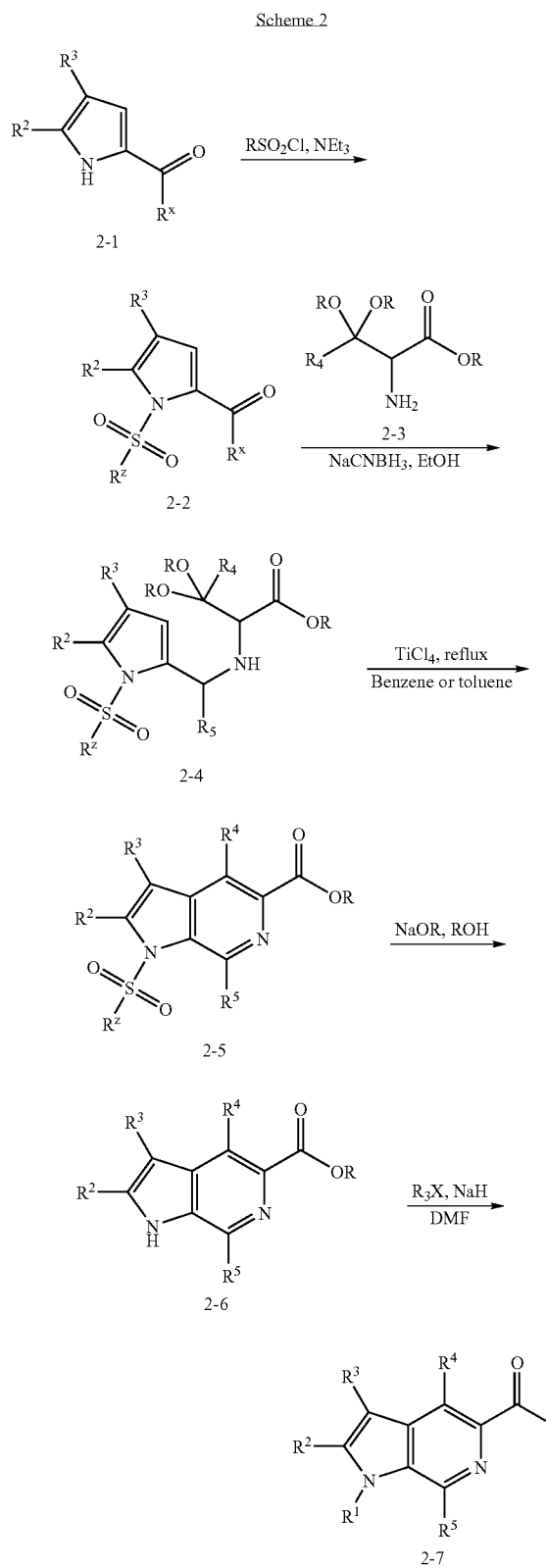

Scheme 3 depicts an alternative method for obtaining intermediate compound 2-5 adapted from the literature (Rousseau, J. F. et al., *J. Org. Chem.*, 63, pp. 2731-2737 (1998) and citations therein) starting from the substituted pyrrole compound 3-1. The pyrrole nitrogen can be protected as a sulfonamide using the same methods described in Scheme 2. Addition of the anion of an N-Cbz glycine ester can provide the intermediate compound 3-4. Removal of the Cbz protecting group can be achieved using palladium catalyzed hydrogenation or other methods, such as those decribed in T. W. Greene, P. G. M. Wuts, *Protective Groups in Organic Chemistry*, 3$^{rd}$ edition, John Wiley & Sons, pp. 531-537 (1999). Pictet-Spengler condensation followed by palladium catalyzed dehydrogenation in xylene can afford the intermediate compound 2-5.

Scheme 3

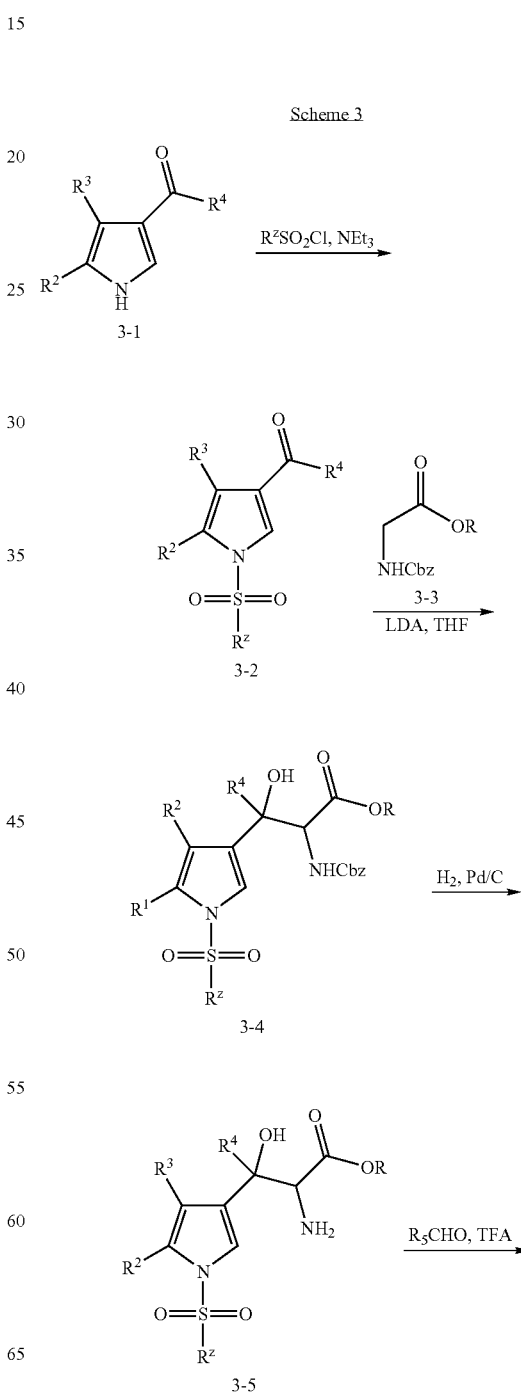

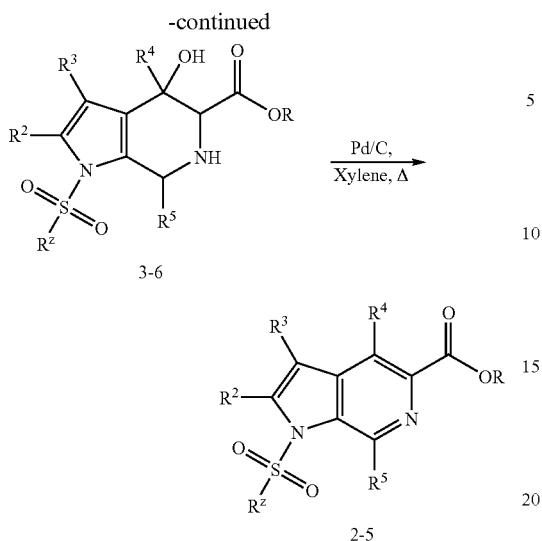

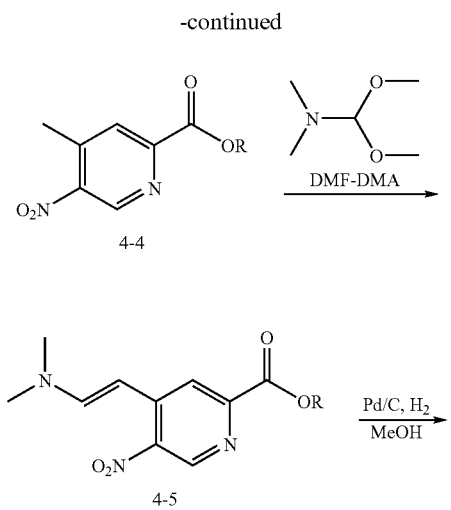

Scheme 4 depicts an alternative method for the formation of the azaindole core 4-9. The hydroxypyridine 4-1 can be converted to the corresponding triflate or bromide 4-2 using POBr$_3$ or trifluoromethanesulfonic anhydride and a base such as triethylamine. Reaction of 4-2 with zinc cyanide in the presence of a catalyst such as Pd(PPh$_3$)$_4$ (D. M. Tschaen et al. *Synthetic Comm.* 1994, 24, 887-890) can provide nitrile 4-3, which can be converted to ester 4-4 under acidic conditions. Reaction of 4-4 with dimethylformamide dimethyacetal followed by reduction can provide azaindole 4-6 (Prokopov, A. A. et al. *Khim. Geterotsikl. Soedin.* 1977, 1135, M. Sloan, R. S. Philipps, *Bioorg. Med. Chem. Lett.*, 1992, 2, 1053-1056), which can be alkylated to 4-7 using a alkyl or benzyl halide and a base such as sodium hydride. Formylation of the pyrrole ring system in 4-7 can be accomplished using 1,1-dichloromethylmethyl ether in the presence of aluminum chloride as described by X. Doisy e. al. *Bioorg. Med. Chem.* 1999, 7, 921-932 to provide compound 4-8, which can react with an amine and a reducing agent such as sodium triacetoxy borohydride to provide 4-9.

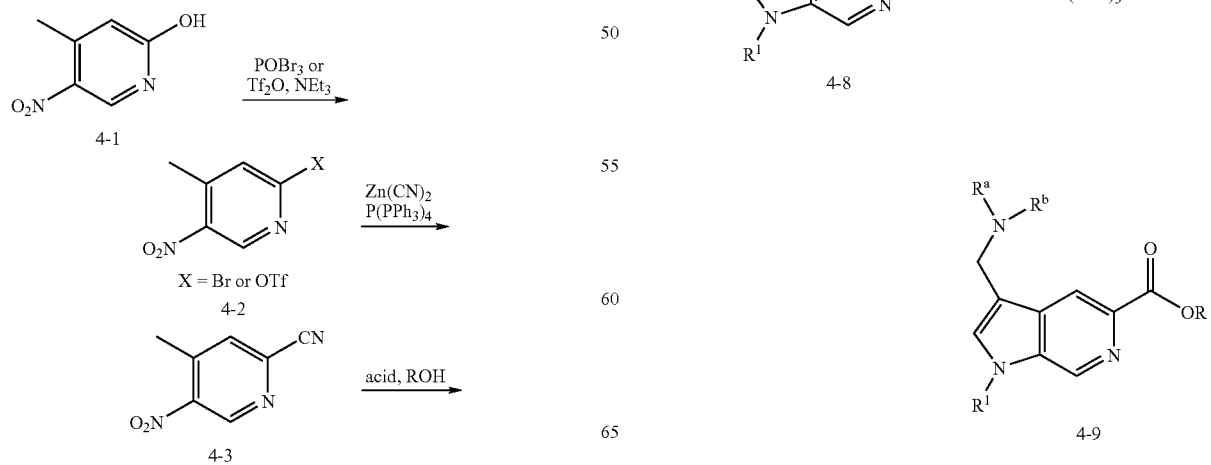

An alternative route that can provide 3-substituted pyrrolo[2,3-c]pyridines 5-6 and 5-7 from the unsubstituted precursor 5-1 is depicted in Scheme 5. Reaction of compound 5-1 with dimethylmethyleneimmonium chloride (A. P. Kozikowski, H. Ishida, *Heterocycles* 1980, 14, 55-58) can give the dimethylaminomethyl derivative 5-2. Alternatively, this step can be performed using classic Mannich reaction conditions (review: J. H. Brewster, E. L. Eliel, *Org. Reactions,* 1953, 7, 99). Upon treatment of 5-2 with sodium acetate and acetic anhydride in acetonitrile (J. N. Cocker, O. B. Mathre, W. H. Todd, *J. Org. Chem.*, 1963, 28, 589-590) the corresponding acetate 5-3 can be obtained, which, on hydrolysis with a base such as potassium carbonate in methanol, can provide the precursor 5-5. Alkylation of the alcohol 5-5 can be achieved using an alkylhalide in the presence of a base such as sodium hydride in DMF as solvent to give 5-7. Alternatively, 5-2 can be treated with with ethyl chloroformate (Shinohara, H.; Fukuda, T. and Iwao, M. *Tetrahedron* 1999, 55, 10989-11000) to form chloride 5-4 which can react with a thiol or alcohol to form 5-6. as described by Naylor, M. A. et al. *J. Med. Chem.* 1998, 41, 2720-2731.

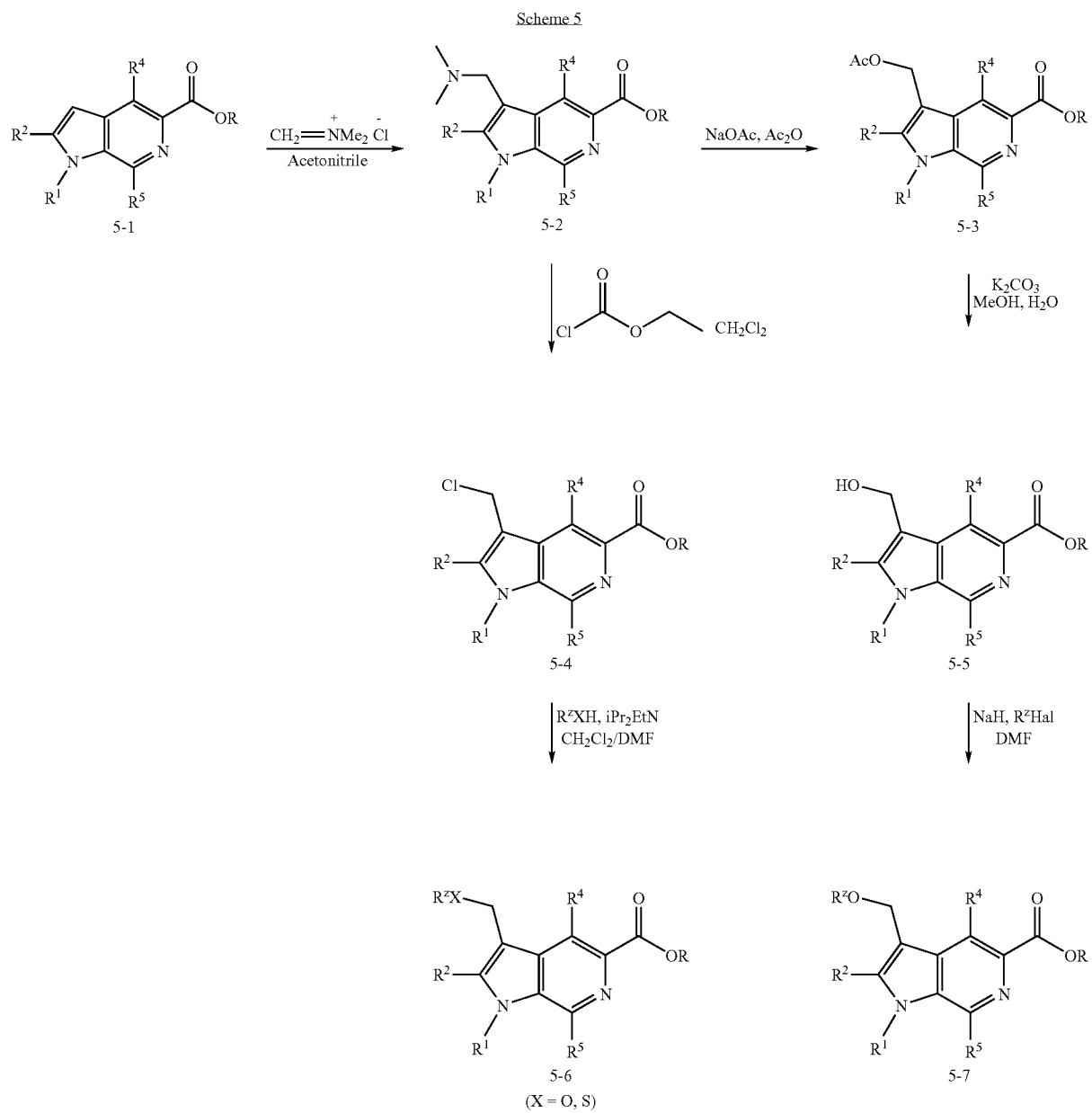

Imidazo[4,5-c]pyridine derivatives of type 1-1 (X=N, Y=C, Z=N) can be obtained according to Scheme 6. The histidine precursor 6-1 is commercially available or can be prepared according published methods (J. L. Kelley, C. A. Miller, E W. McLean, *J. Med. Chem.* 1977, 20, 721-723, G. Trout, *J. Med. Chem.* 1972, 15, 1259-1261). Pictet-Spengler reaction of 6-1 (F. Guzman et al., *J. Med. Chem.* 1984, 27, 564-570, M. Cain, F. Guzman, M. Cook, *Heterocycles*, 1982, 19, 1003-1007) can give the 1,2,3,4-tetrahydro-imidazo[4,5-c]pyridine-3-carboxylate 6-2, which can be converted to the methyl ester 6-3 via the corresponding acyl chloride or similar methods of ester formation known to those skilled in the art. Dehydrogenation to the unsaturated intermediate 6-4 can be achieved with selenium dioxide (J. G. Lee, K. C. Kim, *Tetrahedron Lett,* 1992, 33, 6363-6366), or a catalyst such as palladium or platinum in a solvent such as xylene at the boiling temperature of the solvent (D. Soerens et al. *J. Org. Chem.* 1979, 44, 535-545). Alkylation of 6-4 with an alkyl-halide in the presence of a base such as sodium hydride similar to the methods described in Scheme 2 can provide the desired precursors as a mixture of regioisomers 6-5 and 6-6 that can be separated by column chromatography or other methods known to those skilled in the art.

Scheme 6

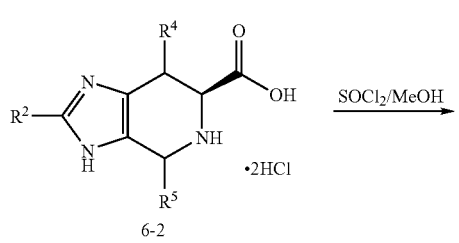

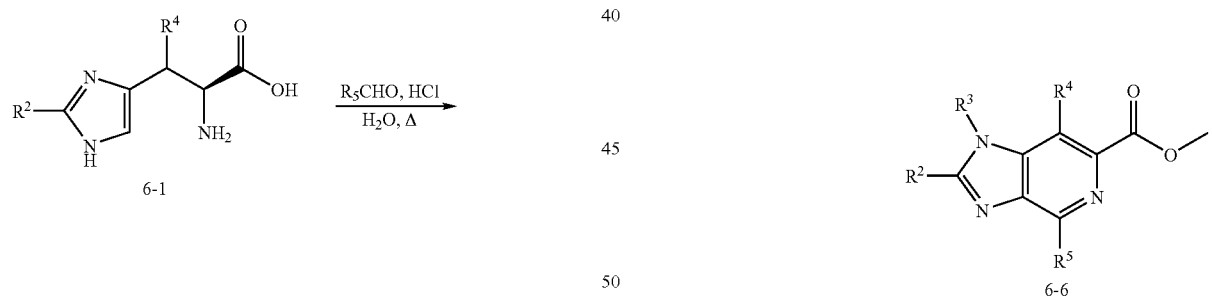

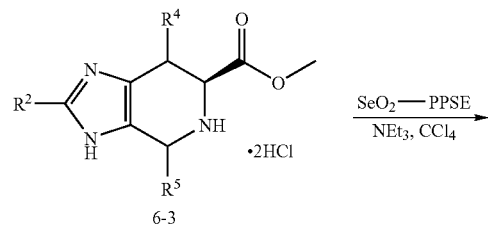

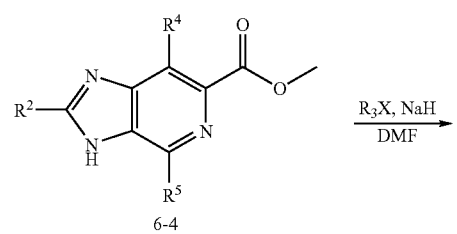

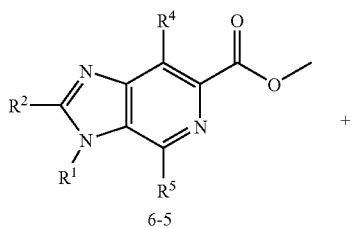

Scheme 7 sets forth a method for producing pyrrolo[3,2-c]pyridine derivatives 1-1 where X=C, Y=C, Z=N, and preferably R=an alkyl group (compound 7-3) via a substituted pyrrole compound of type 7-1 and a 2-azabutadiene compound of type 7-2 (Kantlehner, W. et al., *Liebigs Ann. Chem.*, pp. 344-357 (1980)) under proton catalysis, following the procedures described in Biere, H. et al., *Liebigs Ann. Chem.*, pp. 491-494 (1987). Friedel-Crafts acylation can provide ketone 7-5 which upon reduction with a reducing agent such as borane-t-butyl amine complex in THF can give compound 7-6 and alcohol 7-7.

Scheme 7

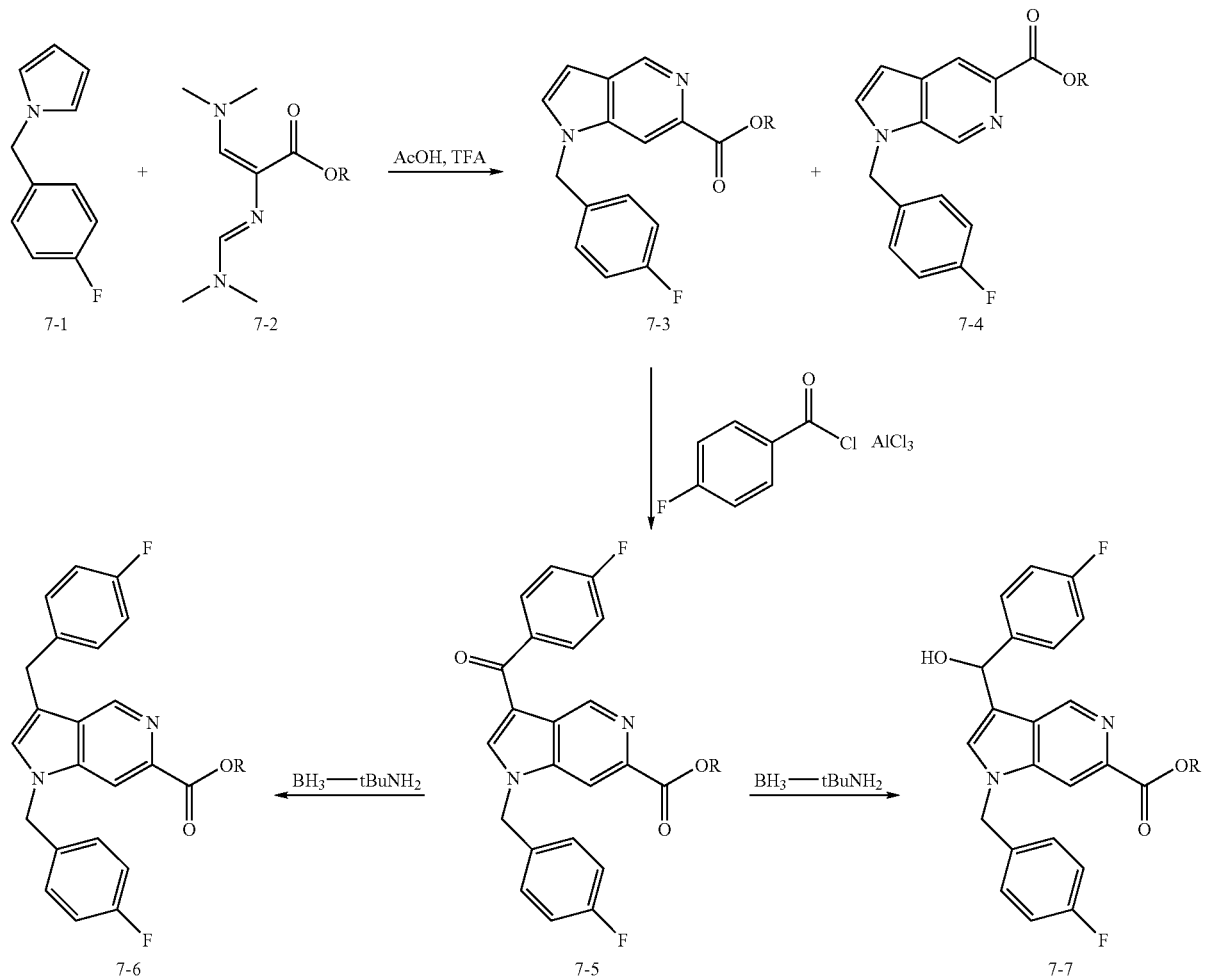

Scheme 8 depicts a general method (T. L. Gilchrist, C. W. Rees, J. A. R. Rodriguez, J. C. S. Chem. Comm. 1979, 627-628, L. Henn, D. M. B. Hickey, C. J. Moody, C. W. Rees, J. Chem. Soc. Perkin Trans. 1 1984, 2189-2196, A. Shafiee, H. Ghazar, J. Heterocyclic Chem. 1986, 23, 1171-1173) for the formation of compounds of general structure 1-1. Reaction of a substituted heteroaromatic aldehyde or ketone 8-1 with ethyl or methyl azidoacetate 8-2 in the presence of a base such as sodium hydride can provide azidocinnamate 8-3, which on thermolysis in boiling toluene or xylenes, can provide the desired product 8-4.

-continued

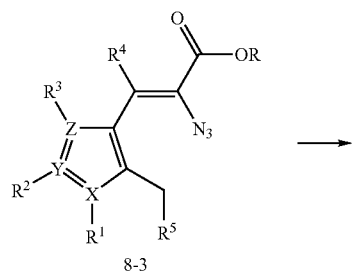

Scheme 8

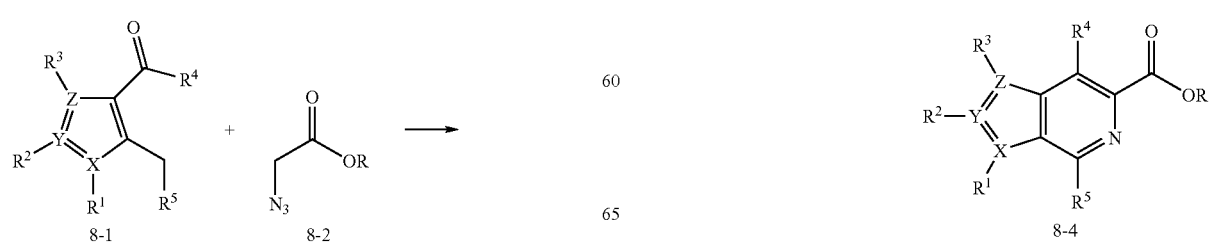

Another general method for formation the desired precursors (R⁵=H, Scheme 9) relies on the condensation of a dicarbonyl compound 9-1 with ethyl glycinate 9-2 (S. Mataka, K. Takahashi, M. Tashiro, *J. Heterocyclic. Chem.* 1981, 18, 1073-1075, R. P. Kreher, J. Pfister *Chemiker-Zeitung* 1984, 9, 275-277) that can provide a mixture of regioisomers 9-3 and 9-4, that can be separated by column chromatography or any other methods known to those skilled in the art.

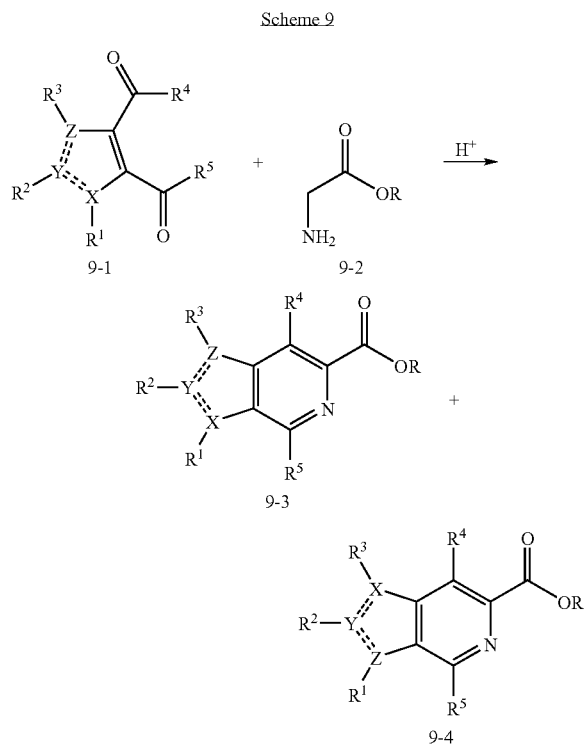

Scheme 9

N-Alkylated hydroxylamines can be prepared by various methods described in the literature [for a review see H. J. Wroblowsky in Houben-Weyl, *Methoden der Organischen Chemie, Suppl.* Vol. E16, Part 1, Thieme, Stuttgart, N.Y., 1990, page 1-96. Scheme 11 describes a method developed by G. Doleschall, *Tetrahedron Lett.* 1987, 28, 2993-2994, which is based on N-alkylation of 3-methyl 5-hydroxy-4-isoxazole carboxylate 10-1 followed by treatment of 10-2 with hydrochloric acid. Another viable approach relies on the alkylation of bis-t-BOC hydroxylamine 10-4 followed by deprotection of the intermediate 10-5 with hydrochloric acid as described by M. A. Staszak C. W. Doecke, *Tetrahedron Lett.* 1994, 35, 6021-6024.

Scheme 10

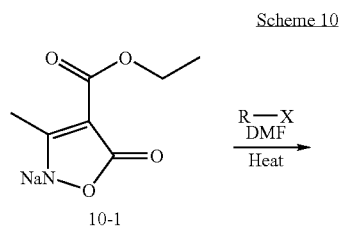

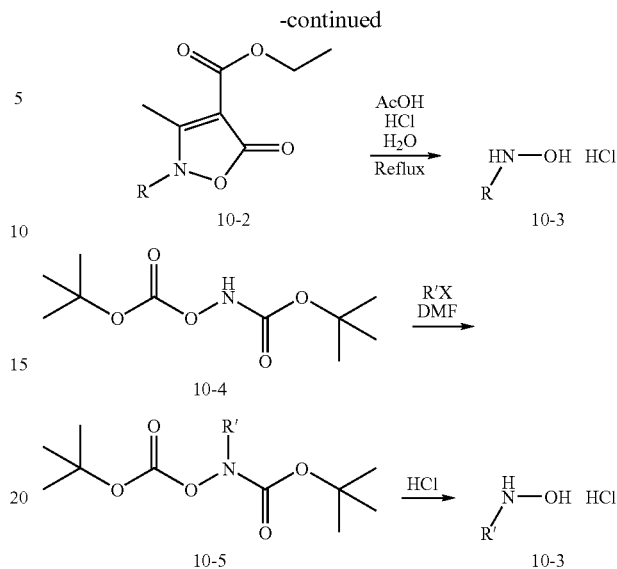

Scheme 11 shows a method for preparation of azaindazole 11-3 and 11-4 from 4-nitro-5-methylpyridine 11-1. Hydrogenation of 11-1 followed by treatment of the intermediate with sodium nitrite in acetic acid can provide azaindazole 11-2. This intermediate can be treated with 4-fluorobenzyl bromide and a base such as potassium carbonate to give both azaindazaole isomers 11-3 and 11-4, which can be separated by chromatography or other methods known to those of ordinary skill in the art. Alternative routes to 5-azaindazoles 11-3 and 11-4 have been described in the literature (Henn, L. *J. Chem. Soc. Perkin Trans.* 1 1984, 2189; Molina, P. *Tetrahedron* 1991, 47, 6737).

Scheme 11

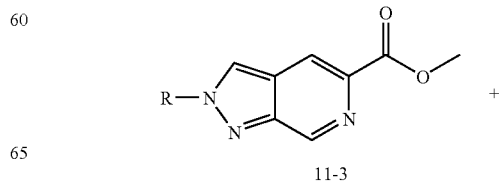

-continued

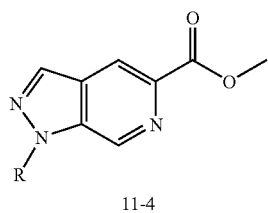

11-4

Scheme 12 depicts the synthesis of a 4-substituted azaindole 12-12. Ethyl 2-methyl-1H-pyrrole-3-carboxylate 12-1 (Wee, A. G. H.; Shu, A. Y. L.; Djerassi, C. *J. Org. Chem.* 1984, 49, 3327-3336) can be treated with a organo halide in the presence of a base such as NaH to provide pyrrole 12-3. Bromination using a bromine source such as NBS followed by radical bromination after the addition of a radical initiator such as benzoyl peroxide can give compound 12-4 which can react with a tosyl glycine ester 12-5 (Ginzel K. D., Brungs, P.; Steckan, E. *Tetrahedron*, 1989, 45, 1691-1701) to provide 12-6. Cyclization of 12-6 to 12-7 can be effected upon treatment with a base such as lithium hexamethyl disilazide. Catalytic hydrogenolysis (with e.g. Pd/C) can provide ester 12-8. Treatment of 12-8 with an organo halide and a base such as NaH can give 12-9. The hydroxy group in 12-8 can be converted to the triflate 12-10 using trifluoromethanesulfonic anhydride and a base such as triethyl amine. Triflate 12-10 can undergo palladium catalyzed couplings such as the Stille coupling with tributylstannylethene 12-11 in the presence of LiCl (J. K. Stille, *Angew. Chem.* 1986, 98, 504; *Angew. Chem. Int. Ed. Engl.* 1986, 25, 508; W. J. Scott, J. K. Stille, *J. Am. Chem. Soc.* 1986, 108, 3033; C. Amatore, A. Jutand, and A. Suarez *J. Am. Chem. Soc.* 1993, 115, 9531-9541) using a catalyst such Pd(PPh$_3$)$_2$Cl$_2$ (T. Sakamoto, C. Satoh, Y. Kondo, H. Yamanaka, *Chem. Pharm. Bull.* 1993, 41, 81-86).

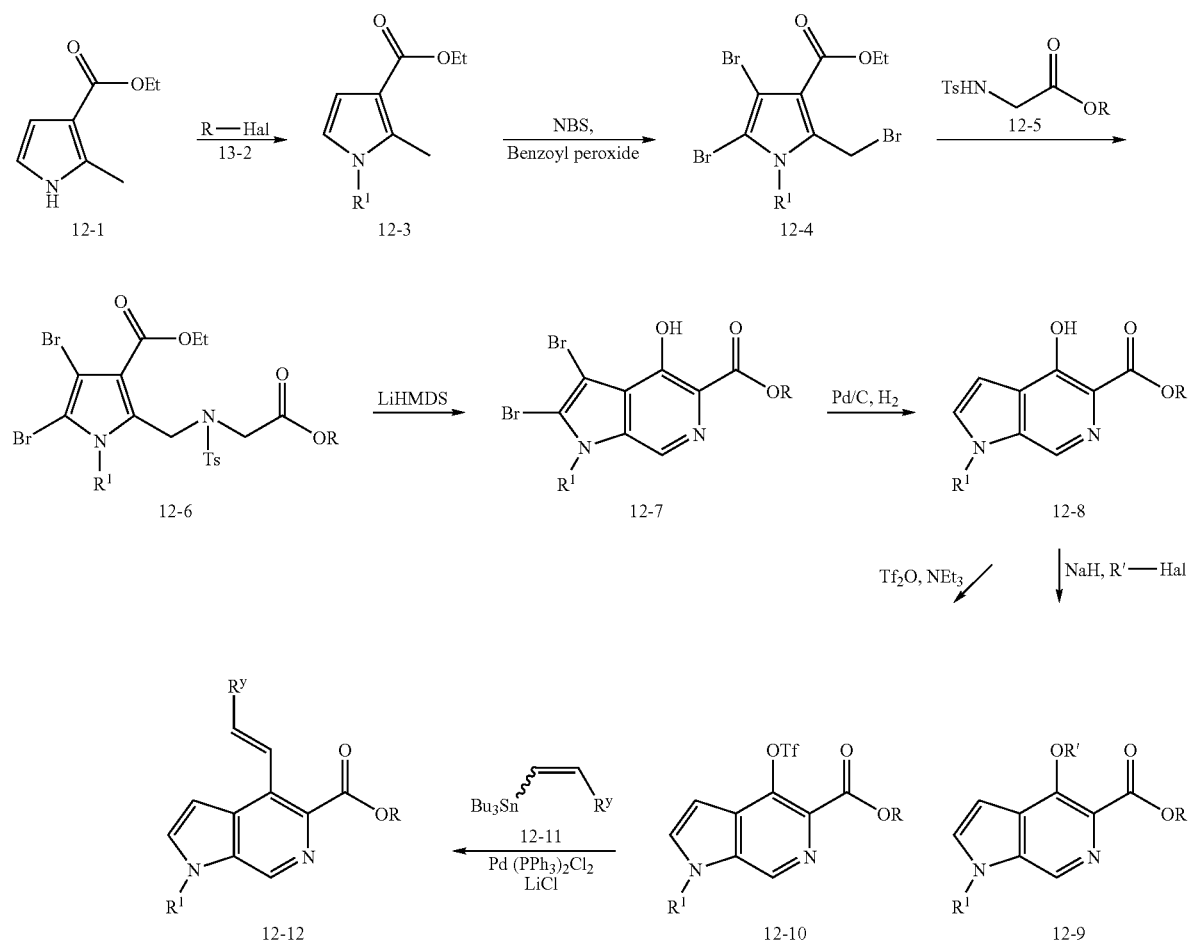

Scheme 12

EXAMPLES

The examples below are intended only to illustrate particular embodiments of the present invention and are not meant to limit the scope of the invention in any manner.

In the examples described below, unless otherwise indicated, all temperatures in the following description are in degrees Celsius (° C.) and all parts and percentages are by weight, unless indicated otherwise.

Various starting materials and other reagents were purchased from commercial suppliers, such as Aldrich Chemical Company or Lancaster Synthesis Ltd., and used without further purification, unless otherwise indicated.

The reactions set forth below were performed under a positive pressure of nitrogen, argon or with a drying tube, at ambient temperature (unless otherwise stated), in anhydrous solvents. Analytical thin-layer chromatography was performed on glass-backed silica gel 60° F. 254 plates (Analtech (0.25 mm)) and eluted with the appropriate solvent ratios (v/v). The reactions were assayed by high-pressure liquid chromatagraphy (HPLC) or thin-layer chromatography (TLC) and terminated as judged by the consumption of starting material. The TLC plates were visualized by UV, phosphomolybdic acid stain, or iodine stain.

Unless otherwise indicated, $^1$H-NMR spectra were recorded on a Bruker instrument operating at 300 MHz and $^{13}$CNMR spectra were recorded at 75 MHz. NMR spectra were obtained as DMSO-d6 or CDCl$_3$ solutions (reported in ppm), using chloroform as the reference standard (7.25 ppm and 77.00 ppm) or DMSO-d6 ((2.50 ppm and 39.52 ppm)). Other NMR solvents were used as needed. When peak multiplicities are reported, the following abbreviations are used: s=singlet, d=doublet, t=triplet, m=multiplet, br=broadened, dd=doublet of doublets, dt=doublet of triplets. Coupling constants, when given, are reported in Hertz.

Infrared spectra were recorded on a Perkin-Elmer FT-IR Spectrometer as neat oils, as KBr pellets, or as CDCl$_3$ solutions, and when reported are in wave numbers (cm$^{-1}$). The mass spectra were obtained using LC/MS or APCI. All melting points are uncorrected.

All final products had greater than 95% purity (by HPLC at wavelengths of 220 nm and 254 nm).

All elemental analyses for compounds herein, unless otherwise specified, provided values for C, H, and N analysis that were within 0.4% of the theoretical value, and are reported as "C, H, N."

In the following examples and preparations, "LDA" means lithium diisopropyl amide, "Et" means ethyl, "Ac" means acetyl, "Me" means methyl, "Ph" means phenyl, (PhO)$_2$POCl means chlorodiphenylphosphate, "HCl" means hydrochloric acid, "EtOAc" means ethyl acetate, "Na$_2$CO$_3$" means sodium carbonate, "NaOH" means sodium hydroxide, "NaCl" means sodium chloride, "NEt$_3$" means triethylamine, "THF" means tetrahydrofuran, "DIC" means diisopropylcarbodiimide, "HOBt" means hydroxy benzotriazole, "H$_2$O" means water, "NaHCO$_3$" means sodium hydrogen carbonate, "K$_2$CO$_3$" means potassium carbonate, "MeOH" means methanol, "i-PrOAc" means isopropyl acetate, "MgSO$_4$" means magnesium sulfate, "DMSO" means dimethylsulfoxide, "AcCl" means acetyl chloride, "CH$_2$Cl$_2$" means methylene chloride, "MTBE" means methyl t-butyl ether, "DMF" means dimethyl formamide, "SOCl$_2$" means thionyl chloride, "H$_3$PO$_4$" means phosphoric acid, "CH$_3$SO$_3$H" means methanesulfonic acid, "Ac$_2$O" means acetic anhydride, "CH$_3$CN" means acetonitrile, and "KOH" means potassium hydroxide.

Example 1

1-(2,4-Difluorobenzyl)-N-hydroxy-1H-pyrrolo[2,3-c]pyridine-5-carboxamide

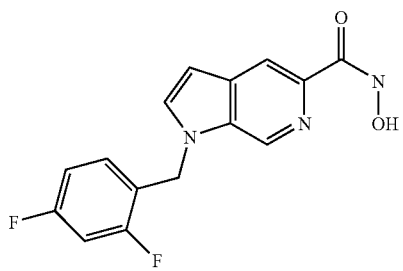

Step 1A: Bromo-4-methyl-5-nitropyridine: A solution of 4-methyl-5-nitropyridin-2-ol (82 g, 0.53 mol) and POBr$_3$ (229 g, 0.8 mol, 1.5 eq.) in dichloromethane (2 L) was heated under a nitrogen atmosphere in a 3 L 3-neck flask with overhead stirrer for 24 h. The mixture was filtered cold. The solid consisted of a 1:1 mixture of desired product 2 and unreacted starting material 4-methyl-5-nitropyridin-2-ol, the filtrate contained the desired product and unreacted POBr$_3$. The solid (46 g) and fresh POBr$_3$ were dissolved in dichloromethane and refluxed for 10 h. The liquid was decanted and combined with the filtrate of the first reaction. The combined solutions were concentrated to a volume of 1.5 L. The mixture was cooled in an ice bath and stirred while ice (500 g) was added to quench the excess POBr$_3$. The organic layer was separated, and the aqueous layer was extracted with dichloromethane. The combined organic extracts were dried (magnesium sulfate) and concentrated. The product was recrystallized from hexanes. Yield: 104 g (90%). $^1$H NMR (300 MHz, CDCl$_3$) δ ppm 2.63 (s, 3H) 7.52 (s, 1H) 8.95 (s, 1H). LCMS: (APCI, M-H)=215 and 217 u/e (bromine isotope pattern); Retention Time: 3.01 min; Purity by TIC: 95%; Purity by UV: 95%.

Step 1B: 4-Methyl-5-nitropyridin-2-yl trifluoromethanesulfonate: To a stirred solution of the 4-methyl-5-nitropyridin-2-ol (5.00 g, 32 mmol) and triethylamine (9.0 mL, 87 mmol) in dichloromethane (150 mL) at 0° C. was added trifluoromethanesulfonic anhydride (7.3 mL, 43 mmol) dropwise and the reaction was stirred for 2 h. The reaction mixture was poured into cold saturated sodium bicarbonate solution and extracted 3× with dichloromethane. The combined organic extracts were dried over sodium sulfate, filtered and the solvent was removed under reduced pressure. The crude material was dissolved in ether and passed through a short column of silica gel using ether as eluent to provide the title compound (8.65 g, 94%) as a white solid. $^1$H NMR (CDCl$_3$) δ ppm 9.00 (s, 1H), 7.17 (s, 1H), 2.73 (s, 3H).

Step 2: 4-Methyl-5-nitropyridine-2-carbonitrile: Method 1: 2-Bromo-4-methyl-5-nitropyridine (104 g, 0.479 mol), Zn(CN)$_2$ (79 g, 0.673 mol, 1.4 eq.), and Pd(PPh$_3$)$_4$ (27 g, 0.023 mol, 5 mol %) were added to a round bottom flask. NOTE: Using catalyst purchased from STREM resulted in shorter reaction times and better yields. DMF (900 mL) was degassed for 10 min before adding to the solid mixture. The mixture was heated in an oil bath to an inside temp of 80° C. The color changed from light yellow to light brown as the inside temperature reached 80° C. The mixture was stirred at the same temperature for 3 h, and monitored by TLC. The solvent was removed in vacuo. The residue was dissolved in a mixture of dichloromethane and water, and insoluble material was removed by filtration through Celite. The organic layer was separated and the aqueous layer was extracted with dichloromethane. The combined organic extracts were dried (magnesium sulfate), and concentrated. The residue was purified by column chromatography starting with 100% hexanes to hexanes/ethyl acetate 4:1. Recrystallization from hexanes yielded 65.8 g (83%) of the desired product. $^1$H NMR (300 MHz, CDCl$_3$) δ ppm 2.71 (s, 3H) 7.73 (s, 1H) 9.20 (s, 1H). LCMS: APCI, M−H$^-$)=162 u/e Purity by TIC: 95%; Purity by UV: 95%.

Method B: To a stirred solution of the 4-methyl-5-nitropyridin-2-yl trifluoromethanesulfonate (8.65 g, 30.2 mmol) in DMF (200 mL) was added zinc cyanide (3.53, 30.2 mmol) followed by Pd(PPh$_3$)$_4$ (2.00 g, 1.7 mmol). The mixture was degassed for 10 min. The solution was heated to 80° C. for 18 h. The solvent was removed in vacuo. The residue was dissolved in a mixture of dichloromethane and water, and insoluble material was removed by filtration through Celite. The organic layer was separated and the aqueous layer was extracted with dichloromethane. The combined organic extracts were dried (magnesium sulfate), and concentrated. The residue was purified by column chromatography starting with 100% hexanes to hexane/ethyl acetate 4:1. Recrystallization from hexanes yielded 4.43 g (90%) of the desired product.

Step 3: Ethyl 4-methyl-5-nitropyridine-2-carboxylate: Concentrated sulfuric acid (768 mL) was added slowly to ethanol (1.6 L) with cooling (exothermic reaction!). 4-Methyl-5-nitropyridine-2-carbonitrile (62.4 g, 0.38 mol) was added to the cold solution. After the addition was complete, the solution was refluxed under nitrogen for 2 h. Part of the solvent (500 mL) was removed using an oil pump at 30° C. The remaining thick solution was poured onto ice (1 kg). After stirring for 15 min, the mixture was extracted with ether (2×1 L) and multiple times with dichloromethane. At first, the organic layer was the TOP layer. As the extraction continued, the organic layer changed from the top layer to the bottom layer due to change in density as less ethanol was extracted. The combined organic extracts were dried (magnesium sulfate) and concentrated. Recrystallization from hexanes yielded 44.4 g (56%) of the desired product. $^1$H NMR (300 MHz, CDCl$_3$) δ ppm 1.46 (t, 3H, J=7.5 Hz), 2.71 (s, 3H), 4.51 (q, 2H, J=7.5 Hz), 8.13 (s, 1H), 9.22 (s, 1H). LCMS: (APCI, M+H$^+$)=209

Step 4: Ethyl 4-[(E)-2-(dimethylamino)vinyl]-5-nitropyridine-2-carboxylate: A mixture of ethyl 4-methyl-5-nitropyridine-2-carboxylate (39.5 g, 0.19 mol), dimethylformamide-dimethylacetal (DMF-DMA) (30.6 g, 0.26 mol, 1.35 eq) in DMF (470 mL) was heated to 90° C. for 30 min. The solvent was removed in vacuo. The residue (78 g) was used without further purification in the next step.

Step 5: Ethyl 1H-pyrrolo[2,3-c]pyridine-5-carboxylate: A solution of crude ethyl 4-[(E)-2-(dimethylamino)vinyl]-5-nitropyridine-2-carboxylate (78 g) in ethanol (350 mL) was degassed. Pd (10%)/C (12 g, 30 wt %) was added. The mixture was shaken in a Parr shaker under hydrogen (40 psi) for 16 h. The initial reaction was exothermic, the temperature rose to 65° C. within 2 h, the pressure dropped by 30 psi, and the color changed from red to light green. After the solution reached room temperature, the flask was shaken under hydrogen (50 psi) for 16 h. The reaction was monitored by LCMS. The solution contained 30% of desired product. After shaking under hydrogen (50 psi, 50° C.) for additional 2.5 days the LCMS showed 70% of the desired product. The mixture was filtered. The filter cake was extracted twice with refluxing in ethanol (2×1 L) and the hot mixture was filtered. The combined filtrates were concentrated and the residue was recrystallized from ethanol to give 20 g of pure product. The mother liquor containing the desired product and the intermediate was concentrated and dissolved in ethanol (300 mL). The mixture was hydrogenated at 50° C. and 50 psi for 3 days using Pd (10%)/C (5 g), and then was worked up as before to provide additional 3 g of desired product. The total yield was 23 g (64%). $^1$H NMR (DMSO-d6): δ ppm 1.34 (t, 3H, J=7.5 Hz), 4.32 (q, 2H, J=7.5 Hz), 6.69 (s, 1H), 7.73 (s, 1H), 8.37 (s, 1H), 8.82 (s, 1H), 11.99 (s, 1H). LCMS ((APCI, M+H$^+$): 191.

Step 6: Ethyl 1-(2,4-difluorobenzyl)-1H-pyrrolo[2,3-c]pyridine-5-carboxylate. To a stirred solution of ethyl 1H-pyrrolo[2,3-c]pyridine-5-carboxylate (0.50 g, 2.63 mmol) in DMF (10 mL) under a nitrogen atmosphere was added sodium hydride (0.087 g, 80% in mineral oil, 2.89 mmol) and 2,4-difluorobenzyl bromide (0.60 g, 2.89 mmol). The resulting mixture was stirred for 16 hours at ambient temperature. It was quenched with water (30 mL), and extracted with ethyl acetate (3×30 mL). The combined organic extracts were washed with water (2×30 mL), dried over sodium sulfate, concentrated in vacuo, and purified by flash chromatography. Elution with hexane/ethyl acetate (1:1) provided the title compound as a light yellow solid (0.40 g, 48% yield). $^1$H NMR (CD$_3$OD) δ ppm. 8.86 (s, 1H), 8.47 (s, 1H), 7.71 (d, 1H, J=3.2 Hz), 7.31 (dd, 1H, J=6.3 Hz), 6.94-7.05 (m, 2H), 6.79 (d, 1H, J=3.2 Hz), 5.63 (s, 2H), 4.46 (q, 2H, J=7.3 Hz), 1.45 (t, 3H, J=7.3 Hz). LCMS (API-ES, M+H$^+$): 317.0

Step 7: 1-(2,4-Difluorobenzyl)-1H-pyrrolo[2,3-c]pyridine-5-carboxylic acid. To ethyl 1-(2,4-difluorobenzyl)-1H-pyrrolo[2,3-c]pyridine-5-carboxylate (0.30 g, 1.58 mmol) in methanol (3 mL) was added sodium hydroxide (0.076 g, 3.16 mmol) in water (0.5 mL). The reaction was heated in a Smith-Creator™ (microwave reactor from Personal Chemistry) to 100° C. for five minutes. The reaction solution was poured into water (30 mL) and the pH was adjusted to 2-3 by addition of citric acid. The precipitate that formed was collected by filtration and dried in vacuo to provide the title compound as a white powder (0.15 g, 55%). $^1$H NMR (DMSO-d6): δ ppm 8.97 (s, 1H), 8.35 (s, 1H), 7.82 (d, 1H, J=3.2 Hz), 7.28-7.38 (m, 2H), 7.09 (t, 1H, J=8.4 Hz), 6.76 (d, 1H, J=3.2 Hz), 5.67 (s, 2H). LCMS (API-ES, M+H$^+$): 289.1

Step 8: 1-(2,4-Difluorobenzyl)-N-hydroxy-1H-pyrrolo[2,3-c]pyridine-5-carboxamide. To 1-(2,4-difluorobenzyl)-1H-pyrrolo[2,3-c]pyridine-5-carboxylic acid (0.15 g, 0.52 mmol) in DMF (10 mL) were added O-(7-azabenzotriazol-1-yl)-1,1,3,3-tetramethyluronium hexafluorophosphate (HATU; 0.20 g, 0.52 mmol), triethylamine (0.15 mL, 1.05 mmol), and hydroxylamine hydrochloride (0.036 g, 0.52 mmol). The resulting mixture was stirred for 16 hours at ambient temperature. It was quenched with water (30 mL) and extracted with ethyl acetate (3×30 mL). The combined organic extracts were washed with water (2×30 mL), dried over sodium sulfate, concentrated in vacuo and purified by preparative HPLC to provide the title compound as a white powder (0.075 g, 48% yield). $^1$H NMR (DMSO-d6) δ ppm 11.14 (s, 1H), 8.92 (s, 1H), 8.85 (s, 1H), 8.21 (s, 1H), 7.78 (s, 1H), 7.26-7.38 (m, 2H), 7.08 (t, 1H, J=8.3 Hz), 6.71 (d, 1H, J=3.0 Hz), 5.64 (s, 2H). LCMS (API-ES, M+H$^+$): 304.1 HRMS (M+H): 304.0886; cal: 304.0898 with $C_{15}H_{12}N_3O_2F_2$. HPLC: 98% purity.

Example 2

1-(2,4-difluorobenzyl)-N-hydroxy-3-(morpholin-4-ylmethyl)-1H-pyrrolo[2,3-c]pyridine-5-carboxamide

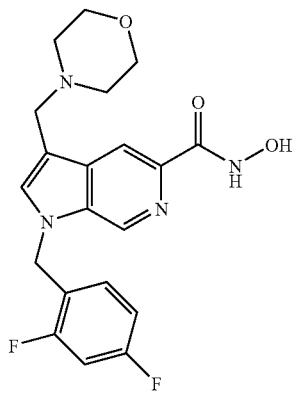

Step 1: Ethyl 1-(2,4-difluorobenzyl)-3-formyl-1 pyrrolo[2,3-c]pyridine-5-carboxylate To a stirring solution of ethyl 3-formyl-1H-pyrrolo[2,3-c]pyridine-5-carboxylate [prepared according to X. Doisy et al., *Bioorg. Med. Chem.*, 1999, 7, 921-932] (0.47 g, 2.15 mmol) in THF (100 mL) under a nitrogen atmosphere was added sodium hydride (0.103 g, 60% in mineral oil, 1.2 eq) and 2,4-difluorobenzyl bromide (0.414 mL, 1.5 eq). The resulting mixture was stirred for 16 hours at ambient temperature. It was quenched with water (30 mL), and extracted with ethyl acetate (3×30 mL). The combined organic extracts were washed with brine, dried over sodium sulfate, concentrated in vacuo and purified by flash chromatography. Elution with 4% MeOH/CH$_2$Cl$_2$ provided the title compound as a light yellow solid (0.59 g, 79% yield). $^1$H NMR (CD$_3$OD) δ ppm 10.07 (s, 1H), 8.98 (s, 1H), 8.92 (s, 1H), 7.95 (s, 1H), 7.23 (m, 1H), 6.86-6.92 (m, 2H), 5.48 (s, 2H), 4.46 (q, 2H, J=7.2 Hz), 1.43 (t, 3H, J=7.2 Hz). LCMS (API-ES, M+H$^+$): 345.0. Step 2:1-(2,4-Difluorobenzyl)-N-hydroxy-3-(morpholin-4-ylmethyl)-1H-pyrrolo[2,3-c]pyridine-5-carboxamide. A solution of ethyl 1-(2,4-difluorobenzyl)-3-formyl-1H-pyrrolo[2,3-c]pyridine-5-carboxylate (0.050 g, 0.145 mmol) and morpholine (0.019 mL, 1.5 eq) in EtOH (1 mL) and CH$_2$Cl$_2$ (0.5 mL) was stirred for 1 h at rt. Decaborane (0.011 g, 0.6 eq) was then added and stirring was continued for 3 h. The reaction mixture was evaporated to dryness under reduced pressure and the residue was treated with a solution of 1.5 M hydroxylamine in 25% NaOMe (1 mL) for 1 h at rt. The reaction mixture was purified by prep-HPLC to provide the title compound as a white solid (0.014 g, 24%). $^1$H NMR (MeOH-d$_4$) δ ppm 8.76 (s, 1H), 8.43 (s, 1H), 7.60 (s, 1H), 7.23-7.31 (m, 1H), 6.90-7.06 (m, 2H), 5.57 (s, 2H), 3.78 (s, 2H), 3.68 (b, 4H), 2.53 (b, 4H). HRMS calcd for C$_{20}$H$_{21}$N$_4$O$_3$F$_2$ (M+H$^+$) 403.1582, found 403.1568. Anal. (C$_2$H$_2$F$_2$N$_5$O$_2$.0.5HOAc) C, H, N. HPLC: >95% purity.

Example 3

1-(2,4-Difluorobenzyl)-N-hydroxy-3-{[(2-hydroxyethyl)amino]methyl}-1 ]pyrrolo[2,3-c]pyridine-5-carboxamide

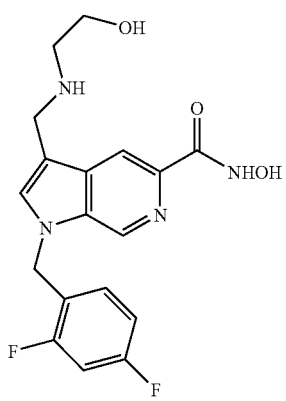

The title compound was prepared in the same manner as described in step 2 of example 2 using 2-hydroxy ethylamine instead of morpholine. $^1$H NMR (MeOH-d$_4$) δ ppm 8.79 (s, 1H), 8.39 (s, 1H), 7.65 (s, 1H), 7.24-7.32 (m, 1H), 6.90-7.05 (m, 2H), 5.56 (s, 2H), 4.12 (s, 2H), 3.70 (t, 2H, J=5.3 Hz), 2.87 (t, 2H, J=5.5 Hz). HRMS calcd for C$_{18}$H$_{19}$F$_2$N$_4$O$_3$ (M+H$^+$) 377.1425, found 377.1409. HPLC: >95% purity.

Example 4

1-(2,4-Difluorobenzyl)-3-({[3-(dimethylamino)propyl]aminomethyl})-N-hydroxy-1H-pyrrolo[2,3-c]pyridine-5-carboxamide

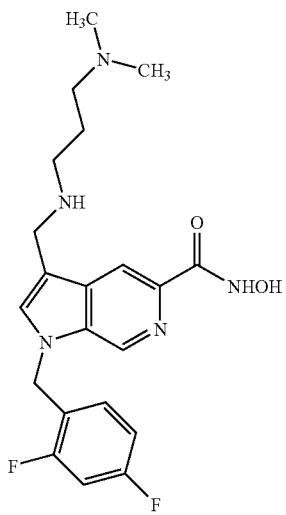

The title compound was prepared in the same manner as described in step 2 of example 2 using 3-(dimethylamino) propylamine instead of morpholine. $^1$H NMR (MeOH-d$_4$) δ ppm 8.79 (s, 1H), 8.39 (s, 1H), 7.63 (s, 1H), 7.26-7.34 (m, 1H), 6.91-7.06 (m, 2H), 5.57 (s, 2H), 4.05 (s, 2H), 2.76 (t, 2H, J=7.1 Hz), 2.43 (t, 2H, J=7.6 Hz), 2.26 (s, 6H), 1.70-1.80 (m, 2H). HRMS calcd for $C_{21}H_{26}F_2N_5O_2$ (M+H$^+$) 418.2055, found 418.2076. HPLC: >95% purity.

Example 5

1-(2,4-Difluorobenzyl)-N-hydroxy-3-[(4-methylpiperazin-1-yl)methyl]-1H pyrrolo[2,3-c]pyridine-5-carboxamide

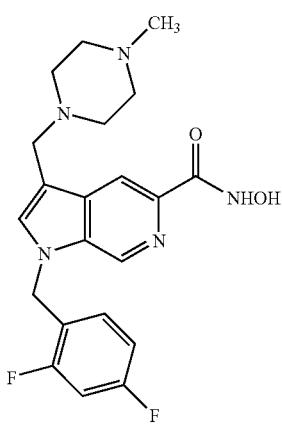

The title compound was prepared in the same manner as described in step 2 of example 2 using 1-methylpiperazine instead of morpholine. $^1$H NMR (MeOH-d$_4$) δ ppm 8.76 (s, 1H), 8.41 (s, 1H), 7.58 (s, 1H), 7.23-7.31 (m, 1H), 6.90-7.05 (m, 2H), 5.55 (s, 2H), 3.81 (s, 2H), 2.66 (b, 8H), 2.39 (s, 3H). LCMS (API-ES M+H$^+$) 416.2 Anal. ($C_{21}H_{23}F_2N_5O_2$·0.8HOAc) C, H, N. HPLC: >95% purity.

Example 6

1-(2,4-difluorobenzyl)-N-hydroxy-3-(piperidin-1-ylmethyl)-1H-pyrrolo[2,3-c]pyridine-5-carboxamide

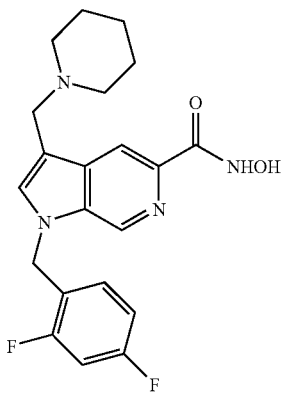

The title compound was prepared in the same manner as described in the step 2 of example 2 using piperidine instead of morpholine. $^1$H NMR (MeOH-d$_4$) δ: 8.82 (s, 1H), 8.41 (s, 1H), 7.72 (s, 1H), 7.29-7.37 (m, 1H), 6.92-7.07 (m, 2H), 5.60 (s, 2H), 4.10 (s, 2H), 2.84 (b, 4H), 1.70 (b, 4H), 1.53 (b, 2H). LCMS (API-ES M+H$^+$) 401.1. Anal. ($C_{21}H_{22}F_2N_4O_2$·HOAc) C, H, N. HPLC: >95% purity.

Example 7

1-(2,4-Difluorobenzyl)-A-hydroxy-N-methyl-3-(morpholin-4-ylmethyl)-1H-pyrrolo[2,3-c]pyridine-5-carboxamide

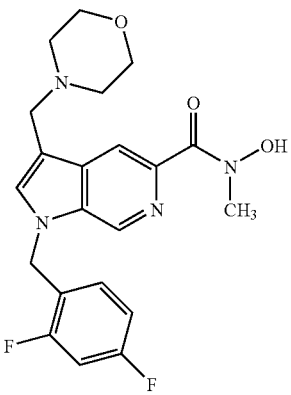

The title compound was prepared in the same manner as described in the step 2 of example 2 except for using 2.0M N-methylhydroxylamine instead of 1.5 M hydroxylamine in 25% NaOMe. $^1$H NMR (MeOH-d$_4$) δ: 8.80 (s, 1H), 8.34 (s, 1H), 7.67 (s, 1H), 7.33 (m, 1H), 6.92-7.06 (m, 2H), 5.59 (s, 2H), 3.77 (s, 2H), 3.67 (t, 4H, J=4.5 Hz), 3.44 (s, 3H), 2.50 (m, 4H). HRMS calcd for $C_{21}H_{23}F_2N_4O_3$ (M+H$^+$) 417.1738, found 417.1730. Anal. ($C_{21}H_{22}F_2N_4O_3$) C, H, N. HPLC: >95% purity.

Example 8

1-(2,4-Difluorobenzyl)-N-hydroxy-3-{[methyl(pyridin-3-ylmethyl)amino]methyl}-1H-pyrrolo[2,3-c]pyridine-5-carboxamide

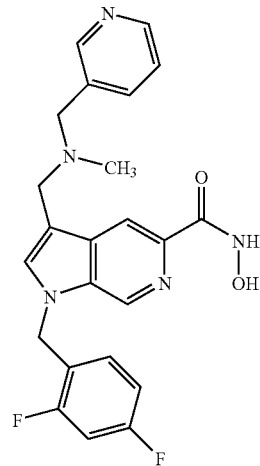

The title compound was prepared in the same manner as described in the step 2 of example 2 using 3-(methylaminomethyl)pyridine instead of morpholine. $^1$H NMR (MeOH-d$_4$)

δ: 8.75 (s, 1H), 8.41 (m, 3H), 7.83 (m, 1H), 7.59 (s, 1H), 7.38 (m, 1H), 7.22-7.29 (q, 1H, J=4.5 Hz), 6.89-7.05 (m, 2H), 5.56 (s, 2H), 3.82 (s, 2H), 3.60 (s, 2H), 2.92 (s, 3H). HRMS calcd for $C_{23}H_{22}F_2N_5O_2$ (M+H$^+$) 438.1742, found 438.1744. HPLC: >95% purity.

Example 9

1-(2,4-Difluorobenzyl)-3-[(1,1-dioxidoth iomorpholin-4-yl)methyl]-N-hydroxy-1H-pyrrolo[2,3-c]pyridine-5-carboxamide

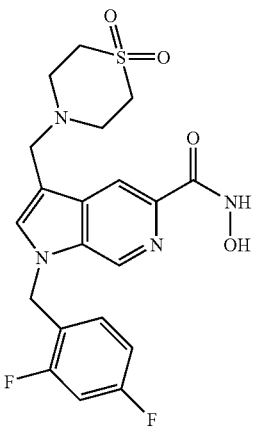

The title compound was prepared in the same manner as described in the step 2 of example 2 using thiomorpholine 1,1-dioxide instead of morpholine. $^1$H NMR (MeOH-d$_4$) δ: 8.76 (s, 1H), 8.45 (s, 1H), 7.59 (s, 1H), 7.22-7.30 (m, 1H), 6.90-7.05 (m, 2H), 5.55 (s, 2H), 3.91 (s, 2H), 3.10 (b, 4H), 3.01 (b, 4H), HRMS calcd for $C_{20}H_{21}F_2N_4O_4S$ (M+H$^+$) 451.1252, found 451.1257. Anal. ($C_{20}H_{20}N_4F_2O_4S.0.3H_2O$) C, H, N. HPLC: >95% purity.

Example 10

3-{[(2-Amino-2-oxoethyl)amino]methyl}-1-(2,4-difluorobenzyl)-N-hydroxy-1H-pyrrolo[2,3-c]pyridine-5-carboxamide

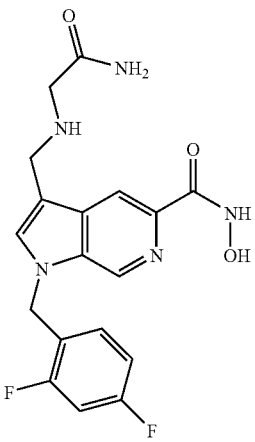

The title compound was prepared in the same manner as described in step 2 of example 2 using glycinamide instead of morpholine. $^1$H NMR (DMSO-d6) δ ppm 11.11 (b, 1H), 8.90 (b, 1H), 8.80 (s, 1H), 8.26 (s, 1H), 7.64 (s, 1H), 7.23-7.35 (m, 3H), 7.02-7.08 (m, 2H), 5.57 (s, 2H), 3.83 (s, 2H), δ 3.05 (s, 2H). HRMS calcd for $C_{18}H_{18}N_5O_3F_2$ (M+H$^+$) 390.1378, found 390.1397. HPLC: >95% purity.

Example 11

1-(2,4-Difluorobenzyl)-N-hydroxy-3-[(pyridin-3-ylamino)methyl]-1 pyrrolo[2,3-c]pyridine-5-carboxamide

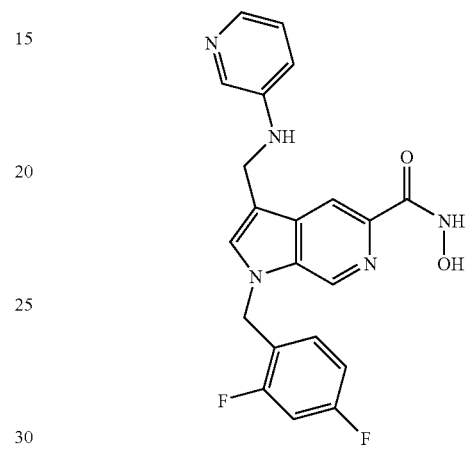

The title compound was prepared in the same manner as described in step 2 of example 2 using pyridin-3-amine instead of morpholine. $^1$H NMR (MeOH-d$_4$) δ ppm 8.75 (s, 1H), 8.39 (s, 1H), 7.96 (d, 1H, J=2.26), 7.73 (m, 1H), 7.61 (s, 1H), 7.06-7.22 (m, 3H), 6.86-7.03 (m, 2H), 5.54 (s, 2H), 4.53 (s, 2H). HRMS calcd for $C_{21}H_{18}F_2N_5O_2$ (M+H$^+$) 410.1429, found 410.1424. HPLC: >95% purity.

Example 12

1-(2,4-Difluorobenzyl)-3-{[(1,1-dioxidotetrahydrothien-3-yl)amino]methyl}-N-hydroxy-1H-pyrrolo[2,3-c]pyridine-5-carboxamide

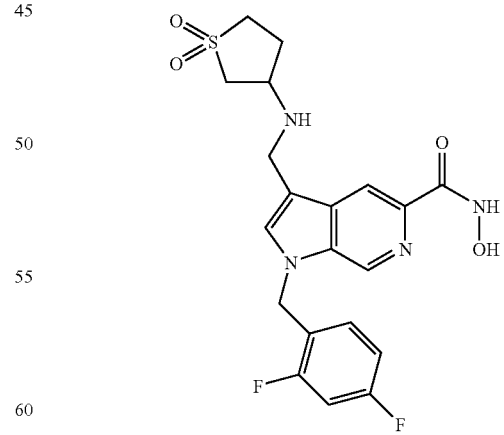

The title compound was prepared in the same manner as described in step 2 of example 2 using 1,1-dioxidotetrahydrothien-3-ylamine instead of morpholine. $^1$H NMR (DMSO-d6) δ ppm 11.12 (s, 1H), 8.90 (s, 1H), 8.82 (s, 1H), 8.28 (s, 1H), 7.65 (s, 1H), 7.23-7.38 (m, 2H), 7.03-7.10 (m, 1H), 5.58 (s, 2H), 3.46 (m, 1H), 3.35 (m, 1H), 3.22 (m, 1H), 3.04 (m, 1H), 2.91 (m, 1H), 2.27 (m, 1H), 2.00 (m, 1H). HRMS calcd for $C_{20}H_2, F_2N_4O_4S$ (M+H$^+$) 451.1252, found 451.1256. HPLC: >95% purity.

Example 13

1-(2,4-Difluorobenzyl)-N-hydroxy-3-(4-methylpiperazin-1-yl)-1H-pyrrolo[2,3-c]pyridine-5-carboxamide

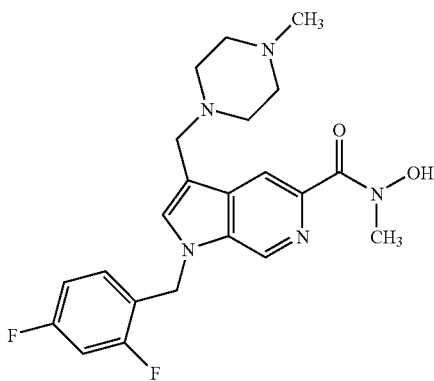

A solution of methyl 1-(2,4-difluorobenzyl)-3-formyl-1H-pyrrolo[2,3-c]pyridine-5-carboxylate (0.220 g, 0.666 mmol) and 1-methylpiperazine (0.120 mL, 1.08 mmol) in MeOH (1.5 mL) and dichloromethane (2.5 mL) was stirred for 4 h at room temperature. Decaborane (0.081 g, 0.666 mmol) was then added and stirring was continued for 2 more hours. The reaction mixture was evaporated to dryness under the reduced pressure and the residue was treated with a solution of 2.0 M N-methyl hydroxylamine in 25% NaOMe (0.7 mL) for 1 h at room temperature. The reaction mixture was purified by prep-HPLC to provide the title compound as a white solid (0.11 g, 39%). $^1$H NMR (DMSO-d6) δ ppm 8.85 (s, 1H), 8.08 (s, 1H), 7.68 (s, 1H), 7.25-7.36 (m, 2H), 7.02-7.09 (m, 1H), 5.58 (s, 2H), 3.62 (s, 2H), 3.32 (s, 3H), 2.15-2.45 (m, 8H), 2.12 (s, 3H). HRMS calcd for $C_{22}H_{26}F_2N_5O_2$(M+H$^+$) 430.2055, found 430.2062.

Example 14

1-(4-Fluorobenzyl)-AN-hydroxy-N-methyl-3-[(4-methylpiperazin-1-yl)methyl]-1H-pyrrolo[2,3-c]pyridine-5-carboxamide

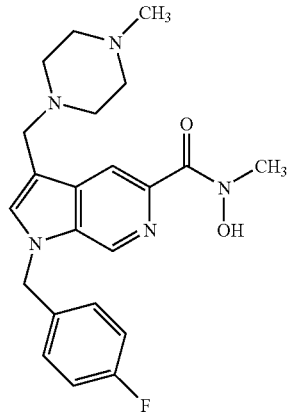

Step 1: Methyl 1-(4-fluorobenzyl)-3-formyl-1H-pyrrolo[2,3-c]pyridine-5-carboxylate. The title compound was prepared in the same manner as described in step 1 of example 2 using 4-fluorobenzyl bromide instead of 2,4-difluorobenzyl bromide. $^1$H NMR (CD$_3$OD) δ ppm 10.08 (s, 1H), 9.03 (s, 1H), 8.84 (s, 1H), 7.89 (s, 1H), 7.22 (m, 2H), 7.08 (m, 2H), 5.46 (s, 2H), 4.01 (s, 3H).

Step 2: 1-(4-Fluorobenzyl)-N-hydroxy-N-methyl-3-[(4-methylpiperazin-1-yl)methyl]-1H pyrrolo[2,3-c]pyridine-5-carboxamide. The title compound was prepared from methyl 1-(4-fluorobenzyl)-3-formyl-1H-pyrrolo[2,3-c]pyridine-5-carboxylate using the methods in example 13.

$^1$H NMR (MeOH-d$_4$) δ ppm 8.72 (s, 1H), 8.32 (s, 1H), 7.68 (s, 1H), 7.27 (m, 2H), 7.06 (m, 2H), 5.53 (s, 2H), 3.80 (s, 2H), 3.42 (s, 3H), 2.55 (b, 8H), 2.31 (s, 3H). HRMS calcd for $C_{22}H_{27}FN_5O_2$ (M+H$^+$) 412.2149, found 412.2143. HPLC: >95% purity.

Example 15

1-(4-Fluorobenzyl)-N-hydroxy-3-[(3-oxopiperazin-1-yl)methyl]-1 pyrrolo[2,3-c]pyridine-5-carboxamide

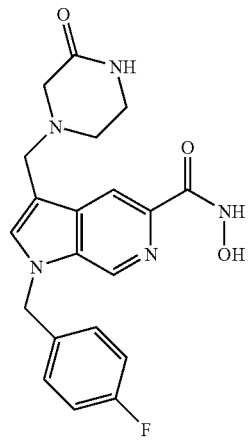

The title compound was prepared in the same manner as described in step 2 of example 2 using methyl 1-(4-fluorobenzyl)-3-formyl-1H-pyrrolo[2,3-c]pyridine-5-carboxylate and piperazin-2-one instead of ethyl 1-(2,4-difluorobenzyl)-3-formyl-1H-pyrrolo[2,3-c]pyridine-5-carboxylate and morpholine respectively. $^1$H NMR (DMSO-d6) δ ppm 11.10 (b, 1H), 8.94 (b, 1H), 8.79 (s, 1H), 8.27 (s, 1H), 7.78 (s, 1H), 7.72 (s, 1H), 7.34 (m, 2H), 7.16 (t, 2H, J=8.86 Hz), 5.54 (s, 2H), 3.74 (s, 2H), 3.11 (b, 2H), 2.92 (s, 2H), 2.55 (m, 2H). HRMS calcd for $C_{20}H_{21}FN_5O_3$ (M+H$^+$) 398.1628, found 398.1613. HPLC: >95% purity.

Example 16 rac 1-(2,4-difluorobenzyl)-N-hydroxy-3-{[(3aR*,7aS*)-1-oxooctahydro-5H-pyrrolo[3,4-c]pyridin-5-yl]methyl}-1H-pyrrolo[2,3-c]pyridine-5-carboxamide

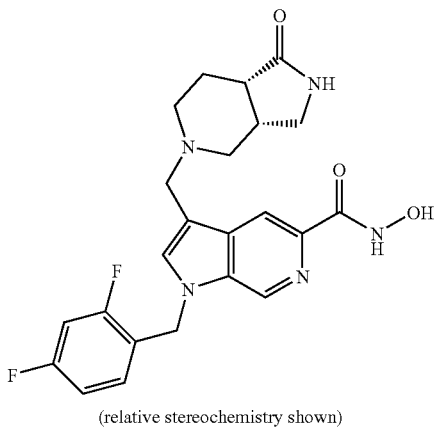

(relative stereochemistry shown)

Step 1: Methyl 4-methyl-5-nitropyridine-2-carboxylate: HCl gas was bubbled into the solution of 2-cyano-4-methyl-5-nitropyridine (30 g) in methanol (200 mL) with cooling in a ice-water bath for 5 minutes. Then 3.3 mL water (1 eq.) was added to the flask. The resulting solution was heated to reflux for 3 hrs. The desired product precipitated as HCl salt (white crystals). The mixture was cooled to room temperature and the precipitate was collected by vacuum filtration. The solid was transferred to a 1 L separation funnel, neutralized with satd. aqueous $NaHCO_3$ (400 mL), and extracted with $CH_2Cl_2$ (400 mL). The organic layer was dried over $Na_2SO_4$, concentrated and dried in vacuum to give the title compound as white solid (33 g, 92% yield). $^1H$ NMR (DMSO-d6) δ ppm 9.19 (s, 1H), 8.21 (s, 1H), 3.91 (s, 3H), 2.63 (s, 3H). LCMS (APCI, M+H$^+$): 197.0.

Step 2: Methyl 4-[(E)-2-(dimethylamino)vinyl]-5-nitropyridine-2-carboxylate: Method 1. A mixture of methyl 4-methyl-5-nitropyridine-2-carboxylate (3.5 g, 17.8 mmol), dimethylformamide dimethylacetal (DMF-DMA) (3.6 ml, 1.5 eq) in acetonitrile (35 mL) was heated in a microwave at 140° C. for 20 min. The solvent was removed. The residue (5.1 g) was carried onto the next step without further purification. Method 2. A mixture of methyl 4-methyl-5-nitropyridine-2-carboxylate (39.5 g, 0.19 mol) and DMF-DMA (30.6 g, 0.26 mol, 1.35 eq) in DMF (470 mL) was heated to 90° C. for 30 min. The solvent was removed in vacuo. The residue (78 g) was used without further purification in the next step.

Step 3: Methyl 1H-pyrrolo[2,3-c]pyridine-5-carboxylate. To a 500 mL Parr bottle was added methyl 4-[(E)-2-(dimethylamino)vinyl]-5-nitropyridine-2-carboxylate (18.9 g, 75.2 mmol) and anhydrous methanol (200 mL). The mixture was purged with nitrogen gas for 10 min. To this suspension was added Pd(10%)/C (1.90 g, 10 w/w %), and the suspension was degassed for 5 more minutes. The hydrogenation began with 43 psi $H_2$ without heating. The reaction became exothermic as indicated by the rising temperature (about 2-3° C. per min) inside the Parr bottle (monitored by a thermal coupling thermometer). As the temperature inside of the reaction reached 45° C., the hydrogen gas flow into the Parr bottle was stopped, and the mixture was allowed to cool down to 25° C. for 30 min. The color of the liquid of the suspension changed from purple red to light green and then colorless in the first hour of the reduction, and about 30 psi $H_2$ was consumed. The hydrogen pressure was brought to 50 psi, and the hydrogenation was continued at 50° C. for 20 h. There was no more hydrogen gas consumed in the last 20 h. After cooling the reaction mixture to 20° C., the solid mixture, which contained Pd(10%)/C and product, was filtered. The solid mixture was suspended in DMSO (200 mL), and the suspension was heated on a hot plate to 80° C. internal temperature with stirring for 10 min. The hot suspension was filtered and the Pd(10%)/C solid was washed with a small portion of DMSO (50 mL). The DMSO filtrate and washing were combined and poured into water (600 mL). Off white solid product precipitated out, and the suspension was stirred for 1 h before filtering, and lyophilizing. The title compound was obtained as an off-white solid product was obtained (11.3 g, >95% pure, 86% yield). $^1H$ NMR (300 MHz, DMSO-d6) δ ppm 3.84 (s, 3H) 6.68 (d, J=2.8 Hz, 1H) 7.73 (d, J=3.0 Hz, 1H) 8.36 (s, 1H) 8.80 (s, 1H) 11.99 (s, 1H). LCMS: (APCI, M-H—)=175

Step 4: Methyl 1-(4-fluorobenzyl)-1H-pyrrolo[2,3-c]pyridine-5-carboxylate. To a stirred solution of methyl 1H-pyrrolo[2,3-c]pyridine-5-carboxylate (15.0 g, 85.1 mmol) in DMF (120 mL) at 10° C. was added sodium hydride (3.75 g, 60% in mineral oil, 93.7 mmol, 1.1 eq.) in three portions over 5 min. The slurry became a homogeneous solution. After 130 min at 10° C. 4-fluorobenzyl bromide (0.60 g, 2.89 mmol) was added at such a rate that the temperature did not exceed 15° C. The resulting mixture was stirred for 2.5 hours at ambient temperature. It was quenched with water (120 mL), and extracted with ethyl acetate (3×30 mL). The combined organic extracts were washed with water (2×30 mL), dried over sodium sulfate, concentrated in vacuo and purified by flash chromatography. Elution with hexane:ethyl acetate (2:1 v/v) provided the title compound as a white solid (21.3 g, 88% yield). $^1H$ NMR (300 MHz, DMSO-d6) δ ppm 3.84 (s, 3H), 5.59 (s, 2H), 6.73 (d, J=2.8 Hz, 1H), 7.15 (t, J=8.9 Hz, 2H), 7.34 (dd, J=8.3, 5.7 Hz, 2H), 7.87 (d, J=2.8 Hz, 1H), 8.3 (s, 1H), 8.97 (s, 1H). LCMS (APCI, M+H$^+$): 285.3.

Step 5: Methyl 1-(4-fluorobenzyl)-3-formyl-1 pyrrolo[2,3-c]pyridine-5-carboxylate. To a stirred 0° C. solution of methyl 1-(4-fluorobenzyl)-1H-pyrrolo[2,3-c]pyridine-5-carboxylate (13.1 g, 43.3 mmol) in a 1:1 (v/v) solution of $CH_3NO_2$/1,2-dichloroethane (350 ml) were added $Cl_2CHOCH_3$ (19.6 ml, 5.0 eq) and $AlCl_3$ (19.07 g, 3.3 eq). The resulting mixture was stirred at 0° C. for 30 minutes. The addition of $Cl_2CHOCH_3$ (19.6 ml, 5.0 eq) and $AlCl_3$ (19.07 g, 3.3 eq) was repeated at 30 minutes and 60 minutes. After the last addition, the reaction mixture was poured onto 350 g of ice. The organic phase was removed, and the aqueous phase was extracted with a 1:1 solution of $CH_3NO_2$/1,2-dichloroethane (3×200 ml). The combined organic extracts were washed with Saturated $NaHCO_3$, brine, dried over $Na_2SO_4$, concentrated in vacuo, and purified by column chromatography. Elution with 25% hexanes/ethyl acetate provided the title compound as a tan solid (9.30 g, 65% yield). $^1H$ NMR (300 MHz, DMSO-d6) d ppm 10.04 (s, 1H), 9.13 (s, 1H), 8.79 (s, 1H), 8.75 (s, 1H), 7.47 (dd, J=8.59, 5.38 Hz, 2H), 7.20 (t, J=8.88 Hz, 2H), 5.70 (s, 2H), 3.88 (s, 3H). LCMS (APCI, M+H$^+$): 313.1.

Step 6: rac-Methyl 1-(2,4-difluorobenzyl)-3-[(3aR*,7aS*)-1-oxooctahydro-5H-pyrrolo[3,4-c]pyridin-5-yl]methyl}-1H-pyrrolo[2,3-c]pyridine-5-carboxylate. To a stirring solution of methyl 1-(2,4-difluorobenzyl)-3-formyl-1H-pyrrolo[2,3-c]pyridine-5-carboxylate (1 g, 3.03 mmol) and rac-3aR*,7aR*-1-oxooctahydro-5H-pyrrolo[3,4-c]pyridine hydrochloride (0.535 g, 1.0 eq) in dichloromethane (20 ml)

was added NaBH(OAc)$_3$ (1.606 g, 2.5 eq). The resulting mixture was stirred for 16 hours at ambient temperature. The solvent was evaporated, the residue was taken into 6:3:1 ethyl acetate/dichloromethane/methanol (30 ml) and washed with 10% K$_2$CO$_3$ (aq) (30 mL). The aqueous layer was extracted with 6:3:1 ethyl acetate/dichloromethane/methanol (3×30 ml). The combined organic extracts were washed with brine, dried over Na$_2$SO$_4$ and concentrated in vacuo. The crude material was used without further purification in the next step. LC-MS (APCI, M+H$^+$): 455.10; 1.959 min. HPLC: 90% purity.

Step 7: rac-1-(2,4-Difluorobenzyl)-N-hydroxy-3-{[(3aR,7aS)-1-oxooctahydro-5H-pyrrolo[3,4-c]pyridin-5-yl]methyl}-1H-pyrrolo[2,3-c]pyridine-5-carboxamide. To a stirring solution of rac-methyl 1-(2,4-difluorobenzyl)-3-{[(3aR*,7aS*)-1-oxooctahydro-5H-pyrrolo[3,4-c]pyridin-5-yl]methyl}-1H-pyrrolo[2,3-c]pyridine-5-carboxylate (0.09 g, 0.198 mmol) in MeOH (5 ml) was added 10% NaOH$_{(aq)}$ (0.5 ml, excess) and H$_2$NOH (1 ml, excess, 50% wt. sol. in water). The resulting mixture was stirred for 16 hours at ambient temperature. The solvent was evaporated and the crude product was purified by reverse phase Prep-HPLC (20-60% acetonitrile:water) to provide the title compound as a white solid (0.032 g, 35%). $^1$H NMR (MeOH-d$_4$) δ: 8.77 (s, 1H), 8.38 (s, 1H), 7.68 (s, 1H), 7.29-7.25 (m, 1H), 7.03-7.00 (m, 1H), 6.94-6.92 (m, 1H), 5.57 (s, 2H), 3.95-3.93 (m, 2H), 3.44-3.41 (m, H), 3.27-3.25 (m, 1H), 2.99-2.95 (m, 1H), 2.95-2.89 (m, 1H), 2.56-2.52 (m, 2H), 2.50-2.46 (m, 1H), 2.46-2.35 (m, H), 1.84-1.82 (m, H), 1.63-1.62 (m, H). LCMS (APCI, M+H$^+$): 456.15. HPLC: 99% purity.

Example 17 rac 1-(2,4-Difluorobenzyl)-N-methoxy-3-{[(3aR*,7aS*)-1-oxooctahydro-5H-pyrrolo[3,4-c]pyridin-5-yl]methyl}-1H-pyrrolo[2,3-c]pyridine-5-carboxamide

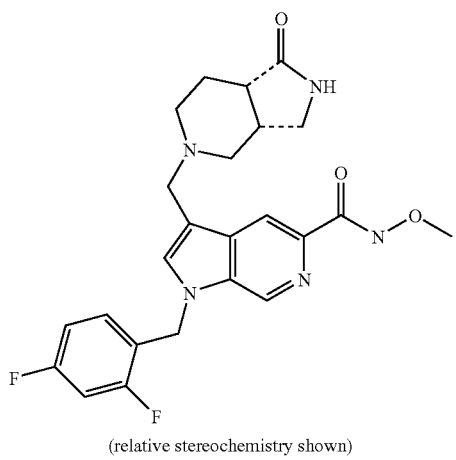

(relative stereochemistry shown)

Step 1: rac-1-(2,4-Difluorobenzyl)-3-{[(3aR*,7aS-1-oxooctahydro-5H-pyrrolo[3,4-c]pyridin-5-yl]methyl)-1H-pyrrolo[2,3-c]pyridine-5-carboxylic acid. Crude rac-methyl 1-(2,4-difluorobenzyl)-3-[[(3aR*,7aS*)-1-oxooctahydro-5H-pyrrolo[3,4-c]pyridin-5-yl]methyl}-1H-pyrrolo[2,3-c]pyridine-5-carboxylate (0.22 g, 0.484 mmol) was dissolved in methanol (10 mL). To this stirring solution was added 3M LiOH$_{(aq)}$ (0.484 ml, 3 eq), and the resulting mixture was stirred for 16 hr at ambient temperature and acidified by the addition of 1M HCl$_{(aq)}$ (1.452 mL, 3 eq). The resulting solution was stirred for 30 minutes at ambient temperature. The solution was then concentrated in vacuo yielding a white solid (0.194 g). $^1$H NMR (MeOH-d$_4$) δ ppm 8.91 (s, 1H), 8.56 (s, 1H), 8.04 (s, 1H), 7.39-7.37 (m, 1H), 7.01-6.95 (m, 2H), 5.66 (s, 2H), 4.00-3.96 (m, 2H), 3.44-3.42 (m, 1H), 3.31-3.26 (m, 2H), 2.99-2.97 (m, 2H), 2.60-2.58 (m, 1H), 2.55-2.30 (m, 2H), 1.88-1.72 (m, 1H), 1.64-1.50 (m, 1H). LCMS (APCI, M+H$^+$): 441.10; 0.748 min. HPLC: 97% purity Step 2: rac-6-(2,4-Difluorobenzyl)-N-methoxy-3-{[(3aR*,7aS*)-1-oxooctahydro-5H-pyrrolo[3,4-c]pyridin-5-yl]methyl}-1H-pyrrolo[2,3-c]pyridine-5-carboxamide. To a stirred solution of crude rac-1-(2,4-difluorobenzyl)-3-{[(3aR*,7aS*)-1-oxooctahydro-5H-pyrrolo[3,4-c]pyridin-5-yl]methyl}-1H-pyrrolo[2,3-c]pyridine-5-carboxylic acid (0.120 g) in DMF (5 mL) and TEA (0.16 mL, 4.2 eq) were added HATU (0.103 g, 1.0 eq) and O-methylhydroxylamine hydrochloride (0.068 g, 3.0 eq). The resulting mixture was stirred for 16 hours at ambient temperature. The solvent was removed in vacuo, and the crude material taken into dichloromethane (10 mL). The organic material was washed with saturated NaHCO$_3$ (3×10 mL). The aqueous phase was extracted with dichloromethane (3×10 mL). The combined organic extracts were washed with brine, dried over Na$_2$SO$_4$, and concentrated in vacuo. The compound was purified by reverse phase Prep-HPLC (20-60% acetonitrile: water), which yielded a white solid (0.060 g, 47%). $^1$H NMR (MeOH-d$_4$) δ ppm 8.76 (s, 1H), 8.40 (s, 1H), 7.64 (s, 1H), 7.27-7.25 (m, 1H), 7.03-7.01 (m, 1H), 6.95-6.93 (m, 1H), 5.57 (s, 2H), 3.85 (s, 2H), 3.82 (s, 3H), 3.43-3.41 (m, 1H), 3.18-3.14 (m, 1H), 2.98-2.96 (m, 1H), 2.83-2.80 (m, 1H), 2.53-2.51 (m, 1H), 2.43-2.40 (m, 2H), 2.31-2.24 (m, 1H), 1.85-1.82 (m, 1H), 1.63-1.59 (m, 1H). LCMS (APCI, M+H$^+$): 470.15; 1.676 min. HPLC: 98% purity.

Example 18 rac 1-(2,4-difluorobenzyl)-N-hydroxy-N-methyl-3-{[(3aR*,7aS*)-1-oxooctahydro-5H-pyrrolo[3,4-c]pyridin-5-yl]methyl}-1H-pyrrolo[2,3-c]pyridine-5-carboxamide

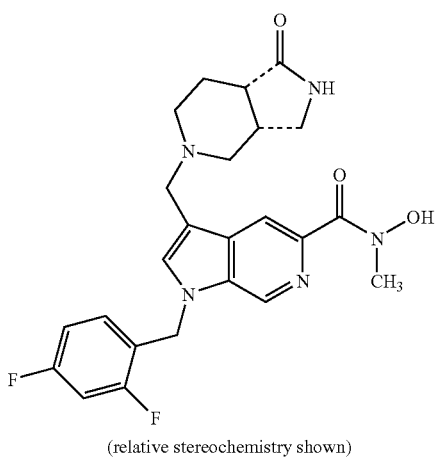

(relative stereochemistry shown)

The title compound was prepared from rac-1-(2,4-difluorobenzyl)-3-{[(3aR*,7aS*)-1-oxooctahydro-5H-pyrrolo[3,4-c]pyridin-5-yl]methyl}-1H-pyrrolo[2,3-c]pyridine-5-carboxylic acid and N-methylhydroxylamine hydrochloride in a manner similar to step 2 of example 17. $^1$H NMR (MeOH-d4)

δ ppm 8.80 (s, 1H), 8.28 (b, 1H), 7.72 (s, 1H), 7.32-7.31 (m, 1H), 7.05-7.02 (m, 1H), 7.00-6.93 (m, 1H), 5.59 (s, 2H), 3.88 (s, 2H), 3.42 (s, 3H), 3.28-3.26 (m, 2H), 2.98-2.96 (m, 1H), 2.83-2.80 (m, 1H), 2.58-2.56 (m, 1H), 2.48-2.44 (m, 2H), 2.27-2.25 (m, 1H), 1.85-1.82 (m, 1H), 1.63-1.59 (m, 1H). LCMS (APCI, M+H+): 470.15. HPLC: 96% purity.

Example 19

1-(2,4-Difluorobenzyl)-N-hydroxy-4-(methoxymethyl)-1-H-pyrrolo[2,3-c]pyridine-5-carboxamide

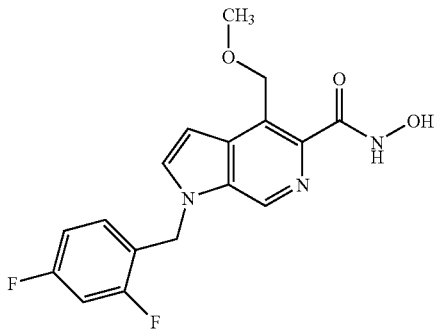

Step 1: Methyl 1-(2,4-difluorobenzyl)-4-methoxymethyl-1-H-pyrrolo[2,3-c]pyridine-5-carboxylate. The title compound was prepared by alkylation of methyl 4-methoxymethyl-1H-pyrrolo[2,3-c]pyridine-5-carboxylate [prepared according to X. Doisy et al., Bioorg. Med. Chem. 1999, 7, 921-932) with 2,4-difluorobenzyl bromide in a manner similar to step 1 of example 2. ¹H NMR (CDCl₃) δ ppm: 8.70 (s, 1H), 7.31 (d, 1H, J=4.0 Hz), 6.71-6.98 (m, 4H), 5.36 (s, 2H), 5.12 (s, 2H), 3.92 (s, 3H), 3.38 (s, 3H). LCMS (API-ES, M+H+): 347.1

Step 2: 1-(2,4-Difluorobenzyl)-N-hydroxy-4-methoxymethyl-1H-pyrrolo[2,3-c]pyridine-5-carboxamide. The title compound was prepared from methyl 1-(2,4-difluorobenzyl)-4-methoxymethyl-1H-pyrrolo[2,3-c]pyridine-5-carboxylate using the methods described in step 7 of example 16. ¹H NMR (MeOH-d₄) δ ppm 8.71 (s, 1H), 7.64 (d, 1H, J=4.0 Hz), 6.85-7.27 (m, 4H), 5.57 (s, 2H), 5.08 (s, 2H), 3.38 (s, 3H). LCMS (APCI, M+H+): 348.1. HRMS calcd for C₁₇H₁₆F₂N₃O₃ (M+H) 348.1160, found 348.1179. HPLC: 100% purity.

Example 20

1-(2,4-Difluorobenzyl)-N-methoxy]-4-(methoxymethyl)-1H-pyrrolo[2,3-c]pyridine-5-carboxamide

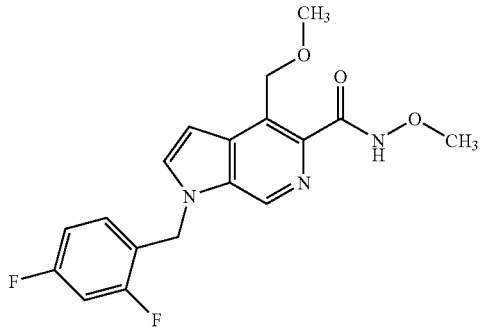

Step 1:1-(2,4-Difluorobenzyl)-4-methoxymethyl-1H-pyrrolo[2,3-c]pyridine-5-carboxylic acid.

The title compound was prepared from methyl-1-(2,4-difluorobenzyl)-4-methoxymethyl-1H-pyrrolo[2,3-c]pyridine-5-carboxylate in a manner similar to step 8 of example 1. ¹H NMR (CD₃OD) δ ppm 8.88 (s, 1H), 8.05 (d, 1H, J=4.0 Hz), 6.95-7.40 (m, 4H), 5.69 (s, 2H), 5.40 (s, 2H), 3.41 (s, 3H). HRMS calcd for C₁₇H₁₅F₂N₂O₃ (M+H) 333.1051, found 333.1040.

Step 2: 1-(2,4-Difluorobenzyl)-N-methoxy]-4-(methoxymethyl)-1H-pyrrolo[2,3-c]pyridine-5-carboxamide. The title compound was prepared from 1-(2,4-difluorobenzyl)-4-methoxymethyl-1H-pyrrolo[2,3-c]pyridine-5-carboxylic acid in a manner similar to step 2 of example 17. ¹H NMR (CD₃OD) δ ppm 8.70 (s, 1H), 7.62 (br, 1H), 6.85-7.25 (m, 4H), 5.55 (s, 2H), 5.10 (s, 2H), 3.83 (s, 3H), 3.38 (s, 3H). HRMS calcd for C₁₈H₁₈F₂N₃O₃ (M+H) 362.1316, found 362.1325.

Example 21

3-(4-Fluorobenzyl)-N-hydroxy-3H-imidazo[4,5-c]pyridine-6-carboxamide

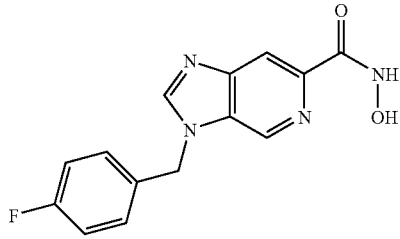

Step 1: (6S)-4,5,6,7-Tetrahydro-3H-imidazo[4,5-c]pyridine-6-carboxylic acid dihydrochloride. L-Histidine (204.8 g, 1.32 mol) was added to water (1.2 L) and cooled in an ice/water bath. Concentrated hydrochloric acid (116.0 mL, 1.39 mol, 1.05 mol eq.) was added slowly. Formaldehyde (37 wt/wt % in water, 112.5 g, 1.39 mol, 1.05 mol eq.) was added in one portion. The reaction mixture was stirred for 30 min upon cooling with an ice/water bath, and then refluxed for 75 min. After cooling to room temperature, the solvent was removed under reduced pressure. The residue was suspended in isopropanol (2 L) and HCl (400 mL of a 4 M solution in dioxane) for 30 min. The white solid was filtered and washed with ether. After drying in a vacuum oven (40° C.), the title product was obtained. (313.0 g, 99% yield, 95% pure). ¹H NMR (DMSO-d6): δ ppm 3.05-3.33 (m, 2H), 4.30 (s, 2H), 4.54 (m, 1H), 9.00 (s, 1H), 12.60 (br s, 3H). LCMS: R$_t$=0.59 min, and M+1=168.1 m/z (M+1 of free base).

Step 2: Methyl (6S)-4,5,6,7-tetrahydro-3H-imidazo[4,5-c]pyridine-6-carboxylate dihydrochloride. Thionylchloride (200 mL, 2.74 mol, 3.0 mol eqv.) was added dropwise to methanol (3.5 L), which was cooled to 0-5° C. (6S)-4,5,6,7-tetrahydro-3H-imidazo[4,5-c]pyridine-6-carboxylic acid dihydrochloride (210.0 g, 0.87 mol) was added The suspension was allowed to warm up to room temperature, and refluxed for 3.5 h. After cooling to room temperature, the solvent was removed under reduced pressure. The white residue was suspended in ether (3 L). The solid was filtered and washed with ether. After drying in a vacuum oven (40° C.), the title compound was obtained (225.0 g, 100% yield, 95% pure). ¹H NMR (DMSO-d6): δ ppm 12.65 (br s, 2H), 9.04 (s, 1H), 4.71 (m, 1H), 4.33 (t, J=16.2 Hz, 2H), 3.81 (s, 3H), 3.10-3.33 (m, 2H), LCMS: R$_t$=0.61 min and M+1=182.1 u/e (M+1 of free base).

Step 3: Methyl 3-H-imidazo[4,5-c]pyridine-6-carboxylate. Methyl (6S)-4,5,6,7-tetrahydro-3H-imidazo[4,5-c]pyridine-6-carboxylate dihydrochloride (156.5 g, 0.62 mol), triethylamine (445.0 g, 4.4 mol, 7.0 mol eqv.), selenium dioxide (158.2 g, 1.43 mol, 2.3 mol eqv.), and polyphosphatesilyl ether (PPSE) (15.0 g) were added to CCl$_4$ (1.5 L). The mixture was refluxed for 6 h. After cooling to room temperature, the solvent was removed under reduced pressure. The residue was suspended in methanol (1.5 L), and triethylamine was added to adjust to pH 8. The brown solid was filtered and washed well with methanol. This brown solid (117.0 g) was recrystallized from hot DMF (2 L, 140° C.). The solution was filtered hot to remove black side products. Upon cooling to room temperature, the desired product crystallized out as a yellow solid (51.3 g, 47% yield, 95% pure). $^1$H NMR (DMSO-d6): δ 13.20 (br s, 1H), 9.02 (s, 1H), 8.58 (s, 1H), 8.31 (s, 1H), 3.89 (s, 3H); LCMS: R$_t$=1.33 min, and M+1=178.1 u/e.

Step 4: Methyl 3-(4-fluorobenzyl)-3-H-imidazo[4,5-c]pyridine-6-carboxylate and methyl 1-(4-fluorobenzyl)-1H-imidazo[4,5-c]pyridine-6-carboxylate. The title compounds were prepared by alkylation of methyl 1H-imidazo[4,5-c]pyridine-6-carboxylate with fluorobenzyl bromide in a manner similar to step 6 of example 1. The two regioisomers were separated by column chromatography using ethyl acetate as eluent. Methyl 3-(4-fluorobenzyl)-3H-imidazo[4,5-c]pyridine-6-carboxylate. R$_f$: 0.29 (ethyl acetate). $^1$H NMR (300 MHz, CDCl$_3$) δ ppm 8.80 (d, 1H) 8.65 (d, 1H) 8.17 (s, 1H) 7.21-7.30 (m, 4H) 7.10 (t, 2H) 5.48 (s, 2H) 4.05 (s, 3H). Methyl 1-(4-fluorobenzyl)-1H-imidazo[4,5-c]pyridine-6-carboxylate. R$_f$: 0.18 (ethyl acetate); $^1$H NMR (300 MHz, CDCl$_3$) δ ppm 9.20 (s, 1H) 8.21 (s, 1H) 8.10 (s, 1H) 7.15-7.24 (m, 2H) 7.03-7.14 (m, 2H) 5.40 (s, 2H) 4.01 (s, 3H).

Step 5: 3-(4-Fluoro-benzyl)-N-hydroxy-3-H-imidazo[4,5-c]pyridine-6-carboxamide. The title compound was prepared from methyl 3-(4-fluoro-benzyl)-3H-imidazo[4,5-c]pyridine-6-carboxylate using the methods in example 26. $^1$H NMR (300 MHz, DMSO-d6) δ:11.23 (s, 1H), 9.00 (s, 1H), 8.89 (s, 1H), 8.74 (s, 1H), 8.21 (s, 1H), 7.49 (pseudo t, J=6.0 Hz, 2H), 7.20 (pseudo t, J=9.0 Hz, 2H), 5.64 (s, 2H). LCMS (API-ES, M+H$^+$): 287.0. HRMS calcd for C$_{14}$H$_{12}$FN$_4$O$_2$ (M+H) 287.0944, found 287.0935. HPLC: >97% purity.

Example 22

3-(4-Fluorobenzyl)-N-methoxy-3H-imidazo[4,5-c]pyridine-6-carboxamide

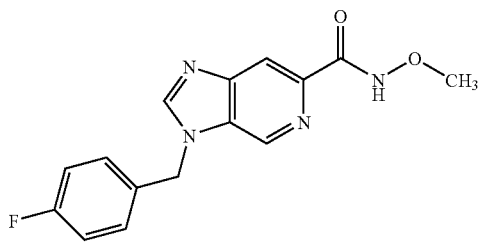

Step 1: 3-(4-Fluorobenzyl)-3H-imidazo[4,5-c]pyridine-6-carboxylate. This compound was prepared from methyl 3-(4-fluorobenzyl)-3H-imidazo[4,5-c]pyridine-6-carboxylate in a manner similar to step 7 of example 1. $^1$H NMR (300 MHz, DMSO-d6) δ ppm 8.99 (s, 1H) 8.76 (s, 1H) 8.31 (s, 1H) 7.41-7.52 (m, 2H) 7.13-7.25 (m, 2H) 5.64 (s, 2H)). LCMS (APCI, M+H$^+$): 272.0

Step 2: 3-(4-Fluorobenzyl)-N-methoxy-3H-imidazo[4,5-c]pyridine-6-carboxamide. The title compound was prepared by coupling of 3-(4-fluorobenzyl)-3H-imidazo[4,5-c]pyridine-6-carboxylic acid with N-methyl hydroxylamine hydrochloride in analogy to step 8 of example 1. $^1$H NMR (DMSO-d6) δ; 11.89 (s, 1H), 8.91 (s, 1H), 8.75 (s, 1H), 8.22 (s, 1H), 7.47 (dd, 2H), 7.19 (dd, 2H), 5.65 (s, 2H), 3.68 (s, 3H). LCMS (APCI, M+H$^+$): 301.1 Anal. (C$_{15}$H$_{13}$FN$_4$O$_2$×0.1H$_2$O)C, H, N. HPLC: 98% purity.

Example 23

3-(4-Fluorobenzyl)-N-hydroxy-N-methyl-3-H-imidazo[4,5-c]pyridine-6-carboxamide

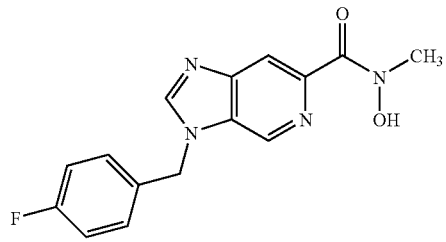

The title compound was prepared by coupling of 3-(4-fluorobenzyl)-3H-imidazo[4,5-c]pyridine-5-carboxylic acid with N-methyl hydroxylamine hydrochloride in a manner similar to step 9 of example 1. $^1$H NMR (DMSO-d6) δ ppm 8.92 (s, 1H), 8.74 (s, 1H), 7.92 (s, 1H), 7.49 (s, 2H), 7.20 (d, 2H, J=8.8 Hz), 5.62 (s, 2H), 3.29 (s, 3H). (API-ES, M+H$^+$): 301.0. HRMS calcd for C$_{15}$H$_{13}$FN$_4$O$_2$ (M+H) 301.1096, found 301.1107. HPLC: 99% purity.

Example 24

3-(2,3-Difluoro-benzyl)-N-hydroxy-3H-imidazo[4,5-c]pyridine-6-carboxamide

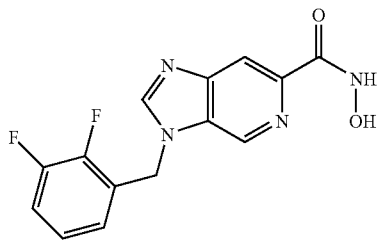

The title compound was prepared using the methods described in steps 4 and 5 of example 21 using 2,3-difluorobenzyl bromide instead of 4-fluorobenzyl bromide. $^1$H NMR (300 MHz, DMSO-d6) δ ppm 11.20 (s, 1H), 8.95 (s, 1H), 8.83 (s, 1H), 8.62 (s, 1H), 8.16 (s, 1H), 7.40-7.36 (m, 1H), 7.18-7.10 (m, 2H), 5.74 (s, 2H). LCMS (API-ES, M+H$^+$): 305.0. HRMS calcd for C$_{14}$H$_{11}$F$_2$N$_4$O$_2$ (M+H) 305.0850, found 305.0854. HPLC: >97% purity.

Example 25

3-(2-Cyclohexylethyl)-N-hydroxy-3-H-imidazo[4,5-c]pyridine-6-carboxamide

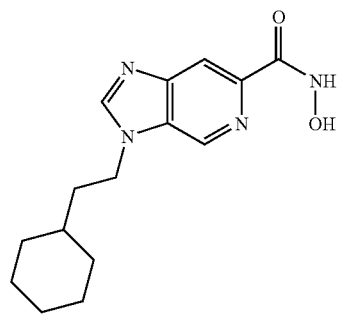

The title compound was prepared using the methods described in steps 4 and 5 of example 21 using (2-bromoethyl)cyclohexane instead of 4-fluorobenzyl bromide compound. $^1$H NMR (300 MHz, DMSO-d6) δ ppm 11.28 (s, 1H), 9.01 (s, 1H), 8.99 (s, 1H), 8.59 (s, 1H), 8.22 (s, 1H), 4.43 (t, J=6.0 Hz, 2H), 1.80-1.65 (m, 7H), 1.22-1.12 (m, 4H), 0.10-0.93 (m, 2H). LCMS (API-ES, M+H$^+$): 289.1. HRMS calcd for $C_{15}H_{21}N_4O_2$ (M+H) 289.1665, found 289.1665. HPLC: >98% purity.

Example 26

1-(2-Cyclohexylethyl)-N-hydroxy-1H-pyrrolo[2,3-c]pyridine-5-carboxamide

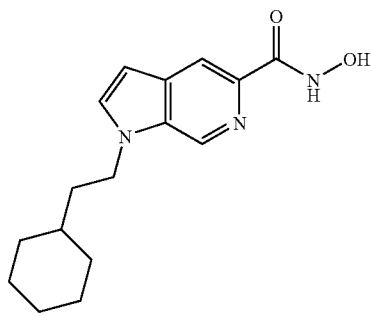

Step 1: Ethyl 1-(2-cyclohexylethyl)-1H-pyrrolo[2,3-c]pyridine-5-carboxylate. The title compound was prepared by alkylation of ethyl 1H-pyrrolo[2,3-c]pyridine-5-carboxylate with (2-bromoethyl)cyclohexane in a manner similar to step 6 of example 1. $^1$H NMR (CDCl$_3$) δ ppm 8.86 (s, 1H), 8.50 (s, 1H), 7.33 (d, 1H, J=3.0 Hz), 6.66 (d, 1H, J=3.0 Hz), 4.52 (q, 2H, J=6.9 Hz), 4.29 (t, 2H, J=7.5 Hz), 1.66-1.83 (m, 7H), 1.48 (t, 3H, J=7.2 Hz), 1.18-1.32 (m, 4H), 0.93-1.05 (m, 2H). LCMS (APCI, M+H$^+$): 301.1

Step 2: 1-(2-Cyclohexylethyl)-N-hydroxy-1H-pyrrolo[2,3-c]pyridine-5-carboxamide. The title compound was prepared from ethyl 1-(2-cyclohexylethyl)-1H-pyrrolo[2,3-c]pyridine-5-carboxylate using the methods in example 16. $^1$H NMR (DMSO-d6) δ ppm. 11.11 (s, 1H), 8.90 (s, 1H), 8.82 (s, 1H), 8.21 (d, 1H, J=3.0 Hz), 7.73 (d, 1H, J=3.0 Hz), 6.65 (d, 1H, J=3.0 Hz), 4.37 (q, 2H, J=7.6 Hz), 1.64-1.74 (m, 7H), 1.14 (m, 4H), 0.96 (m, 2H). LCMS (APCI, M+H$^+$): 288.1.

HRMS calcd for $C_1H_{22}N_3O_2$(M+H) 288.1707, found 288.1710. HPLC: 100% purity.

Example 27

1-(4-Fluorobenzyl)-N-hydroxy-N-isopropyl-1H-pyrrolo[2,3-c]pyridine-5-carboxamide

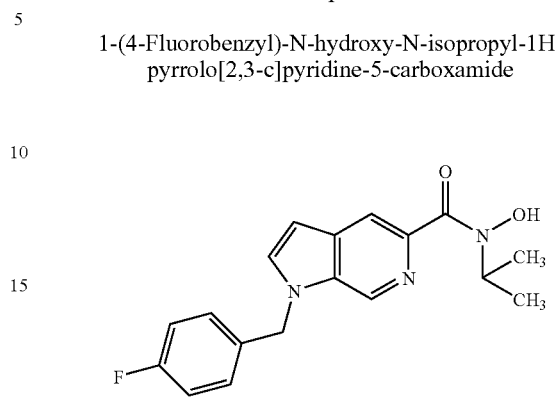

The title compound was prepared by coupling of 1-(4-fluorobenzyl)-1H-pyrrolo[2,3-c]pyridine-5-carboxylic acid with N-isopropyl hydroxylamine hydrochloride in a manner similar to step 8 of example 1. $^1$H NMR (CDCl$_3$) δ ppm 8.59 (s, 1H), 8.46 (s, 1H), 7.39 (s, 1H), 7.10 (m, 2H), 7.02 (d, 2H, J=8.6 Hz), 6.73 (s, 1H), 5.41 (s, 2H), 5.08 (m, 1H), 1.33 (d, 6H, J=6.6 Hz). LCMS (APCI, M+H$^+$): 328.1 HRMS calcd for $C_{18}H_{18}FN_3O_2$ (M+H) 328.1456, found 328.1456. HPLC: 95.8% purity.

Example 28

1-(4-Fluorobenzyl)-N-hydroxy-N-propyl-1H-pyrrolo[2,3-c]pyridine-5-carboxamide

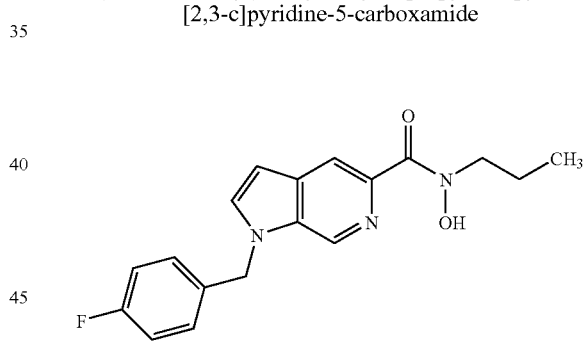

Step 1: Ethyl 3-methyl-5-oxo-2-propyl-2,5-dihydroisoxazole-4-carboxylate. To a stirred solution of ethyl 3-methyl-5-oxo-2,5-dihydroisoxazole-4-carboxylate sodium salt [prepared according G. Doleschall, Tetrahedron Lett. 1987, 28, 2993-2994] (3.5 g, 18.1 mmol) in DMF (20 mL) was added 1-iodopropane (1.70 g, 18.1 mmol). The resulting mixture was heated to 120° C. for 1 hr. When cooled down, it was poured into ice-water (30 mL), and extracted with dichloromethane (2×50 mL). The organic layer was washed with water (2×50 mL), dried over sodium sulfate, concentrated and purified by flash chromatography with ethyl acetate/hexanes (1/1) to provide a solid product (0.52 g, 13% yield). $^1$H NMR (CDCl$_3$) δ ppm 4.33 (q, 2H, J=7.1 Hz), 3.86 (t, 2H, J=6.8 Hz), 2.57 (s, 3H), 1.81-1.88 (m, 2H), 1.37 (t, 3H, J=7.1 Hz), 0.98 (t, 3H, J=7.6 Hz). LCMS (APCI, M+H$^+$): 214.1.

Step 2: N-Propylhydroxylamine hydrochloride. To a stirred solution of ethyl 3-methyl-5-oxo-2-propyl-2,5-dihydroisoxazole-4-carboxylate (0.52 g, 2.44 mmol) in water (10 mL) were added acetic acid (10 mL) and hydrochloric acid (37% in water). The resulting solution was heated at reflux for 8 h. Then all solvents were evaporated at reduced pressure and the desired product was dried in vacuo to provide the title compound as a glue-like liquid (0.30 g, quant.). $^1$H NMR (CDCl$_3$) δ ppm 10.94 (s, 2H), 3.24 (s, 2H), 2.77 (m, 2H), 1.89 (m, 2H), 1.03 (t, 3H, J=7.5 Hz).

Step 3: 1-(4-Fluorobenzyl)-N-hydroxy-N-propyl-1H-pyrrolo[2,3-c]pyridine-5-carboxamide. The title compound was prepared by coupling of 1-(4-fluorobenzyl)-1H-pyrrolo[2,3-c]pyridine-5-carboxylic acid with N-propyl hydroxylamine hydrochloride in a manner similar to step 8 of example 1. $^1$H NMR (DMSO-d6) δ ppm 11.93 (br s, 1H), 8.88 (s, 1H), 7.99 (s, 1H), 7.88 (d, 1H, J=3.0 Hz), 7.34 (m, 2H), 7.15 (d, 2H, J=8.8 Hz), 6.69 (d, 1H, J=3.0 Hz), 5.56 (s, 2H), 3.66 (t, 2H, J=7.1 Hz), 1.64 (m, 2H), 0.83 (s, 3H). LCMS (API-ES, M+H$^+$): 328.1. HRMS calcd for C$_{18}$H$_{19}$FN$_3$O$_2$ (M+H) 328.1456, found 328.1458. HPLC: 100% purity.

Example 29

1-(4-Fluorobenzyl)-N-hydroxy-N-isobutyl-1H-pyrrolo[2,3-c]pyridine-5-carboxamide

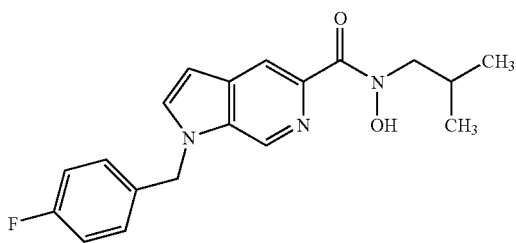

Step 1: Ethyl 3-methyl-5-oxo-2-isobutyl-2,5-dihydroisoxazole-4-carboxylate. The title compound was prepared by alkylation of ethyl 3-methyl-5-oxo-2,5-dihydroisoxazole-4-carboxylate sodium salt with 1-iodo-3-methylbutane in a manner similar to step 1 of example 28. $^1$H NMR (CDCl$_3$) δ ppm 4.12 (q, 2H, J=7.1 Hz), 3.47 (t, 2H, J=6.8 Hz), 2.35 (s, 3H), 1.97-2.07 (m, 1H), 1.16 (t, 3H, J=7.0 Hz), 0.77 (d, 6H, J=6.8 Hz). LCMS (APCI, M+H$^+$): 228.2.

Step 2: N-Isobutylhydroxylamine hydrochloride. The title compound was prepared from ethyl 3-methyl-5-oxo-2-isobutyl-2,5-dihydroisoxazole-4-carboxylate in a manner similar to step 2 of example 28. $^1$H NMR (DMSO-d6) δ ppm 11.22 (s, 2H), 10.78 (s, 1H), 2.95 (d, 2H, J=7.0 Hz), 2.01-2.06 (m, 1H), 0.95 (d, 6H, J=6.8 Hz).

Step 3: 1-(4-Fluorobenzyl)-N-hydroxy-N-isobutyl-1 pyrrolo[2,3-c]pyridine-5-carboxamide.

The title compound was prepared by coupling of 1-(4-fluorobenzyl)-1H-pyrrolo[2,3-c]pyridine-5-carboxylic acid with N-isobutyl hydroxylamine hydrochloride in a manner similar to step 8 of example 1. $^1$H NMR (DMSO-d6) δ ppm 12.00 (br s, 1H), 8.83 (s, 1H), 7.95 (s, 1H), 7.84 (d, 1H, J=3.0 Hz), 7.29 (m, 2H), 7.10 (d, 2H, J=8.8 Hz), 6.64 (d, 1H, J=3.0 Hz), 5.51 (s, 2H), 3.50 (d, 2H, J=7.2 Hz), 1.98-2.05 (m, 1H), 0.80 (s, 6H). LCMS (API-ES, M+H$^+$): 342.1. HRMS calcd for C$_{19}$H$_{21}$FN$_3$O$_2$ (M+H) 342.1613, found 342.1608. Anal. (C$_{19}$H$_{20}$FN$_3$O$_2$) C, H, N. HPLC: 100% purity.

Example 30

1-(4-Fluorobenzyl)-N-hydroxy-N-(3-hydroxypropyl)-1H-pyrrolo[2,3-c]pyridine-5-carboxamide

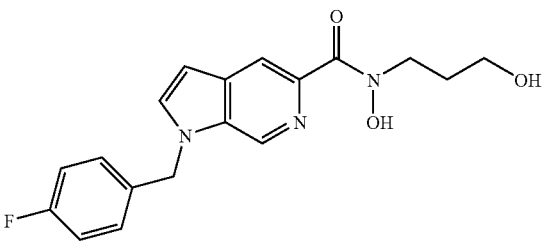

Step 1: Ethyl 3-methyl-5-oxo-2-[(3-tert-butyldimethylsilanoxyl)propyl]-2,5-dihydroisoxazole-4-carboxylate. The title compound was prepared by alkylation of ethyl 3-methyl-5-oxo-2,5-dihydroisoxazole-4-carboxylate sodium salt with (3-bromopropoxy)(tert-butyl)dimethylsilane in a manner similar to step 1 of example 28. $^1$H NMR (CDCl$_3$) δ ppm 4.30 (q, 2H, J=7.2 Hz), 4.00 (t, 2H, J=6.4 Hz), 3.58 (t, 2H, J=5.5 Hz), 2.55 (s, 3H), 1.93-1.96 (m, 2H), 1.34 (t, 3H, J=7.0 Hz), 0.88 (s, 9H), 0.04 (s, 6H). LCMS (APCI, M+H$^+$): 344.1.

Step 2: N-(3-Hydroxypropyl)hydroxylamine hydrochloride. The title compound was prepared from ethyl 3-methyl-5-oxo-2-[(3-tert-butyldimethylsilanoxyl)propyl]-2,5-dihydroisoxazole-4-carboxylate in a manner similar to step 2 of example 28. $^1$H NMR (DMSO-d6) δ ppm 11.32 (s, 3H), 10.80 (s, 1H), 3.47 (d, 2H, J=6.1 Hz), 3.10-3.17 (m, 2H), 1.17-1.78 (m, 2H).

Step 3: 1-(4-Fluorobenzyl)-N-hydroxy-N-(3-hydroxypropyl)-1H-pyrrolo[2,3-c]pyridine-5-carboxamide. The title compound was prepared by coupling of 1-(4-fluorobenzyl)-1H-pyrrolo[2,3-c]pyridine-5-carboxylic acid with N-(3-hydroxypropyl)hydroxylamine hydrochloride in a manner similar to step 8 of example 1. $^1$H NMR (CD$_3$OD) δ ppm 8.71 (s, 1H), 8.20 (s, 1H), 7.71 (d, 1H, J=3.0 Hz), 7.26 (m, 2H), 7.05 (d, 2H, J=8.9 Hz), 6.75 (d, 1H, J=3.0 Hz), 5.55 (s, 2H), 3.90 (m, 2H), 3.65 (t, 2H, J=6.0 Hz), 1.94-2.00 (m, 2H). LCMS (API-ES, M+H$^+$): 344.1. HRMS calcd for C$_{18}$H$_{19}$FN$_3$O$_3$ (M+H) 344.1405, found 344.1402. HPLC: 99.1% purity.

Example 31

1-(4-Fluorobenzyl)-3-[(4-fluorophenyl)(hydroxy)methyl]-N-hydroxy-1H pyrrolo[3,2-c]pyridine-6-carboxamide

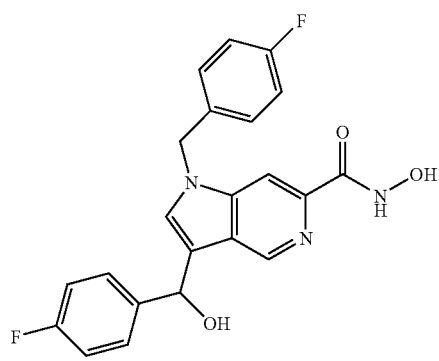

Step 1: 1-(4-Fluorobenzyl)-1H-pyrrole. To a stirred solution of pyrrole (10.0 mL, 9.67 g, 144.13 mmol) in dichloromethane (200 mL) were added tetrabutylammonium bromide (46.5 g, 144.13 mmol), 4-fluorobenzyl bromide (17.7 mL, 158.54 mmol) and 50% NaOH aqueous solution (120 mL) with cooling in an ice-water bath. The resulting mixture was heated to reflux for 5 hr. After cooling down, it was quenched with saturated aqueous NH$_4$Cl solution (200 mL), and extracted with dichloromethane (300 mL). The organic extract was dried over sodium sulfate, concentrated in vacuo and purified by flash chromatography. Elution with dichloromethane:ethyl acetate:hexanes (1:1:5) provided the title compound (20 g, 79% yield). $^1$H NMR (CDCl$_3$) δ ppm 6.96-7.09 (m, 4H), 6.67 (d, 2H, J=2.0 Hz), 6.19 (t, 2H, J=2.0 Hz), 5.03 (s, 2H). LCMS (APCI, M+H$^+$): 176.1.

Step 2: Ethyl 1-(4-fluorobenzyl)-1H-pyrrolo[3,2-c]pyridine-6-carboxylate. A solution of 1-(4-fluorobenzyl)-1H-pyrrole (11.1 g, 63.4 mmol), ethyl 3-dimethylamino-2-(dimethylamino-methyleneamino)-acrylate (14.84 g, 69.7 mmol) [prepared according to W. Kantlehner, F. Wagner, H. Bredereck, *Liebigs Ann. Chem.* 1980, 344-357] and trifluoroacetic acid (19.4 mL, 253.6 mmol) in acetic acid (80 mL) was stirred for 16 h at ambient temperature. Then the solution was heated to reflux for 4 hr. After cooling down, it was concentrated. The residue was poured into satd. potassium carbonate solution (1000 mL) and extracted with ethyl acetate (3×500 mL). The combined organic extracts were washed with brine (2×500 mL), dried over sodium sulfate, and concentrated. Purification by column chromatography with toluene:acetonitrile (2:1) provided the title compound. (3.6 g, 19% yield). $^1$H NMR (CDCl$_3$) δ ppm 9.15 (s, 1H), 8.23 (s, 1H), 7.37 (d, 1H, J=3.0 Hz), 7.0-7.11 (m, 4H), 6.83 (d, 1H, J=3.0 Hz), 5.40 (s, 2H), 4.52 (q, 2H, J=7.0 Hz), 1.48 (t, 3H, J=7.0 Hz). LCMS (APCI, M+H$^+$): 299.

Step 3: Ethyl 3-(4-fluorobenzoyl)-1-(4-fluorobenzyl)-1H-pyrrolo[3,2-c]pyridine-6-carboxylate.

To a stirred solution of ethyl 1-(4-fluorobenzyl)-1H-pyrrolo[3,2-c]pyridine-6-carboxylate (4.0 g, 13.4 mmol) in dichloromethane (60 mL) were added aluminum chloride (3.6 g, 26.8 mmol) and 4-fluorobenzoyl bromide (3.2 mL, 26.8 mmol). The resulting mixture was stirred for three days at ambient temperature. It was quenched with ice-water (100 mL), and extracted with dichloromethane (3×100 mL). The combined organic extracts were washed with water (2×100 mL), dried over sodium sulfate, concentrated in vacuo and purified by flash chromatography. Elution with hexane:ethyl acetate (1:1) provided the title compound as a solid (2.2 g, 39% yield). $^1$H NMR (CDCl$_3$) δ ppm 9.62 (s, 1H), 8.23 (s, 1H), 7.85-7.87 (m, 2H), 7.74 (s, 1H), 7.12-7.18 (m, 4H), 7.03-7.06 (m, 2H), 5.43 (s, 2H), 4.51 (q, 2H, J=7.2 Hz), 1.47 (t, 3H, J=7.2 Hz). LCMS (APCI, M+H$^+$): 421.1.

Step 4: Ethyl 1-(4-fluorobenzyl)-3-[(4-fluorophenyl)(hydroxy)methyl]-1H-pyrrolo[3,2-c]pyridine-6-carboxylate and ethyl 1-(4-fluorobenzyl)-3-[(4-fluorobenzyl]-1H-pyrrolo[3,2-c]pyridine-6-carboxylate. To ethyl 3-(4-fluorobenzoyl)-1-(4-fluorobenzyl)-1H-pyrrolo[3,2-c]pyridine-6-carboxylate (2.2 g, 5.24 mmol) in tetrahydrofuran (60 mL) were added borane tert-butylamine complex (4.6 g, 52.4 mmol) and two drops of methanol. The resulting solution was heated at reflux for 3 days. After cooling down, the reaction mixture was quenched with saturated aqueous ammonium chloride solution (50 mL), and extracted with ethyl acetate (3×100 mL). The organic layer was dried over sodium sulfate, and concentrated. Purification by chromatography with ethyl acetate provided the title compounds ethyl 1-(4-fluorobenzyl)-3-[(4-fluorophenyl)(hydroxy)methyl]-1H-pyrrolo[3,2-c]pyridine-6-carboxylate (0.9 g, 40% yield), $^1$H NMR (CDCl$_3$) δ: 8.77 (s, 1H), 8.21 (s, 1H), 7.57 (s, 1H), 7.46-7.48 (m, 2H), 7.23-7.25 (m, 2H), 7.11-7.19 (m, 4H), 5.99-6.06 (m, 1H), 5.51 (s, 2H), 4.29 (q, 2H, J=7.0 Hz), 1.30 (t, 3H, J=7.0 Hz). LCMS (API-ES, M+H$^+$): 423, and ethyl 1-(4-fluorobenzyl)-3-[(4-fluorobenzyl]-1H-pyrrolo[3,2-c]pyridine-6-carboxylate (0.8 g, 38% yield), $^1$H NMR (CDCl$_3$) δ ppm 8.79 (s, 1H), 8.22 (s, 1H), 7.61 (s, 1H), 7.31-7.33 (m, 2H), 7.19-7.24 (m, 2H), 7.10-7.16 (m, 4H), 5.52 (s, 2H), 4.30 (q, 2H, J=7.0 Hz), 4.14 (s, 2H), 1.31 (t, 3H, J=7.0 Hz). LCMS (API-ES, M+H$^+$): 407.0.

Step 5: 1-(4-Fluorobenzyl)-3-[(4-fluorophenyl)(hydroxy)methyl]-N-hydroxy-1H-pyrrolo[3,2-c]pyridine-6-carboxamide. The title compound was prepared from ethyl 1-(4-fluorobenzyl)-3-[(4fluorophenyl)(hydroxy)methyl]-1H-pyrrolo[3,2-c]pyridine-6-carboxylate using the method of step 7 in example 16. $^1$H NMR (DMSO-d6) δ: 11.16 (s, 1H), 8.90 (s, 1H), 8.62 (s, 1H), 8.06 (s, 1H), 7.49-7.52 (m, 3H), 7.23-7.26 (m, 2H), 7.11-7.19 (m, 4H), 5.96-6.06 (m, 1H), 5.49 (s, 2H). LCMS (APCI, M+H$^+$): 410.0. Anal. (C$_{22}$H$_{17}$F$_2$N$_3$O$_3$) C, H, N.

Example 32

1,3-Bis(4-fluorobenzyl)-N-hydroxy-1H-pyrrolo[3,2-c]pyridine-6-carboxamide

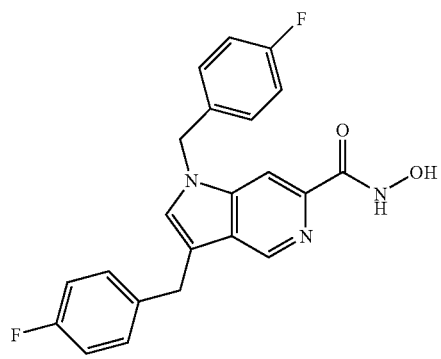

The title compound was prepared from ethyl 1-(4-fluorobenzyl)-3-[(4-fluorobenzyl]-1H-pyrrolo[3,2-c]pyridine-6-carboxylate using the methods of step 7 of example 16. $^1$H NMR (DMSO-d6) δ: 11.16 (s, 1H), 8.92 (s, 1H), 8.65 (s, 1H), 8.08 (s, 1H), 7.53 (s, 1H), 7.32-7.34 (m, 2H), 7.21-7.24 (m, 2H), 7.07-7.16 (m, 4H), 5.50 (s, 2H), 4.13 (s, 2H). LCMS (API-ES, M+H$^+$): 394.0. Anal. (C$_{22}$H$_{17}$F$_2$N$_3$O$_2$·0.5H$_2$O)C, H, N.

Example 33

1-(4-Fluorobenzyl)-N-hydroxy-N-methyl-3-[(2-methyl-3-oxopiperazin-1-yl)methyl]-1H-pyrrolo[2,3-c]pyridine-5-carboxamide

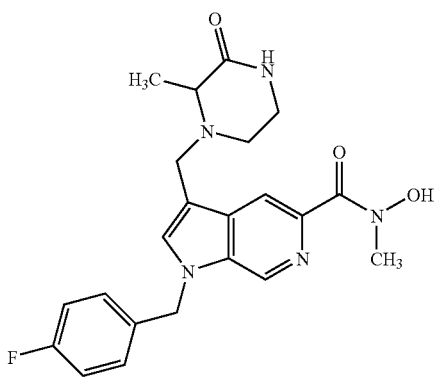

A solution of methyl 1-(4-fluorobenzyl)-3-formyl-1H-pyrrolo[2,3-c]pyridine-5-carboxylate (312 mg, 1.0 mmol, 1.0 eq) in 4 mL anhydrous dichloromethane) was mixed with a solution of 3-methylpiperazin-2-one (114 mg, 1.0 mmol, 1.0 eq) in 4 mL dichloromethane. After the reaction mixture was stirred for 1 h at room temp., sodium triacetoxyborohydride (530 mg, 2.5 mmol, 2.5 eq.) was added, and the resulting mixture was stirred at room temp. overnight. The solvent was removed under reduced pressure, and the residue was dissolved in 8 mL of a 6:3:1 (v/v) mixture of ethylacetate/dichloromethane/methanol. The organic phase was washed with 8 mL of 1.0 M aqueous potassium carbonate, and the aqueous layer was extracted with the 6:3:1 mixture of ethylacetate/dichloromethane/methanol (2×8 mL). The organic phases were combined, dried over anhydrous sodium sulfate, and concentrated to dryness under reduced pressure. The residue was dissolved in 4 mL methanol. Then 1 mL 3.0 M LiOH (3.0 eq) solution was added. After the solution was stirred at rt for 3 h, 3 mL 1.0 M HCl (3.0 eq) was added, and the mixture was stirred for another 15 min. Then the solvent and excess HCl were removed under reduced pressure. The residue was dissolved in 4 mL DMF, and N-methylhydroxyamine (4 mL, 0.25 M in DMF, 1.0 eq), HATU (4 mL, 0.25 M in DMF, 1.0 eq), and triethylamine (0.42 mL, neat, 3 eq) were added. The reaction mixture was stirred at 60° C. for 16 h. The solvent was removed under reduced pressure, and the residue was subjected to prep HPLC for purification to afford the title compound (66 mg, 24% overall yield). $^1$HNMR (300 MHz, MeOH-d$_4$) δ ppm: 9.08 (s, 1H), 8.85 (b, 1H), 8.32 (s, 1H), 7.37-7.25 (m, 2H), 7.08-6.96 (m, 2H), 5.62 (s, 2H), 4.75 (d, 1H), 4.47 (d, 1H), 3.90-3.77 (m, 1H), 3.54-3.32 (m, 2H), 3.35 (s, 3H), 3.25-3.12 (m, 2H), 1.65 (d, 3H). HRMS calcd for $C_{22}H_{25}N_5O_3F$ (M+H$^+$) 426.1941, found 426.1947. HPLC: >99% purity.

Example 34

(4-Fluorobenzyl)-N-hydroxy-N-methyl-3-{[(1R,5S)-2-oxo-3,8-diazabicyclo[3.2.1]oct-8-yl]methyl}-1H-pyrrolo[2,3-c]pyridine-5-carboxamide

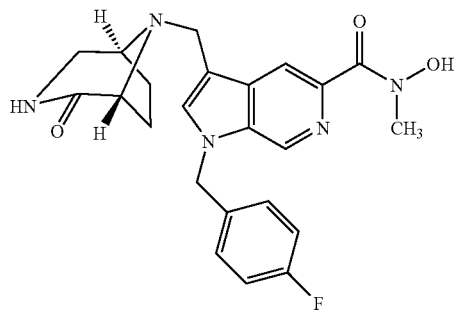

The title compound was prepared in the same manner as described in the example 33 using (1R,5S)-3,8-diazabicyclo[3.2.1]octan-2-one instead of 3-methylpiperazin-2-one. $^1$HNMR (300 MHz, MeOH-d$_4$) δ ppm: 9.08 (s, 1H), 8.78 (b, 1H), 8.35 (s, 1H), 7.37-7.25 (m, 2H), 7.10-6.95 (m, 2H), 5.63 (s, 2H), 4.60 (s, 2H), 4.28-4.13 (m, 1H), 3.98-3.88 (m, 1H), 3.73-3.58 (m, 1H), 3.40 (s, 3H), 3.30-3.18 (m, 1H), 2.60-2.42 (m, 2H), 2.35-2.20 (m, 1H), 2.18-2.03 (m, 1H). HRMS calcd for $C_{23}H_{25}N_5O_3F$ (M+H$^+$) 438.1941, found 438.1968. HPLC: 97% purity.

Example 35

1-(4-Fluorobenzyl)-N-hydroxy-1H-pyrazolo[3,4-c]pyridine-5-carboxamide

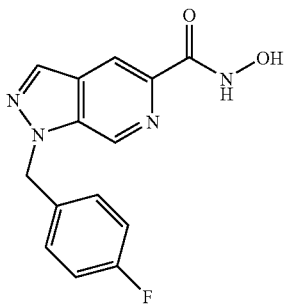

Step 1: Methyl 1H-pyrazolo[3,4-c]pyridine-5-carboxylate. To a stirring solution of methyl 4-methyl-5-nitro-pyridine-2-carboxylate (3.00 g) in THF (40 mL) was added Pd/C catalyst (300 mg). The flask was evacuated and back-filled with hydrogen from a balloon three times and then stirred under hydrogen overnight. The mixture was filtered through Celite, and the filter cake was extracted several times with ethyl acetate. The combined organic extracts were concentrated and the resulting white powder (2.58 g, 100%) consisting of methyl 5-amino-4-methyl-pyridine-2-carboxylate was used in the next step without further purification and characterization. To a stirring solution of methyl 5-amino-4-methyl-pyridine-2-carboxylate (2.58 g, 15.53 mmol) in AcOH (60 mL), was added 2.0 M sodium nitrite in water (9.3 mL, 18.63 mmol) and the mixture was stirred for 4 h at room temperature. The acetic acid and other volatiles were removed at high vacuum, the resulting solid was suspended in water and filtered to give the title compound as a yellowish solid (2.18 g, 79% yield). $^1$HNMR (DMSO-d6): δ ppm 13.98 (bs, 1H), 9.10 (s, 1H), 8.57 (s, 1H), 8.39 (s, 1H), 3.88 (s, 3H). LCMS (API-ES M+Na$^+$) 200.

Step 2: Methyl 1-(4-fluorobenzyl)-1H-pyrazolo[3,4-c]pyridine-5-carboxylate. To a stirring solution of methyl 1H-pyrazolo[3,4-c]pyridine-5-carboxylate (0.628 g, 3.545 mmol) in DMF (15 mL) was added 4-fluorobenzyl bromide (0.442 mL, 3.545 mmol) followed by potassium carbonate (0.490 g, 3.545 mmol), and the mixture was stirred overnight at room temperature. Saturated sodium bicarbonate was added and the mixture was extracted with ethyl acetate (3×50 mL). The combined organic extracts were dried over sodium sulfate, filtered and concentrated. The crude solid was purified by flash column chromatography (silica gel, 0-20% acetonitrile:chloroform v/v) to provide pure desired methyl 1-(4-fluorobenzyl)-1H-pyrazolo[3,4-c]pyridine-5-carboxylate (0.66 g, 30% yield over three steps) and the undesired methyl 2-(4-fluoro-benzyl)-2H-pyrazolo[3,4-c]pyridine-5-carboxylate (0.73 g, 33% yield) as white solids. Methyl 1-(4-fluorobenzyl)-1H-pyrazolo[3,4-c]pyridine-5-carboxylate: $^1$HNMR (CDCl$_3$, 300 MHz) δ ppm 8.91 (s, 1H), 8.59 (s, 1H), 8.22 (s, 1H), 7.26 (m, 2H), 7.02 (m, 2H), 5.69 (s, 2H), 4.03 (s, 3H). LCMS (API-ES M+H$^+$) 286. Methyl 2-(4-fluoro-benzyl)-2H-pyrazolo[3,4-c]pyridine-5-carboxylate: $^1$HNMR (CDCl$_3$, 300 MHz): 6 ppm 9.32 (s, 1H), 8.51 (s, 1H), 8.10 (s, 1H), 7.36 (m, 2H), 7.09 (m, 2H), 5.65 (2H, s), 4.02 (s, 3H). LCMS (API-ES M+H$^+$) 286.

Step 3: 1-(4-Fluorobenzyl)-N-hydroxy-1H-pyrazolo[3,4-c]pyridine-5-carboxamide. To a stirring solution of methyl 1-(4-fluorobenzyl)-1H-pyrazolo[3,4-c]pyridine-5-carboxylate (96 mg, 0.33 mmol) in methanol (4 mL) was added a 50% v/v solution of hydroxylamine in water (2 mL) followed by 10% sodium hydroxide solution in water (1 mL). The mixture was stirred for 2 hours, then 10% hydrochloric acid solution in water (1 mL) was added until a neutral pH was obtained, and the mixture was concentrated under reduced pressure. Methanol was added and the mixture was purified by reverse phase preparative HPLC (Dionex, 0-40% acetonitrile:water v/v, 40 minutes) to provide a white solid (50 mg, 52% yield). $^1$H NMR (DMSO-d6): δ ppm 9.22 (s, 1H), 8.39 (s, 1H), 8.37 (s, 1H), 7.37 (m, 2H), 7.15 (m, 2H), 5.83 (s, 2H). Anal. HPLC: >95% (@ 254, 222 nM). HRMS calcd for C$_{14}$H$_{11}$FN$_4$O$_2$ (M+H) 287.0939, found 287.0936.

Example 36

1-(4-Fluorobenzyl)-N-hydroxy-N-methyl-1H-pyrazolo[3,4-c]pyridine-5-carboxamide

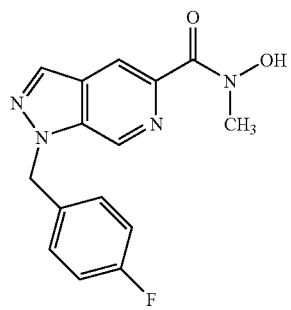

To a stirring solution of methyl 1H-pyrazolo[3,4-c]pyridine-5-carboxylate (100 mg, 0.351 mmol) in methanol (4 mL) was added a 3.0 M solution of LiOH in water (0.351 mL, 1.05 mmol) and the mixture was stirred overnight, then 1.0 M hydrochloric acid in diethyl ether was added (1.05 mL, 1.05 mmol) and the solvent was evaporated under reduced pressure. The crude solid was dissolved in DMF and N-methylhydroxylamine hydrochloride (58 mg, 0.698 mmol) was added followed by triethylamine (214 mL, 1.154 mmol) and HATU (266 mg, 0.698 mmol). The mixture was stirred overnight. Water was added and the mixture was extracted with dichloromethane (3×20 mL). The combined organic extracts were dried over sodium sulfate, filtered and concentrated. The crude solid was dissolved in DMSO and purified by reverse phase preparative HPLC to provide a white solid (105 mg, 100% yield). $^1$H NMR (DMSO-d6): & 10.24 (bs, 1H), 9.26 (s, 1H), 8.07 (s, 1H), 7.37 (m, 2H), 7.15 (m, 2H), 5.81 (s, 2H), 3.31 (s, 3H). Anal. HPLC: >95% (@ 254, 222 nM). HRMS calcd for C$_{15}$H$_{13}$FN$_4$O$_2$ (M+H) 301.1088, found 301.1096.

Example 37

1-(2,4-Difluorobenzyl)-N-methoxy-3-[(4-methylpiperazin-1-yl)methyl]-1H-pyrrolo[2,3-c]pyridine-5-carboxamide

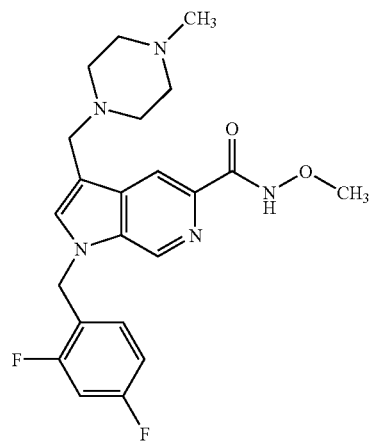

The title compound was prepared by coupling of 1-(2,4-difluorobenzyl)-3-[(4-methylpiperazin-1-yl)methyl]-1H-pyrrolo[2,3-c]pyridine-5-carboxylic acid and O-methylhydroxylamine hydrochloride in analogy to step 2 of example 17. $^1$H NMR (MeOH-d$_4$) δ 8.77 (s, 1H), 8.43 (s, 1H), 7.59 (s, 1H), 7.27-7.03 (m, 1H) 7.01-6.93 (m, 2H), 5.55 (s, 2H), 3.82 (s, 5H), 2.82 (m, 4H), 2.66 (m, 4H), 2.50 (s, 3H). LCMS (APCI, M+H$^+$): 430.2. Anal. (C$_{22}$H$_{22}$F$_2$N$_5$O$_3$×1.5H$_2$O× 0.8AcOH)C, H, N.

Example 38

4-[(E)-2-Ethoxyvinyl]-1-(4-fluorobenzyl)-N-hydroxy-1H-pyrrolo[2,3-c]pyridine-5-carboxamide

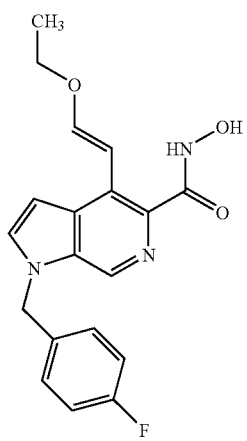

Step 1: Ethyl 1-(4-fluorobenzyl)-2-methyl-1H-pyrrole-3-carboxylate.

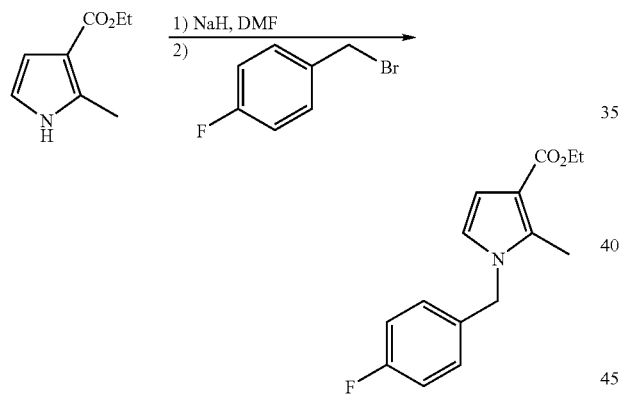

To a solution of ethyl 2-methyl-1H-pyrrole-3-carboxylate (106.26 g, 0.694 mol) (prepared by the method of: Wee, A. G. H.; Shu, A. Y. L.; Djerassi, C. *J. Org. Chem.* 1984, 49, 3327-3336) in anhydrous DMF (1.0 L), under nitrogen, was added sodium hydride (60% in oil, 30.5 g, 0.763 mol, 1.1 eq.) in 5 portions over 1 hour. When gas evolution ceased, 4-fluorobenzyl bromide (131.13 g, 0.694 mol) in anhydrous DMF (0.2 L) was added via pressure equalized addition funnel over 45 minutes. The mixture was allowed to stir at room temperature for 16 hours after the addition was complete, then was poured into water (1.4 L) in a 4 L separatory funnel. The mixture was extracted with diethyl ether (5×1.0 L) and the combined organic phases were washed with brine (3.0 L) and dried ($Na_2SO_4$). Filtration, rinsing of the filter cake with diethyl ether (0.5 L) and concentration in vacuo (approx. 20 Torr) gave the crude product and DMF. Residual DMF was removed on a cold finger trap rotary evaporator at full pump vacuum in a 40° C. water bath to give the crude benzylate pyrrole as an orange oil. The crude product was purified by chromatography on a column of silica gel (125 mm OD, 1 kg 230-400 mesh, packed with hexanes-EtOAc 95:5) eluted with hexanes:EtOAc (95:5, 2.0 L) and hexanes:EtOAc (90:10, 8.0 L) while collecting 500 mL fractions, using the flash technique. Fractions 4-18 were combined to afford ethyl 1-(4-fluorobenzyl)-2-methyl-1H-pyrrole-3-carboxylate (172.3 g, 95%) as a clear, pale yellow, viscous liquid.

TLC (Merck, hexanes:EtOAc 85:15, UV-+, cerium molybdate-+): $R_f$=0.26

LCMS (Eclipse XDB-C8, 0.8 mL/min, gradient 80:20 to 5:95$H_2O$ (+0.1% HOAc):$CH_3CN$—5 minutes, APCI, +mode): RT—3.711 min, m/e=262.1 (base), 263.2 (30)

$^1$H-NMR (300 MHz, $CDCl_3$): δ=1.33 (t, J=7.06 Hz, 3H), 2.43 (s, 3H), 4.26 (q, J=7.06 Hz, 2H), 5.00 (s, 2H), 6.52 (d, J=3.20 Hz, 1H), 6.58 (d, J=3.20 Hz, 1H), 6.92-7.04 (m, 4H).

Step 2: Ethyl 4,5-dibromo-2-(bromomethyl)-1-(4-fluorobenzyl)-1H-pyrrole-3-carboxylate.

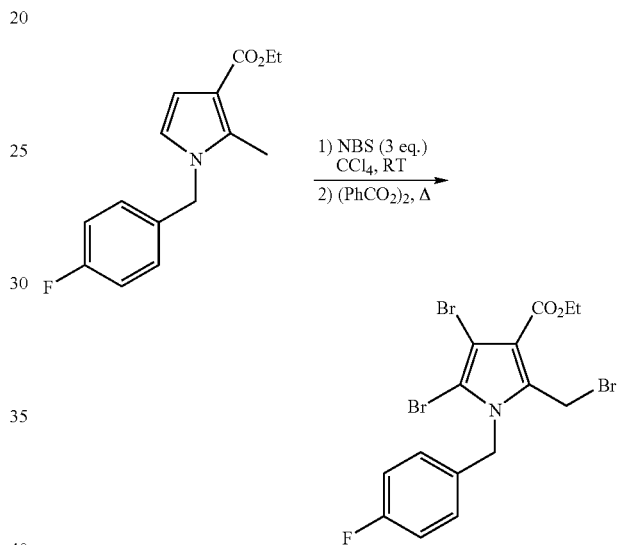

To NBS (267.5 g, 1.503 mol, 3 eq.) in anhydrous $CCl_4$ (0.5 L) in a 3 L, 3N round bottom flask, equipped with an internal temperature monitoring probe, addition funnel, and reflux condenser, was added ethyl 1-(4-fluorobenzyl)-2-methyl-1H-pyrrole-3-carboxylate (130.9 g, 0.501 mol) in anhydrous $CCl_4$ (0.5 L) over 15 minutes. The internal temperature rose to 43° C. during the addition and a transient red color developed, which faded upon completion of the addition. The mixture was allowed to stir for 15 minutes, then benzoyl peroxide (1.21 g, 5 mmol, 0.01 eq.) was added and the mixture was heated to an internal temperature of 77° C. (reflux) and maintained at that temperature for 1.5 hours. At this time point LCMS (APCI) indicated complete reaction. The mixture was cooled to room temperature, the precipitated solid was removed by filtration, the filter cake was rinsed with $CCl_4$ (0.3 L), and the combined filtrates were concentrated in vacuo to give the crude tribromide as a red-brown semi-solid. The crude material was treated with dichloromethane (50 mL) and hexanes (250 mL) to produce a tan solid and a red-brown liquid. The solid was isolated by filtration, was rinsed with dichloromethane:hexanes (10:90, 0.5 L) and was dried in vacuo at room temperature to furnish 170.03 g (69%) of ethyl 4,5-dibromo-2-(bromomethyl)-1-(4-fluorobenzyl)-1H-pyrrole-3-carboxylate as a pale, tan solid. The filtrates were concentrated in vacuo to give a mother liquor that was purified by chromatography on a column of silica gel (70 mm OD, 400 g 230-400 mesh, hexanes:EtOAc 90:10, 250 mL fractions) using the flash technique. Fractions 3-6 provided an additional 29.57 g of ethyl 4,5-dibromo-2-(bromomethyl)-1-(4-fluorobenzyl)-1H-pyrrole-3-carboxylate as a pale, tan solid. Total: 199.6 g (81%).

TLC (Merck, hexanes:EtOAc 90:10, UV-+, cerium molybdate-+): $R_f$=0.33

LCMS (Eclipse XDB-C8, 0.8 mL/min, gradient 80:20 to 5:95$H_2O$ (+0.1% HOAc):$CH_3CN$—5 minutes, APCI, +mode): RT—4.109 min, m/e=416.0 (50), 417.9 (base), 419 (50), M-Br $^1$H-NMR (300 MHz, $CDCl_3$): δ=1.39 (t, J=7.16 Hz, 3H), 4.35 (q, J=7.16 Hz, 2H), 4.77 (s, 2H), 5.36 (s, 2H), 6.96-7.07 (m, 4H).

Step 3: Ethyl 4,5-dibromo-1-(4-fluorobenzyl)-2-({(2-methoxy-2-oxoethyl)[(4-methylphenyl)sulfonyl]amino}methyl)-1H-pyrrole-3-carboxylate

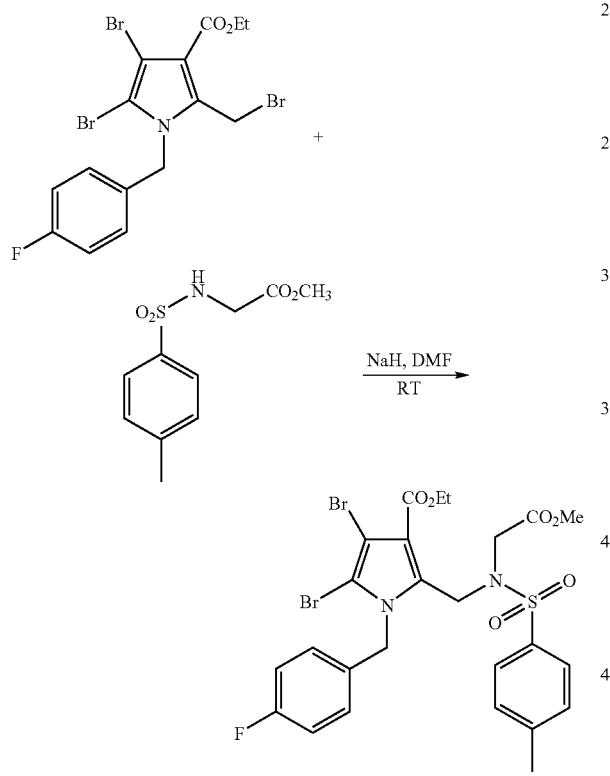

To a stirring solution of methyl N-[(4-methylphenyl)sulfonyl]glycinate (51.75 g, 0.213 mol, prepared by the method of: Ginzel, K. D.; Brungs, P.; Steckhan, E. Tetrahedron 1989, 45, 1691-1701) in anhydrous DMF (0.5 L) was added NaH (60% in oil, 8.59 g, 0.215 mol) in one portion. The mixture was allowed to stir for 30 minutes (warms and returns to room temperature) at which time a solution ethyl 4,5-dibromo-2-(bromomethyl)-1-(4-fluorobenzyl)-1H-pyrrole-3-carboxylate (105.92 g, 0.213 mol) in anhydrous DMF (0.5 L) was added over 1 hour. The mixture was allowed to stir at room temperature for 16 hours, then the DMF was removed in vacuo (approx 2 Torr, 40° C. water bath) and the oily residue was dissolved in dichloromethane (0.75 L), the solution was washed with saturated aq. $NH_4Cl$ (0.5 L), brine (0.5 L), and dried ($Na_2SO_4$). Filtration and concentration in vacuo provided the crude alkylated material as a viscous reddish oil. The crude material was heated in the presence of MeOH (0.75 L) until the MeOH was boiling, then dichloromethane was added slowly until solution was achieved. The red solution was cooled to room temperature (see off-white crystals) and the crystallization was completed by cooling in a refrigerator (4° C.) for 16 hours. The ivory solid was isolated by filtration, the solid was rinsed with diethyl ether:hexanes (0.5 L, 10:90 v/v) and the solid was dried in a vacuum oven (approx. 20 Torr, 50° C.) overnight to furnish ethyl 4,5-dibromo-1-(4-fluorobenzyl)-2-({(2-methoxy-2-oxoethyl)[(4-methylphenyl)sulfonyl]amino}methyl)-1H-pyrrole-3-carboxylate (108.2 g, 77%) as a free flowing, fine, ivory solid. TLC (Merck, hexanes:EtOAc 75:25, UV-+, cerium molybdate-+-purple): $R_f$=0.38 LCMS (Eclipse XDB-C8, 0.8 mL/min, gradient 80:20 to 5:95$H_2O$ (+0.1% HOAc):$CH_3CN$—5 minutes, ESI, +mode): RT—4.436 min, m/e=680.8 (55), 681.8 (18), 682.9 (base), 683.9 (30), 684.8 (62), 686.8 (10)—M+Na $^1$H-NMR (300 MHz, $CDCl_3$): δ=1.24 (t, J=7.16 Hz, 3H), 2.14 (s, 3H), 3.49 (s, 3H), 3.89 (s, 2H), 4.19 (q, J=7.16 Hz, 2H), 4.55 (s, 2H), 7.02 (d, J=2.45 Hz, 2H), 7.04 (s, 2H), 7.28 (d, J=8.19 Hz, 2H), 7.59 (d, J=8.19 Hz, 2H)

Step 4: Methyl 2,3-dibromo-1-(4-fluorobenzyl)-4-hydroxy-1 pyrrolo[2,3-c]pyridine-5-carboxylate

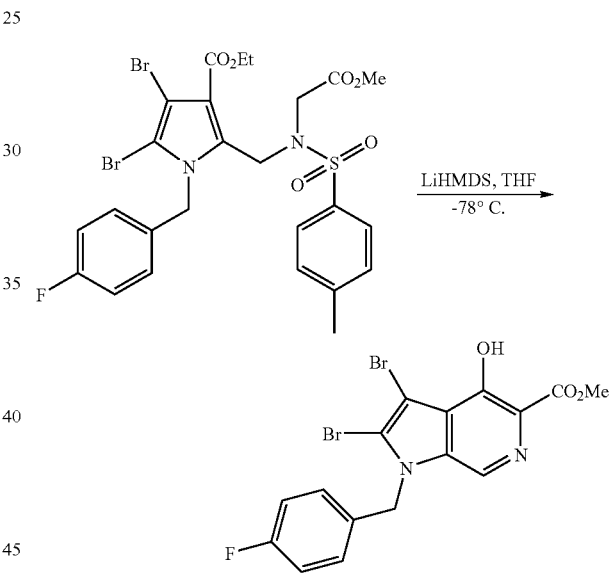

To solid LiHMDS (61.27 g, 0.366 mol), in a 3 L 3-neck round bottom flask equipped with a 0.5 L pressure equalized addition funnel and an internal temperature probe, was added anhydrous THF (0.5 L). The mixture was placed under nitrogen and immersed in a dry ice-i-PrOH bath. The solution was allowed to stir until the internal temperature reached –78° C. (1.25 h). To this stirring cold solution was added a solution of ethyl 4,5-dibromo-1-(4-fluorobenzyl)-2-({(2-methoxy-2-oxoethyl)[(4-methylphenyl) sulfonyl]amino}methyl)-1H-pyrrole-3-carboxylate (107.43 g, 0.163 mol) in anhydrous THF (0.5 L) at such a rate that the internal temperature does not exceed –70° C. (2 hours). During the course of the addition, a yellow color was first noticed giving way to an orange/yellow solution, which then produced a precipitate and an orange/yellow solution. The reaction was allowed to stir for 30 minutes after the addition was complete, at which point LCMS (sample taken at 15 minutes after addition) indicated the reaction was complete. The mixture was rapidly poured into a 6 L separatory funnel, which had been charged with saturated aq. $NH_4Cl$ (1.5 L) and dichloromethane-methanol (95:5, 2 L). The mixture was rapidly shaken to distribute the reaction mixture and quench the reaction. The organic phase was separated, the aq. layer was extracted with dichloromethane-methanol (95:5 v/v, 1 L). The combined organic phases were filtered to remove a fine white precipitate and then dried ($Na_2SO_4$). Concentration in vacuo afforded the crude cyclized material as a yellow solid, which was triturated with EtOH (0.6 L) and the resulting white solid was isolated by filtration, washed with anhydrous ethyl ether (50 mL), and dried in a vacuum oven (approx. 20 Torr, 50° C., 16 hours) to give 40.51 g (54.4%) of methyl 2,3-dibromo-1-(4-fluorobenzyl)-4-hydroxy-1H-pyrrolo[2,3-c]pyridine-5-carboxylate as a powdery white solid after drying in a vacuum oven. The filtrate was concentrated in vacuo and the residue was triturated with diethyl ether/hexanes (50:50 v/v, 0.25 L) to give 10.69 g (14.3%) of methyl 2,3-dibromo-1-(4-fluorobenzyl)-4-hydroxy-1H-pyrrolo[2,3-c]pyridine-5-carboxylate as a powdery white solid after drying in a vacuum oven (approx. 20 Torr, 50° C., 16 hours). The filtrate was again treated under the same conditions (0.1 L, 50:50 v/v diethyl ether-hexanes) to give an additional 2.39 g (3.2%) for a total yield of 53.59 g (72%).

TLC (Merck, $CH_2Cl_2$:EtOAc 50:50, UV-+, cerium molybdate-+): $R_f$=0.57

LCMS (Eclipse XDB-C8, 0.8 mL/min, gradient 80:20 to 5:95$H_2O$ (+0.1% HOAc):$CH_3CN$—5 minutes, ESI, +mode): RT—3.790 min, m/e=456.9 (55), 458.8 (base), 459.9 (15)—M+, 480.9—M+Na.

$^1$H-NMR (300 MHz, $CDCl_3$): δ=4.03 (s, 3H), 5.48 (s, 2H), 6.96-7.04 (m, 2H), 7.05-7.12 (m, 2H), 8.28 (s, 1H), 11.60 (s, 1H).

Step 5: Methyl 1-(4-fluorobenzyl)-4-hydroxy-1H-pyrrolo[2,3-c]pyridine-5-carboxylate

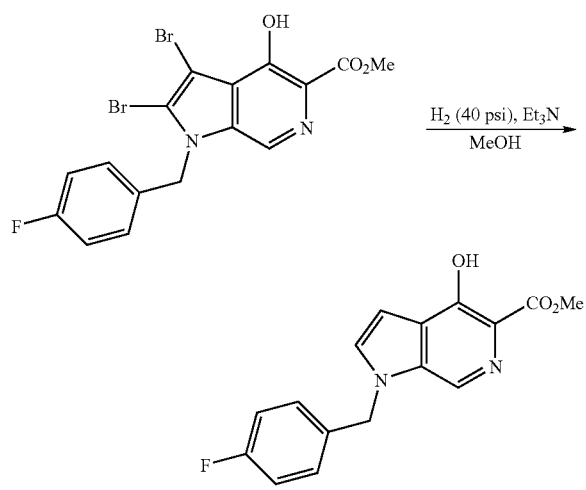

To a 2.5 L Parr flask was added methyl 2,3-dibromo-1-(4-fluorobenzyl)-4-hydroxy-1H-pyrrolo[2,3-c]pyridine-5-carboxylate (67.28 g, 0.147 mol), methanol (1.5 L) and triethyl amine (32.70 g, 0.323 mol, 2.2 eq.). Into this mixture was bubbled nitrogen for 10 minutes, then 10% Pd/C (15.6 g) was carefully added. The bottle was placed on a Parr apparatus, evacuated/purged with nitrogen (3×) and hydrogen was added to 40 psi. Shaking was commenced and after 5 minutes the pressure had gone to zero and the bottle was re-pressurized to 40 psi. This was repeated 2× at which point the pressure lowered to 35 psi and remained. TLC and LCMS then indicated the reaction was complete (total time ca. 1 hour). The palladium was removed by filtration through a pad of Celite, the filter cake was rinsed with dichloromethane (1.0 L) and the combined filtrates were concentrated in vacuo to give the crude product plus amine salts. The mixture was taken into EtOAc (2 L) and water (1.0 L), the organic phase was separated, the aqueous layer was extracted with EtOAc (0.6 L), and the combined organic phases were washed with brine (1.0 L) and dried ($Na_2SO_4$). Filtration and concentration in vacuo gave a powdery white solid which was dried in a vacuum oven (approx. 20 Torr, 50° C., 16 hours) to afford 43.13 g (98%) of methyl 1-(4-fluorobenzyl)-4-hydroxy-1H-pyrrolo[2,3-c]pyridine-5-carboxylate as a free flowing, powdery white solid.

TLC (Merck, $CH_2Cl_2$:EtOAc 50:50, UV-+, cerium molybdate-+): $R_f$=0.45 (fluorescent blue)

LCMS (Eclipse XDB-C8, 0.8 mL/min, gradient 80:20 to 5:95 v/v $H_2O$ (+0.1% HOAc):$CH_3CN$—5 minutes, APCI, +mode): RT—3.217 min, m/e=301.1 (base, M+H).

$^1$H-NMR (300 MHz, $CDCl_3$): δ=4.02 (s, 3H), 5.36 (s, 2H), 6.83 (d, J=3.10 Hz, 1H), 6.96-7.04 (m, 2H), 7.07-7.13 (m, 2H), 7.17 (d, J=3.10 Hz, 1H), 8.31 (s, 1H), 11.40 (s, 1H).

Step 6: Methyl 1-(4-fluorobenzyl)-4-{[(trifluoromethyl) sulfonyl]oxy}-1H-pyrrolo[2,3-c]pyridine-5-carboxylate. To a stirred solution of the methyl 1-(4-fluorobenzyl)-4-hydroxy-1H-pyrrolo[2,3-c]pyridine-5-carboxylate (20.0 g, 66.7 mmol) and triethylamine (46.5 mL, 333 mmol) in dichloromethane (200 mL) at 0° C. was added trifluoromethanesulfonic anhydride (33.6 mL, 200 mmol) dropwisely and the reaction stirrred at 0° C. for 10 minutes. It was quenched with water and extracted with ethyl acetate. The organic layer was dried over sodium sulfate, filtered, concentrated, and purified by chromatography with ethyl acetate/hexanes (1/1) to provide the title compound as brown solid (25.28 g, 88% yield). $^1$H NMR ($CDCl_3$): δ; 8.73 (s, 1H), 7.39 (d, 1H), 7.18 (t, 2H), 7.05 (t, 2H), 6.80 (d, 1H), 5.43 (s, 2H), 4.02 (s, 3H). LCMS (API-ES, M+H$^+$): 433.0. HPLC: 96% purity.

Step 7: Methyl 4-[(E)-2-ethoxyvinyl]-1-(4-fluorobenzyl)-1H-pyrrolo[2,3-c]pyridine-5-carboxylate. To a stirred solution of methyl 1-(4-fluorobenzyl)-4-{[(trifluoromethyl)sulfonyl]oxy}-1H-pyrrolo[2,3-c]pyridine-5-carboxylate (1.4 g, 3.24 mmol) and (E)-2-ethoxyvinyl tributyltin [prepared according to A. Leusik, H. A. Budding, J. W. Marsman, *J. Organomet. Chem.*, 1967, 9, 285-294] (2.2 g, 6.48 mmol) in DMF (10 mL) under a nitrogen atmosphere were added triethylamine (0.48 mL, 3.24 mmol) and dichlorobis(triphenylphosphine)palladium(II) (0.24 g, 0.32 mmol). The resulting mixture was heated to 140° C. for 2 hours. It was quenched with water, and extracted with ethyl acetate three times. The combined organic extracts were washed with water (2×30 mL), dried over sodium sulfate, concentrated in vacuo and purified by Biotage flash chromatography. Elution with hexane:ethyl acetate (1:1) provided the title compound as brown glue (0.40 g, 35% yield). $^1$H NMR (MeOD) δ; 8.50 (s, 1H), 7.64 (d, 1H, J=3.3 Hz), 7.22 (t, 2H, J=6.8 Hz), 7.05 (t, 2H, J=6.8 Hz), 6.89 (d, 1H, J=3.3 Hz), 5.53 (s, 2H), 4.02 (q, 2H, J=7.1 Hz), 1.37 (t, 3H, J=7.1 Hz). LCMS (APCI, M+H$^+$): 355.2.

Step 8: 4-[(E)-2-Ethoxyvinyl]-1-(4-fluorobenzyl)-N-hydroxy-1H-pyrrolo[2,3-c]pyridine-5-carboxamide. The title compound was prepared from methyl 4-[(E)-2-ethoxyvinyl]-1-(4-fluorobenzyl)-1H-pyrrolo[2,3-c]pyridine-5-carboxylate in a manner similar to step 7 of example 16. $^1$H NMR (DMSO-d6) 6; 11.76 (d, 1H, J=1.9 Hz), 8.88 (d, 1H, J=1.9 Hz), 8.60 (s, 1H), 7.83 (d, 1H, J=3.0 Hz), 7.31 (t, 2H, J=8.9

Hz), 7.22 (d, 1H, J=13.2 Hz), 7.05 (t, 2H, J=8.9 Hz), 6.82 (d, 1H, J=3.0 Hz), 6.66 (d, 1H, J=13.2 Hz), 5.54 (s, 2H), 3.96 (q, 2H, J=7.0 Hz), 1.28 (t, 3H, J=7.0 Hz).

LCMS (APCI, M+H$^+$): 356. Anal. ($C_{19}H_{18}FN_3O_3$) C, H, N. HPLC: 95% purity.

Method 2

Step 1: Ethyl 4,5-dibromo-1-(4-fluorobenzyl)-2-({(2-ethoxy-2-oxoethyl)[(4-methylphenyl) sulfonyl]amino}methyl)-1H-pyrrole-3-carboxylate

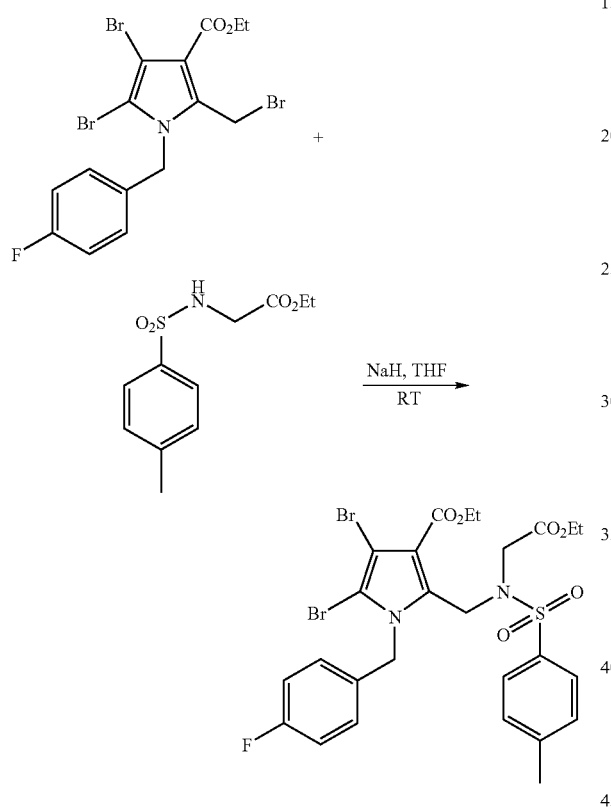

To a stirring solution of ethyl 4,5-dibromo-2-(bromomethyl)-1-(4-fluorobenzyl)-1H-pyrrole-3-carboxylate (104.0 g, 0.209 mol) and ethyl N-[(4-methylphenyl)sulfonyl]glycinate (53.7 g, 0.209 mol, prepared by the method of: Ginzel, K. D.; Brungs, P.; Steckhan, E. Tetrahedron 1989, 45, 1691-1701) in anhydrous THF (1.5 L) was added NaH (60% in mineral oil, 8.40 g, 0.210 mol) in several small portions. The mixture was allowed to stir at room temperature for 16 hours. It was quenched with aq. NH$_4$Cl solution, and extracted with ethyl acetate. The organic layer was dried over Na$_2$SO$_4$, concentrated and the residue was purified by column chromatography with ethyl acetate/hexane (1:4, v:v) to provide the title compound as glue-like material (124 g, 88% yield).

$^1$H NMR (CDCl$_3$) δ ppm 7.61 (d, J=4.7 Hz, 2H), 7.30 (d, J=5.7 Hz, 2H), 7.04 (d, J=5.6 Hz, 4H), 5.60 (s, 2H), 4.55 (s, 2H), 4.20 (q, J=7.1 Hz, 2H), 3.94 (q, J=7.2 Hz, 2H), 3.89 (s, 2H), 2.42 (s, 2H), 1.25 (t, J=7.2 Hz, 3H), 1.14 (t, J=7.1 Hz, 3H).

Step 2: Ethyl 2,3-dibromo-1-(4-fluorobenzyl)-4-hydroxy-1H-pyrrolo[2,3-c]pyridine-5-carboxylate

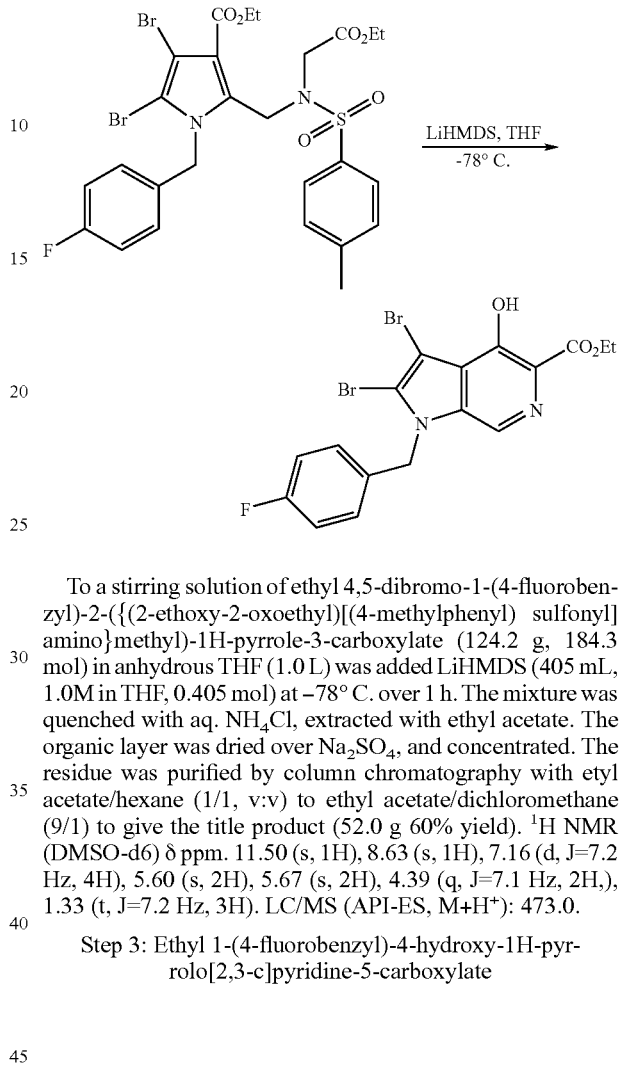

To a stirring solution of ethyl 4,5-dibromo-1-(4-fluorobenzyl)-2-({(2-ethoxy-2-oxoethyl)[(4-methylphenyl) sulfonyl]amino}methyl)-1H-pyrrole-3-carboxylate (124.2 g, 184.3 mmol) in anhydrous THF (1.0 L) was added LiHMDS (405 mL, 1.0M in THF, 0.405 mol) at –78° C. over 1 h. The mixture was quenched with aq. NH$_4$Cl, extracted with ethyl acetate. The organic layer was dried over Na$_2$SO$_4$, and concentrated. The residue was purified by column chromatography with etyl acetate/hexane (1/1, v:v) to ethyl acetate/dichloromethane (9/1) to give the title product (52.0 g 60% yield). $^1$H NMR (DMSO-d6) δ ppm. 11.50 (s, 1H), 8.63 (s, 1H), 7.16 (d, J=7.2 Hz, 4H), 5.60 (s, 2H), 5.67 (s, 2H), 4.39 (q, J=7.1 Hz, 2H,), 1.33 (t, J=7.2 Hz, 3H). LC/MS (API-ES, M+H$^+$): 473.0.

Step 3: Ethyl 1-(4-fluorobenzyl)-4-hydroxy-1H-pyrrolo[2,3-c]pyridine-5-carboxylate

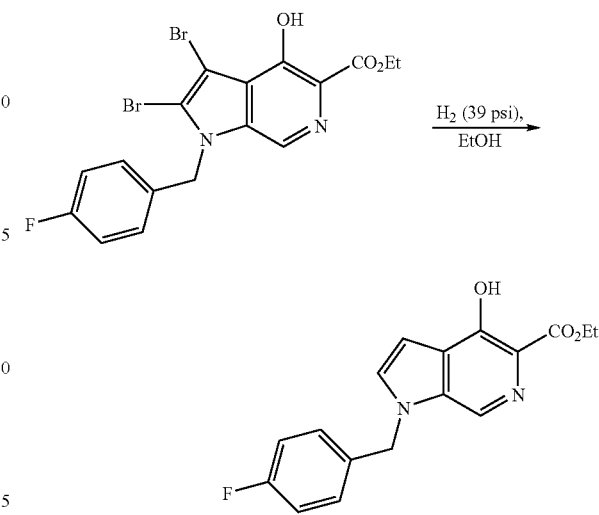

A suspension of ethyl 2,3-dibromo-1-(4-fluorobenzyl)-4-hydroxy-1H-pyrrolo[2,3-c]pyridine-5-carboxylate (52.0 g, 0.110 mol) and 10% Pd/C (0.5 g) in ethanol (2.0 L) was shaken in a Parr shaker under hydrogen (39 psi) for 23 h. The catalyst was removed by filtration. On concentration of the filtrate, the product precipitated out. It was collected by filtration and dried under vacuum to provide the title compound. (34 g, 98% yield) $^1$H NMR (DMSO-d6) δ ppm 11.66 (s, 1H), 8.89 (s, 1H), 8.14 (d, J=3.0 Hz, 1H) 7.37 (d, J=5.7 Hz, 2H), 7.19 (d, J=6.6 Hz, 2H), 7.11 (d, J=3.0 Hz, 1H), 5.71 (s, 2H), 4.45 (q, J=7.1 Hz, 2H), 1.37 (t, J=7.2 Hz, 3H). LC/MS (API-ES, M+H$^+$): 315.1.

Step 4: Ethyl 1-(4-fluorobenzyl)-4-[[(trifluoromethyl)sulfonyl]oxy}-1-H-pyrrolo[2,3-c]pyridine-5-carboxylate. To a stirred solution of the ethyl 1-(4-fluorobenzyl)-4-hydroxy-1H-pyrrolo[2,3-c]pyridine-5-carboxylate (20.0 g, 63.7 mmol) and triethylamine (44.4 mL, 318.5 mmol) in dichloromethane (150 mL) at 0° C. was added trifluoromethanesulfonic anhydride (32.0 mL, 190.1 mmol) dropwise and the reaction stirred for 1 h. It was quenched with water, extracted with ethyl acetate. The organic layer was dried over sodium sulfate, filtered, concentrated and purified by chromatography with ethyl acetate/hexane (1/1) to provide the title compound as brown solid (17.6 grams, 78% yield). $^1$H NMR (DMSO-d6): δ: 8.10 (s, 1H), 8.08 (d, 1H), 7.41 (t, 2H), 7.18 (t, 2H), 6.74 (d, 1H), 5.64 (s, 2H), 4.34 (q, 2H), 1.31 (t, 3H). LC/MS (API-ES, M+H$^+$): 447.0.

Step 5: Ethyl 4-[(E)-2-ethoxyvinyl]-1-(4-fluorobenzyl)-1H-pyrrolo[2,3-c]pyridine-5-carboxylate. To a stirred solution of ethyl 1-(4-fluorobenzyl)-4-{[(trifluoromethyl)sulfonyl]oxy}-1H-pyrrolo[2,3-c]pyridine-5-carboxylate (10.0 g, 22.4 mmol) and ethoxyvinyl tributyltin [prepared according to A. Leusik, H. A. Budding, J. W. Marsman, *J. Organomet. Chem.*, 1967, 9, 285-294] (9.7 g, 26.9 mmol, mixture of E-1,2: Z-1,2: 1:1, ratio=1:0.3:0.1) in DMF (30 mL) under a nitrogen atmosphere were added triethylamine (3.2 mL, 22.4 mmol) and dichlorobis(triphenylphosphine)palladium(II) (1.0 g, 1.4 mmol). The resulting mixture was heated to 140° C. for 10 minutes. It was quenched with aq NaHCO$_3$ solution, and extracted with ethyl acetate. The organic layer was washed with brine (2×), dried over sodium sulfate, concentrated in vacuo and purified by Biotage flash chromatography. Elution with hexane:ethyl acetate (3:2) provided the title compound as a brown glue (1.0 g pure E-isomer) and 7.7 g of a mixture of E, Z and alpha with ratio=1:0.3:0.4). $^1$H NMR (DMSO-d6) δ; 8.69 (s, 1H), 7.85 (d, J=3.3 Hz, 1H), 7.33 (t, J=6.8 Hz, 2H), 7.13-7.20 (m, 3H), 6.86 (d, J=3.3 Hz, 1H), 6.43 (d, J=13 Hz, 1H), 5.55 (s, 2H), 4.27 (q, J=7.2 Hz, 2H), 3.98 (q, J=7.0 Hz, 2H), 1.29 (t, J=7.1 Hz, 6H). LCMS (APCI, M+H$^+$): 369.1.

Step 6: 4-[(E)-2-ethoxyvinyl]-1-(4-fluorobenzyl)-N-hydroxy-1H-pyrrolo[2,3-c]pyridine-5-carboxamide. To ethyl 4-[(E)-2-ethoxyvinyl]-1-(4-fluorobenzyl)-1H-pyrrolo[2,3-c]pyridine-5-carboxylate (0.2 g, 0.54 mmol) in methanol (5 mL) were added hydroxylamine (1 mL, 50% in water, 15.2 mmol) and sodium hydroxide (0.0763 g, 1.9 mmol). The mixture was stirred at room temperature for 5 h, neutralized with 4N aq. HCl solution (0.48 mL, 1.9 mmol), and extracted with ethyl acetate. The organic extract was concentrated and recrystallized from ethyl acetate/ethyl ether/hexane to give the title compound (0.12 g, 62% yield). $^1$H NMR (DMSO-d6) 6; 11.76 (d, 1H, J=1.9 Hz), 8.88 (d, 1H, J=1.9 Hz), 8.60 (s, 1H), 7.83 (d, 1H, J=3.0 Hz), 7.31 (t, 2H, J=8.9 Hz), 7.22 (d, 1H, J=13.2 Hz), 7.05 (t, 2H, J=8.9 Hz), 6.82 (d, 1H, J=3.0 Hz), 6.66 (d, 1H, J=13.2 Hz), 5.54 (s, 2H), 3.96 (q, 2H, J=7.0 Hz), 1.28 (t, 3H, J=7.0 Hz). LCMS (APCI, M+H$^+$): 356.1. Anal. ($C_{19}H_{18}FN_3O_3$) C, H, N. HPLC: 95% purity.

Example 39

1-(4-Fluorobenzyl)-N-hydroxy-4-vinyl-1H-pyrrolo[2,3-c]pyridine-5-carboxamide

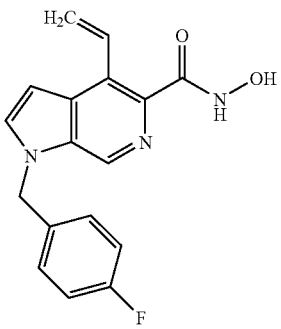

Step 1: Ethyl 1-(4-fluorobenzyl)-4-vinyl-1H-pyrrolo[2,3-c]pyridine-5-carboxylate. To a stirring solution of ethyl 1-(4-fluorobenzyl)-4-[(trifluoromethyl)sulfonyl]-1H-pyrrolo[2,3-c]pyridine-5-carboxylate (0.100 g, 0.224 mmol) in DMF (1 mL) was added vinyl tributyltin (78 mg, 0.246 mmol), lithium chloride (28 mg, 0.672 mmol), followed by dichloro-bis-diphenylphosphino palladium (II) (3 mg, 0.0045 mmol). After the addition, argon was bubbled through the mixture using a balloon attached to a needle for 10 min. The mixture was sealed and heated to 50° C. for 48 hr. The reaction mixture was concentrated under reduced pressure, water was added and the mixture was extracted with dichloromethane (3×10 mL). The combined organic extracts were dried over sodium sulfate, filtered, and concentrated under reduced pressure. The crude material was purified by flash column chromatography (silica gel, 20%-60% hexanes:ethyl acetate) to provide the vinylated ester (0.073 g, 79%) as a clear, thick oil. $^1$H NMR (CDCl$_3$) 5; 8.65 (s, 1H), 7.50 (1H, dd, J=17.9, 11.5 Hz), 7.34 (1H, d, J=3.1 Hz), 7.15-7.09 (2H, m), 7.05-6.96 (2H, m), 6.88 (1H, dd, J=3.2, 0.8 Hz), 5.78 (1H, dd, J=17.9, 1.7 Hz), 5.68 (1H, dd, J=11.5, 1.7 Hz), 5.40 (2H, s), 4.46 (2H, q, J=7.1 Hz), 1.44 (1H, t, J=7.1 Hz). LCMS (API-ES M+H$^+$) 325.

Step 2: 1-(4-Fluorobenzyl)-N-hydroxy-4-vinyl-1H-pyrrolo[2,3-c]pyridine-5-carboxamide. To a stirring solution of ethyl 1-(4-fluorobenzyl)-4-vinyl-1H-pyrrolo[2,3-c]pyridine-5-carboxylate (0.058 g, 0.179 mmol) in methanol (2 mL) at room temperature was added hydroxylamine (1 mL, 50% solution in water) followed by 10% sodium hydroxide solution in water (0.5 mL). The mixture was stirred overnight and quenched with 10% hydrochloride acid solution in water (0.5 mL) and concentrated under reduced pressure. The crude material was dissolved in DMSO and purified by reverse phase HPLC (20-60% acetonitrile:water, 30 minutes). Removal of the solvent provided the pure hydroxamic acid (40 mg, 71%) as a white solid. $^1$H NMR (DMSO-d6) δ: 8.45 (1H, s), 7.55 (1H, d, J=3.2 Hz), 7.27 (1H, dd, J=17.9, 11.5 Hz), 7.14-1.07 (2H, m), 6.96-6.88 (2H, m), 6.80 (1H, d, J=3.2 Hz), 5.79 (1H, dd, J=17.9, 1.7 Hz), 5.53 (1H, dd, J=11.5, 1.7 Hz), 5.40 (2H, s). Anal. HPLC: >93% (© 254, 222 nM). LCMS (API-ES M+H$^+$) 312.

Example 40

1-(2,4-Difluorobenzyl)-N-hydroxy-3-[(phenylthio)methyl]-1H-pyrrolo[2,3-c]pyridine-5-carboxamide

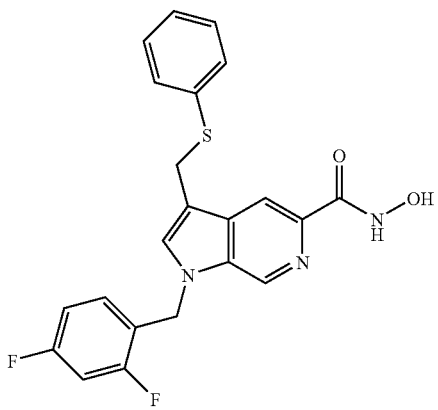

Step 1: Methyl 1-(2,4-difluorobenzyl)-3-[(dimethylamino)methyl]-11 pyrrolo[2,3-c]pyridine-5-carboxylate. A stirring solution of methyl 1-(2,4-difluorobenzyl)-1H-pyrrolo[2,3-c]pyridine-5-carboxylate (20.83 g, 68.91 mmol) and N-methyl-N-methylenemethaniminium chloride (12.89 g, 137.8 mmol) in acetonitrile (200 mL) was refluxed for 2 hours. The resulting white precipitate was filtered. The white solid was taken into DCM (700 mL) and washed with saturated NaHCO$_3$. The aqueous phase was extracted with DCM (1×400 mL). The combined organic phases were washed with brine (400 mL), dried over Na$_2$SO$_4$, and concentrated in vacuo yielding a white solid (22.32 g, 90%). $^1$H NMR (300 MHz, DMSO-d6) δ ppm 2.13 (s, 6H) 3.56 (s, 2H) 3.85 (s, 3H) 5.60 (s, 2H) 7.02-7.11 (m, 1H) 7.24-7.36 (m, 2H) 7.66 (s, 1H) 8.38 (d, J=0.75 Hz, 1H) 8.93 (s, 1H). LCMS (APCI, M+H): 360.1.

Step 2: Methyl 1-(2,4-difluorobenzyl)-3-[(phenylthio)methyl]-1H-pyrrolo[2,3-c]pyridine-5-carboxylate. To a stirring solution of methyl 1-(2,4-difluorobenzyl)-3-[(dimethylamino)methyl]-1H-pyrrolo[2,3-c]pyridine-5-carboxylate (0.906 g, 2.52 mmol) in DCM (20 mL) was added ethyl chloroformate (0.240 mL, 2.52 mmol). The pale yellow homogeneous solution was stirred for 20 minutes. To this stirring solution was added a solution of benzenethiol (0.416 g, 3.78 mmol) and diisopropyl ethylamine (0.814 g, 6.3 mmol) in DMF (10 mL). The reaction was stirred for 16 hours at ambient temperature. The reaction was concentrated in vacuo and purified by flash chromatography yielding a white powder (0.405 g, 40%). $^1$H NMR (400 MHz, CDCl$_3$) δ ppm 4.01 (s, 3H) 4.27 (s, 2H) 5.32 (s, 2H) 6.74-6.80 (m, 1H) 6.81-6.90 (m, 2H) 7.12 (s, 1H) 7.17-7.24 (m, 3H) 7.26-7.29 (m, 2H) 8.50 (s, 1H) 8.78 (s, 1H). LCMS (APCI, M+H): 425.1.

Step 3: 1-(2,4-Difluorobenzyl)-N-hydroxy-3-[(phenylthio)methyl]-1 pyrrolo[2,3-c]pyridine-5-carboxamide. To a stirring solution of methyl 1-(2,4-difluorobenzyl)-3-[(phenylthio)methyl]-1H-pyrrolo[2,3-c]pyridine-5-carboxylate (0.099 g, 0.233 mmol) in MeOH (4 mL) was added 50 wt. % solution of hydroxylamine in water (0.275 mL, 4.66 mmol) and 1M NaOH$_{(aq)}$ (0.233 mL, 0.233 mmol). The homogeneous solution stirred for 16 hours at ambient temperature. The reaction was concentrated in vacuo. Purification by prep-HPLC yielded a white solid (0.071 g, 72%). $^1$H NMR (300 MHz, DMSO-d6) δ ppm 4.46 (s, 2H) 5.54 (s, 2H) 6.98-7.07 (m, 1H) 7.12-7.20 (m, 2H) 7.21-7.33 (m, 5H) 7.60 (s, 1H) 8.33 (s, 1H) 8.80 (s, 1H) 8.95 (s, 1H) 11.14 (s, 1H). LCMS (APCI, M+H): 426.0.

Example 41

3-[(Benzylthio)methyl]-1-(2,4-difluorobenzyl)-N-hydroxy-1H-pyrrolo[2,3-c]pyridine-5-carboxamide

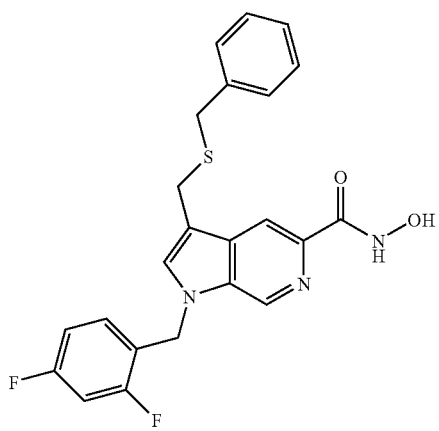

The title compound was prepared in the same manner as described in example 41 using benzylmercaptan instead of benzenethiol. $^1$H NMR (300 MHz, DMSO-d6) δ ppm 3.65 (s, 2H) 3.86 (s, 2H) 5.59 (s, 2H) 7.07 (td, J=8.52, 2.35 Hz, 1H) 7.22-7.38 (m, 7H) 7.64 (s, 1H) 8.26 (s, 1H) 8.82 (s, 1H) 8.92 (s, 1H) 11.14 (s, 1H). LCMS (APCI, M+H): 439.9.

Example 42

1-(4-Fluorobenzyl)-N,4-dihydroxy-1H-pyrrolo[2,3-c]pyridine-5-carboxamide

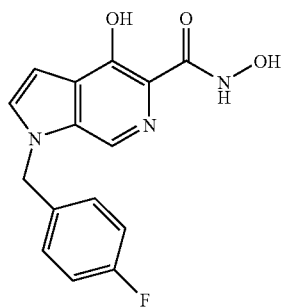

To methyl 1-(4-fluorobenzyl)-4-hydroxy-1H-pyrrolo[2,3-c]pyridine-5-carboxylate (0.22 g, 0.73 mmol) in methanol (10 mL) were added hydroxylamine (2 mL, 30.3 mmol, 50% in water) and sodium hydroxide (2.0 mL. 2.0 mmol, 1 N aqueous solution). The resulting solution was stirred for 16 h at ambient temperature. After addition of 1N hydrochloric acid (2.0 mL. 2.0 mmol) the product precipitated out. It was collected by filtration, washed with water and ethyl acetate, and dried in vacuo to provide the title compound as a solid (0.18 g, 82% yield). $^1$H NMR (DMSO-d6) δ: 13.19 (s, 1H), 11.41 (s, 1H), 9.17 (s, 1H), 8.39 (s, 1H), 7.71 (d, 1H, 7.34 (t, 2H, 7.16 (t, 2H) 6.68 (d, 1H), 5.54 (s, 2H). LCMS (APCI, M+H⁺): 302.1. HRMS calcd for $C_{15}H_{12}FN_3O_3$ (M+H) 302.0936, found 302.0935. HPLC: 100% purity.

Example 43

1-(4-Fluorobenzyl)-4-hydroxy-N-methoxy-1H-pyrrolo[2,3-c]pyridine-5-carboxamide

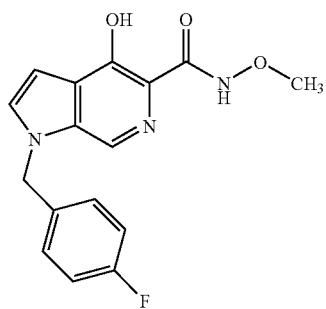

To methyl 1-(4-fluorobenzyl)-4-hydroxy-1H-pyrrolo[2,3-c]pyridine-5-carboxylate (0.6 g, 2 mmol) in methanol (10 ml) and water (1 ml) were added sodium hydroxide (0.56 g, 14 mmol) and O-methylhydroxylamine (0.668 g, 8 mmol). The resulting mixture was stirred for 28 hours at 63° C. Acetic acid (2 mL) was added to precipitate undesired byproduct, 1-(4-fluorobenzyl)-4-hydroxy-1H-pyrrolo[2,3-c]pyridine-5-carboxylic acid, which was removed by filtration. The filtrate was concentrated in under reduced pressure; the residue was dissolved in methanol and purified by preparative HPLC to provide the title compound as a white powder (0.035 g, 5.6% yield). ¹H NMR (300 MHz, DMSO-d6) d ppm 3.76 (s, 3H) 5.60 (s, 2H) 6.75 (d, J=2.83 Hz, 1H) 7.17-7.24 (m, 2H) 7.32-7.39 (m, J=5.46 Hz, 2H) 7.76 (d, J=3.20 Hz, 1H) 8.47 (s, 1H) 12.08 (s, 1H) 12.89 (s, 1H). LC-MS (APCI, M+H⁺): 316.1. HPLC: 95% purity.

Example 44

1-(4-Fluorobenzyl)-N-hydroxy-4-methoxy-N-methyl-1H-pyrrolo[2,3-c]pyridine-5-carboxamide

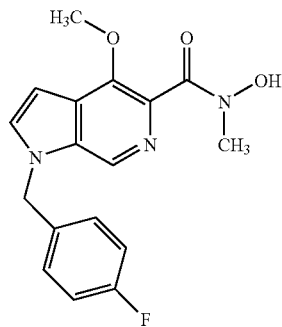

Step 1: Methyl 1-(4-fluorobenzyl)-4-methoxy-1H-pyrrolo[2,3-c]pyridine-5-carboxylate. To methyl 1-(4-fluorobenzyl)-4-hydroxy-1H-pyrrolo[2,3-c]pyridine-5-carboxylate (0.25 g, 0.83 mmol) in DMF (10 mL) were added sodium hydride (0.037 g, 0.92 mmol, 60% in mineral oil) and iodomethane (0.057 mL. 0.92 mmol). The solution was stirred for 3 h at ambient temperature. The reaction mixture was quenched with saturated aqueous ammonium chloride solution (10 mL), and extracted with ethyl acetate (3×50 mL). The organic extracts were washed with brine (3×50 mL), dried over sodium sulfate, concentrated in vacuo and purified by flash chromatography. Elution with ethyl acetate provided the title compound as a solid (0.10 g, 38% yield). ¹H NMR (CD₃OD) δ: 8.43 (s, 1H), 7.61 (d, 1H, J=3.1 Hz), 7.24 (t, 2H, J=8.8 Hz), 7.05 (t, 2H, J=8.8 Hz), 6.92 (d, 1H, J=3.1 Hz), 5.52 (s, 2H), 4.16 (s, 3H), 3.91 (s, 3H). LCMS (APCI, M+H⁺): 315.0.

Step 2: 1-(4-Fluorobenzyl)-4-methoxy-1H-pyrrolo[2,3-c]pyridine-5-carboxylic acid. The title compound was prepared by hydrolysis of methyl 1-(4-fluorobenzyl)-4-methoxy-1H-pyrrolo[2,3-c]pyridine-5-carboxylate in a manner similar to step 7 of example 1. ¹H NMR (DMSO-d6): 6; 8.30 (s, 1H), 7.65 (d, 1H, J=3.1 Hz), 7.24 (t, 2H, J=8.8 Hz), 7.14 (t, 2H, J=8.8 Hz), 6.58 (d, 1H, J=3.1 Hz), 5.47 (s, 2H), 3.92 (s, 3H). LCMS (APCI, M+H⁺): 301.1.

Step 3: 1-(4-Fluorobenzyl)-N-hydroxy-4-methoxy-N-methyl-1H-pyrrolo[2,3-c]pyridine-5-carboxamide. The title compound was prepared by coupling of 1-(4-fluorobenzyl)-4-methoxy-1H-pyrrolo[2,3-c]pyridine-5-carboxylic acid with N-methyl hydroxylamine hydrochloride in a manner similar to step 8 of example 1. ¹H NMR (DMSO-d6) 6; 9.70 (s, 1H), 8.50 (s, 1H), 7.76 (s, 1H), 7.33 (m, 2H), 7.16 (d, 2H, J=8.9 Hz), 6.76 (s, 1H), 5.51 (s, 2H), 4.00 (s, 3H), 2.96 (s, 3H). LCMS (APCI, M+H⁺): 330.1. HRMS calcd for $C_{17}H_{17}FN_3O_3$ (M+H) 330.1249, found 330.1250. HPLC: 98% purity.

Example 45

1-(2,4-Difluorobenzyl)-3-({[(1-ethylpyrrolidin-2-yl)methyl]amino}methyl)-N hydroxy-1H-pyrrolo[2,3-c]pyridine-5-carboxamide

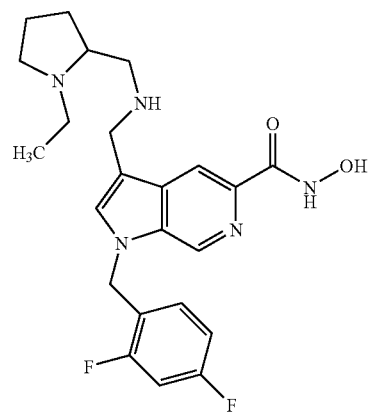

The title compound was prepared in the same manner as described in the step 6 and 7 of example 16 using [(1-ethylpyrrolidin-2-yl)methyl]amine as amine reagent to provide a white solid. $^1$H NMR (CDCl$_3$) δ: 10.35 (bs), 8.69 (1H, s), 8.44 (1H, s), 7.66 (1H, s), 7.06 (2H, m), 6.83 (2H, m), 5.37 (2H, s), 4.37 (2H, s), 3.40-3.10 (3H, m), 3.10-2.80 (2H, s), 2.60-2.25 (2H, m), 2.15 (1H, m), 1.90-1.70 (3H, m), 1.10 (3H, t, J=7.2 Hz). LCMS (API-ES M+H$^+$) 444. Anal. HPLC: >95% purity.

Example 46

1-(2,4-Difluorobenzyl)-3-({[(1-ethylpyrrolidin-2-yl)methyl]amino}methyl)-N-methoxy-1H-pyrrolo[2,3-c]pyridine-5-carboxamide

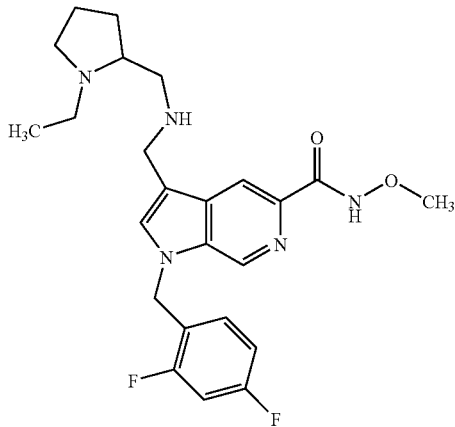

The title compound was prepared in the same manner as described in example 33 using [(1-ethylpyrrolidin-2-yl)methyl]amine instead of 3-methylpiperazin-2-one and O-methyl hydroxylamine instead of N-methylhydroxylamine. $^1$H NMR (MeOH-d4) δ: 8.84 (1H, s), 8.49 (1H, s), 7.68 (1H, s), 7.36 (1H, m), 7.10-6.90 (2H, m), 5.60 (2H, s), 4.15 (2H, s), 3.87 (3H, s), 3.53 (1H, m), 3.45-3.30 (2H, m), 3.20 (1H, m), 2.97 (2H, q), 2.91 (2H, m), 2.20 (1H, m), 1.99 (1H, m), 1.94 (3H, s), 1.81 (1H, m), 1.20 (3H, t). LCMS (API-ES M+H$^+$) 458.20. Anal. HPLC: >95% purity. Anal. (C$_{24}$H$_{29}$F$_2$N$_5$O$_2$×1.54H$_2$O× 3.00 HCl) C, H, N.

Example 47

1-(2,4-Difluorobenzyl)-N-hydroxy-3-[(2-methoxyethoxy)methyl]-1H-pyrrolo[2,3-c]pyridine-5-carboxamide

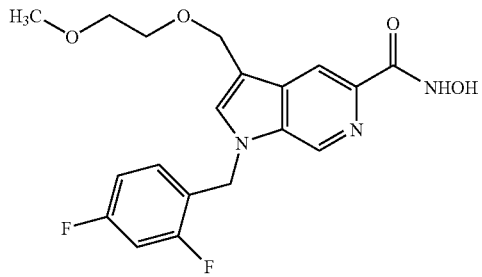

Step 1: Methyl 1-(2,4-difluorobenzyl)-3-[(2-methoxyethoxy)methyl]-1H-pyrrolo[2,3-c]pyridine -5-carboxylate

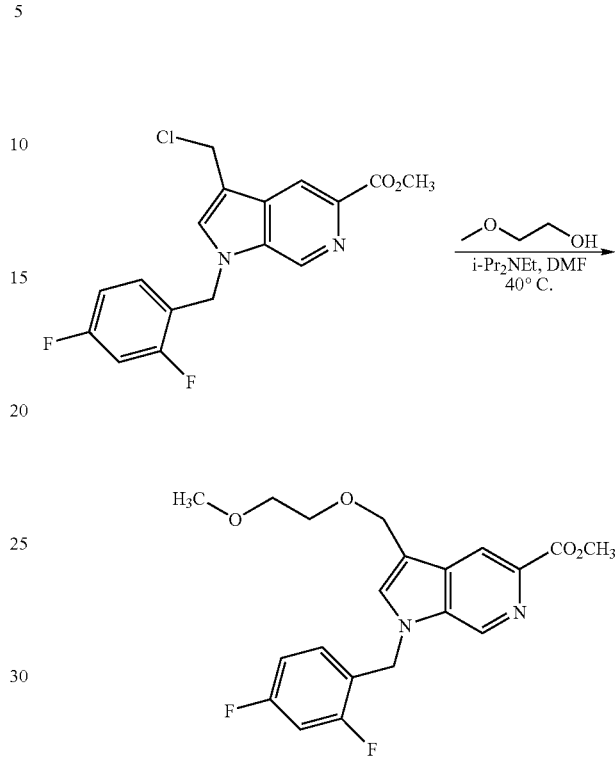

To a solution of methyl 3-(chloromethyl)-1-(2,4-difluorobenzyl)-1H-pyrrolo[2,3-c]pyridine-5-carboxylate (3 mL, 0.197M in CH$_2$Cl$_2$, 0.591 mmol) [prepared as described in step 2 of example 40] in anhydrous DMF (5 mL) was added methoxyethanol (0.25 g, 3.29 mmol, 0.26 mL, 5.5 eq.) followed by i-Pr$_2$NEt (0.407 g, 3.14 mmol, 0.55 mL, 4 eq.). The mixture, under nitrogen, was placed in an oil bath and the bath was warmed to 40° C. After stirring for 24 hours (40° C.) the reaction was judged to by complete by HPLC-MS analysis and the volatiles were removed in vacuo (ca. 2 torr) to give a golden yellow oil. The crude material was purified by chromatography on a column of silica gel (40 mm OD, 100 g, 230-400 mesh, packed with CH$_2$Cl$_2$, eluted with CH$_2$Cl$_2$-EtOAc 70:30 v/v, 1.0 L, and CH$_2$Cl$_2$-EtOAc-MeOH 68:30:2, 1.0 L, 25 mL fractions) using the flash technique. Fractions 55-64 were combined to afford 0.148 g (77%) of methyl 1-(2,4-difluorobenzyl)-3-[(2-methoxyethoxy)methyl]-1H-pyrrolo[2,3-c]pyridine-5-carboxylate as a white, crystalline solid.

TLC (Merck, CH$_2$Cl$_2$:EtOAc 70:30, UV-+, cerium molybdate-+): R$_f$=0.19

LC-MS (Eclipse XDB-C8, 0.8 mL/min, gradient 80:20 to 5:95H$_2$O (+0.1% HOAc):CH$_3$CN—5 minutes, APCI, +mode): RT—3.041 min, m/e=391.0 (M+H$^+$, base).

$^1$H-NMR (300 MHz, CDCl$_3$): δ=3.37 (s, 3H), 3.57 (m, 2H), 3.66 (m, 2H), 4.01 (s, 3H), 4.76 (s, 2H), 5.39 (s, 2H), 6.83 (m, 2H), 7.06 (m, 1H), 7.35 (s, 1H), 8.54 (s, 1H), 8.81 (s, 1H).

Step 2: 1-(2,4-Difluorobenzyl)-N-hydroxy-3-[(2-methoxyethoxy)methyl]-1H-pyrrolo[2,3-c]pyridine-5-carboxamide Step 1: Methyl 1-(2,4-difluorobenzyl)-3-{[2-(2-methoxyethoxy)ethoxy]methyl}-1H-pyrrolo[2,3-c]pyridine-5-carboxylate

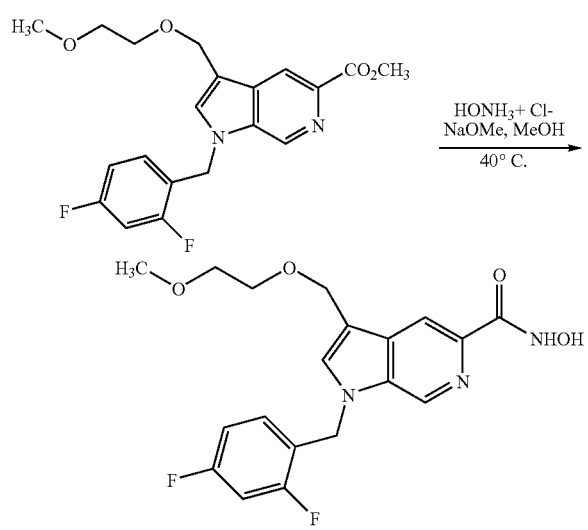

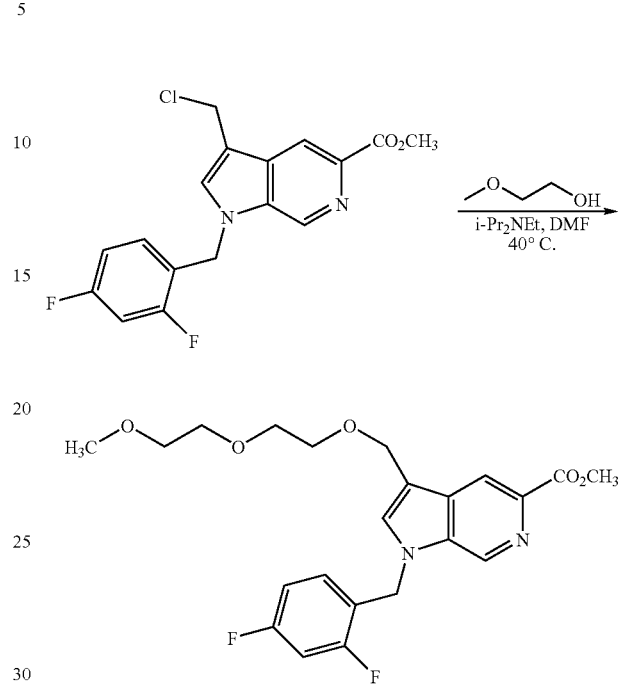

To a solution of methyl 1-(2,4-difluorobenzyl)-3-[(2-methoxyethoxy)methyl]-1H-pyrrolo[2,3-c]pyridine-5-carboxylate (0.100 g, 0.256 mmol) in anhydrous methanol (7 mL) was added hydroxylamine hydrochloride (0.09 g, 1.28 mmol, 5 eq.) followed by NaOMe (25 wt % solution in MeOH, 0.333 g, 1.54 mmol, 6 eq., 0.35 mL). The mixture was allowed to stir at room temperature under nitrogen for 1 hour, whereupon HPLC-MS analysis indicated no reaction. The mixture was immersed in an oil bath and heated to 45° C. (bath temperature) for 3.5 hours (ca. 40% complete) and additional aliquot of hydroxylamine hydrochloride (0.09 g, 1.28 mmol, 5 eq.) followed by NaOMe (25 wt % solution in MeOH, 0.333 g, 1.54 mmol, 6 eq., 0.35 mL) was added and heating was continued for an additional 4 hours. At this juncture the reaction was judged to be complete (HPLC-MS). The mixture was cooled to room temperature, poured into $CH_2Cl_2$: EtOAc:MeOH (0.125 L, 60:30:10 v/v) and brine (0.12 L) containing saturated ammonium chloride (50 mL). The organic phase was separated, dried ($Na_2SO_4$), and concentrated in vacuo to afford 67 mg (67%) of the target compound as a pale yellow semi-solid.

LC-MS (Eclipse XDB-C8, 0.8 mL/min, gradient 80:20 to 5:95 $H_2O$ (+0.1% HOAc): $CH_3CN$—5 minutes, ESI, +mode): RT—2.895 min, m/e=436.0 ($M+H^+2Na^+$, 35), 414.0 ($M+H^+Na^+$, 62), 392.0 ($M+H^+$, base)

Example 48

1-(2,4-Difluorobenzyl)-AN-hydroxy-3-{[2-(2-methoxyethoxy)ethoxy]methyl}-1H-pyrrolo[2,3-c]pyridine-5-carboxamide

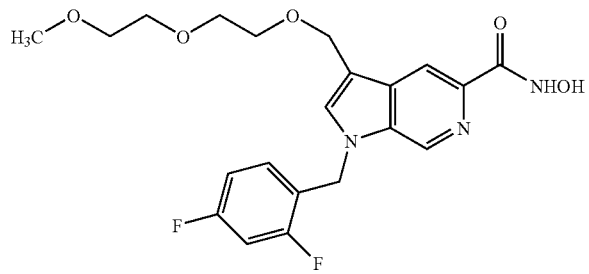

To a solution of methyl 3-(chloromethyl)-1-(2,4-difluorobenzyl)-1H-pyrrolo[2,3-c]pyridine-5-carboxylate (4 mL, 0.197M in $CH_2Cl_2$, 0.788 mmol)) [prepared as described in step 2 of example 40] in anhydrous DMF (10 mL) was added 2-(methoxyethoxy)-ethanol (0.47 g, 3.94 mmol, 0.43 mL, 5 eq.) followed by i-$Pr_2NEt$ (0.407 g, 3.14 mmol, 0.55 mL, 4 eq.). The mixture, under nitrogen, was placed in an oil bath and the bath was warmed to 40° C. After stirring for 24 hours (40° C.) the reaction was judged to by complete by HPLC-MS analysis and the volatiles were removed in vacuo (ca. 2 torr) to give a golden yellow oil. The crude material was purified by chromatography on a column of silica gel (40 mm OD, 100 g, 230-400 mesh, packed and eluted with $CH_2Cl_2$-EtOAc 70:30 v/v, 0.4 L, $CH_2Cl_2$-EtOAc-MeOH 80:18:2 1.0 L, and $CH_2Cl_2$-EtOAc-MeOH 80:17.5:2.5 1.0 L, 25 mL fractions) using the flash technique. Fractions 42-80 were combined to afford 0.339 g (78%) of methyl 1-(2,4-difluorobenzyl)-3-{[2-(2-methoxyethoxy)ethoxy]methyl}-1H-pyrrolo[2,3-c]pyridine-5-carboxylate: 2-(methoxyethoxy)-ethanol (1:1) as a clear, colorless, viscous oil.

TLC (Merck, $CH_2Cl_2$:MeOH 95:5, UV-+, cerium molybdate-+): $R_f$=0.14

LC-MS (Eclipse XDB-C8, 0.8 mL/min, gradient 80:20 to 5:95$H_2O$ (+0.1% HOAc):$CH_3CN$—5 minutes, ESI, +mode): RT—3.101 min, m/e=457.0 ($M+Na^+$, 20), 435.1 ($M+H^+$, base).

$^1$H-NMR (300 MHz, $CDCl_3$): δ=3.39 (s, 3H), 3.50-3.80 (m, 8H), 4.02 (s, 3H), 4.77 (s, 2H), 5.40 (s, 2H), 6.84 (m, 2H), 7.07 (m, 1H), 7.35 (s, 1H), 8.54 (s, 1H), 8.82 (s, 1H).

Step 2: 1-(2,4-Difluorobenzyl)-N-hydroxy-3-{[2-(2-methoxyethoxy)ethoxy]methyl}-1H-pyrrolo[2,3-c]pyridine-5-carboxamide

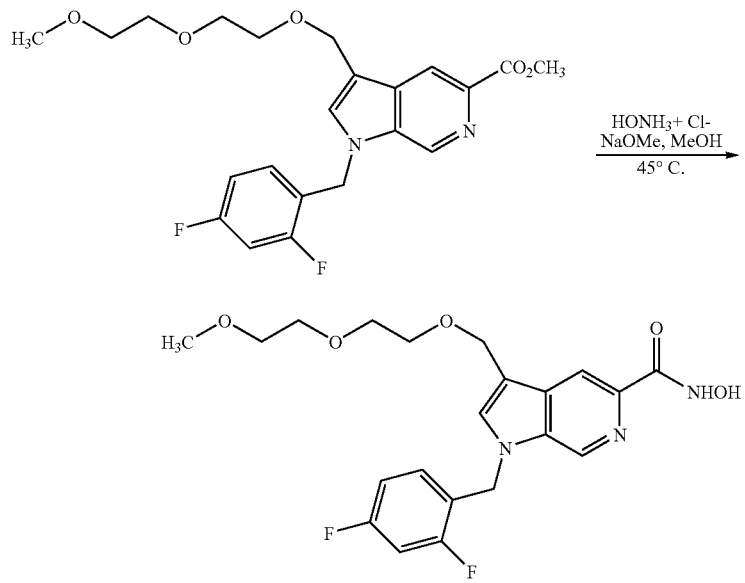

To a solution of methyl 1-(2,4-difluorobenzyl)-3-{[2-(2-methoxyethoxy)ethoxy]methyl}-1H-pyrrolo[2,3-c]pyridine-5-carboxylate:2-(methoxyethoxy)-ethanol (1:1) (0.142 g, 0.256 mmol) in anhydrous methanol (7 mL) was added hydroxylamine hydrochloride (0.09 g, 1.28 mmol, 5 eq.) followed by NaOMe (25 wt % solution in MeOH, 0.333 g, 1.54 mmol, 6 eq., 0.35 mL). The mixture was allowed to stir at room temperature under nitrogen for 1 hour, whereupon HPLC-MS analysis indicated no reaction. The mixture was immersed in an oil bath and heated to 45° C. (bath temperature) for 3.5 hours (ca. 50% complete) and additional aliquot of hydroxylamine hydrochloride (0.09 g, 1.28 mmol, 5 eq.) followed by NaOMe (25 wt % solution in MeOH, 0.333 g, 1.54 mmol, 6 eq., 0.35 mL) was added and heating was continued for an additional 4 hours. At this juncture the reaction was judged to be complete (HPLC-MS). The mixture was cooled to room temperature, poured into $CH_2Cl_2$: EtOAc:MeOH (0.125 L, 60:30:10 v/v) and brine (0.12 L) containing saturated ammonium chloride (50 mL). The organic phase was separated, dried ($Na_2SO_4$), and concentrated in vacuo to afford 81.4 mg (73%) of the target compound as a pale yellow viscous oil.

LC-MS (Eclipse XDB-C8, 0.8 mL/min, gradient 80:20 to 5:95$H_2O$ (+0.1% HOAc):$CH_3CN$—5 minutes, ESI, +mode): RT—2.861 min, m/e=480.0 ($M+H^+2Na^+$, 40), 458.0 ($M+H+2Na^+$, 85), 436.0 (M+H+, base).

Example 49

1-(2,4-Difluorobenzyl)-3-({[(4R)-2,2-dimethyl-1,3-dioxolan-4-yl]methoxy}methyl)-N-hydroxy-1H-pyrrolo[2,3-c]pyridine-5-carboxamide

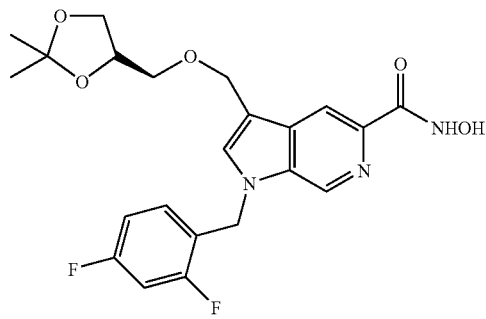

Step 1: Methyl 1-(2,4-difluorobenzyl)-3-({[(4R)-2,2-dimethyl-1,3-dioxolan-4-yl]methoxy}methyl)-1H-pyrrolo[2,3-c]pyridine-5-carboxylate

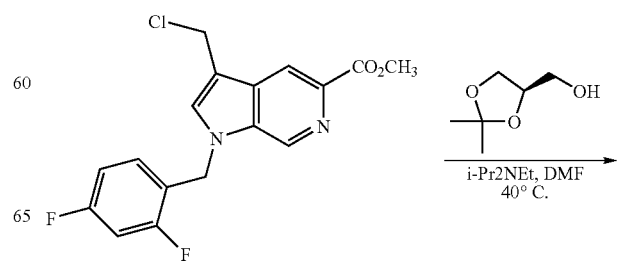

-continued

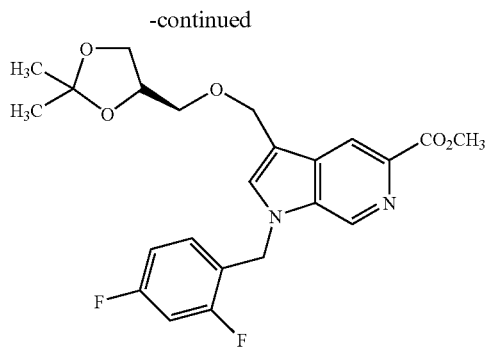

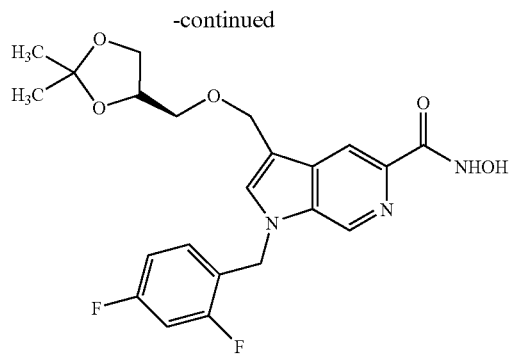

To a solution of methyl 3-(chloromethyl)-1-(2,4-difluorobenzyl)-1H-pyrrolo[2,3-c]pyridine-5-carboxylate (3 mL, 0.197M in $CH_2Cl_2$, 0.591 mmol)) [prepared as described in step 2 of example 40] in anhydrous DMF (5 mL) was added (R)-(−)-2,2-Dimethyl-1,3-dioxolane-4-methanol (0.37 ml, 2.955 mmol, 5.0 eq.) followed by i-$Pr_2$NEt (0.4079, 3.14 mmol, 0.55 mL, 4 eq.). The mixture, under nitrogen, was placed in an oil bath and the bath was warmed to 40° C. After stirring for 24 hours (40° C.) the reaction was judged to by complete by HPLC-MS analysis and the volatiles were removed in vacuo (ca. 2 torr) to give a golden yellow oil. The crude material was purified by chromatography on a column of silica gel (40 mm OD, 100 g, 230-400 mesh, packed with $CH_2Cl_2$, eluted with $CH_2Cl_2$-EtOAc 50:50 v/v, 1.0 L, 25 mL fractions) using the flash technique. Fractions 30-54 were combined to afford 0.224 g (85%) of Methyl 1-(2,4-difluorobenzyl)-3-({[(4R)-2,2-dimethyl-1,3-dioxolan-4-yl]methoxy}methyl)-1H-pyrrolo[2,3-c]pyridine-5-carboxylate as a colorless oil.

TLC (Merck, $CH_2Cl_2$:EtOAc 50:50, UV-+, cerium molybdate-+): $R_f$=0.26

LC-MS (Eclipse XDB-C8, 0.8 mL/min, gradient 80:20 to 5:95$H_2O$ (+0.1% HOAc):$CH_3CN$—5 minutes, APCI, +mode): RT—3.456 min, m/e=447.2 (M+H$^+$, base).

$^1$H-NMR (300 MHz, $CDCl_3$): δ=1.33 (s, 3H), 1.40 (s, 3H) 3.46 (m, 2H), 3.67 (m, 1H), 3.98 (s, 3H), 4.00 (m, 1H), 4.20 (m, 1H), 4.68 (q, 2H), 5.33 (s, 2H), 6.82 (m, 2H), 6.93 (q, 1H), 7.31 (s, 1H), 8.50 (s, 1H), 8.86 (s, 1H).

Step 2: 1-(2,4-Difluorobenzyl)-3-({[(4R)-2,2-dimethyl-1,3-dioxolan-4-yl]methoxy}methyl)-N-hydroxy-1H-pyrrolo[2,3-c]pyridine-5-carboxamide

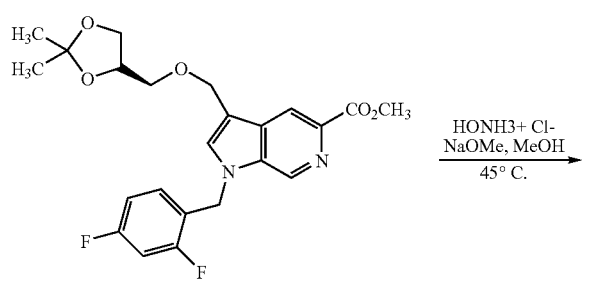

To a solution of Methyl 1-(2,4-difluorobenzyl)-3-({[(4R)-2,2-dimethyl-1,3-dioxolan-4-yl]methoxy}methyl)-1H-pyrrolo[2,3-c]pyridine-5-carboxylate (0.110 g, 0.247 mmol) in anhydrous methanol (5 mL) was added hydroxylamine hydrochloride (0.07 g, 0.988 mmol, 4 eq.) followed by NaOMe (25 wt % solution in MeOH, 0.28 ml 1.235 mmol, 5 eq.). The mixture was allowed to stir at room temperature under nitrogen for 1 hour. The mixture, under nitrogen, was placed in an oil bath and the bath was warmed to 40° C. After stirring for 4 hours (40° C.) the reaction was judged to by complete by HPLC-MS and the volatiles were removed in vacuo to give a cream colored solid. The crude material was taken up in EtOAc, DCM, MeOH (60:30:10 50 ml) and washed with $NH_4Cl$ and brine. The organics were dried ($Na_2SO_4$) volatiles were removed in vacuo to give a light yellow oil that was purified by prep HPLC.

LC-MS (Eclipse XDB-C8, 0.8 mL/min, gradient 80:20 to 5:95$H_2O$ (+0.1% HOAc):$CH_3CN$—5 minutes, APCI, +mode): RT—3.075 min, m/e=448.2 (M+H$^+$, base).

Example 50

1-(4-Fluorobenzyl)-AN-hydroxy-4-(3-hydroxypropyl)-1 pyrrolo[2,3-c]pyridine-5-carboxamide

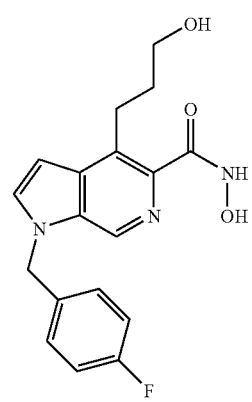

Step 1: Ethyl 1-(4-Fluorobenzyl)-4-(3-hydroxyprop-1-yn-1-yl)-1H-pyrrolo[2,3-c]pyridine-5-carboxylate. To a solution of ethyl 1-(4-fluorobenzyl)-4-{[(trifluoromethyl)sulfonyl]oxy}-1H-pyrrolo[2,3-c]pyridine-5-carboxylate (1.50 g, 3.36 mmol) in DMF (4 mL) was added propargyloxytrimethylsilane (0.73 g, 5.72 mmol), lithium chloride (0.214 g, 5.1 mmol), copper iodide (0.028 g ml, 0.15 mmol), triethylamine (7 ml, 50.4 mmol) and dichlorobis(triphenylphosphine)palladium(II) (0.052 g, 0.074 mmol). The resulting mixture was stirred for 20 min at 140° C. in a microwave reactor (Personal Chemistry). The solvent was evaporated and 10 mL ethyl acetate was added. After stirring for 10 min, the mixture was filtered through Celite and the filtrate was concentrated. Purification by flash chromatography (Biotage) over silica gel (1:3, hexane/ethyl acetate) afforded the title product as yellow oil (0.46 g, 46% yield). $^1$H NMR (400 MHz, CHLOROFORM-D) δ ppm 8.69 (s, 1H) 7.36 (d, J=3.28 Hz, 1H) 7.06-7.14 (m, 2H) 6.98-7.06 (m, 2H) 6.84 (d, J=2.53 Hz, 1H) 5.40 (s, 2H) 4.67 (s, 2H) 4.48 (q, J=7.07 Hz, 2H) 1.46 (t, J=7.20 Hz, 3H). LC-MS (APCI, M+H$^+$): 353.1. HPLC: 96% purity.

Step 2: Ethyl 1-(4-fluorobenzyl)-4-(3-hydroxypropyl)-1H-pyrrolo[2,3-c]pyridine-5-carboxylate.

To a solution of ethyl 1-(4-fluorobenzyl)-4-(3-hydroxyprop-1-yn-1-yl)-1H-pyrrolo[2,3-c]pyridine-5-carboxylate (0.46 g, 1.31 mmol) in MeOH (6 mL) was added palladium, (10 wt. % on activated carbon, 15 mg, 0.014 mmol). The resulting mixture was stirred for 4 h at room temperature under H$_2$ at 60 psi. The mixture was filtered and concentrated to afford the title product as yellow oil (0.41 g, 88% yield). LC-MS (APCI, M+H$^+$): 357.2. HPLC: 96% purity.

Step 3: 1-(4-Fluorobenzyl)-N-hydroxy-4-(3-hydroxypropyl)-1H-pyrrolo[2,3-c]pyridine-5-carboxamide. To a solution of ethyl 1-(4-fluorobenzyl)-4-(3-hydroxypropyl)-1H-pyrrolo[2,3-c]pyridine-5-carboxylate (22 mg, 0.06 mmol) in MeOH (3 mL) was added sodium hydroxide (15 mg, 0.38 mmol) and hydroxylamine (50 wt. % in water) (82.5 mg, 1.25 mmol). The resulting mixture was stirred for 18 h at room temperature. The mixture was neutralized by acetic acid and concentrated. The title compound was purified by preparative HPLC to provide the title compound as a white powder (4 mg, 19% yield). 1H NMR (300 MHz, MeOH) δ ppm 8.53 (s, 1H) 7.63 (d, J=3.20 Hz, 1H) 7.20-7.27 (m, J=8.57, 5.37 Hz, 2H) 7.05 (t, J=8.76 Hz, 2H) 6.81 (d, J=2.83 Hz, 1H) 5.52 (s, 2H) 3.60 (t, J=6.31 Hz, 2H) 1.90-2.04 (m, 4H). LC-MS (APCI, M+H$^+$): 344.2. HPLC: 90% purity.

Preparation of rac-(3aR*,7aR*)-octahydro-3H-pyrrolo[3,4-c]pyridin-3-one

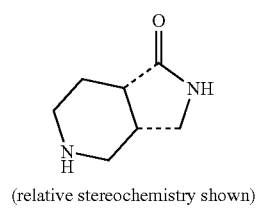

(relative stereochemistry shown)

Step 1: 1,2-dihydro-3H-pyrrolo[3,4-c]pyridin-3-one. Pyridinedicarboximide (60 g, 0.405 mol) and zinc (160.2 g, 1.626 mol) were added to glacial acidic acid (1800 mL) at ambient temperature. The mixture was stirred and heated at 100° C. for 4 h and left over night to cool to ambient temperature. The mixture was analyzed by TLC (20% MeOH/80% EtOAc, Rf SM=0.86, Rf P=0.24). An additional 5 g of zinc was added and the reaction was stirred for 3 h more. No changes in the TLC were observed. The acidic acid was evaporated. The pH of the residue was adjusted to pH 8 by addition of aq. NaHCO$_3$. The mixture was extracted with CHCl$_3$ (8×1 L). The water of the aq. phase was evaporated and the residue extracted with chloroform (2×2 L). The solvent of the organic phases was evaporated and the combined residue recrystallized from isopropanol. Yield: 23.1 g. $^1$H NMR (300 MHz, d6-DMSO) δ=8.87 (s, 1H), 8.71 (s, 2H), 7.64 (br s, 1H), 4.44 (s, 2H). LCMS: 9.38 min, M+H=134.03 u/e.

Step 2: rac-(3aR*,7aR*)-octahydro-3H-pyrrolo[3,4-c]pyridin-3-one. 1,2-dihydro-3H-pyrrolo[3,4-c]pyridine-3-one (19.6 g, 0.146 mol) was placed into a hydrogenation reactor together with 250 mL AcOH and 1 g of PtO$_2$ (Colonial Metals). An H$_2$ pressure of 60 PSI was applied and the mixture hydrogenated until a pressure of 26 PSI was measured. The reaction mixture was filtered and the solvent evaporated. At the end of the evaporation, 4 N HCl in 1,4-dioxane (50 mL, 0.2 mol) was added. The solvent was evaporated to dryness. Ether (800 mL) was added and the mixture was stirred and filtered. The filter, a white solid, was dried to give 28.3 g of the desired product. $^1$H NMR (300 MHz, d6-DMSO) δ=9.42 (br s, 1H), 8.33 (br s, 1H), 7.88 (s, 1H), 3.44-3.25 (m, overlaps with water peak, observed integral of 6H includes water), 3.11-3.01 (m, 2H), 2.88-2.76 (m, 2H), 2.64 (br t, 1H), 2.55-2.45 (m, 3H) 1.90-1.75 (m, 1H), 1.61-1.42 (m, 1H). LCMS: 1.0 min, M+H=144.1 u/e.

Preparation of 3-Amino-N,3-dicyclopropylamide

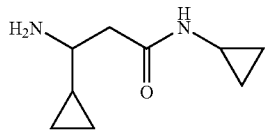

Step 1: 3-Amino-3-cyclopropylpropanoic acid

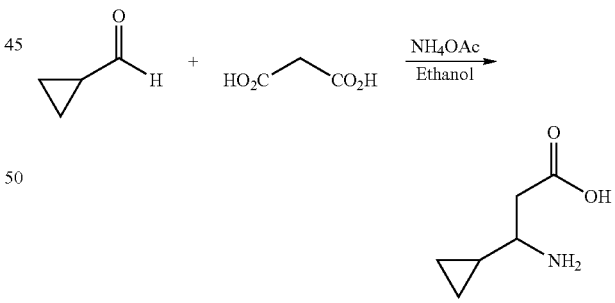

A mixture of cyclopropanecarboxaldehyde (150.2 g, 2.1 mol), ammonium acetate (329.9 g, 4.3 mol), malonic acid (223 g, 2.1 mol), and ethanol (850 mL) was stirred at reflux for 19 h. The reaction was analyzed by LCMS and determined to be complete. The mixture was allowed to cool to room temperature. The heterogeneous mixture was further cooled with an ice-bath and stirred 3 h prior to collecting the solid precipitate by suction filtration. The cake was washed with cold ethanol (displacement wash: 250 mL) and the solids dried under vacuum to provide 146.5 g of the desired compound (53% yield) as a white solid. mp: 206-208° C.

Step 2: 3-[(t-Butoxycarbonyl)amino]-3-cyclopropylpropanoic acid

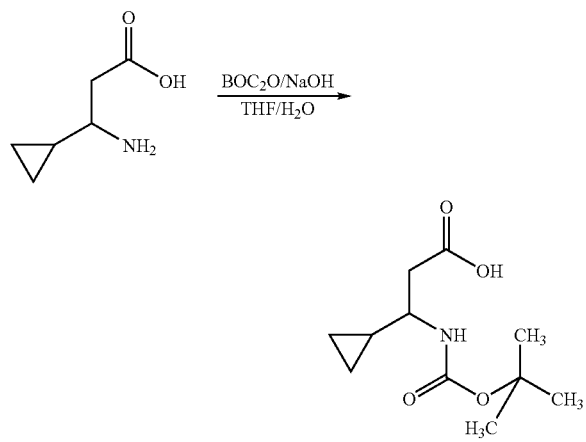

To a mixture of 3-amino-3-cyclopropylpropanoic acid (146 g, 1.13 mol), water (300 mL), and tetrahydrofuran (1 L) was added an aqueous solution of sodium hydroxide (95 g, 2.37 mol; 200 mL of water) while maintaining the internal temperature below 30° C. A solution of di-t-butyl dicarbonate (271.7 g, 1.24 mol) in tetrahydrofuran (250 mL) was added to the reaction via addition funnel while maintaining the internal temperature below 30° C. with the aid of a water bath. The reaction was stirred at ambient temperature for a period of 17 h, at which point LCMS analysis indicated that the starting material had been consumed. The reaction mixture was quenched by portionwise addition of oxalic acid to a pH of 4 and the precipitated salts removed by filtration. The salts were rinsed with ethyl acetate (slurry-wash: 1×500 mL; displacement wash: 1×500 mL) and the phases were split. The aqueous layer was extracted with ethyl acetate (2×250 mL), the combined organic layers washed with brine (1×400 mL), dried over sodium sulfate, filtered and the majority of the solvent removed to provide a thick slurry. The product slurry was diluted with hexanes (500 mL) and cooled to 0° C. prior to filtration. The cake was washed with cold hexanes (displacement wash: 1×300 mL) and dried under vacuum to afford the desired compound (236.3 g, 91.3% yield) as a white solid. mp: 104-106° C.

Step 3: tert-Butyl 1-cyclopropyl-3-(cyclopropylamino)-3-oxopropylcarbamate

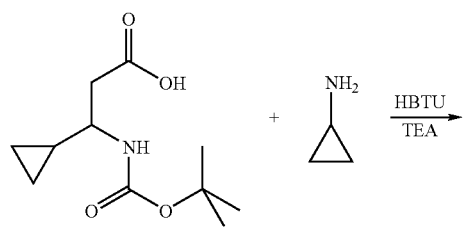

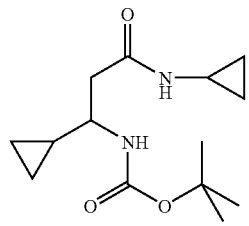

A 1 L 3-neck flask equipped with a mechanical stirrer was charged with a solution of 3-[(t-butoxycarbonyl)amino]-3-cyclopropylpropanoic acid (34.44 g, 160 mmol) in THF (150 mL). HBTU (66.75 g, 176 mmol) was added in small portions followed by triethylamine (35.62 g, 352 mmol) in THF (100 mL). The reaction mixture was stirred for 20 min at room temperature. A solution cyclopropylamine (10.00 g, 176 mmol) in THF (100 mL) was added slowly with an addition funnel. The reaction was stirred overnight at room temperature. The reaction mixture became thick as product started forming. After 17 h LC/ELSD/HMS indicated the completion of the reaction. Water (200 mL) was added to the reaction mixture and the mixture was stirred for 30 min. The solid product was filtered and dried in a vacuum oven overnight to afford analytically pure tert-butyl 1-cyclopropyl-3-(cyclopropylamino)-3-oxopropylcarbamate (39.60 g, 93% yield) mp=166-168° C.

Step 4: 3-Amino-N,3-dicyclopropylpropanamide hydrochloride

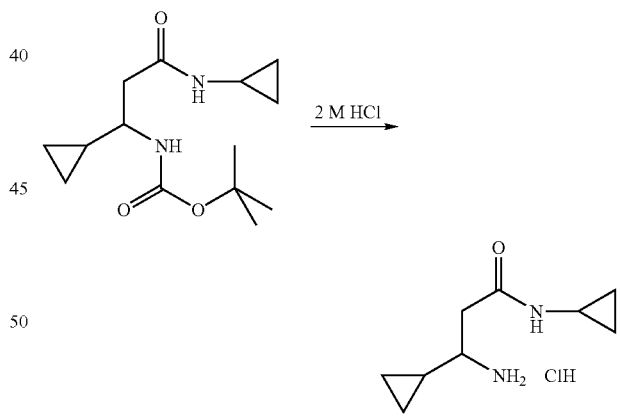

To the solution of tert-butyl 1-cyclopropyl-3-(cyclopropylamino)-3-oxopropylcarbamate (38.10 g, 150 mmol) in dichloromethane (600 mL) and methyl alcohol (40 mL) was added 2 M solution of hydrochloric acid in diethyl ether (300 mL, 600 mmol) with an addition funnel at such a rate that the temperature of the reaction remained below 30° C. The reaction was allowed to stir at room temperature overnight. After 18 h, the reaction was complete as indicated by ELSD/MS. The reaction mixture was evaporated under reduced pressure. Diethyl ether (2×200 mL) was added to the residue, and the mixture was stirred for 15 min, and then decanted. This pro cess was repeated to remove excess of hydrochloric acid. It was further dried in a vacuum oven overnight to afford 3-amino-N,3-dicyclopropylpropanamide hydrochloride (30 g, >100% yield).

Step 5: 3-Amino-N,3-dicyclopropylpropanamide

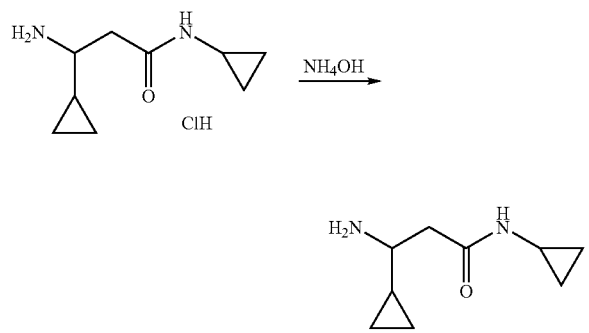

To 1 L round-bottom flask was charged a solution of 3-amino-N,3-dicyclopropylpropanamide hydrochloride (12 g, 38 mmol) in THF (400 mL). To this was added 30% ammonium hydroxide (7 mL, 57 mmol) dropwise. The mixture was stirred at room temperature for 30 min. Some ammonium chloride was separated. The reaction mixture was diluted with dichloromethane (1 L), washed with water (2×100 mL), brine (100 mL) and dried over sodium sulfate. Removal of the solvent under reduced pressure and drying in a vacuum oven overnight afforded the title compound as an oil which solidified after 2 days (9 g, 85% yield) mp=116-118° C. $^1$H NMR (300 MHz, DMSO-d6) δ ppm 7.93 (s, 1H), 2.85 (s, 2H), 2.50-2.42 (m, 1H), 2.29-2.16 (m, 1H) 2.22-1.91 (m, 2H) 0.64-0.50 (m, 1H) 0.5-0.05 (m, 2H); LCMS (API-ES, M+H$^+$): 169.2.

General Procedure A for synthesis of compounds of formula:

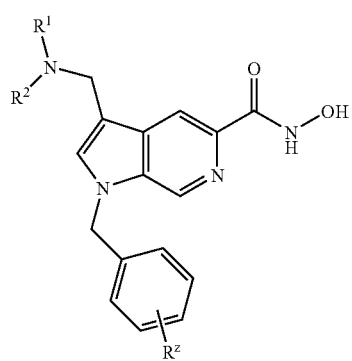

One stir bar, the appropriate aldehyde-ester (Reactant A, 320 μL, 80 μmol, 1 eq, 0.25 M in anhydrous acetonitrile), and the appropriate amine (Reactant B, 320 μL, 80 μmol, 1 eq, 0.25 M in anhydrous acetonitrile) were added to a 10×70 mm test tube. The test tube was capped and the reaction mixture was stirred for 1 h at ambient temperature. NaBH(OAc)$_3$ (320 μL, ~200 μmol, ~2.5 eq, 0.625 M suspension in anhydrous acetonitrile) was added and the reaction was stirred for 16 h at ambient temperature. The solvent was evaporated and the residue dissolved in of a 6:3:1 (v:v) mixture of ethylacetate/CH$_2$Cl$_2$/methanol (1.1 mL). The organic phase was washed with aq. 10% K$_2$CO$_3$ (320 μL) and the aq. layer was extracted once with of the 6:3:1 mixture of ethylacetate/CH$_2$Cl$_2$/methanol (1.1 mL). The organic phases were combined and the solvent was evaporated. In a glove box, the residue was dissolved or suspended in MeOH (2 mL). The solution/suspension was treated at ambient temperature with a) 50% aq NH$_2$OH (20 eg) and NaOH (1 eq) for 16 h, b) 50% aq NH$_2$OH (20 eq) for 24 h, c) 50% NH$_2$OH (20 eq) and NaOH (1 eq) for 16 h, and finally with d) 1 M HCl (1.88 eq) for 10 min. The solvent was evaporated and the residue dissolved in DMSO (1340 μL, containing 0.01% BHT). The DMSO solution was filtered and the desired product purified and isolated by HPLC.

Example 51

1-(2,4-Difluorobenzyl)-N-hydroxy-3-({[2-(1-methylpyrrolidin-2-yl)ethyl]amino}methyl)-1H-pyrrolo [2,3-c]pyridine-5-carboxamide

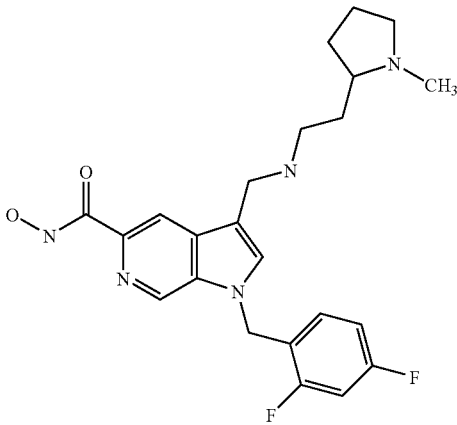

The compound was synthesized using the General Procedure A and 2-(2-aminoethyl)-1-methypyrrolidine as the amine component. $^1$H NMR (500 MHz, d6-DMSO) δ ppm 11.17 (s, 1H) 8.91 (s, 1H) 8.67-8.72 (m, 2H) 8.48 (s, 1H) 7.80 (s, 1H) 7.43 (q, 1H) 7.28 (t, 1H) 7.07 (t, 1H) 5.63 (s, 2H) 4.34-4.37 (m, 2H) 2.94-3.02 (m, 4H) 2.76-2.78 (m, 3H) 2.13-2.19 (m, 2H) 1.93-1.97 (m, 1H) 1.83-1.88 (m, 1H) 1.74-1.79 (m, 1H) 1.52-1.56 (m, 1H). LCMS: Mass of Compound: 443.2 D; Mass obs. (M+H$^+$)=445 u/e; Retention Time: 1.08 min; Purity by TIC: 100%; Purity by UV: 100%.

Example 52

1-(2,4-Difluorobenzyl)-N-hydroxy-3-({[3-(4-methylpiperazin-1-yl)propyl]amino}methyl)-1H-pyrrolo[2,3-c]pyridine-5-carboxamide

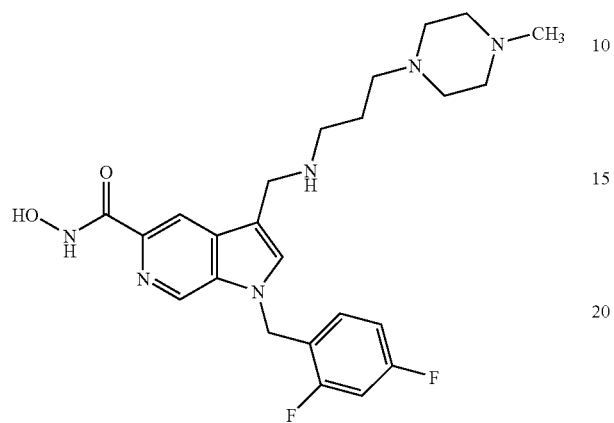

The compound was synthesized using the General Procedure A and 1-(3-aminopropyl)-4-methylpiperazine as the amine component. $^1$H NMR (500 MHz, d6-DMSO) δ ppm 11.18 (s, 1H), 8.91 (s, 1H) 8.55 (m, 1H) 8.48 (s, 1H) 7.80 (s, 1H) 7.42 (q, 1H) 7.27 (t, 1H) 7.07 (t, 1H) 5.63 (s, 2H) 4.34 (m, 2H) 2.94 (m, 2H) 2.73 (s, 3H) 1.74 (m, 2H) (Note: DMSO peak supression supresses also piperazin protons and other N—CH$_2$ singals). LCMS: Mass of Compound: 472.2 D; Mass obs. (M+H$^+$)=474 u/e; Retention Time: 1.07 min; Purity by TIC: 100%; Purity by UV: 100%.

Example 53

1-(2,4-Difluorobenzyl)-N-hydroxy-3-{[(2-hydroxy-1-methylethyl)amino]methyl}-1H-pyrrolo[2,3-c]pyridine-5-carboxamide

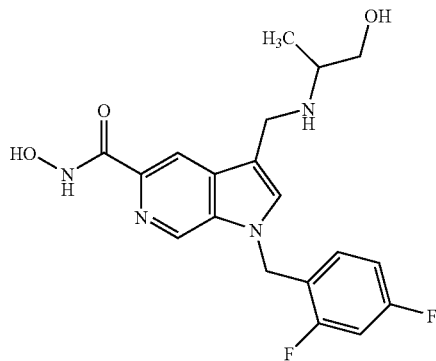

The compound was synthesized using the General Procedure A and DL-2-amino-1-propanol as the amine component. $^1$H NMR (500 MHz, d6-DMSO) & ppm 11.15 (s, 1H) 8.89 (s, 1H) 8.57 (s, 1H) 8.48 (s, 1H) 7.41 (q, 1H) 7.27 (t, 1H) 7.07 (t, 1H) 5.62 (s, 2H) 4.32-4.38 (m, 2H) 1.21 (d, 2H) (DMSO supression supresses signal of CHCH$_3$ and signal of CH$_2$OH.

LCMS: Mass of Compound: 390.2 D; Mass obs. (M+H$^+$)=391 u/e; Retention Time: 1.1 min; Purity by TIC: 100%; Purity by UV: 100%.

Example 54

1-(2,4-Difluorobenzyl)-N-hydroxy-3-{[(2-morpholin-4-ylethyl)amino]methyl-1H-pyrrolo[2,3-c]pyridine-5-carboxamide

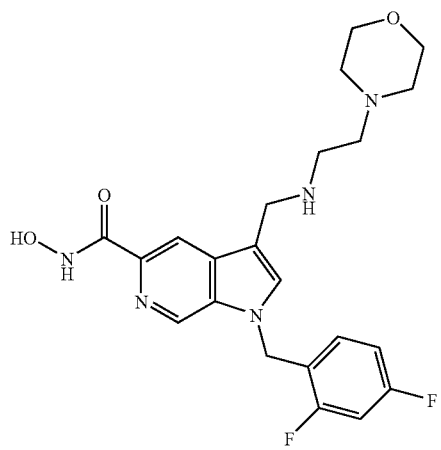

The compound was synthesized using the general procedure A and 4-(2-aminoethyl)morpholine as the amine component. $^1$H NMR (500 MHz, d6-DMSO) δ ppm 11.17 (s, 1H) 8.91 (s, 1H) 8.50 (s, 1H) 7.82 (s, 1H) 7.42 (q, 1H) 7.27 (t, 1H) 7.07 (t, 1H) 5.63 (s, 2H) 4.36-4.41 (m, 2H) (DMSO Peak supression supresses signals CH$_2$ group). LCMS: Mass of Compound: 445.2 D; Mass obs. (M+H$^+$)=447 u/e; Retention Time: 1.08 min; Purity by TIC: 100%; Purity by UV: 99%.

Example 55

1-(2,4-Difluorobenzyl)-N-hydroxy-3-{[(pyridin-2-ylmethyl)amino]methyl}-1H-pyrrolo[2,3-c]pyridine-5-carboxamide

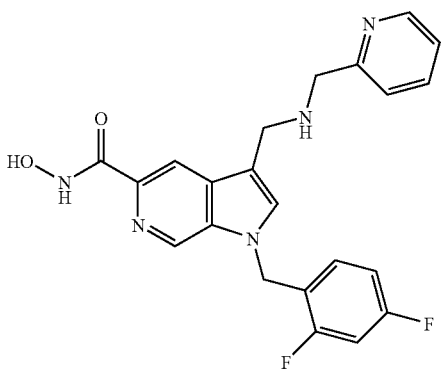

The compound was synthesized using the General Procedure A and 2-(aminomethyl)pyridine as the amine component. $^1$H NMR (500 MHz, d6-DMSO) δ ppm 11.15 (s, 1H) 9.27 (s, 1H) 8.88 (s, 1H) 8.59 (d, 1H) 8.53 (s, 1H) 7.80-7.85 (m, 2H) 7.39-7.43 (m, 2H) 7.36-7.39 (m, 1H) 7.26 (t, 1H) 7.07

(t, 1H) 5.62 (s, 2H) 4.42 (s, 2H) 4.31 (s, 2H). LCMS: Mass of Compound: 423.2 D; Mass obs. (M+H+)=425 u/e; Retention Time: 1.19 min; Purity by TIC: 98%; Purity by UV: 98%.

Example 56

1-(2,4-Difluorobenzyl)-N-hydroxy-3-H[(2-pyridin-2-ylethyl)amino]methyl}-1H-pyrrolo[2,3-c]pyridine-5-carboxamide

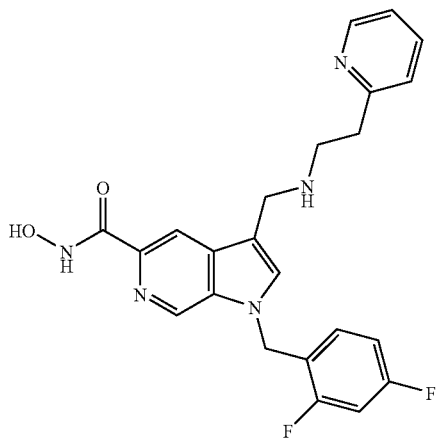

The compound was synthesized using the General Procedure A and 2-(2-aminoethyl)pyridine as the amine component. ¹H NMR (500 MHz, d6-DMSO) δ ppm 11.17 (s, 1H) 8.90 (s, 1H) 8.75 (s, 1H) 8.54 (s, 1H) 8.48 (d, 1H) 7.84 (s, 1H) 7.73-7.78 (m, 1H) 7.42 (q, 1H) 7.24-7.32 (m, 3H) 7.05 (td, 1H) 5.63 (s, 2H) 4.39-4.45 (m, 2H) 3.08 (t, 2H) (DMSO peak suppression supresses signal of CH2). LCMS: Mass of Compound: 437.2 D; Mass obs. (M+H+)=438 u/e; Retention Time: 1.11 min; Purity by TIC: 100%; Purity by UV: 96%.

Example 57

1-(2,4-Difluorobenzyl)-N-hydroxy-3-{[(2-pyrrolidin-1-ylethyl)amino]methyl}-1H-pyrrolo[2,3-c]pyridine-5-carboxamide

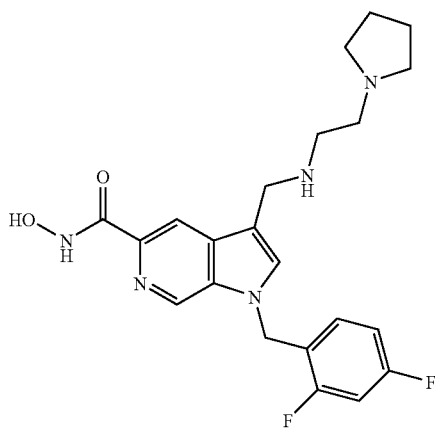

The compound was synthesized using the General Procedure A and N-(2-aminoethyl)pyrrolidine as the amine component. ¹H NMR (500 MHz, d6-DMSO) δ ppm 11.17 (s, 1H) 8.92 (s, 1H) 8.50 (s, 1H) 7.81 (s, 1H) 7.42 (q, 1H) 7.27 (t, 1H) 7.07 (t, 1H) 5.63 (s, 2H) 4.41 (s, 2H) 1.94-2.03 (m, 2H) 1.79-1.88 (m, 2H) (DMSO peak suppression supresses signal of CH2). LCMS: Mass of Compound: 429.2 D; Mass obs. (M+H+)=431 u/e; Retention Time: 1.09 min; Purity by TIC: 100%; Purity by UV: 94.

Example 58

1-(2,4-Difluorobenzyl)-N-hydroxy-3-({[2-(2-hydroxyethoxy)ethyl]amino}methyl)-1H-pyrrolo[2,3-c]pyridine-5-carboxamide

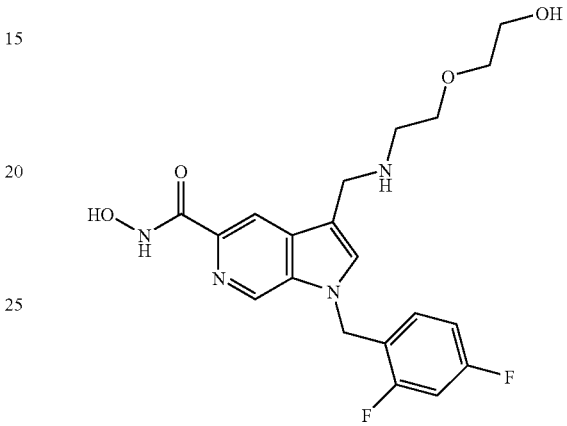

The compound was synthesized using the General Procedure A and 2-(2-aminoethoxy)ethanol as the amine component. ¹H NMR (500 MHz, d6-DMSO) δ ppm 11.15 (s, 1H) 8.89 (s, 1H) 8.60-8.69 (m, 2H) 8.49 (m, 1H) 7.82 (s, 1H) 7.41 (q, 1H) 7.26 (td, 1H) 7.07 (td, 1H) 5.62 (s, 2H) 4.37 (t, 2H) 3.62 (t, 2H) 3.32-3.38 (m, 4H) 3.10 (s, 3H) (Signals and integration from 3.62 to 3.10 ppm are effected by DMSO supression). LCMS: Mass of Compound: 420.2 D; Mass obs. (M+H+)=421 u/e; Retention Time: 1.11 min; Purity by TIC: 100%; Purity by UV: 97%.

Example 59

1-(2,4-Difluorobenzyl)-N-hydroxy-3-({[(1R)-2-hydroxy-1-phenylethyl]amino}methyl)-1H-pyrrolo[2,3-c]pyridine-5-carboxamide

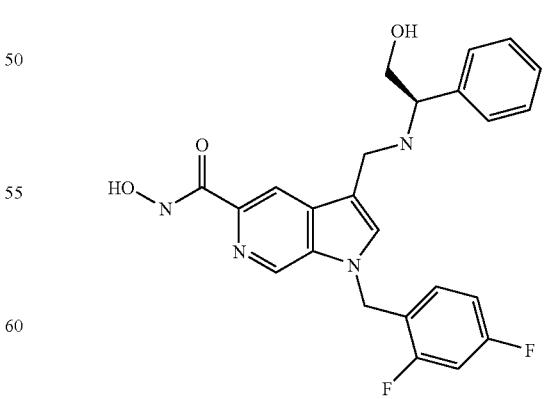

The compound was synthesized using the General Procedure A and D-(−)-alpha-phenylglycinol as the amine component. ¹H NMR (500 MHz, d6-DMSO) δ ppm 11.14 (s, 1H)

9.14-9.24 (m, 2H) 8.88 (s, 1H) 8.33 (s, 1H) 7.65 (s, 1H) 7.37-7.44 (m, 6H) 7.29 (td, 1H) 7.08 (td, 1H) 5.59 (s, 2H) 4.27-4.34 (m, 2H) 4.10-4.16 (m, 1H) 3.73-3.79 (m, 2H). LCMS: Mass of Compound: 452.2 D; Mass obs. (M+H⁺)=453 u/e; Retention Time: 1.22 min; Purity by TIC: 100%; Purity by UV: 100%.

Example 60

1-(2,4-Difluorobenzyl)-N-hydroxy-3-{[(tetrahydrofuran-2-ylmethyl)amino]methyl}-1H-pyrrolo[2,3-c]pyridine-5-carboxamide

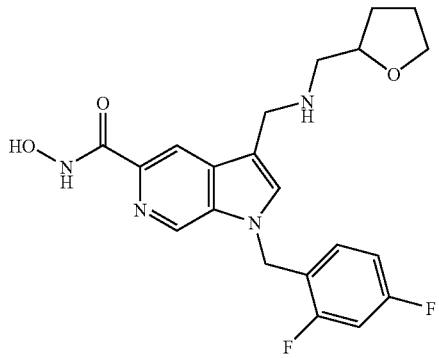

The compound was synthesized using the General Procedure A and tetrahydrofurfurylamine as the amine component. ¹H NMR (500 MHz, d6-DMSO) δ ppm 11.15 (s, 1H) 8.89 (s, 1H) 8.69-8.78 (m, 2H) 8.48 (s, 1H) 7.82 (s, 1H) 7.40 (q, 1H) 7.28 (td, 1H) 7.07 (s, 1H) 5.62 (s, 2H) 4.31-4.38 (m, 2H) 4.01-4.07 (m, 1H) 3.72-3.77 (m, 2H) 3.02-3.08 (m, 1H) 2.83-2.90 (m, 1H) 1.91-1.99 (m, 1H) 1.75-1.83 (m, 2H) 1.43-1.48 (m, 1H). LCMS: Mass of Compound: 416.2 D; Mass obs. (M+H⁺)=418 u/e; Retention Time: 1.17 min; Purity by TIC: 100%; Purity by UV: 98%.

Example 61

1-(2,4-Difluorobenzyl)-3-({[3-(dimethylamino)-2,2-dimethylpropyl]amino}methyl)-N-hydroxy-1H-pyrrolo[2,3-c]pyridine-5-carboxamide

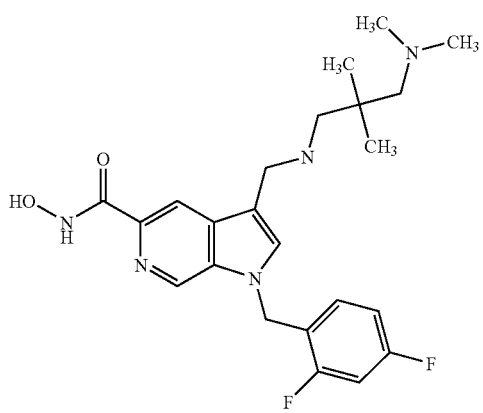

The compound was synthesized using the General Procedure A and N,N,2,2-tetramethyl-1,3-propanediamine as the amine component. ¹H NMR (500 MHz, d6-DMSO) δ ppm 11.17 (s, 1H) 8.91 (s, 1H) 8.55 (br. s, 1H) 8.47 (s, 1H) 7.85 (s, 1H) 7.42 (q, 1H) 7.28 (dt, 1H) 7.07 (td, 1H) 5.64 (s, 2H) 4.38 (s, 2H) 3.06 (s, 1H) 2.89-2.95 (m, 2H) 2.77 (s, 6H) 1.03 (s, 6H). LCMS: Mass of Compound: 445.2 D; Mass obs. (M+H⁺)=447 u/e; Retention Time: 1.08 min; Purity by TIC: 100%; Purity by UV: 100%.

Example 62

1-(2,4-Difluorobenzyl)-3-({[(1-ethylpyrrolidin-2-yl)methyl]amino}methyl)-N-hydroxy-1H-pyrrolo[2,3-c]pyridine-5-carboxamide

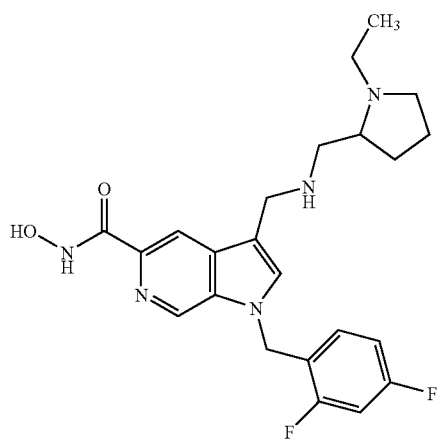

The compound was synthesized using the General Procedure A and 2-(aminomethyl)-1-ethyl-pyrrolidine as the amine component. ¹H NMR (500 MHz, d6-DMSO) δ ppm 11.18 (s, 1H) 8.92 (s, 1H) 8.50 (s, 1H) 7.80 (s, 1H) 7.42 (q, 1H) 7.28 (t, 1H) 7.07 (t, 1H) 5.64 (s, 2H) 4.42 (s, 2H) 3.02-3.10 (m, 2H) 2.20-2.27 (m, 1H) 1.95 (s, 1H) 1.82-1.91 (m, 1H) 1.73-1.80 (m, 1H) 1.19 (t, 5H). LCMS: Mass of Compound: 443.2 D; Mass obs. (M+H⁺)=445 u/e; Retention Time: 1.09 min; Purity by TIC: 100%; Purity by UV: 100%.

Example 63

1-(2,4-Difluorobenzyl)-N-hydroxy-3-{[methyl(2-pyridin-2-ylethyl)amino]methyl}-1H-pyrrolo[2,3-c]pyridine-5-carboxamide

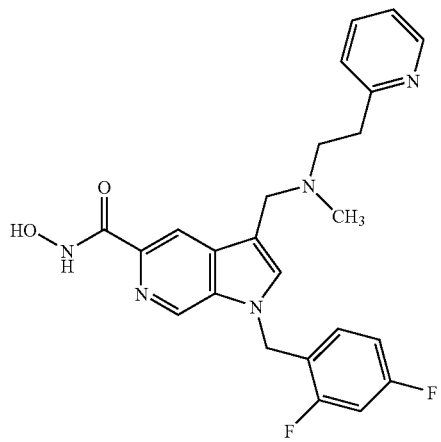

The compound was synthesized using the General Procedure A and 2-(2-methylaminoethyl)pyridine as the amine component. ¹H NMR (500 MHz, d6-DMSO) δ ppm 11.18 (s, 1H) 8.90 (s, 1H) 8.56 (s, 1H) 8.46 (d, 1H) 7.94 (s, 1H) 7.73 (t, 1H) 7.38 (q, 1H) 7.31 (d, 1H) 7.23-7.29 (m, 2H) 7.04 (td, 1H) 5.64 (s, 2H) 4.58-4.64 (m, 2H) 3.18 (t, 2H) 2.77 (s, 3H)

(DMSO suppression supresses CH₂ signal). LCMS: Mass of Compound: 451.2 D; Mass obs: (M+H⁺)=453 u/e; Retention Time: 1.17 min; Purity by TIC: 100%; Purity by UV: 93%.

Example 64

3-({[(1S)-1-Benzyl-2-hydroxyethyl]amino}methyl)-1-(2,4-difluorobenzyl)-N-hydroxy-1H-pyrrolo[2,3-c]pyridine-5-carboxamide

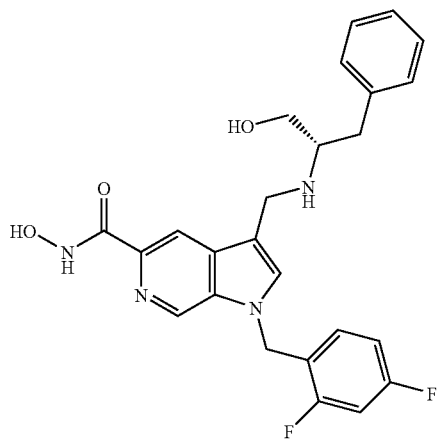

The compound was synthesized using the General Procedure A and L-phenylalaninol as the amine component. ¹H NMR (500 MHz, d6-DMSO) δ ppm 11.16 (s, 1H) 8.91 (s, 1H) 8.82 (br. s, 1H) 8.72 (br. s, 1H) 8.53 (s, 1H) 7.85 (s, 1H) 7.43 (q, 1H) 7.26-7.31 (m, 3H) 7.18-7.24 (m, 3H) 7.05-7.10 (m, 1H) 5.64 (s, 2H) 4.40-4.50 (m, 2H) 3.35 (s, 1H) 3.08 (d, 1H) 2.80 (t, 1H). LCMS: Mass of Compound: 466.2 D; Mass obs. (M+H⁺)=467 u/e; Retention Time: 1.3 min; Purity by TIC: 100%; Purity by UV: 94%.

Example 65

1-(2,4-Difluorobenzyl)-N-hydroxy-3-{[(2-hydroxypropyl)amino]methyl}-1H-pyrrolo[2,3-c]pyridine-5-carboxamide

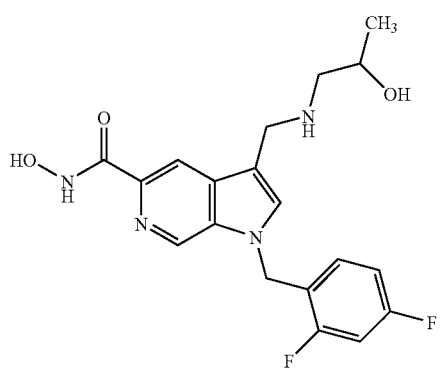

The compound was synthesized using the General Procedure A and 1-amino-2-propanol as the amine component. ¹H NMR (500 MHz, d6-DMSO) δ ppm 11.15 (s, 1H) 8.89 (s, 1H) 8.56-8.64 (m, 2H) 8.48 (s, 1H) 7.84 (s, 1H) 7.40 (q, 1H) 7.26 (td, 1H) 7.06 (td, 1H) 5.62 (s, 2H) 4.30-4.37 (m, 2H) 3.83-3.89 (m, 1H) 2.89-2.95 (m, 1H) 2.66-2.73 (m, 1H) 1.04 (d, 3H). LCMS: Mass of Compound: 390.2 D; Mass obs. (M+H⁺)=391 u/e; Retention Time: 1.1 min; Purity by TIC: 100%; Purity by UV: 98%.

Example 66

1-(2,4-Difluorobenzyl)-N-hydroxy-3-({[(5-methylpyrazin-2-yl)methyl]amino}methyl)-1H-pyrrolo[2,3-c]pyridine-5-carboxamide

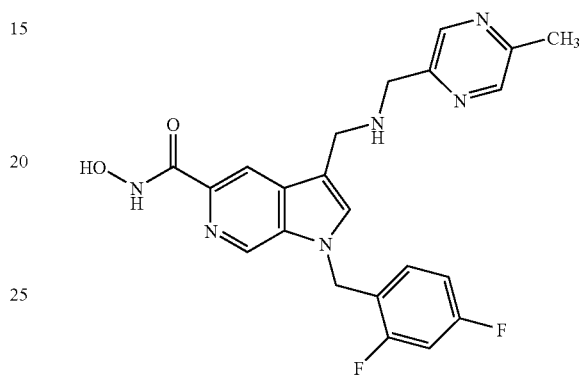

The compound was synthesized using the General Procedure A and 2-(aminomethyl)-5-methylpyrazine as the amine component. ¹H NMR (500 MHz, d6-DMSO) δ ppm 9.25-9.33 (m, 2H) 8.88 (s, 1H) 8.55 (s, 1H) 8.54 (s, 1H) 8.50 (s, 1H) 7.83 (s, 1H) 7.39 (q, 1H) 7.27 (dt, 1H) δ 7.07 (td, 1H) 5.62 (s, 2H) 4.41-4.46 (m, 2H) 4.31-4.36 (m, 2H) (DMSO suppression suppresses CH₃ signal). LCMS: Mass of Compound: 438.2 D; Mass obs. (M+H⁺)=439 u/e; Retention Time: 1.18 min; Purity by TIC: 100%; Purity by UV: 95%.

Example 67

1-(2,4-Difluorobenzyl)-N-hydroxy-3-({[2-(1H-indol-3-yl)ethyl]amino}methyl)-1H-pyrrolo[2,3-c]pyridine-5-carboxamide

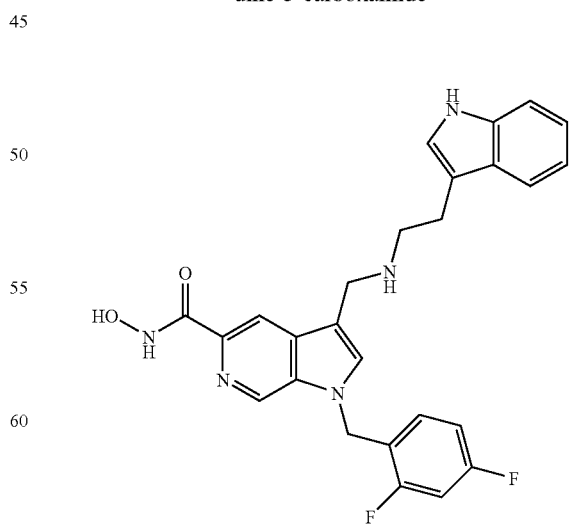

The compound was synthesized using the General Procedure A and tryptamine as the amine component. ¹H NMR (500 MHz, d6-DMSO) δ ppm 11.16 (s, 1H) 10.90 (s, 1H) 8.90 (s, 1H) 8.64 (s, 2H) 8.52 (s, 1H) 7.81 (s, 1H) 7.48 (d, 1H) 7.40 (q, 1H) 7.32 (d, 1H) 7.25 (t, 1H) 7.17 (d, 1H) 7.02-7.07 (m, 2H) 6.96 (t, 1H) 5.62 (s, 2H) 4.40 (t, 2H) 3.19 (t, 2H) 3.02 (t, 2H). LCMS: Mass of Compound: 475.2 D; Mass obs. (M+H$^+$)=477 u/e; Retention Time: 1.34 min; Purity by TIC: 100%; Purity by UV: 91%.

Example 68

1-(2,4-Difluorobenzyl)-N-hydroxy-3-({[3-(2-oxopyrrolidin-1-yl)propyl]amino}methyl)-1H-pyrrolo[2,3-c]pyridine-5-carboxamide

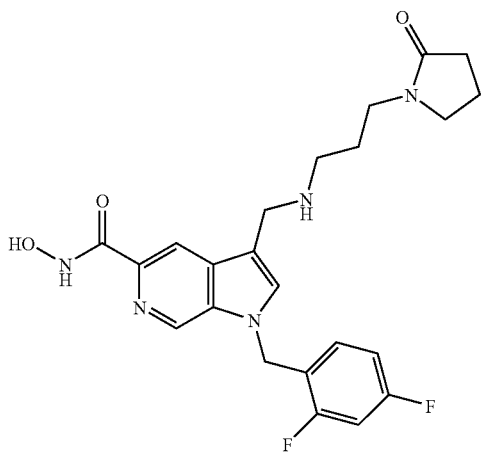

The compound was synthesized using the General Procedure A and 1-(3-aminopropyl)-2-pyrrolidinone as the amine component. $^1$H NMR (500 MHz, d6-DMSO): ppm 11.16 (s, 1H) 8.90 (s, 1H) 8.55 (br. s, 2H) 8.49 (s, 1H) 7.80 (s, 1H) 7.41 (q, 1H) 7.27 (dt, 1H) 7.07 (td, 1H) 5.63 (s, 2H) 4.34 (t, 2H) 2.84-2.91 (m, 2H) 2.17 (t, 2H) 1.83-1.90 (m, 2H) 1.75 (s, 2H). LCMS: Mass of Compound: 457.2 D; Mass obs. (M+H$^+$)=459 u/e; Retention Time: 1.15 min; Purity by TIC: 100%; Purity by UV: 97.

Example 69

1-(2,4-Difluorobenzyl)-3-{[ethyl(2-hydroxyethyl)amino]methyl}-N-hydroxy-1H-pyrrolo[2,3-c]pyridine-5-carboxamide

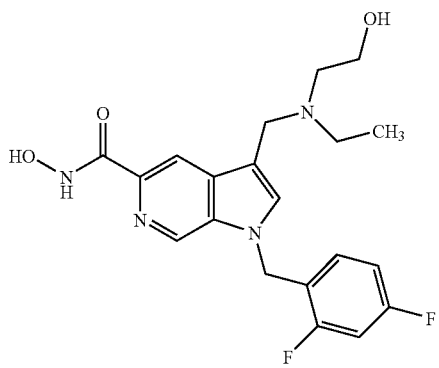

The compound was synthesized using General Procedure A and 2-ethylaminoethanol as the amine component. $^1$H NMR (500 MHz, d6-DMSO) δ ppm 9.20-9.26 (br. s, 1H) 8.89 (s, 1H) 8.49 (s, 1H) 7.94 (s, 1H) 7.38 (q, 1H) 7.26 (dt, 1H) 7.06 (dt, 1H) 5.64 (s, 2H) 4.50-4.59 (m, 2H) 3.06-3.15 (m, 4H) 1.23 (t, 3H). LCMS: Mass of Compound: 404.2 D; Mass obs. (M+H$^+$)=405 u/e; Retention Time: 1.14 min; Purity by TIC: 100%; Purity by UV: 99%.

Example 70

1-(2,4-Difluorobenzyl)-3-{[(4-fluorobenzyl)amino]methyl}-N-hydroxy-1H-pyrrolo[2,3-c]pyridine-5-carboxamide

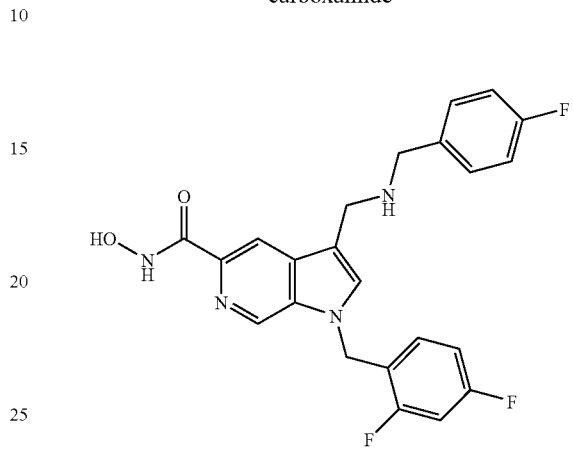

The compound was synthesized using the General Procedure A and 4-fluorobenzylamine as the amine component. $^1$H NMR (500 MHz, d6-DMSO) δ ppm 11.15 (s, 1H) 8.98 (s, 2H) 8.89 (s, 1H) 8.47 (s, 1H) 7.80 (s, 1H) 7.48 (dd, 2H) 7.41 (q, 1H) 7.27 (dt, 1H) 7.23 (t, 2H) 7.06 (dt, 1H) 5.62 (s, 2H) 4.34-4.41 (m, 2H) 4.15-4.20 (m, 2H). LCMS: Mass of Compound: 440.1 D; Mass obs. (M+H$^+$)=442 u/e; Retention Time: 1.31 min; Purity by TIC: 100%; Purity by UV: 89%.

Example 71

1-(2,4-Difluorobenzyl)-N-hydroxy-3-{[(1-phenylethyl)amino]methyl}-1H-pyrrolo[2,3-c]pyridine-5-carboxamide

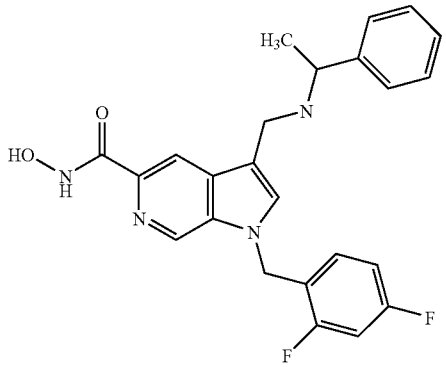

The compound was synthesized using the General Procedure A and alpha-methylbenzylamine as the amine component. $^1$H NMR (500 MHz, d6-DMSO) δ ppm 11.15 (s, 1H) 9.10 (br. s, 1H) 9.03 (br. s, 1H) 8.88 (s, 1H) 8.37 (s, 1H) 7.73 (s, 1H) 7.45-7.49 (m, 2H) 7.37-7.45 (m, 4H) 7.27 (dt, 1H) 7.07 (dt, 1H) 5.60 (s, 2H) 4.39-4.45 (m, 1H) 4.31-4.37 (m, 1H) 4.01-4.08 (m, 1H) 1.55 (d, 3H). LCMS: Mass of Compound: 436.2 D; Mass obs. (M+H⁺)=437 u/e; Retention Time: 1.3 min; Purity by TIC: 100%; Purity by UV: 98%.

Example 72

1-(2,4-Difluorobenzyl)-3-({[2-(dimethylamino)ethyl]amino}methyl)-N-hydroxy -1H-pyrrolo[2,3-c]pyridine-5-carboxamide

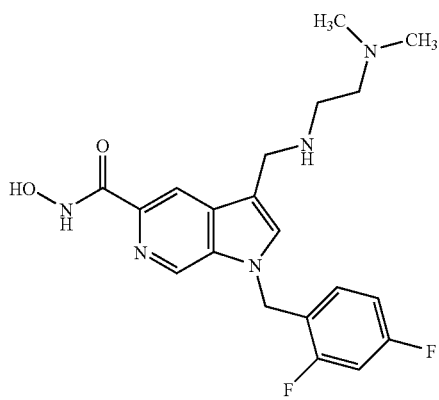

The compound was synthesized using the General Procedure A and N,N-dimethylethylenediamine as the amine component. ¹H NMR (500 MHz, d6-DMSO) δ ppm 11.17 (s, 1H) 8.92 (s, 1H) 8.50 (s, 1H) 7.81 (s, 1H) 7.42 (q, 1H) 7.27 (t, 1H) 7.07 (t, 1H) 5.63 (s, 2H) 4.40 (s, 2H) 2.80 (s, 6H) (DMSO suppression suppresses CH₂ signals). LCMS: Mass of Compound: 403.2 D; Mass obs. (M+H⁺)=405 u/e; Retention Time: 1.07 min; Purity by TIC: 100%; Purity by UV: 93%.

Example 73

3-{[(Cyclopropylmethyl)(propyl)amino]methyl}-1-(2,4-difluorobenzyl)-N-hydroxy -1H-pyrrolo[2,3-c]pyridine-5-carboxamide

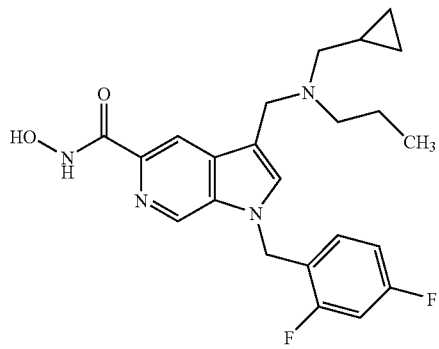

The compound was synthesized using General Procedure A and N-propylcyclopropanemethylamine as the amine component. ¹H NMR (500 MHz, d6-DMSO) δ ppm 11.15 (s, 1H) 9.21 (s, 1H) 8.90 (s, 1H) 8.46 (s, 1H) 7.94 (s, 1H) 7.41 (q, 1H) 7.25 (dt, 1H) 7.06 (dt, 1H) 5.65 (s, 2H) 4.60 (dd, 1H) 4.54 (dd, 1H) 2.95-3.03 (m, 3H) 1.66-1.71 (m, 1H) 1.60-1.64 (m, 1H) 1.06-1.12 (m, 1H) 0.81 (t, 3H) 0.56-0.62 (m, 2H) 0.24-0.34 (m, 2H). LCMS: Mass of Compound: 428.2 D; Mass obs. (M+H⁺)=430 u/e; Retention Time: 1.33 min; Purity by TIC: 100%; Purity by UV: 92%.

Example 74

3-{[(1R,2R,4S)-Bicyclo[2.2.1]hept-2-ylamino]methyl}-1-(2,4-difluorobenzyl)-N-hydroxy -1H-pyrrolo[2,3-c]pyridine-5-carboxamide

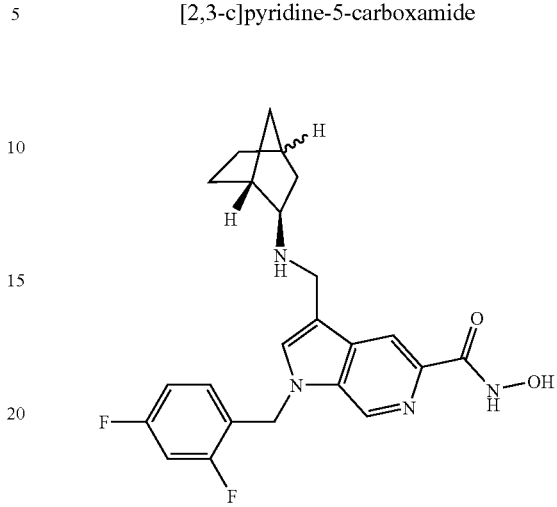

The compound was synthesized using the General Procedure A and exo-2-aminonorbornane as the amine component. ¹H NMR (500 MHz, d6-DMSO) δ ppm 11.15 (s, 1H) 8.90 (s, 1H) 8.47 (s, 1H) 8.34-8.44 (m, 2H) 7.82 (s, 1H) 7.43 (q, 1H) 7.28 (td, 1H) 7.08 (td, 1H) 5.62 (s, 2H) 4.29-4.36 (m, 2H) 3.35 (m, 1H) 3.02-3.07 (m, 1H) 2.24-2.27 (m, 1H) 1.58-1.64 (m, 2H) 1.50-1.35 (m, 4H) 1.09-1.13 (m, 1H) 1.02-1.08 (m, 2H). LCMS: Mass of Compound: 426.2 D; Mass obs. (M+H⁺)=428 u/e; Retention Time: 1.3 min; Purity by TIC: 100%; Purity by UV: 99%.

Example 75 rac-1-(2,4-Difluorobenzyl)-N-hydroxy-3-({[(1S,2R)-2-phenylcyclopropyl]amino}methyl)-1H-pyrrolo[2,3-c]pyridine-5-carboxamide

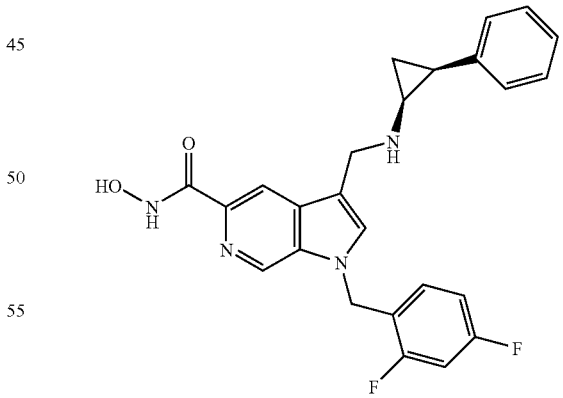

The compound was synthesized using the General Procedure A and trans-2-phenylcyclopropylamine hydrochloride as the amine component. ¹H NMR (500 MHz, d6-DMSO) δ ppm 11.14 (s, 1H) 9.04 (br. s, 1H) 8.89 (s, 1H) 8.50 (s, 1H) 7.76 (s, 1H) 7.40 (q, 1H) 7.29 (dt, 1H) 7.22 (t, 2H) 7.17 (t, 1H) 7.06 (dt, 1H) 7.01 (d, 2H) 5.59 (d, 1H) 5.56 (d, 1H) 4.47-4.56 (m, 2H) 2.92-2.98 (m, 1H) 2.27-2.31 (m, 1H) 1.33-1.39 (m, 1H) 1.18-1.25 (m, 1H). LCMS: Mass of Compound: 448.2 D;

Example 76

3-({[(1R)-1-Cyclohexylethyl]amino}methyl)-1-(2,4-difluorobenzyl)-N-hydroxy-1H-pyrrolo[2,3-c]pyridine-5-carboxamide

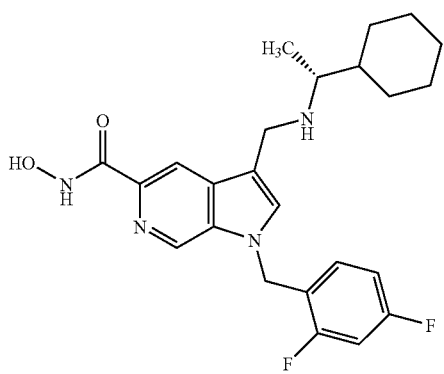

The compound was synthesized using the General Procedure A and (R)-(−)-1-cyclohexylethylamine as the amine component. $^1$H NMR (500 MHz, d6-DMSO) δ ppm 11.15 (s, 1H) 8.90 (s, 1H) 8.53 (br s, 1H) 8.47 (s, 1H) 8.19 (br. s, 1H) 7.83 (s, 1H) 7.42 (q, 1H) 7.27 (dt, 1H) 7.07 (dt, 1H) 5.63 (s, 2H) 4.37-4.41 (m, 1H) 4.31-4.36 (m, 1H) 3.33 (s, 1H) 1.63-1.70 (m, 3H) 1.53-1.60 (m, 2H) 1.45-1.50 (m, 1H) 1.11-1.18 (m, 1H) 1.15 (d, 3H) 1.01-1.06 (m, 2H) 0.94-1.00 (m, 2H).

LCMS: Mass of Compound: 442.2 D; Mass obs. (M+H$^+$)=443 u/e; Retention Time: 1.4 min; Purity by TIC: 100%; Purity by UV: 100%.

Example 77

1-(2,4-Difluorobenzyl)-N-hydroxy-3-({[(1S)-2-hydroxy-1-(1H-indol-3-ylmethyl)ethyl]amino}methyl)-1H-pyrrolo[2,3-c]pyridine-5-carboxamide

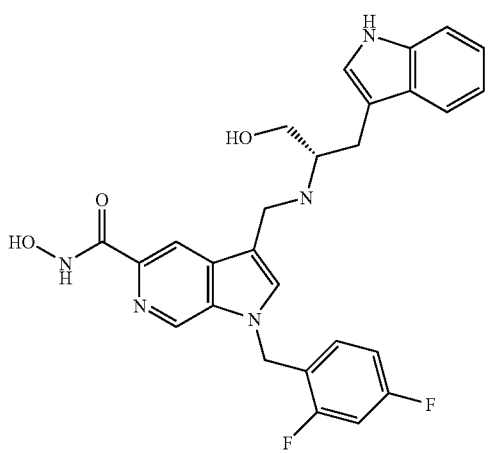

The compound was synthesized using the General Procedure A and L-(−)-tryptophanol as the amine component. $^1$H NMR (500 MHz, d6-DMSO) δ ppm 11.16 (s, 1H) 10.92 (s, 1H) 8.91 (s, 1H) 8.70-8.80 (m, 2H) 8.54 (s, 1H) 7.83 (s, 1H) 7.43 (d, 1H) 7.40 (q, 1H) 7.32 (d, 1H) 7.27 (dt, 1H), 7.17-7.20 (m, 1H) 7.02-7.08 (m, 2H) 6.92 (t, 1H) 5.63 (s, 2H) 4.45-4.54 (m, 2H) 3.12 (dd, 1H) 2.99 (dd, 1H) DMSO suppression suppresses CH$_2$ Signal). LCMS: Mass of Compound: 505.2 D; Mass obs. (M+H$^+$)=507 u/e; Retention Time: 1.28 min; Purity by TIC: 100%; Purity by UV: 92%.

Example 78

1-(2,4-Difluorobenzyl)-N-hydroxy-3-({[1-(hydroxymethyl)-2-methylpropyl]amino}methyl)-1H-pyrrolo[2,3-c]pyridine-5-carboxamide

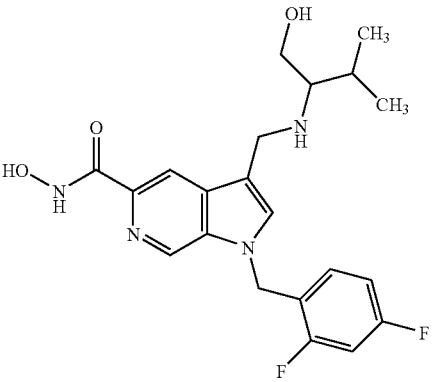

The compound was synthesized using General Procedure A and DL-2-amino-3-methyl-1-butanol as the amine component. $^1$H NMR (500 MHz, d6-DMSO) δ ppm 8.90 (s, 1H) 8.57-8.64 (m, 1H) 8.47 (s, 1H) 8.25-8.33 (m, 1H) 7.86 (s, 1H) 7.40 (q, 1H) 7.27 (dt, 1H) 7.06 (dt, 1H) 5.63 (s, 2H) 4.37-4.46 (m, 2H) 3.71 (dd, 2H) 2.88-2.94 (m, 1H) 2.05 (sep, 1H) 0.87 (d, 3H) 0.84 (d, 3H). LCMS: Mass of Compound: 418.2 D; Mass obs. (M+H$^+$)=419 u/e; Retention Time: 1.19 min; Purity by TIC: 100%; Purity by UV: 98%.

Example 79

1-(2,4-Difluorobenzyl)-N-hydroxy-3-{[(3-methylbenzyl)amino]methyl}-1H-pyrrolo[2,3-c]pyridine-5-carboxamide

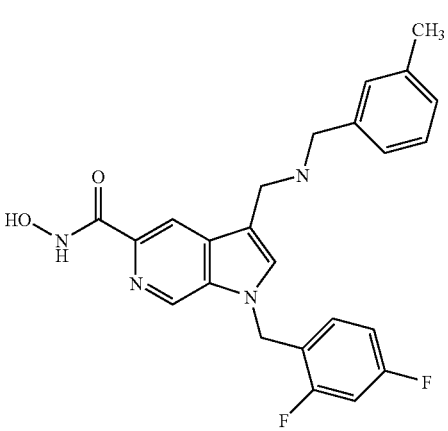

The compound was synthesized using the General Procedure A and 3-methylbenzylamine as the amine component. $^1$H NMR (500 MHz, d6-DMSO) δ ppm 11.15 (s, 1H) 8.98 (br.

s, 2H) 8.89 (s, 1H) 8.47 (s, 1H) 7.80 (s, 1H) 7.40 (q, 1H) 7.24-7.30 (m, 2H) 7.20-7.24 (m, 2H) 7.18 (t, 1H) 7.06 (dt, 1H) 5.62 (s, 2H) 4.34-4.41 (m, 2H) 4.10-4.15 (m, 2H) 2.27 (s, 3H). LCMS: Mass of Compound: 436.2 D; Mass obs. (M+H$^+$)=437 u/e; Retention Time: 1.34 min; Purity by TIC: 100%; Purity by UV: 97%.

Example 80

1-(2,4-Difluorobenzyl)-N-hydroxy-3-{[(2-hydroxyethyl)amino]methyl}-1H-pyrrolo[2,3-c]pyridine-5-carboxamide

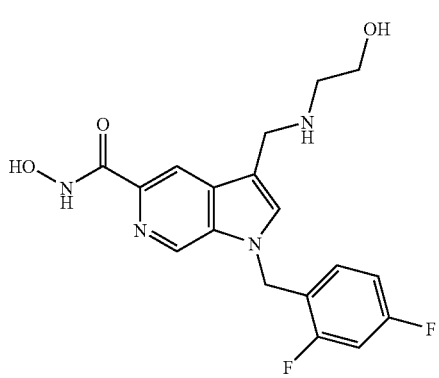

The compound was synthesized using the General Procedure A and ethanolamine as the amine component. $^1$H NMR (500 MHz, d6-DMSO) δ ppm 11.15 (s, 1H) 8.89 (s, 1H) 8.59-8.68 (m, 2H) 8.49 (s, 1H) 7.83 (s, 1H) 7.39 (q, 1H) 7.28 (dt, 1H) 7.07 (dt, 1H) 5.62 (s, 2H) 4.31-4.39 (m, 2H) 2.97 (s, 2H) 2.93-2.96 (m, 2H) (DMSO suppession suppresses CH2 signal). LCMS: Mass of Compound: 376.1 D; Mass obs. (M+H$^+$)=377 u/e; Retention Time: 1.07 min; Purity by TIC: 96%; Purity by UV: 83%.

Example 81

1-(2,4-Difluorobenzyl)-N-hydroxy-3-[(2-methylpyrrolidin-1-yl)methyl]-1H-pyrrolo[2,3-c]pyridine-5-carboxamide

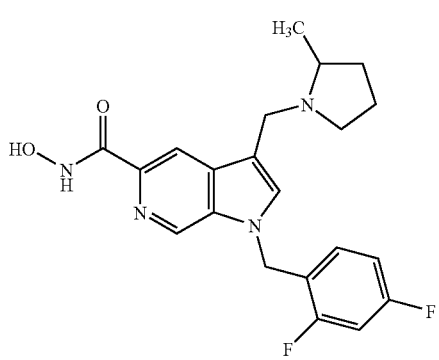

The compound was synthesized using the General Procedure A and 2-methylpyrrolidine as the amine component. $^1$H NMR (500 MHz, d6-DMSO) δ ppm 11.17 (s, 1H) 9.26-9.34 (m, 1H) 8.90 (s, 1H) 8.46 (s, 1H) 7.93 (s, 1H) 7.40 (q, 1H) 7.25 (dt, 1H) 7.07 (dt, 1H) 5.64 (s, 2H) 4.69 (dd, 1H) 4.42 (dd, 1H) 3.37 (s, 1H) 2.15-2.23 (m, 1H) 1.85-1.94 (m, 1H) 1.73-1.82 (m, 1H) 1.50-1.55 (m, 1H) 1.30 (m, 1H) 1.29 (d, 3H). LCMS: Mass of Compound: 400.2 D; Mass obs. (M+H$^+$) 402 u/e; Retention Time: 1.19 min; Purity by TIC: 100%; Purity by UV: 95%.

Example 82

1-(2,4-Difluorobenzyl)-3-{[(1-ethylpropyl)amino]methyl}-N-hydroxy-1H-pyrrolo[2,3-c]pyridine-5-carboxamide

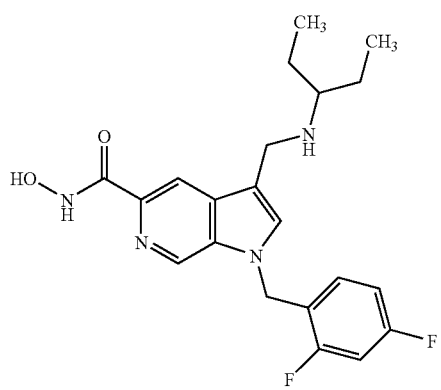

The compound was synthesized using the General Procedure A and 3-aminopentane as the amine component. $^1$H NMR (500 MHz, d6-DMSO) δ ppm 11.16 (s, 1H) 8.91 (s, 1H) 8.46 (s, 1H) 8.40 (br. s, 1H) 7.84 (s, 1H) 7.42 (q, 1H) 7.28 (dt, 1H) 7.07 (dt, 1H) 5.63 (s, 2H) 4.34-4.39 (m, 2H) 2.94-3.01 (m, 1H) 1.68 (td, 2H) 1.60 (dt, 2H) 0.84 (t, 6H). LCMS: Mass of Compound: 402.2 D; Mass obs. (M+H$^+$)=403 u/e; Retention Time: 1.25 min; Purity by TIC: 100%; Purity by UV: 98%.

Example 83

1-(2,4-Difluorobenzyl)-N-hydroxy-3-H{[(3-isopropoxypropyl)amino]methyl}-1H-pyrrolo[2,3-c]pyridine-5-carboxamide

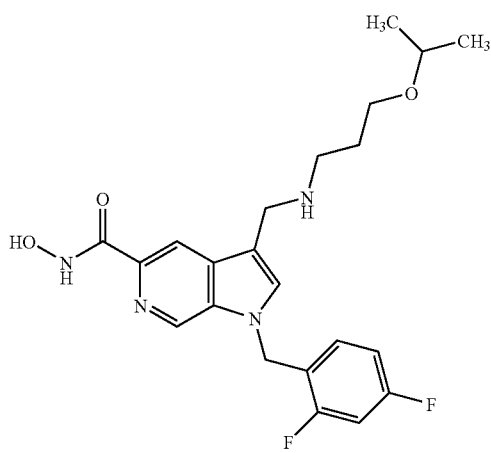

The compound was synthesized using the General Procedure A and 3-isopropoxypropylamine as the amine component. ¹H NMR (500 MHz, d6-DMSO) δ ppm 11.15 (s, 1H) 8.90 (s, 1H) 8.49 (s, 1H) 8.45 (br. s, 2H) 7.80 (s, 1H) 7.41 (q, 1H) 7.27 (dt, 1H) 7.07 (dt, 1H) 5.62 (s, 2H) 4.32-4.37 (m, 2H) 2.96 (s, 2H) 1.72-1.78 (m, 2H) 0.99 (d, 6H). LCMS: Mass of Compound: 432.2 D; Mass obs. (M+H⁺)=433 u/e; Retention Time: 1.26 min; Purity by TIC: 100%; Purity by UV: 99%.

Example 84

1-(2,4-Difluorobenzyl)-N-hydroxy-3-{[(2-hydroxy-2-phenylethyl)amino]methyl}-1H-pyrrolo[2,3-c]pyridine-5-carboxamide

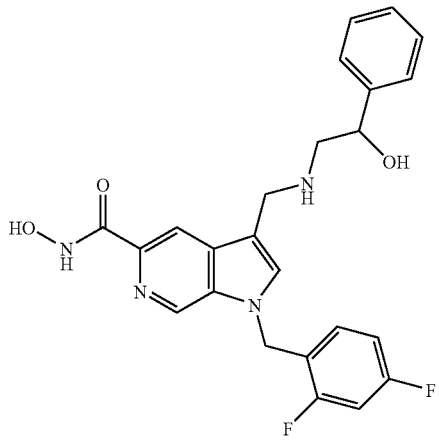

The compound was synthesized using the General Procedure A and 2-amino-1-phenylethanol as the amine component. ¹H NMR (500 MHz, d6-DMSO) δ ppm 11.16 (s, 1H) 8.89 (s, 1H) 8.79-8.85 (m, 2H) 8.50 (s, 1H) 7.84 (s, 1H) 7.23-7.44 (m, 7H) 7.04 (dt, 1H) 5.62 (s, 2H) 4.81-4.87 (m, 1H) 4.35-4.42 (m, 2H) 3.07-3.17 (m, 1H) 2.89-2.97 (m, 1H). LCMS: Mass of Compound: 452.2 D; Mass obs. (M+H⁺)=453 u/e; Retention Time: 1.26 min; Purity by TIC: 100%; Purity by UV: 93%.

Example 85

1-(2,4-Difluorobenzyl)-3-(J[2-(4-fluorophenyl)ethyl]aminomethyl)-N-hydroxy-1H-pyrrolo[2,3-c]pyridine-5-carboxamide

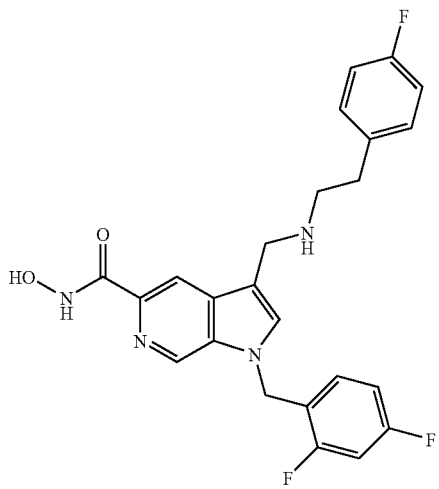

The compound was synthesized using the General Procedure A and 4-fluorophenethylamine hydrochloride as the amine component. ¹H NMR (500 MHz, d6-DMSO) δ ppm 8.90 (s, 1H) 8.65 (br. s, 2H) 8.50 (s, 1H) 7.81 (s, 1H) 7.40 (q, 1H) 7.22-7.29 (m, 3H) 7.12 (t, 2H) 7.06 (dt, 1H) 5.63 (s, 2H) 4.34-4.41 (m, 2H) 3.10-3.17 (m, 2H, distorted by DMSO supression) 2.84-2.89 (m, 2H). LCMS: Mass of Compound: 454.2 D; Mass obs. (M+H⁺)=455 u/e; Retention Time: 1.37 min; Purity by TIC: 97%; Purity by UV: 92%.

Example 86

1-(2,4-Difluorobenzyl)-N-hydroxy-3-{[(2-hydroxy-1-methyl-2-phenylethyl)amino]methyl}-1H-pyrrolo[2,3-c]pyridine-5-carboxamide

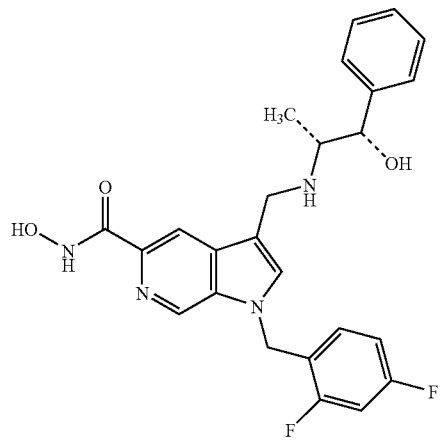

The compound was synthesized using the General Procedure A and phenylpropanolamine hydrochloride as the amine component. ¹H NMR (500 MHz, d6-DMSO) δ ppm 11.16 (s, 1H) 8.92 (s, 1H) 8.78 (br. s, 1H) 8.68 (br. s, 1H) 8.54 (s, 1H) 7.87 (s, 1H) 7.44 (q, 1H) 7.30-7.36 (m, 5H) 7.24-7.29 (m, 2H) 7.07 (dt, 1H) 5.64 (s, 2H) 5.11 (s, 1H) 4.40-4.50 (m, 2H) 3.31-3.39 (m, 1H) 0.93 (d, 3H). LCMS: Mass of Compound: 466.2 D; Mass obs. (M+H⁺)=467 u/e; Retention Time: 1.3 min; Purity by TIC: 97%; Purity by UV: 89%.

Example 87

1-(2,4-Difluorobenzyl)-N-hydroxy-3-({[(1S)-1-(hydroxymethyl)-2,2-dimethylpropyl]amino}methyl)-1H-pyrrolo[2,3-c]pyridine-5-carboxamide

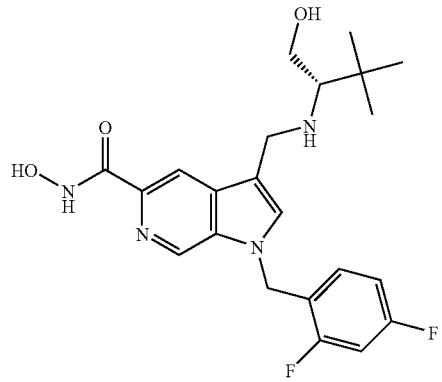

The compound was synthesized using the General Procedure A and L-tert-leucinol as the amine component. ¹H NMR (500 MHz, d6-DMSO) δ ppm 8.90 (s, 1H) 8.83 (br. s, 1H) 8.47 (s, 1H) 7.90 (s, 1H) 7.69 (br. s, 1H) 7.42 (q, 1H) 7.25 (dt, 1H) 7.06 (dt, 1H) 5.60-5.67 (m, 2H) 4.43-4.50 (m, 2H) 3.79

(dd, 1H) 2.73-2.78 (m, 1H) 0.75 (s, 9H). LCMS: Mass of Compound: 432.2 D; Mass obs. (M+H⁺)=433 u/e; Retention Time: 1.22 min; Purity by TIC: 100%; Purity by UV: 98%.

Example 88

1-(2,4-Difluorobenzyl)-N-hydroxy-3-[({[6-(trifluoromethyl)pyridin-3-yl]methyl}amino)methyl]-1H-pyrrolo[2,3-c]pyridine-5-carboxamide

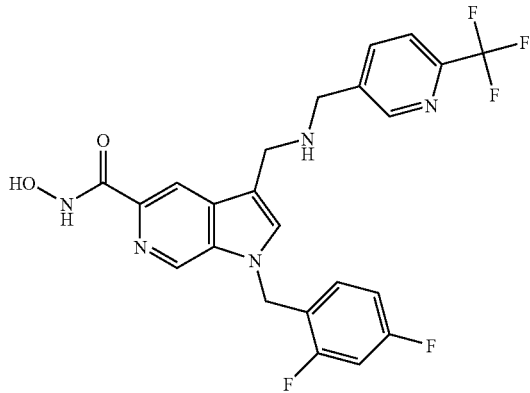

The compound was synthesized using the General Procedure A and 3-aminomethyl-6-(trifluoromethyl)pyridine as the amine component. ¹H NMR (500 MHz, d6-DMSO) δ ppm 11.16 (s, 1H) 9.10 (br. s, 2H) 8.90 (s, 1H) 8.81 (s, 1H) 8.50 (s, 1H) 8.15 (dd, 1H) 7.96 (d, 1H) 7.81 (s, 1H) 7.41 (q, 1H) 7.24 (dt, 1H) 7.07 (dt, 1H) 5.63 (s, 2H) 4.42-4.48 (m, 2H) 4.31-4.39 (m, 2H) 3.36 (s, 1H). LCMS: Mass of Compound: 491.1 D; Mass obs. (M+H⁺)=492 u/e; Retention Time: 1.32 min; Purity by TIC: 100%; Purity by UV: 99%.

Example 89

1-(2,4-Difluorobenzyl)-N-hydroxy-3-{[(1-methylpiperidin-4-yl)amino]methyl}-1H-pyrrolo[2,3-c]pyridine-5-carboxamide

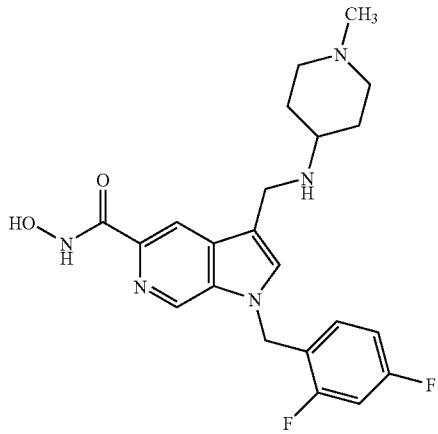

The compound was synthesized using the General Procedure A and 1-methyl-4-piperidinamine as the amine component. ¹H NMR (500 MHz, d6-DMSO) δ ppm 11.17 (s, 1H) 8.92 (s, 1H) 8.82 (br. s, 2H) 8.47 (s, 1H) 7.82 (s, 1H) 7.42 (q, 1H) 7.28 (dt, 1H) 7.08 (dt, 1H) 5.63 (s, 2H) 4.36-4.44 (m, 2H) 2.91-3.00 (m, 2H) 2.74 (s, 3H) 2.28 (d, 2H) 1.68-1.77 (m, 2H) (DMSO suppression suppresses CH₂ signals. LCMS: Mass of Compound: 429.2 D; Mass obs. (M+H⁺)=431 u/e; Retention Time: 1.07 min; Purity by TIC: 1.00%; Purity by UV: 100%.

Example 90

1-(2,4-Difluorobenzyl)-N-hydroxy-3—[(2-methoxypyridin-3-yl)amino-methyl]-1H-pyrrolo[2,3-c]pyridine-5-carboxamide

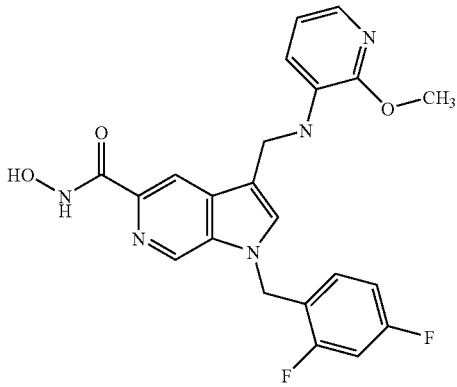

The compound was synthesized using the General Procedure A and 3-amino-2-methoxypyridine as the amine component. ¹H NMR (500 MHz, d6-DMSO) δ ppm 8.88-8.97 (m, 1H) 8.46-8.54 (m, 1H) 7.86-7.92 (m, 1H) 7.21-7.30 (m, 3H) 7.01 (dt, 1H) 6.78 (dd, 1H) 6.66 (dd, 1H) 5.60 (s, 2H) 4.45 (s, 2H) 3.81 (s, 3H). LCMS: Mass of Compound: 439.1 D; Mass obs. (M+H⁺)=440 u/e; Retention Time: 1.32 min; Purity by TLC: 96%; Purity by UV: 95%.

Example 91

1-(2,4-Difluorobenzyl)-N-hydroxy-3-[(tetrahydro-2H-pyran-4-ylamino)methyl]-1H-pyrrolo[2,3-c]pyridine-5-carboxamide

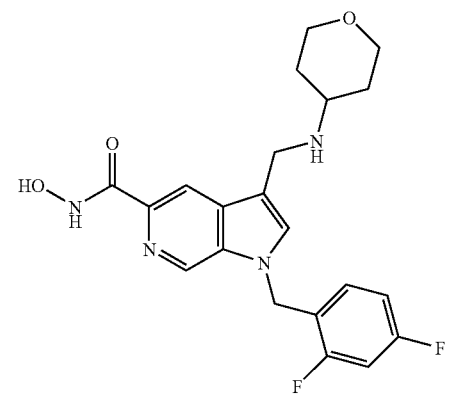

The compound was synthesized using the General Procedure A and tetrahydro-2H-pyran-4-ylamine as the amine component. ¹H NMR (500 MHz, d6-DMSO) δ ppm 8.91 (s, 1H) 8.62 (s, 2H) 8.48 (s, 1H) 7.83 (s, 1H) 7.42 (q, 1H) 7.27 (dt, 1H) 7.08 (dt, 1H) 5.63 (s, 2H) 4.34-4.40 (m, 2H) 3.89 (dd, 2H) 1.97 (d, 2H) 1.49-1.58 (m, 2H). LCMS: Mass of Compound: 416.2 D; Mass obs. (M+H⁺)=417 u/e; Retention Time: 1.15 min; Purity by TIC: 100%; Purity by UV: 98%.

Example 92

1-(2,4-Difluorobenzyl)-N-hydroxy-3-{[(tetrahydro-1H-pyrrolizin-7a(5H)-ylmethyl)amino]methyl}-1H-pyrrolo[2,3-c]pyridine-5-carboxamide

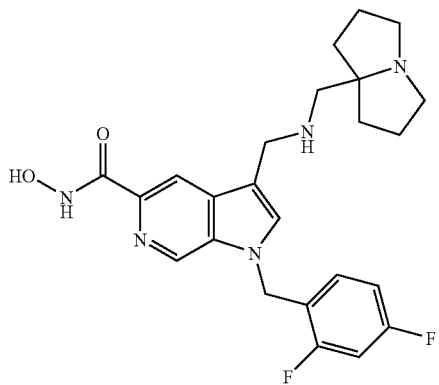

The compound was synthesized using the General Procedure A and tetrahydro-1H-pyrrolizin-7a(5H)-yl-methylamine as the amine component. The amine can be synthesized following the procedure provided by Miyano, Seiji; Yamashita, Osamu; Sumoto, Kunihiro; Shima, Keiyu; Hayashimatsu, Mariko; Satoh, Fumio; *J. Heterocycl. Chem.* 1987, 24, 47-49. ¹H NMR (500 MHz, d6-DMSO) δ ppm 11.17 (s, 1H) 8.91 (s, 1H) 8.49 (s, 1H) 7.82 (s, 1H) 7.41 (q, 1H) 7.28 (dt, 1H) 7.07 (dt, 1H) 5.64 (s, 2H) 4.43 (s, 2H) 3.12 (s, 1H) 3.08-3.11 (m, 2H) 2.02 (m, 4H) 1.85 (m, 4H). LCMS: Mass of Compound: 455.2 D; Mass obs. (M+H⁺)=457 u/e; Retention Time: 1.09 min; Purity by TIC: 100%; Purity by UV: 97%.

Example 93

1-(2,4-Difluorobenzyl)-N-hydroxy-3-({methyl[(1-phenyl-1H-pyrazol-4-yl)methyl]amino}methyl)-1H-pyrrolo[2,3-c]pyridine-5-carboxamide

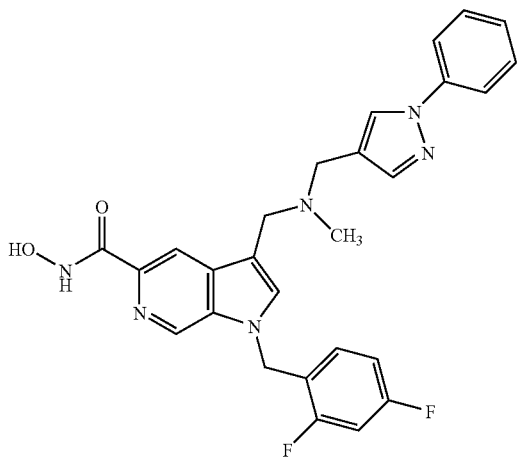

The compound was synthesized using the General Procedure A and N-methyl-1-(1-phenyl-1h-pyrazol-4-yl)methanamine as the amine component. ¹H NMR (500 MHz, d6-DMSO) δ ppm 11.17 (s, 1H) 9.66 (s, 1H) 8.90 (s, 1H) 8.59 (s, 1H) 8.53 (s, 1H) 7.95 (s, 1H) 7.86 (s, 1H) 7.78 (d, 2H) 7.49 (t, 2H) 7.41 (q, 1H) 7.31 (t, 1H) 7.27 (dt, 1H) 7.06 (dt, 1H) 5.65 (s, 2H) 4.65 (dd, 1H) 4.45 (dd, 1H) 4.38 (dd, 1H) 4.23 (dd, 1H) 2.60 (d, 3H). LCMS: Mass of Compound: 502.2 D; Mass obs. (M+H⁺)=503 u/e; Retention Time: 1.38 min; Purity by TIC: 100%; Purity by UV: 90%.

Example 94

1-(2,4-Difluorobenzyl)-3-({[4-(difluoromethoxy)benzyl]amino}methyl)-N-hydroxy-1H-pyrrolo[2,3-c]pyridine-5-carboxamide

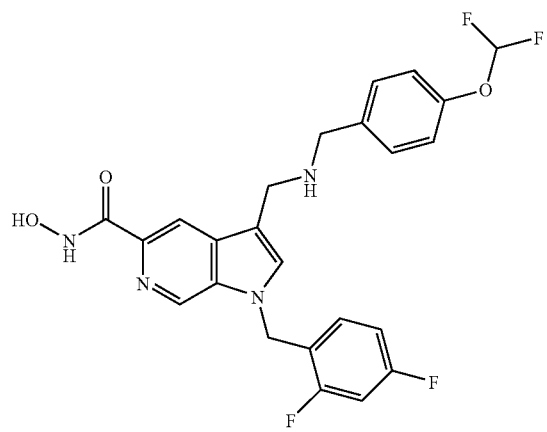

The compound was synthesized using the General Procedure A and 4-(difluoromethoxy)benzylamine as the amine component. ¹H NMR (500 MHz, d6-DMSO) δ ppm 11.15 (s, 1H) 8.99 (s, 2H) 8.89 (s, 1H) 8.47 (s, 1H) 7.80 (s, 1H) 7.48 (d, 2H) 7.39 (q, 1H) 7.27 (dt, 1H) 7.20 (d, 2H) 7.03-7.09 (dt, 1H) 5.62 (s, 2H) 4.34-4.40 (m, 2H) 4.15-4.20 (m, 2H) 3.35 (s, 1H). LCMS: Mass of Compound: 488.1 D; Mass obs. (M+H⁺)=490 u/e; Retention Time: 1.38 min; Purity by TIC: 100%; Purity by UV: 99%.

Example 95

1-(2,4-difluorobenzyl)-N-hydroxy-3-({methyl[2-(methylsulfonyl)ethyl]amino}methyl)-1H-pyrrolo[2,3-c]pyridine-5-carboxamide

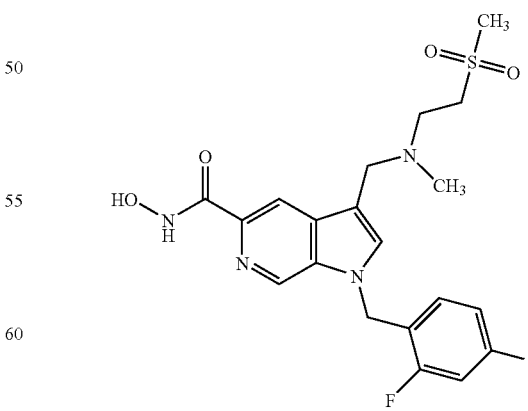

The compound was synthesized using the General Procedure A and 2-(methylamino)-1-(methylsulfonyl)ethane as the amine component. ¹H NMR (500 MHz, d6-DMSO) δ ppm 11.17 (s, 1H) 8.90 (s, 1H) 8.54 (s, 1H) 7.93 (s, 1H) 7.40 (q, 1H) 7.26 (dt, 1H) 7.05 (dt, 1H) 5.65 (s, 2H) 4.63 (d, 1H) 4.53 (d, 1H) 3.05 (s, 3H) 2.70 (s, 3H) (DMSO suppression suppresses CH$_2$ signal). LCMS: Mass of Compound: 452.1 D; Mass obs. (M+H$^+$)=453 u/e; Retention Time: 1.15 min; Purity by TIC: 100%; Purity by UV: 100%.

Example 96

1-(2,4-Difluorobenzyl)-N-hydroxy-3-({[2-(tetrahydro-2H-pyran-4-yl)ethyl]amino}methyl)-1H-pyrrolo[2,3-c]pyridine-5-carboxamide

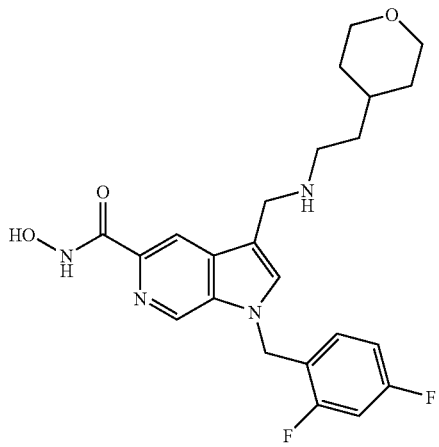

The compound was synthesized using the General Procedure A and 4-(2-aminoethyl)tetrahydropyran as the amine component. $^1$H NMR (500 MHz, d6-DMSO) δ ppm 11.16 (s, 1H) 8.90 (s, 1H) 8.49 (s, 1H) 8.48 (br s, 2H) 7.81 (s, 1H) 7.41 (q, 1H) 7.28 (dt, 1H) 7.07 (dt, 1H) 5.63 (s, 2H) 4.30-4.36 (m, 2H) 3.77 (dd, 2H) 2.89-2.96 (m, 2H) 1.44-1.51 (m, 6H) 1.05-1.14 (m, 2H). LCMS: Mass of Compound: 444.2 D; Mass obs. (M+H$^+$)=446 u/e; Retention Time: 1.21 min; Purity by TIC: 100%; Purity by UV: 97%

Example 97

Ethyl (1R,5S)-3-[({1-(2,4-difluorobenzyl)-5-[(hydroxyamino)carbonyl]-1H-pyrrolo[2,3-c]pyridin-3-yl}methyl)amino]-8-azabicyclo[3.2.1]octane-8-carboxylate

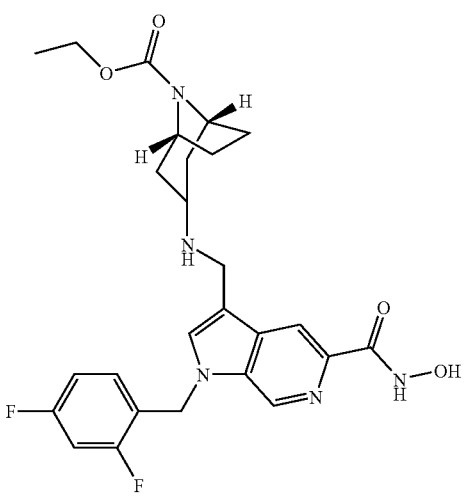

The compound was synthesized using the General Procedure A and N-(ethoxycarbonyl)aminotropane as the amine component. The synthesis procedure for the amine is given in WO 2000038680 A1 20000706. $^1$H NMR (500 MHz, d6-DMSO) δ ppm 11.15 (s, 1H) 8.89 (s, 1H) 8.47 (s, 1H) 8.46 (br. s, 2H) 7.80 (s, 1H) 7.40 (q, 1H) 7.26 (dt, 1H) 7.06 (dt, 1H) 5.62 (s, 2H) 4.31-4.38 (m, 2H) 4.15-4.20 (m, 2H) 3.97 (q, 2H) 1.86-1.95 (m, 2H) 1.65 (d, 3H) 1.47-1.54 (m, 2H) 1.11 (t, 3H). LCMS: Mass of Compound: 513 D; Mass obs. (M+H$^+$)=514 u/e; Retention Time: 1.29 min; Purity by TIC: 100%; Purity by UV: 97%.

Example 98

1-(2,4-difluorobenzyl)-N-hydroxy-3-{[(6-methyl-3,4-dihydro-2H-chromen-4-yl)amino]methyl}-1H-pyrrolo[2,3-c]pyridine-5-carboxamide

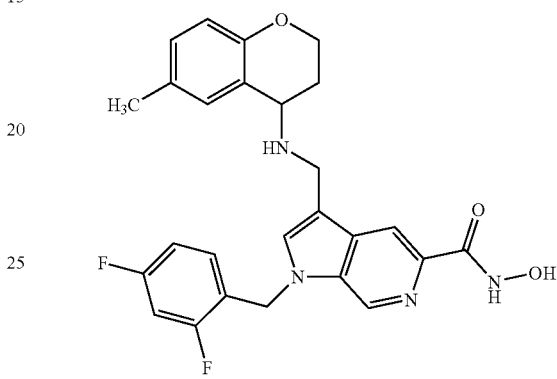

The compound was synthesized using the General Procedure A and 6-methyl-3,4-dihydro-2H-chromen-4-ylamine hydrochloride as the amine component. The synthesis of the amine is outlined in WO 2003106462. $^1$H NMR (500 MHz, d6-DMSO) δ ppm 11.17 (s, 1 h) 8.95 (br. s, 2H), 8.91 (s, 3H) 8.50 (s, 1H) 7.83 (s, 1H) 7.42 (q, 1H) 7.27 (dt, 1H) 7.19 (s, 1H) 7.04-7.09 (m, 2H) 6.74 (d, 1H) 5.63 (s, 2H) 4.50-4.56 (m, 2H) 4.41-4.48 (m, 1H) 4.17-4.27 (m, 2H) 2.34-2.39 (m, 1H) 2.25-2.20 (m, 1H), 2.18 (s, 3H). LCMS: Mass of Compound: 478.2 D; Mass obs. (M+H$^+$)=480 u/e; Retention Time: 1.37 min; Purity by TIC: 100%; Purity by UV: 100%

Example 99

1-(2,4-Difluorobenzyl)-N-hydroxy-3-{[(1,4,5,6-tetrahydrocyclopenta[c]pyrazol-3-ylmethyl)amino]methyl}-1H-pyrrolo[2,3-c]pyridine-5-carboxamide

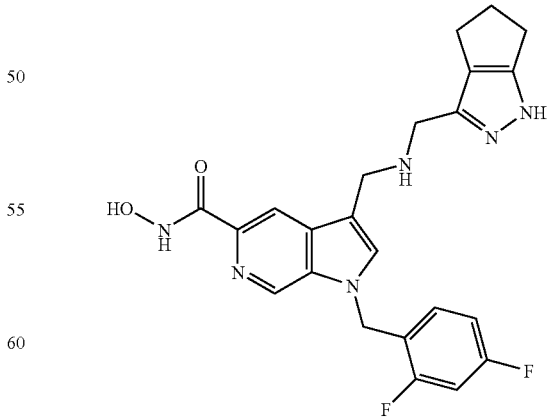

The compound was synthesized using the General Procedure A and 1,4,5,6-tetrahydrocyclopenta[C]pyrazol-3-ylmethylamine hydrochloride as the amine component. $^1$H NMR (500 MHz, d6-DMSO) δ ppm 9.04 (br s, 2H) 8.90 (s, 1H) 8.45 (s, 1H) 7.83 (s, 1H) 7.40 (q, 1H) 7.27 (dt, 1H) 7.06 (dt, 1H) 5.62 (s, 2H) 4.34-4.39 (m, 2H) 4.01-4.06 (m, 2H) 2.60 (t, 1H, distorted by DMSO supression), 2.40 (t, distorted by DMSO supression). LCMS: Mass of Compound: 452.2 D; Mass obs. (M+H$^+$)=454 u/e; Retention Time: 1.23 min; Purity by TIC: 100%; Purity by UV: 100%

Example 100

1-(2,4-Difluorobenzyl)-N-hydroxy-3-({[2-(5-methyl-4H-1,2,4-triazol-3-yl)ethyl]amino}methyl)-1H-pyrrolo[2,3-c]pyridine-5-carboxamide

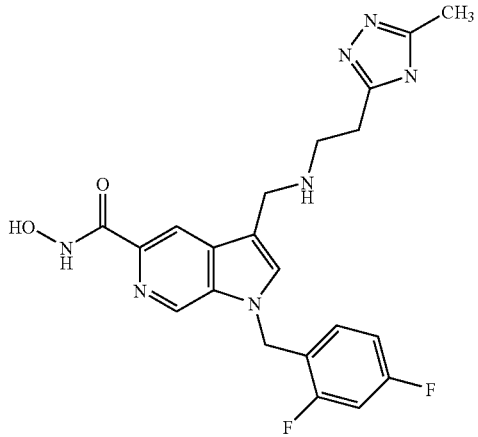

The compound was synthesized using the General Procedure A and 2-(3-methyl-1H-1,2,4-triazol -5-yl)ethanamine dihydrochloride as the amine component. $^1$H NMR (500 MHz, d6-DMSO) δ ppm 8.90 (s, 1H) 8.51 (s, 1H) 7.83 (s, 1H) 7.39 (q, 1H) 7.27 (dt, 1H) 7.06 (dt, 1H) 5.63 (s, 2H) 4.41 (s, 2H) 2.91 (t, 2H) 2.24 (s, 3H) (DMSO suppression suppresses CH$_2$ signal). LCMS: Mass of Compound: 441.2 D; Mass obs. (M+H$^+$)=442 u/e; Retention Time: 1.1 min; Purity by TIC: 100%; Purity by UV: 96%.

Example 101

3-({[1-Cyclopropyl-3-(cyclopropylamino)-3-oxopropyl]amino}methyl)-1-(2,4-difluorobenzyl)-N-hydroxy-1H-pyrrolo[2,3-c]pyridine-5-carboxamide

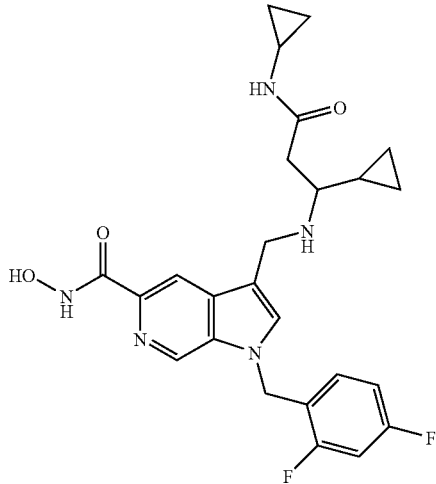

The compound was synthesized using the General Procedure A and 3-amino-n,3-dicyclopropylamide as the amine component. The synthesis of this amine is outlined in another section of this patent application. $^1$H NMR (500 MHz, d6-DMSO) δ ppm 8.91 (s, 1H) 8.84 (br. s, 1H) 8.68 (br. s, 1H) 8.48 (s, 1H) 8.25 (s, 1H) 7.84 (s, 1H) 7.41 (q, 1H) 7.27 (dt, 1H) 7.07 (dt, 1H) 5.63 (s, 2H) 4.40-4.50 (m, 2H) 2.87-2.94 (m, 1H) 0.93-1.00 (m, 1H) 0.57-0.65 (m, 3H) 0.46-0.57 (m, 7H) 0.31-0.38 (m, 2H) 0.19-0.25 (m, 1H). LCMS: Mass of Compound: 483.2 D; Mass obs. (M+H$^+$)=485 u/e; Retention Time: 1.23 min; Purity by TIC: 100%; Purity by UV: 98%.

General Procedure B for Synthesis of Compounds of Formula

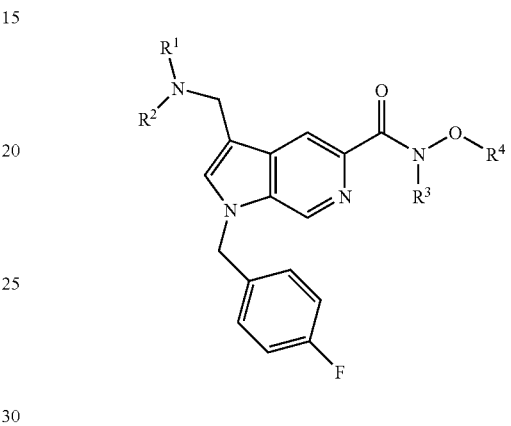

One stir bar, the aldehyde-ester (Reactant A, 320 μL, 80 μmol, 1 eq, 0.25 M in anhydrous dichloromethane), the amine (Reactant B, 320 μL, 80 μmol, 1 eq, 0.25 M in anhydrous dichloromethane) were added to a test tube. The test tube was capped and the reaction mixture was stirred for 1 h at ambient temperature. NaBH(OAc)$_3$ (320 μL, ~200 μmol, ~2.5 eq, 0.625 M suspension in anhydrous dichloromethane) was added and the reaction was stirred for 48 h at ambient temperature. The solvent was evaporated and the residue dissolved in a 6:3:1 (v:v) mixture of ethylacetate/CH$_2$Cl$_2$/methanol (1.1 mL). The solvent was evaporated and the residue dissolved in a 6:3:1 (v:v) mixture (1.1 mL) of ethylacetate/CH$_2$Cl$_2$/methanol. The organic phase was washed with aq. 10% K$_2$CO$_3$ (320 μL) and the aq. layer was extracted once with the 6:3:1 mixture of ethylacetate/CH$_2$Cl$_2$/methanol (1.1 mL). The organic phases were combined and the solvent was evaporated. The residues were dissolved or dispersed in MeOH (0.5 mL) and 3 M aq LiOH (80 μL (240 mmol, 3 eq) was added. The resulting solutions/suspensions were stirred for 3 h at ambient temperature. 1 M aq HCl (240 μL, 3 eq) was added and the reactions were stirred for 30 min at ambient temperature. The solvent and excess HCl were evaporated and the residue was dissolved in anhydrous TEA (400 μL, 200 μmol, 2.5 eq, 0.5 M in anhydrousDMF). The hydroxyamine (Reactant C, 320 μL, 80 μmol, 1 eq, 0.25 M in anhydrous DMF), and HATU (160 μL, 80 μmol, 1 eq, 0.5 M in anhydrous DMF) were added. The reaction mixture was stirred at ambient temperature for 16 h. The solvent was evaporated and the residue dissolved in a 7:2:1 mixture of EtOAc/CH$_2$Cl$_2$/isopropanol (1.3 mL). The mixture was washed with aq. 10% K$_2$CO$_3$ (0.5 mL). The organic layer was transferred into a new test tube. The aq. layer was extracted 2× with the 7:2:1 mixture of ethylacetate/CH$_2$Cl$_2$/isopropanol (1.3 mL). The solvent was evaporated and the residue dissolved in DMSO (1340 μL, containing 0.01% BHT). The DMSO solution was filtered and the desired product purified and isolated by HPLC.

Example 102

N-(Benzyloxy)-1-(4-fluorobenzyl)-3-[(3-oxopiperazin-1-yl)methyl]-1H-pyrrolo[2,3-c]pyridine-5-carboxamide

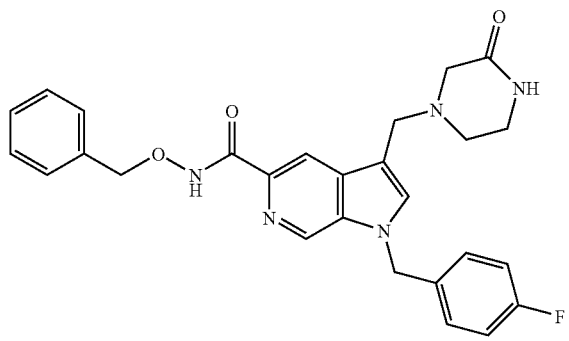

The compound was synthesized using the General Procedure B, piperazin-2-one as Reactant B, and O-benzylhydroxyamine as Reactant C. $^1$H NMR (500 MHz, d6-DMSO) δ ppm 8.86 (s, 1H) 8.57 (s, 1H) 7.99 (s, 1H) 7.40-7.43 (m, 2H) 7.39 (s, 1H) 7.28-7.37 (m, 5H) 7.12-7.17 (m, 2H) 5.60 (s, 2H) 4.90 (s, 2H) 4.83 (s, 1H) 4.60 (br s, 1H) 3.66 (m, 3H) 2.73 (m, 4H). LCMS: Mass of Compound: 487.2 D; Mass obs. (M+H$^+$)=489 u/e; Retention Time: 1.36 min; Purity by TIC: 94%; Purity by UV: 94%.

Example 103

N-(Allyloxy)-1-(4-fluorobenzyl)-3-[(3-oxopiperazin-1-yl)methyl]-1H-pyrrolo[2,3-c]pyridine-5-carboxamide

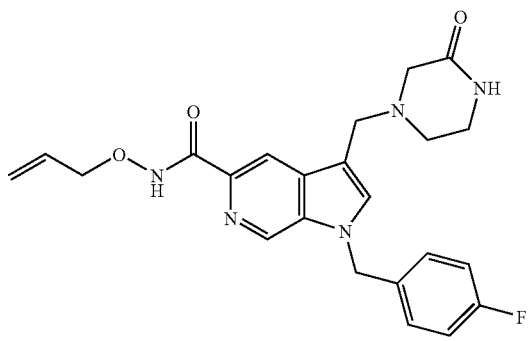

The compound was synthesized using the General Procedure B, piperazin-2-one as Reactant B, and O-allylhydroxyamine as Reactant C. $^1$H NMR (500 MHz, d6-DMSO) δ ppm 11.65 (br s, 1H) 8.86 (s, 1H) 8.55 (s, 1H) 8.35 (br s, 1H) 7.99 (s, 1H) 7.36-7.33 (m, 2H) 7.15 (t, 1H) 5.99-5.91 (m, 1H) 5.60 (s, 2H) 5.28 (d, 1H) 5.18 (d, 1H) 4.60 (br s, 2H) 4.38 (d, 2H) 3.82-3.63 (m, 2H) 2.73 (s, 1H). LCMS: Mass of Compound: 437.2 D; Mass obs. (M+H$^+$)=439 u/e; Retention Time: 1.23 min; Purity by TIC: 100%; Purity by UV: 90%.

Example 104

1-(4-Fluorobenzyl)-3-[(3-oxopiperazin-1-yl)methyl]-N-phenoxy-1H-pyrrolo[2,3-c]pyridine-5-carboxamide

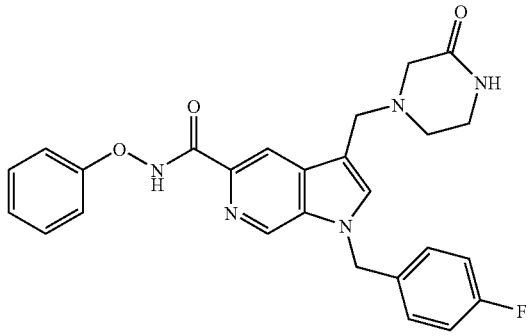

The compound was synthesized using the General B, piperazin-2-one as Reactant B and O-phenylhydroxyamine as Reactant C. $^1$H NMR (500 MHz, d6-DMSO) δ ppm 12.55 (s, 1H) 8.94 (s, 1H) 8.60 (s, 1H) 8.34 (br s, 1H) 8.03 (s, 1H) 7.33-7.39 (m, 2H) 7.25-7.29 (t, 2H) 7.12-7.18 (t, 2H) 6.94-7.01 (m, 3H) 5.62 (s, 1H) 4.62 (br s, 1H) 3.70 (br m, 6H). LCMS: Mass of Compound: 473.2 D; Mass obs. (M+H$^+$)=474 u/e; Retention Time: 1.35 min; Purity by TIC: 100%; Purity by UV: 95%.

Example 105

4-Ethyl-1-(4-fluoro-benzyl)-1H-pyrrolo[2,3-c]pyridine-5-carboxylic acid hydroxyamide

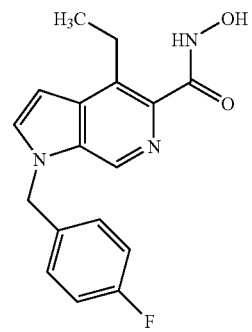

Step 1: 4-Ethynyl-1-(4-fluoro-benzyl)-1H-pyrrolo[2,3-c]pyridine-5-carboxylic acid ethyl ester

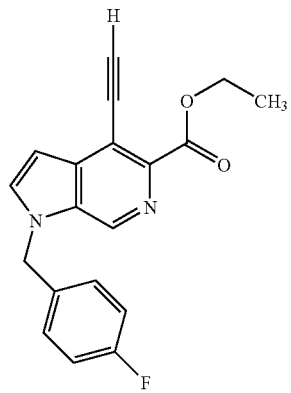

To a solution of 1-(4-fluoro-benzyl)-4-trifluoromethane-sulfonyloxy-1H-pyrrolo[2,3-c]pyridine-5-carboxylic acid ethyl ester (2.0 g, 4.48 mmol) in DMF (4.5 mL) and diisopropylamine (4.5 mL) was added trimethylsilylalkyne (4.4 mL, 31.4 mmol), copper (I) iodide (68 mg, 0.36 mmol), and bis(triphenylphosphine) palladium (II) chloride (126 mg, 0.18 mmol). The reaction was vacuum degassed with nitrogen three times, and then heated in a pre-heated oil bath at 90° C. After thirty minutes, the reaction was cooled to room temperature and diluted with 20 mL of ethyl acetate. The solution was filtered through a silica plug (15 mm×10 mm), and concentrated. The resulting oil was dissolved in EtOH (25 mL), and potassium carbonate (1.24 g, 9 mmol) was added. The reaction was stirred for 18 hours at room temperature, and then the solids were removed by filtration. The solvent was removed by rotary evaporation, and the resulting residue was dissolved in $CH_2Cl_2$ (80 mL). The organic layer was washed with 2×50 mL of water, and then 50 mL of saturated NaCl. After drying the organic liquid over $MgSO_4$, the solids were removed by filtration and then the solvent was removed by rotary evaporation to give the desired product. Yield 0.927 g, 64%. MS (APCI): Calc: 322, Found: (M+H) 323.

Step 2: 4-Ethyl-1-(4-fluoro-benzyl)-1H-pyrrolo[2,3-c]pyridine-5-carboxylic acid ethyl ester

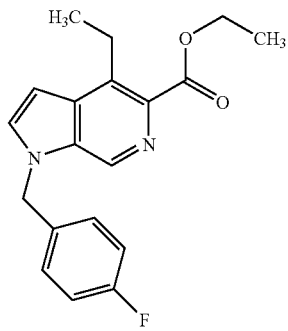

To a solution of 4-ethynyl-1-(4-fluoro-benzyl)-1H-pyrrolo[2,3-c]pyridine-5-carboxylic acid ethyl ester (60 mg, 0.018 mmol, prepared in step 1 above) in EtOH (2 mL) was added Lindlar's catalyst (Aldrich, 20 mg). The atmosphere was vacuum degassed with hydrogen three times, and then a balloon of hydrogen was attached to the reaction. After stirring for 18 hours, the reaction was filtered through a fine filter to remove the palladium. The solvent was removed by rotary evaporation, and the crude oil was carried on without further purification. Yield 57 mg, 94%. MS (APCI): Calc: 326, Found: (M+H) 327.

Step 3: (4-Ethyl-1-(4-fluoro-benzyl)-1H-pyrrolo[2,3-c]pyridine-5-carboxylic acid hydroxyamide)

To a solution of 4-ethyl-1-(4-fluoro-benzyl)-1H-pyrrolo[2,3-c]pyridine-5-carboxylic acid ethyl ester (57 mg, 0.175 mmol) in EtOH (2 mL), was added a 10% wt/wt solution of NaOH in water (0.5 mL) and a 50% wt/wt solution of hydroxylamine in water (1 mL). The reaction was stirred at room temperature for 18 hours, and then 1 N HCl was added till a pH of 7 was reached. The reaction was concentrated by rotary evaporation, and then purified by preparative HPLC to give the desired product. Yield 10 mg, 18%. $^1$H NMR (400 MHz, $CDCl_3$) δ 1.36 (t, J=7.58 Hz, 3H), 3.47 (q, J=7.41 Hz, 2H), 5.38 (s, 2H), 6375 (d, J=3.28 Hz, 1H), 7.02 (m, 2H), 7.13 (m, 2H), 7.30 (m, 1H), 8.43 (s, 1H).

Example 106

1-(2,4-Difluorobenzyl)-3-({[(2R-2,3-dihydroxypropyl]oxy}methyl)-N-hydroxy-1-pyrrolo[2,3-c]pyridine-5-carboxamide

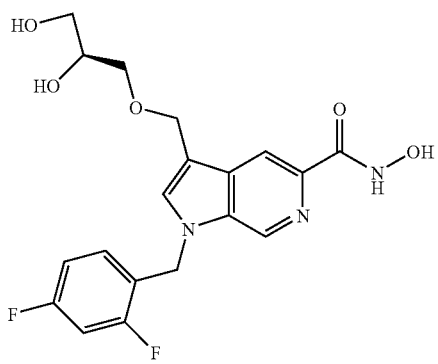

Step 1: Methyl 1-(2,4-difluorobenzyl)-3-({[(4S)-2,2-dimethyl-1,3-dioxolan-4-yl]methoxy}methyl)-1 pyrrolo[2,3-c]pyridine-5-carboxylate

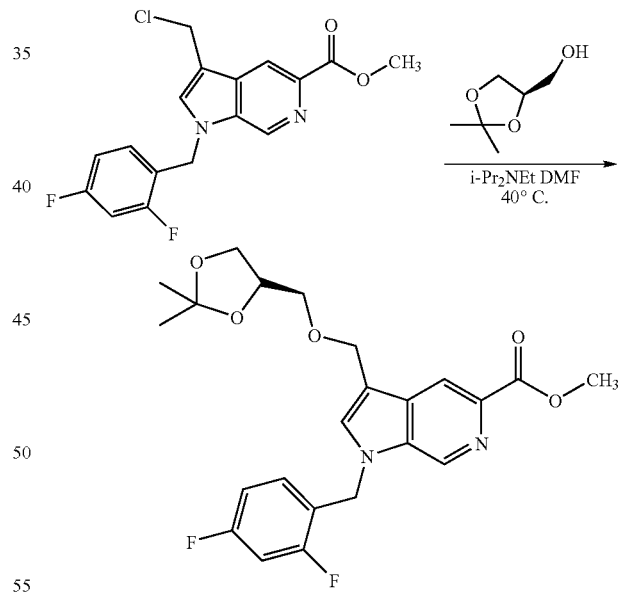

To a solution of methyl 3-(chloromethyl)-1-(2,4-difluorobenzyl)-1H-pyrrolo[2,3-c]pyridine-5-carboxylate (3 mL, 0.197M in $CH_2Cl_2$, 0.591 mmol) [prepared as described in step 2 of example 40] in anhydrous DMF (5 mL) was added (R)-(−)-2,2-dimethyl-1,3-dioxolane-4-methanol (2.955 mmol, 0.37 mL, 5.0 eq.) followed by i-$Pr_2$NEt (0.407 g, 3.14 mmol, 0.55 mL, 4 eq.). The mixture, under nitrogen, was placed in an oil bath and the bath was warmed to 40° C. After stirring for 24 hours (40° C.) the reaction was judged to be complete by HPLC-MS analysis. Water (0.5 mL) was added and after 45 minutes the volatiles were removed in vacuo (ca.

2 torr) to give a golden yellow oil. The crude material was purified by chromatography on a column of silica gel (40 mm OD, 100 g, 230-400 mesh, packed with CH$_2$Cl$_2$, eluted with CH$_2$Cl$_2$-EtOAc 70:30 v/v, 1.0 L, 1.0 L, 25 mL fractions) using the flash technique. Fractions were combined to afford 0.224 g (85%) of 1-[1-(2,4-difluorobenzyl)-3-({[(4R)-2,2-dimethyl-1,3-dioxolan-4-yl]methoxy)methyl)-1H-pyrrolo[2,3-c]pyridin-5-yl]ethanone as a colorless oil. TLC (Merck, CH$_2$Cl$_2$:EtOAc 50:50, UV-+, cerium molybdate-+): R$_f$=0.26. LC-MS (Eclipse XDB-C8, 0.8 mL/min, gradient 80:20 to 5:95H$_2$O (+0.1% HOAc):CH$_3$CN—5 minutes, APCI, +mode): RT—3.456 min, m/e=447.20 (M+H$^+$, base).
$^1$H-NMR (300 MHz, CDCl$_3$): δ=1.33 (s, 3H), 1.40 (s, 3H) 3.46 (m, 2H), 3.67 (m, 1H), 3.98 (s, 3H), 4.00 (m, 1H), 4.20 (m, 1H), 4.68 (q, 2H), 5.33 (s, 2H), 6.82 (m, 2H), 6.93 (q, 1H), 7.31 (s, 1H), 8.50 (s, 1H), 8.86 (s, 1H).

Step 2: 1-[1-(2,4-Difluorobenzyl)-3-({[(2R)-2,3-dihydroxypropyl]oxy}methyl)-1H-pyrrolo[2,3-c]pyridin-5-yl]ethanone

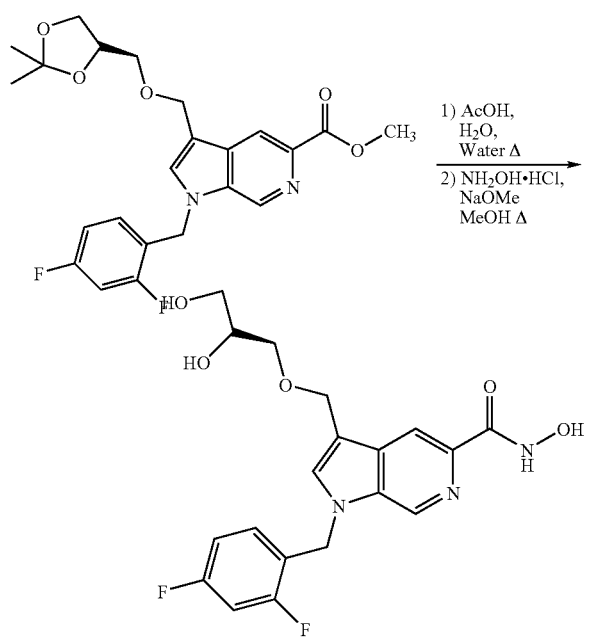

To a solution of 1-[t-(2,4-difluorobenzyl)-3-({[(4R)-2,2-dimethyl-1,3-dioxolan-4-yl]methoxy}methyl)-1H-pyrrolo[2,3-c]pyridin-5-yl]ethanone (358 mg 0.802 mmol) in methanol (20 mL) was added acetic acid (10 mL) and water (10 mL). The mixture was placed in an oil bath and the bath was warmed to 40° C. After stirring for 3 days (40° C.) the reaction was judged to be complete by HPLC-MS analysis. The methanol was removed under vacuum and the residue freeze-dried to remove the acetic acid and water. To a solution of the resulting colorless oil in THF (20 mL) was added powdered molecular sieves 4A (4 g). After stirring for 24 hours the sieves were removed by filtration and the solvent removed under vacuum to yield the crude diol, ester as an oil (410 mg). To a solution of this mixture (0.100 g, 0.2461 mmol) in anhydrous methanol (5 mL) was added hydroxylamine hydrochloride (0.068 g, 0.9843 mmol, 4 eq.) followed by NaOMe (25 wt % solution in MeOH, 0.28 mL 1.235 mmol, 5 eq.). The mixture, under nitrogen, was placed in an oil bath and the bath was warmed to 40° C. After stirring for 2 hours (40° C.) the reaction was judged to be complete by HPLC-MS and the volatiles were removed in vacuo to give a cream colored solid. The crude material was taken up in EtOAc, DCM, MeOH (60:30:10, 50 mL) and washed with saturated aq. NH$_4$Cl and brine. The organics were dried (Na$_2$SO$_4$) volatiles were removed in vacuo to give a light yellow oil that was purified by prep HPLC. To give 8 mg (8%) of 1-[1-(2,4-difluorobenzyl)-3-({[(2R)-2,3-dihydroxypropyl]oxy}methyl)-1H-pyrrolo[2,3-c]pyridin-5-yl]ethanone as a white powder. LC-MS (Eclipse XDB-C8, 0.8 mL/min, gradient 80:20 to 5:95H$_2$O (+0.1% HOAc):CH$_3$CN—5 minutes, APCI, +mode): RT—2.305 min, m/e=408.1 (M+H$^+$, base).
$^1$H-NMR (300 MHz, CD$_3$OD): δ=3.36-3.54 (m, 4H), 3.66 (m, 1H), 4.67 (s, 2H), 5.48 (s, 2H), 6.74-6.96 (m, 2H), 7.14 (m, 1H), 7.53 (s, 1H), 8.27 (s, 1H), 8.68 (s, 1H)

Example 107

1-(2,4-Difluorobenzyl)-3-({[(2S)-2,3-dihydroxypropyl]oxy}methyl)-hydroxy-1H-pyrrolo[2,3-c]pyridine-5-carboxamide

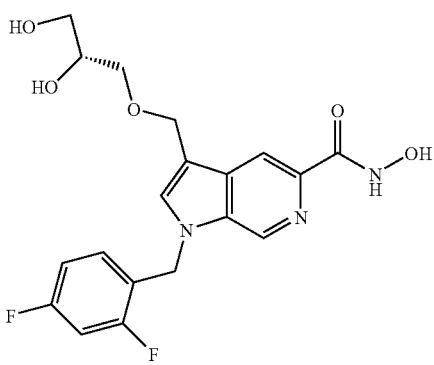

The title compound was prepared as in example 106 starting with methyl 3-(chloromethyl)-1-(2,4-difluorobenzyl)-1H-pyrrolo[2,3-c]pyridine-5-carboxylate and (S)-(+)-2,2-Dimethyl-1,3-dioxolane-4-methanol to give a white powder (10 mg). LC-MS (Eclipse XDB-C8, 0.8 mL/min, gradient 80:20 to 5:95H$_2$O (+0.1% HOAc):CH$_3$CN—5 minutes, APCI, +mode): RT—2.060 min, m/e=408.1 (M+H$^+$, base).
$^1$H-NMR (300 MHz, CD$_3$OD): δ=3.40 (m, 2H), 3.48 (m, 2H), 3.66 (m, 1H), 4.74 (s, 2H), 5.44 (s, 2H), 6.84 (m, 1H), 6.96 (m, 1H), 7.17 (m, 1H), 7.56 (s, 1H), 8.34 (s, 1H), 8.68 (s, 1H)

Example 108

1-(4-Fluorobenzyl)-N-hydroxy-3-[(2-methoxyethoxy)methyl]-N-methyl-1H-pyrrolo[2,3-c]pyridine-5-carboxamide

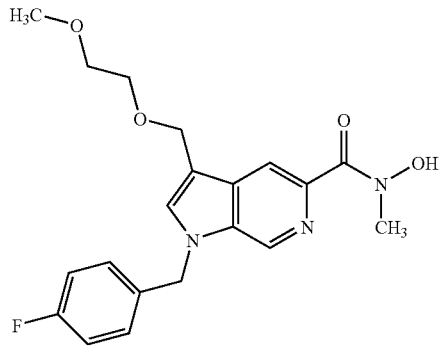

Step 1: Methyl 1-(4-fluorobenzyl)-3-[(2-methoxyethoxy)methyl]-1H-pyrrolo[2,3-c]pyridine-5-carboxylate

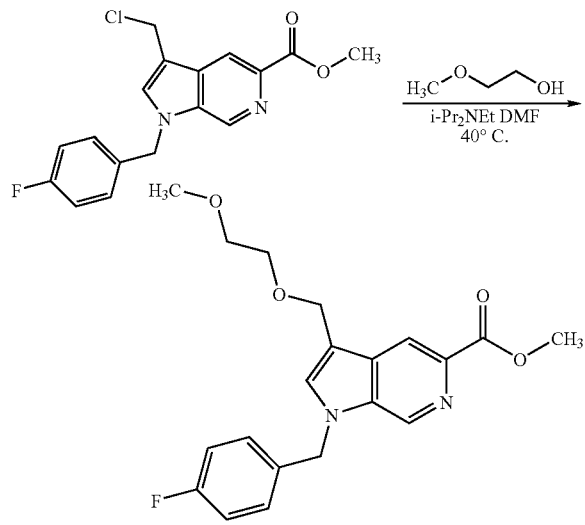

To a solution of methyl 3-(chloromethyl)-1-(2,4-difluorobenzyl)-1H-pyrrolo[2,3-c]pyridine-5-carboxylate (7.43 mL, 0.197M in CH$_2$Cl$_2$, 1.4645 mmol)) [prepared as described in step 2 of example 40] in anhydrous DMF (10 mL) was added 2-(methoxyethoxy)-ethanol (7.32 mmol, 0.58 mL, 5 eq.) followed by i-Pr$_2$NEt (5.86 mmol, 1.02 mL, 4 eq.). The mixture, under nitrogen, was placed in an oil bath and the bath was warmed to 40° C. After stirring for 24 hours (40° C.) the reaction was judged to be complete by HPLC-MS analysis and the volatiles were removed in vacuo (ca. 2 torr) to give a golden yellow oil. The crude material was diluted with EtOAc (40 mL) and washed with water (4×20 mL) and brine (20 mL). The organic phase was separated, dried (Na$_2$SO$_4$), and concentrated in vacuo to afford 542 mg (100%) of the target compound as a pale brown solid. TLC (Merck, CH$_2$Cl$_2$: MeOH 95:5, UV-+, cerium molybdate-+): R$_f$=0.18. LC-MS (Eclipse XDB-C8, 0.8 mL/min, gradient 80:20 to 5:95H$_2$O (+0.1% HOAc):CH$_3$CN—5 minutes, ESI, +mode): RT-2.748 min, m/e=373.1 (M+H$^+$, base). $^1$H-NMR (300 MHz, CDCl$_3$): δ=3.38 (s, 3H), 3.56 (m, 2H), 3.67 (m, 2H), 4.04 (s, 3H), 4.77 (s, 2H), 5.36 (s, 2H), 7.00 (m, 2H), 7.16 (m, 2H), 7.34 (s, 1H), 8.54 (s, 1H), 8.74 (s, 1H).

Step 2: 1-(4-Fluorobenzyl)-3-[(2-methoxyethoxy)methyl]-1H-pyrrolo[2,3-c]pyridine-5-carboxylic acid

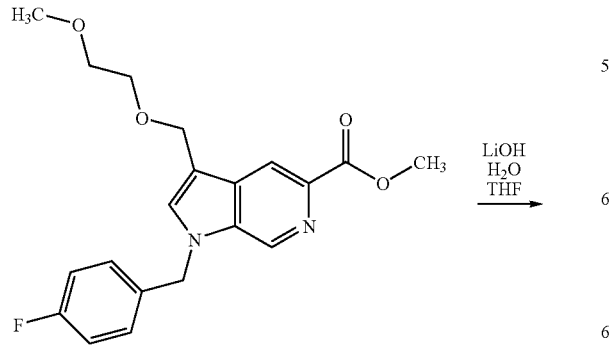

To a solution of methyl 1-(4-fluorobenzyl)-3-[(2-methoxyethoxy)methyl]-1H-pyrrolo[2,3-c]pyridine-5-carboxylate (542 mg 1.4645 mmol) in THF (10 mL) was added lithium hydroxide monohydrate (123 mg 2.929 mmol, 2 eq.) and water (5 mL) and the clear solution was warmed to 40° C. for 3 hours. THF was removed under vacuum and 1 M HCl added (2.93 mL 2.93 mmol, 2 eq.) the crude product was extracted into EtOAc (3×30 mL) then DCM:MeOH 100:5 (3×30 mL). The organics were dried (Na$_2$SO$_4$) volatiles were removed in vacuo to give the title product as a cream colored powder 400 mg (76%). LC-MS (Eclipse XDB-C8, 0.8 mL/min, gradient 80:20 to 5:95H$_2$O (+0.1% HOAc):CH$_3$CN—5 minutes, ESI, +mode): RT—1.753 min, m/e=359.1 (M+H$^+$, base). $^1$H-NMR (300 MHz, CD$_3$OD): δ=3.68 (s, 3H), 3.60 (m, 2H), 3.73 (m, 2H), 4.86 (s, 2H), 5.64 (s, 2H), 7.12 (m, 2H), 7.36 (m, 2H), 8.06 (s, 1H), 8.3 (s, 1H), 8.86 (s, 1H).

Step 3: 1-(4-Fluorobenzyl)-N-hydroxy-3-[(2-methoxyethoxy)methyl]-N-methyl-1H-pyrrolo[2,3-c]pyridine-5-carboxamide

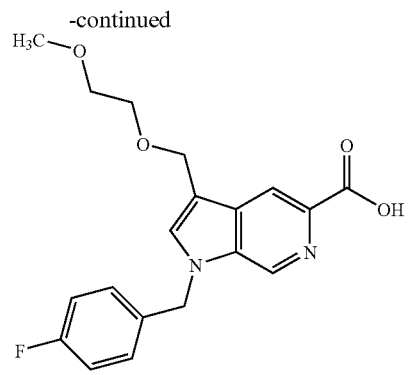

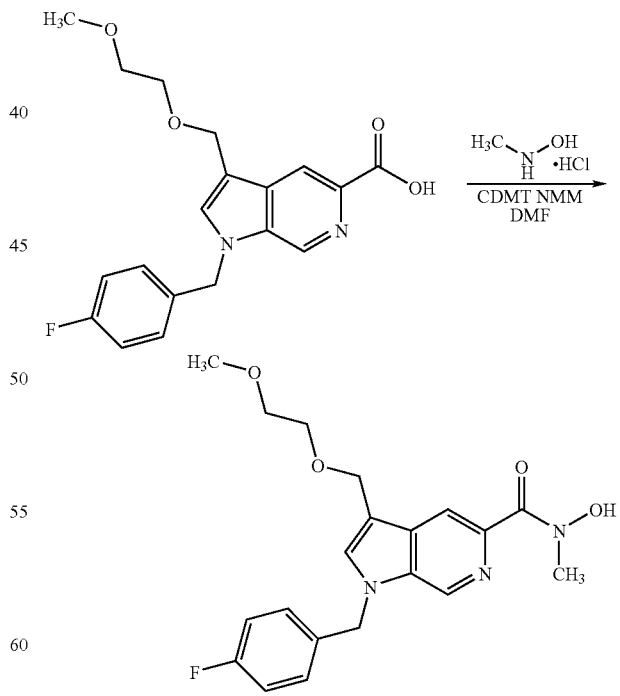

To a solution of 1-(4-fluorobenzyl)-3-[(2-methoxyethoxy)methyl]-1H-pyrrolo[2,3-c]pyridine-5-carboxylic acid (200 mg 0.5581 mmol) in anhydrous DMF (10 mL) was added CDMT (118 mg 0.6695 mmol 1.2 eq.) and NMM (N-methyl morpholine) (0.074 mL 0.67 mmol 1.2 eq.). The mixture, under nitrogen, was stirred for 1.5 hours, during which it slowly darkened to a deep orange. N-Methylhydroxylamine hydrochloride (233 mg 2.79 mmol 5.0 eq) was added and stirring continued for 10 hours. The reaction was judged to be complete by HPLC-MS analysis and the volatiles were removed in vacuo (ca. 2 torr) to give a golden yellow oil. This oil was dissolved in EtOAc (30 mL) and washed with water (3×20 mL) and brine (20 mL). The organic phase was separated, dried ($Na_2SO_4$), and concentrated in vacuo to afford the crude product. Which was purified by chromatography on a column of silica gel (40 mm OD, 100 g, 230-400 mesh, packed with $CH_2Cl_2$, eluted with $CH_2Cl_2$—MeOH—$NH_3$ 97:2:1 v/v, 2.0 L, 25 mL fractions) using the flash technique. Fractions were combined to afford 0.080 g (37%) of 1-(4-fluorobenzyl)-N-hydroxy-3-[(2-methoxyethoxy)methyl]-N-methyl-1H-pyrrolo[2,3-c]pyridine-5-carboxamide. LC-MS (Eclipse XDB-C8, 0.8 mL/min, gradient 80:20 to 5:95$H_2O$ (+0.1% HOAc):$CH_3CN$—5 minutes, ESI, +mode): RT -2.062 min, m/e=388.1 (M+H$^+$, base). $^1$H-NMR (300 MHz, CDCl$_3$): o=3.38 (s, 3H), 3.47 (s, 3H), 3.57 (m, 2H), 3.68 (m, 2H), 4.78 (s, 2H), 5.37 (s, 2H), 7.04 (m, 2H), 7.13 (m, 2H), 7.42 (s, 1H), 8.46 (s, 1H), 8.64 (s, 1H). Found: C, 61.79; H, 5.83; N, 10.7%. $C_{20}H_{22}FN_3O_4$; 0.08$H_2O$, requires C, 61.78; H, 5.74; N, 10.81%.

Example 109

1-(4-Fluorobenzyl)-N-methoxy-3-[(2-methoxyethoxy)methyl]-1H-pyrrolo[2,3-c]pyridine-5-carboxamide

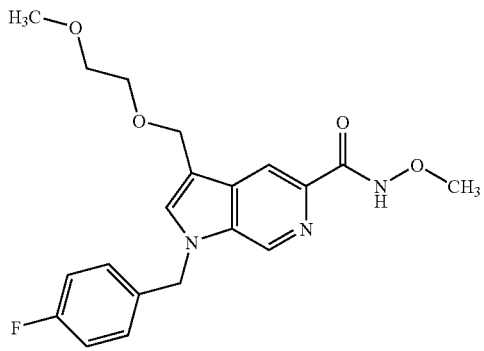

The title compound was prepared in the same manner as described in step 3 of example 108 using O-methylhydroxylamine hydrochloride instead of N-methylhydroxylamine hydrochloride. LC-MS (Eclipse XDB-C8, 0.8 mL/min, gradient 80:20 to 5:95$H_2O$ (+0.1% HOAc):$CH_3CN$—3 minutes, APCI, +mode): RT—1.196 min, m/e=388.2 (M+H$^+$, base). $^1$H-NMR (300 MHz, DMSO): δ=3.26 (s, 3H), 3.46 (m, 2H), 3.57 (m, 2H), 3.72 (s, 3H), 4.72 (s, 2H), 5.62 (s, 2H), 7.14 (t, 2H), 7.36 (m, 2H), 7.86 (s, 1H), 8.27 (s, 1H), 8.87 (s, 1H). Found: C, 61.84; H, 5.63; N, 10.97%. $C_{20}H_{22}FN_3O_4$; 0.05$H_2O$, requires C, 61.86; H, 5.74; N, 10.82%.

Example 110

3-({[(4R)-2,2-Dimethyl-1,3-dioxolan-4-yl]methoxy}methyl)-1-(4-fluorobenzyl)-N-hydroxy-N-methyl-1H-pyrrolo[2,3-c]pyridine-5-carboxamide

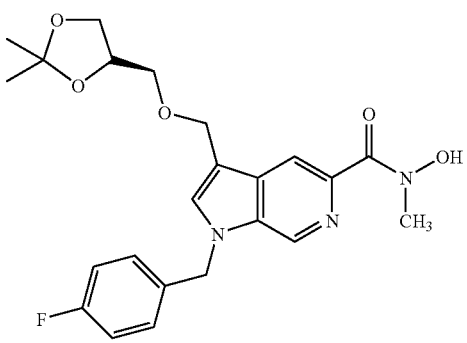

Step 1: Methyl 3-({[(4R)-2,2-dimethyl-1,3-dioxolan-4-yl]methoxy}methyl)-1-(4-fluorobenzyl)-1 H-pyrrolo[2,3-c]pyridine-5-carboxylate

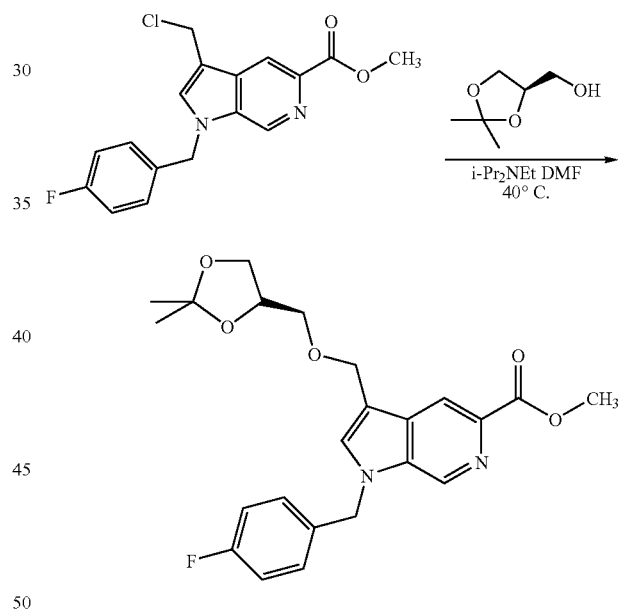

To a solution of methyl 3-(chloromethyl)-1-(2,4-difluorobenzyl)-1H-pyrrolo[2,3-c]pyridine-5-carboxylate (7.43 mL, 0.197M in $CH_2Cl_2$, 1.4645 mmol)) [prepared as described in step 2 of example 40] in anhydrous DMF (10 mL) was added (R)-(-)-2,2-Dimethyl-1,3-dioxolane-4-methanol (7.32 mmol, 0.91 mL, 5 eq.) followed by i-Pr$_2$NEt (5.86 mmol, 1.02 mL, 4 eq.). The mixture, under nitrogen, was placed in an oil bath and the bath was warmed to 40° C. After stirring for 24 hours (40° C.) the reaction was judged to be complete by HPLC-MS analysis and the volatiles were removed in vacuo (ca. 2 torr) to give a golden yellow oil. The crude material was diluted with EtOAc (40 mL) and washed with water (4×20 mL) and brine (20 mL). The organic phase was separated, dried ($Na_2SO_4$), and concentrated in vacuo to afford the target compound, which was purified by chromatography on a column of silica gel (40 mm OD, 150 g, 230-400 mesh, packed with $CH_2Cl_2$, eluted with $CH_2Cl_2$-EtOAc-MeOH 70:30:2 v/v, 2.0 L, 25 mL fractions) using the flash technique. Fractions were combined to afford 0.520 g (83%) of methyl 3-({[(4R)-2,2-dimethyl-1,3-dioxolan-4-yl]methoxy}methyl)-1-(4-fluorobenzyl)-1H-pyrrolo[2,3-c]pyridine-5-carboxylate. LC-MS (Eclipse XDB-C8, 0.8 mL/min, gradient 80:20 to 5:95$H_2O$ (+0.1% HOAc):$CH_3CN$—5 minutes, ESI, +mode): RT-2.98 min, m/e=429.1 (M+H$^+$, base). $^1$H-NMR (300 MHz, $CDCl_3$): o=1.38 (s, 3H), 1.42 (s, 3H), 3.53 (m, 2H), 3.72 (m, 1H), 4.04 (m, 4H), 4.27 (m, 1H), 4.78 (q, 2H), 5.38 (s, 2H), 7.05 (t, 2H), 7.17 (m, 2H), 7.32 (s, 1H), 8.56 (s, 1H), 8.77 (s, 1H).

Step 2: 3-({[(4R)-2,2-Dimethyl-1,3-dioxolan-4-yl]methoxy}methyl)-1-(4-fluorobenzyl)-1 ]pyrrolo[2,3-c]pyridine-5-carboxylic acid

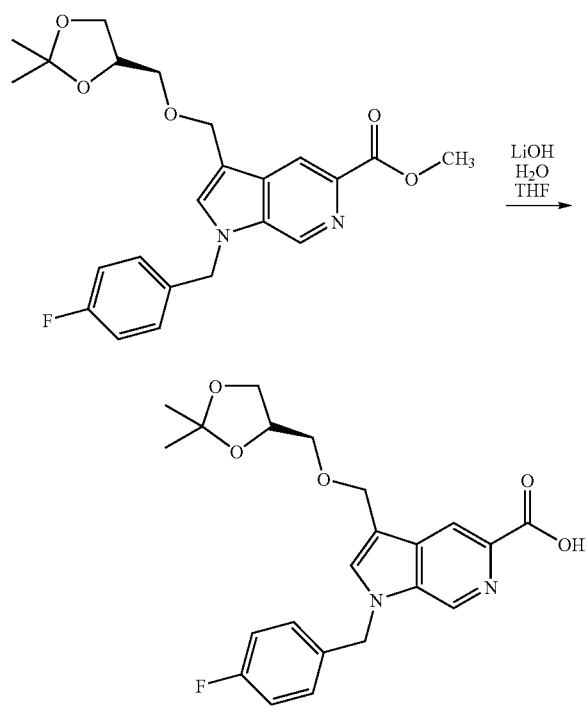

To a solution of methyl 3-({[(4R)-2,2-dimethyl-1,3-dioxolan-4-yl]methoxy}methyl)-1-(4-fluorobenzyl) -1H-pyrrolo[2,3-c]pyridine-5-carboxylate (520 mg 1.2137 mmol) in THF (10 mL) was added lithium hydroxide monohydrate (102 mg 2.4273 mmol, 2 eq.) and water (5 mL) and the clear solution warmed to 45° C. for 3 hours. THF was removed under vacuum and 1M HCl added (2.93 mL 2.93 mmol, 2 eq.) the crude product precipitated and was collected by filtration, washed with water and ether and dried in vacuo to give the title product as a tan powder 386 mg (77%). LC-MS (Eclipse XDB-C8, 0.8 mL/min, gradient 80:20 to 5:95$H_2O$ (+0.1% HOAc):$CH_3CN$—5 minutes, ESI, +mode): RT—2.255 min, m/e=415.2 (M+H$^+$, base). $^1$H-NMR (300 MHz, DMSO): δ=1.26 (d, 6H), 3.52 (m, 2H), 3.61 (t, 1H), 3.97 (t, 1H), 4.24 (m, 1H), 4.74 (s, 2H), 5.5.63 (s, 2H), 7.23 (t, 2H), 7.42 (m, 2H), 7.94 (s, 1H), 8.37 (s, 1H), 8.97 (s, 1H).

Step 3: 3-({[(4R)-2,2-Dimethyl-1,3-dioxolan-4-yl]methoxy}methyl)-1-(4-fluorobenzyl)-N-hydroxy-N-methyl -1H-pyrrolo[2,3-c]pyridine-5-carboxamide

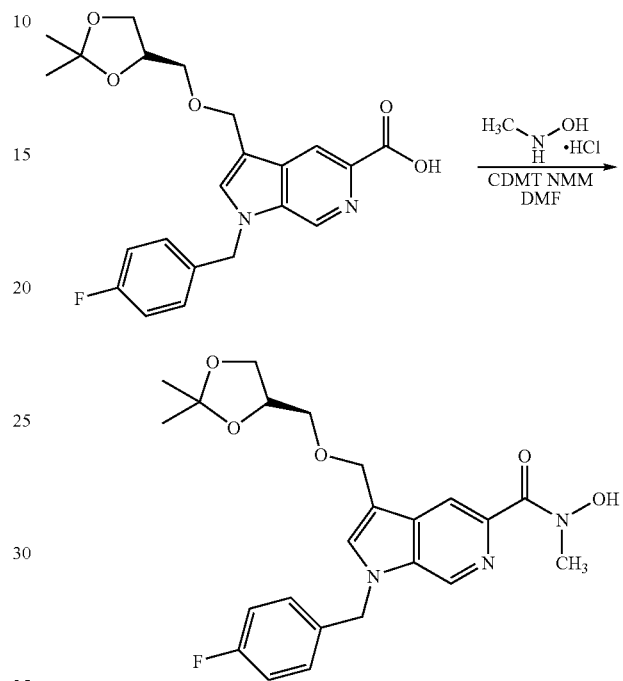

To a solution of 3-({[(4R)-2,2-dimethyl-1,3-dioxolan-4-yl]methoxy}methyl)-1-(4-fluorobenzyl)-1H -pyrrolo[2,3-c]pyridine-5-carboxylic acid (200 mg 0.4828 mmol) in anhydrous DMF (10 mL) was added CDMT (102 mg 0.5793 mmol 1.2 eq.) and NMM (0.064 mL, 0.5793 mmol 1.2 eq.). The mixture, under nitrogen, was stirred for 2 hours, during which it slowly darkened to a deep orange. N-Methylhydroxylamine Hydrochloride (202 mg 2.414 mmol 5.0 eq) was added and stirring continued for 10 hours. The reaction was judged to be complete by HPLC-MS analysis and the volatiles were removed in vacuo (ca. 2 torr) to give a golden yellow oil. This oil was dissolved in EtOAc (30 mL) and washed with water (3×20 mL) and brine (20 mL). The organic phase was separated, dried ($Na_2SO_4$), and concentrated in vacuo to afford the crude product which was purified by prep HPLC to give 95 mg (44%) of 3-({[(4R)-2,2-dimethyl-1,3-dioxolan-4-yl]methoxy)methyl)-1-(4-fluorobenzyl)-N -hydroxy-N-methyl-1H-pyrrolo[2,3-c]pyridine-5-carboxamide as a white powder. LC-MS (Eclipse XDB-C8, 0.8 mL/min, gradient 80:20 to 5:95$H_2O$ (+0.1% HOAc):$CH_3CN$—5 minutes, ESI, +mode): RT—2.278 min, m/e=444.2 (M+H$^+$, base). $^1$H-NMR (400 MHz, $CDCl_3$): δ=1.34 (s, 3H), 1.38 (s, 3H), 3.52 (m, 4H), 3.62 (m, 1H), 3.67 (m, 1H), 4.04 (m, 1H), 4.32 (m, 1H) 4.77 (q, 2H), 5.38 (s, 2H), 7.06 (m, 2H), 7.16 (m, 2H), 7.43 (s, 1H), 8.47 (s, 1H), 8.64 (s, 1H).

Example 111

3-({[(4S)-2,2-dimethyl-1,3-dioxolan-4-yl]methoxy}methyl)-1-(4-fluorobenzyl)-N-hydroxy-1H-pyrrolo[2,3-c]pyridine-5-carboxamide

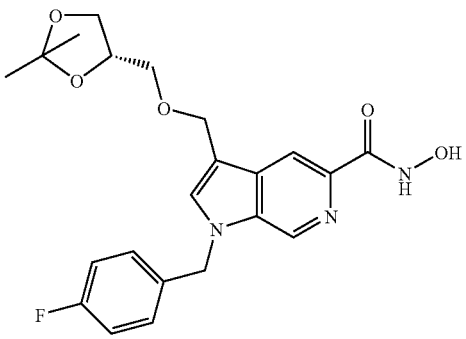

The title compound was prepared as in example 49 starting with methyl 3-(chloromethyl)-1-(2,4-difluorobenzyl)-1H-pyrrolo[2,3-c]pyridine-5-carboxylate and (S)-(+)-2,2-dimethyl-1,3-dioxolane-4-methanol. LC-MS (Eclipse XDB-C8, 0.8 mL/min, gradient 80:20 to 5:95 $H_2O$ (+0.1% HOAc):$CH_3CN$—5 minutes, APCI, +mode): RT—3.014 min, m/e=448.2 (M+H$^+$, base). $^1$H-NMR (300 MHz, DMSO): δ=1.24 (d, 6H), 3.44 (m, 2H), 3.57 (t, 1H), 3.94 (t, 1H), 4.17 (m, 1H), 4.66 (s, 2H), 5.46 (s, 2H), 6.80-6.97 (m, 2H), 7.17 (q, 1H), 7.63 (s, 1H), 8.27 (s, 1H), 8.69 (s, 1H). Found: C, 58.38; H, 5.15; N, 9.04%. $C_{22}H_{23}FN_3O_5$; 0.29$H_2O$, requires C, 58.38; H, 5.25; N, 9.28%.

Example 112

1-(2,4-Difluorobenzyl)-AN-hydroxy-N-methyl-3-{[(3aS,7aS*)-1-oxooctahydro-5H-pyrrolo[3,4-c]pyridin-5-yl]methyl}-1H-pyrrolo[2,3-c]pyridine-5-carboxamide

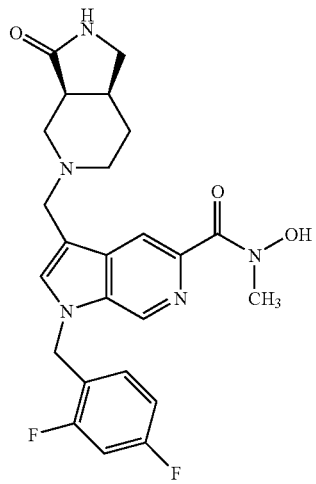

The title compound was prepared as described in example 18 of the using enantiomerically pure (3aS,7aS)-octahydro-3H-pyrrolo[3,4-c]pyridin-3-one. $[α]_d^{22}$=−83+/−17 C=0.003 g/ml, solvent: MeOH).

Example 113

1-(2,4-Difluorobenzyl)-N-hydroxy-N-methyl-3-{[(3aR,7aR)-1-oxooctahydro-5H-pyrrolo[3,4-c]pyridin-5-yl]methyl}-1H-pyrrolo[2,3-c]pyridine-5-carboxamide

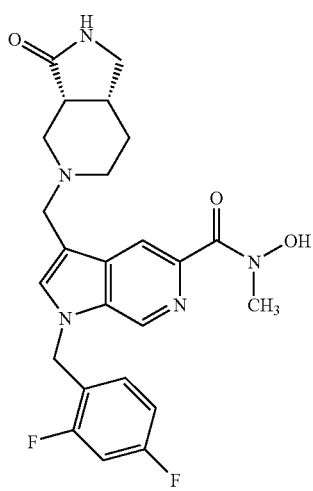

The title compound was prepared as described in example 18 using enantiomerically pure (3aR, 7aR)-octahydro-3H-pyrrolo[3,4-c]pyridin-3-one. $[α]d^{22}$=+83+/−17 (C=0.003 g/ml, solvent: MeOH). Preparation of enantiomerically pure (3aR, 7aR)-octahydro-3H-pyrrolo[3,4-c]pyridin-3-one:

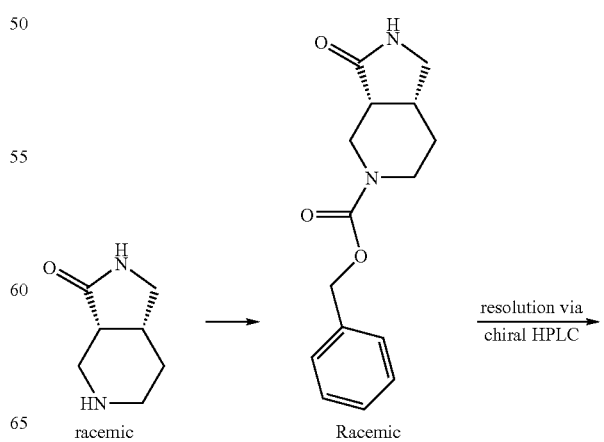

-continued

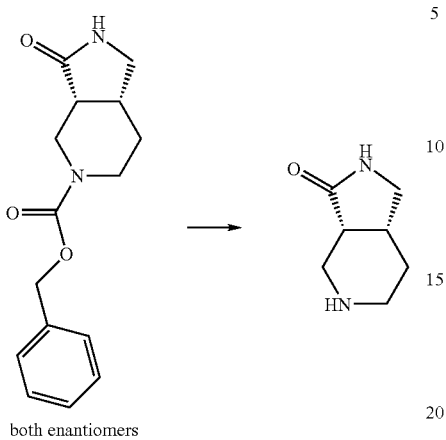

both enantiomers

Step 1: Benzyl (3aR,7aR)-3-oxooctahydro-5H-pyrrolo[3,4-c]pyridine-5-carboxylate and Benzyl (3as,7as)-3-oxooctahydro-5H-pyrrolo[3,4-c]pyridine-5-carboxylate:

To racemic (3aR*,7aR*)-octahydro-3H-pyrrolo[3,4-c]pyridin-3-one (2 g, 14.27 mmol) in DMF (20 mL) was added DIEA (5 ml, 28.54 mmol) and benzyl chloridocarbonate (2.01 mL, 14.27 mmol). The resulting mixture was stirred for 18 hours at room temperature. The solvent and DIEA were evaporated. The residue was dissolved in dichloromethane and extracted four times with diluted HCl aqueous solution (pH=4). The organic phase was evaporated. Recrystallization three times from hot ethyl acetate/methanol (9:1) provided the title compound as a white solid. (1.62 g, 41% yield). LC-MS (APCI, M+H$^+$): 275.1. HPLC: 98% purity. The enantiomers were separated using supercritical fluid chromatography on a Chiralpak(R) AS-H, 250×21 mm, 5 u column at 35° C. at 100 bar isobaric pressure using 50% methanol-modified CO$_2$ and a flow rate of 50 mL/min. LC-MS (APCI, M+H$^+$): 275.1. HPLC: 99% purity. $^1$H NMR (300 MHz, MeOH) d ppm 7.15-7.51 (m, 5H) 4.99-5.21 (m, 2H) 4.17-4.44 (m, 1H) 3.76-3.95 (m, 1H) 3.48 (dd, J=9.98, 6.22 Hz, 1H) 3.24 (d, J=4.90 Hz, 1H) 2.86-3.08 (m, 2H) 2.45-2.73 (m, 2H) 1.75-1.93 (m, 1H) 1.37-1.56 (m, 1H)

Step 2: (3aR,7aR)-Octahydro-3H-pyrrolo[3,4-c]pyridin-3-one and (3aS,7aS)-octahydro-3H pyrrolo[3,4-c]pyridin-3-one: To each pure enantiomer of benzyl (3aR,7aR)-3-oxooctahydro-5H-pyrrolo[3,4-c]pyridine-5-carboxylate and benzyl (3aS,7aS)-3-oxooctahydro-5H-pyrrolo[3,4-c]pyridine-5-carboxylate (500 mg, 1.82 mmol) in MeOH (5 ml) was added Pd/C (Palladium, 10 wt. % on activated carbon) (25 mg). The resulting mixture was stirred for 18 hours at room temperature with a hydrogen balloon. The Pd/C was filtered off. The filtrate was concentrated and to provide the title compounds.

Example 114

1-(4-fluorobenzyl)-N-hydroxy-N-methyl-3-[(3-oxopiperazin-1-yl)methyl]-1H-pyrrolo[2,3-c] pyridine-5-carboxamide

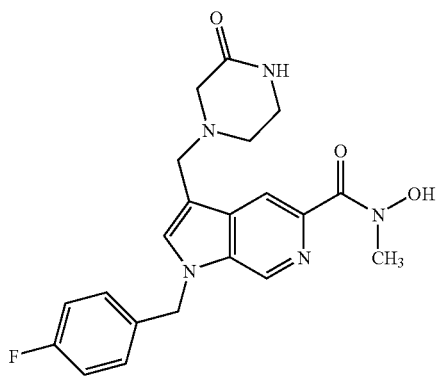

Step 1: Methyl 1-(4-fluorobenzyl)-3-((3-oxopiperazin-1-yl)methyl)-1H-pyrrolo[2,3-c]pyridine-5-carboxylate

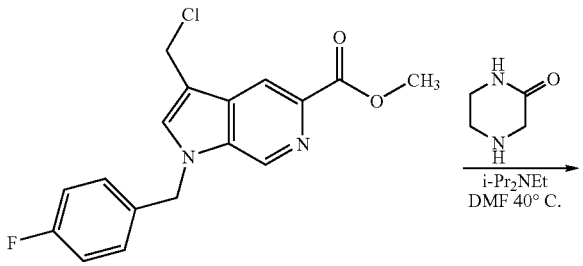

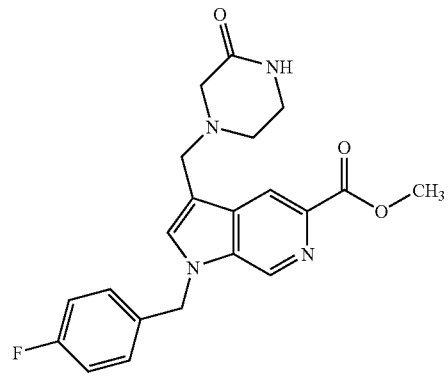

A solution of methyl 3-(chloromethyl)-1-(4-fluorobenzyl)-1H-pyrrolo[2,3-c]pyridine-5-carboxylate (24 mL, 2.0M in CH$_2$Cl$_2$, 48.3 mmol) [prepared as described in step 2 of example 40] was evaporated in vacuo to a residue. To this residue, anhydrous DMF (150 mL) and piperazin-2-one (386.4 mmol, 38.689, 8.0 eq.) were added followed by i-Pr$_2$NEt (18.77 g, 145.2 mmol, 25.29 mL, 3 eq.). The mixture, under nitrogen, was placed in an oil bath and the bath was warmed to 50° C. After stirring for 4 hours (50° C.) the reaction was judged to be complete by HPLC-MS analysis. The volatiles were removed in vacuo (ca. 2 torr, at 60° C.) to give a yellow residue. Saturated aqueous sodium bicarbonate (300 mL) was added. White solid precipitated out, and the mixture was sonicated for 30 min and cooled to 10° C. The solid was filtered, washed with cold water (50 mL), and dried in vacuo to afford 18.2 g (95%) of methyl 1-(4-fluorobenzyl)-3-((3-oxopiperazin-1-yl)methyl)-1H-pyrrolo[2,3-c]pyridine-5-carboxylate. LC-MS (Eclipse XDB-C8, 0.8 mL/min, gradient 80:20 to 5:95H$_2$O (+0.1% HOAc):CH$_3$CN—5 minutes, APCI, +mode): RT—1.41 min, m/e=397.20 (M+H$^+$, base). $^1$H NMR (300 MHz, DMSO-D6) d ppm 2.55 (t, 2H) 2.92 (s, 2H) 3.11 (s, 2H) 3.74 (s, 2H) 3.84 (s, 3H) 5.56 (s, 2H) 7.16 (t, J=8.85 Hz, 2H) 7.34 (dd, J=8.19, 5.75 Hz, 2H) 7.71 (s, 1H) 7.81 (s, 1H) 8.41 (s, 1H) 8.93 (s, 1H).

Step 2: 1-(4-Fluorobenzyl)-3-((3-oxopiperazin-1-yl)methyl)-1H-pyrrolo[2,3-c]pyridine-5-carboxylic acid

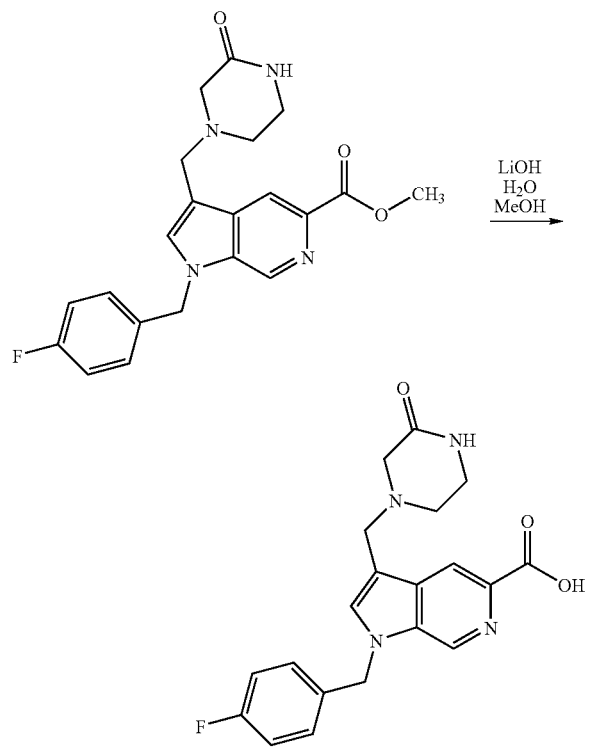

To a suspension of methyl 1-(4-fluorobenzyl)-3-((3-oxopiperazin-1-yl)methyl)-1H-pyrrolo[2,3-c]pyridine-5-carboxylate (18.2 g, 46.0 mmol) in methanol (450 mL) and water (200 mL) was added lithium hydroxide (1.40 g 58.3 mmol, 1.3 eq.). The suspension was heated to reflux for 10 h, and the reaction was judge to be 95% complete by HPLC-MS analysis. Methanol (200 mL) and lithium hydroxide (0.7 g, 29.2 mmol) were added and the reflux continued for 18 h total. The volatiles were removed in vacuo to a residue. Water (200 mL) was added and the mixture was cooled to 10° C. and neutralized with aqueous concentrated hydrochloric acid to pH 7. The white solid precipitated out, and filtered followed by washing with cold water, and dried in vacuoto afford 9.10 g (52%) of 1-(4-fluorobenzyl)-3-((3-oxopiperazin-1-yl)methyl)-1H-pyrrolo[2,3-c]pyridine-5-carboxylic acid LC-MS (Eclipse XDB-C8, 0.8 mL/min, gradient 80:20 to 5:95H$_2$O (+0.1% HOAc):CH$_3$CN—5 minutes, APCI, +mode): RT—1.31 min, m/e=383.20 (M+H$^+$, base). $^1$H NMR (400 MHz, DMSO-D6) d ppm 2.55 (t, J=5.16 Hz, 2H) 2.92 (s, 2H) 3.11 (s, 2H) 3.75 (s, 2H) 5.57 (s, 2H) 7.16 (t, J=8.81 Hz, 2H) 7.35 (dd, J=8.56, 5.54 Hz, 2H) 7.72 (s, 1H) 7.83 (s, 1H) 8.41 (s, 1H) 8.92 (s, 1H).

Step 3: 1-(4-fluorobenzyl)-N-hydroxy-N-methyl-3-((3-oxopiperazin-1-yl)methyl)-1H-pyrrolo [2,3-c]pyridine-5-carboxamide

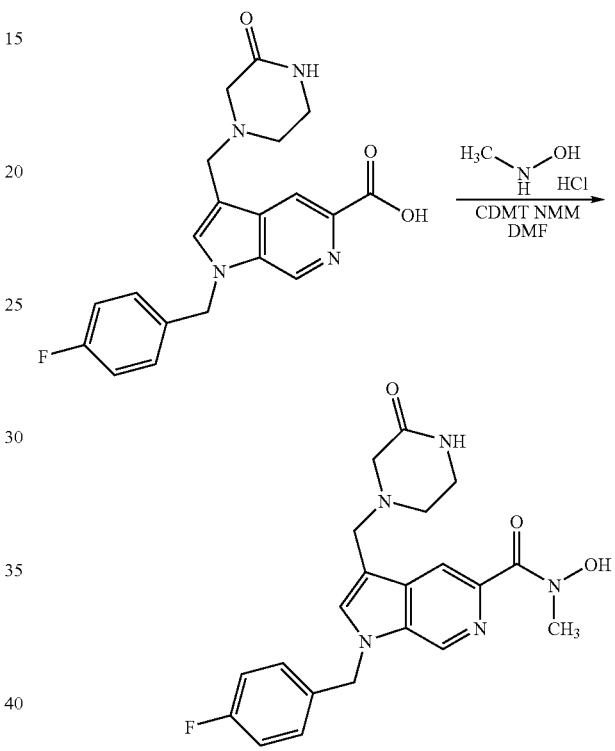

To a solution of 1-(4-fluorobenzyl)-3-((3-oxopiperazin-1-yl)methyl)-1H-pyrrolo[2,3-c]pyridine-5-carboxylic acid (9.0 g 23.50 mmol) in anhydrous DMF (285 mL) was added CDMT (4.95 g 28.20 mmol 1.2 eq.) and NMM (N-methyl morpholine) (2.85 g 28.2 mmol 1.2 eq.). The mixture, under nitrogen, was stirred for 70 min. N-Methylhydroxylamine hydrochloride (23.6 g 282.0 mmol 12.0 eq) was added and stirring continued for 3 hours. The reaction was judged to be complete by HPLC-MS analysis, and was quenched by adding water (100 mL) to the reaction mixture. The volatiles were removed in vacuo (ca. 2 torr, at 60° C.) to give a residue. Saturated aqueous sodium bicarbonate (120 mL) was added to neutralize to pH 7. White solid precipitated out, and the mixture was cooled to 5° C. The solid was filtered, washed with cold water (100 mL), and dried in vacuo to afford 7.7 g (85%) of 1-(4-fluorobenzyl)-N-hydroxy-N-methyl-3-((3-oxopiperazin-1-yl)methyl)-1H-pyrrolo[2,3-c]pyridine-5-carboxamide at >95% purity by $^1$HNMR analysis. To obtain 99% purity, 7.7 g of the product was dissolved in a boiling mixture (700 mL) of methanol and isopropanol (1:9). The hot solution was filtered to remove trace impurities, and the filtrate was allowed to cool to room temperature. The product crystallized out as needle-like crystals, which was filtered, washed with isopropanol, and dried in vacuo to afford (3.0 g) 99% purity.

LC-MS (Eclipse XDB-C8, 0.8 mL/min, gradient 80:20 to 5:95H$_2$O (+0.1% HOAc):CH$_3$CN—5 minutes, APCI, +mode): RT—2.27 min, m/e=412.30 (M+H$^+$, base). $^1$H NMR (400 MHz, DMSO-D6) d ppm 2.55 (t, J=5.29 Hz, 2H) 2.92 (s, 2H) 3.11 (s, 2H) 3.32 (s, 3H) 3.73 (s, 2H) 5.54 (s, 2H) 7.16 (t, J=8.81 Hz, 2H) 7.35 (dd, J=8.56, 5.54 Hz, 2H) 7.71 (s, 1H) 7.83 (s, 1H) 8.09 (s, 1H) 8.86 (s, 1H).

Example 115

N-ethoxy-1-(4-fluorobenzyl)-3-{[(2-hydroxyethyl)(propyl)amino]methyl}-1H-pyrrolo[2,3-c]pyridine-5-carboxamide

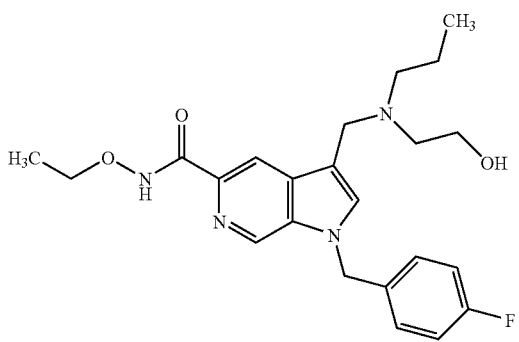

The compound was synthesized using the General Procedure B, 2-(propylamino)ethanol) as Reactant B, and O-ethylhydroxyamine as Reactant C. $^1$H NMR (500 MHz, DEUTERIUM OXIDE) d ppm 9.26 (s, 1H) 8.87 (s, 1H) 8.48 (s, 1H) 8.02 (s, 1H) 7.32 (dd, 2H) 7.14 (t, 2H) 5.60 (s, 2H) 4.55 (m, 2H) 3.88 (q, 2H) 3.69 (s, 6H) 1.70 (m, 2H) 1.15 (t, 3H) 0.83 (t, 3H). LCMS: Mass of Compound: 428.2 D; Mass obs. (M+H$^+$)=429 u/e; Retention Time: 1.2 min; Purity by TIC: 100%; Purity by UV: 98%.

Example 116

3-{[[3-(Dimethylamino)propyl](methyl)amino]methyl}-N-ethoxy-1-(4-fluorobenzyl)-1H-pyrrolo[2,3-c]pyridine-5-carboxamide

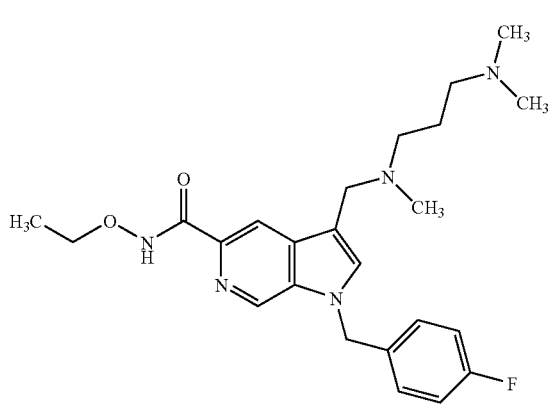

The compound was synthesized using the General Procedure B, N,N,N'-trimethyl-1,3-propandiamine as Reactant B, and O-ethylhydroxyamine as Reactant C. $^1$H NMR (500 MHz, DEUTERIUM OXIDE) d ppm 9.56 (s, 1H) 8.88 (s, 1H) 8.49 (s, 1H) 7.97 (s, 1H) 7.33 (dd, 2H) 7.15 (t, 2H) 5.61 (s, 2H) 4.60 (m, 1H) 4.50 (m, 1H) 3.89 (q, 2H) 3.16-3.11 (m, 1H) 3.00 (s, 3H) 3.00-2.96 (m, 1H), 2.76 (s, 3H) 2.75 (s, 3H) 2.69 (s, 3H) 2.06 (m, 1H) 1.98 (m, 1H) 1.15 (t, 3H) LCMS: Mass of Compound: 441.2 D; Mass obs. (M+H$^+$)=443 u/e; Retention Time: 1.1 min; Purity by TIC: 92%; Purity by UV: 100%.

Example 117

1-(4-Fluorobenzyl)-N-hydroxy-N-methyl-3-{[2-(2-oxopyrrolidin-1-yl)ethoxy]methyl}-1H-pyrrolo[2,3-c]pyridine-5-carboxamide

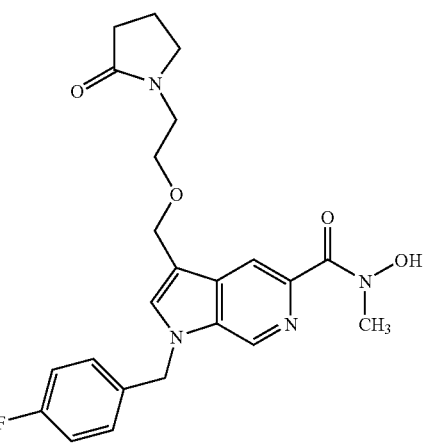

Step 1: Methyl 1-(4-fluorobenzyl)-3-{[2-(2-oxopyrrolidin-1-yl)ethoxy]methyl}-1H-pyrrolo[2,3-c]pyridine-5-carboxylate

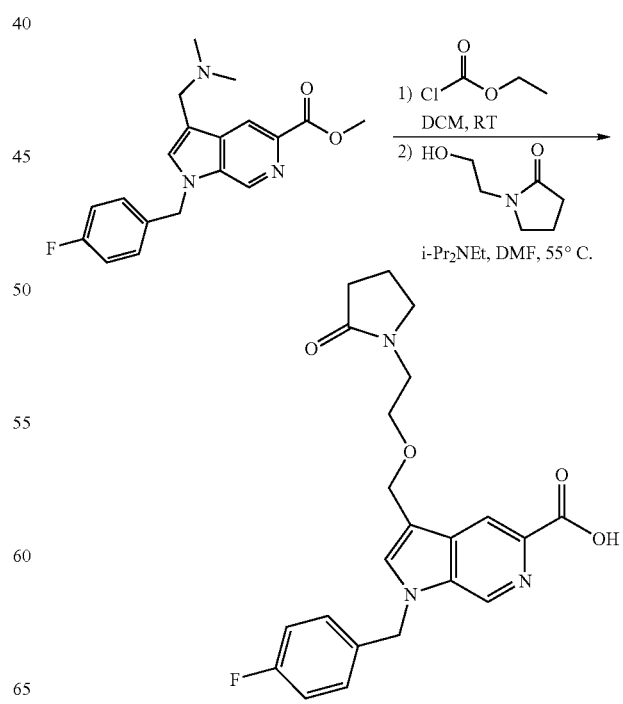

To a stirring solution of methyl 3-[(dimethylamino)methyl]-1-(4-fluorobenzyl)-1H-pyrrolo[2,3-c]pyridine-5-carboxylate (1.04 g, 3.05 mmol) in DCM (16 mL) under nitrogen was added ethyl chloroformate (0.330 g, 3.05 mmol). The solution was stirred for 2 hours at room temperature. At this time, 1-(2-hydroxyethyl)pyrrolidin-2-one (1.57 g, 12.18 mmol), ethyl(diisopropyl)amine (1.97 g, 15.23 mmol), and DMF (16 mL) were added to the reaction and the reaction heated to 55° C. After stirring for 24 hours (55° C.) the reaction was judged to be complete by HPLC-MS analysis and the volatiles were removed in vacuo (ca. 2 torr) to give red oil. The crude material was diluted with EtOAc (40 mL) and washed with water (4×20 mL) and brine (20 mL). The organic phase was separated, dried (Na$_2$SO$_4$), and concentrated in vacuo to afford the target compound, which was purified by chromatography on a column of silica gel. Fractions were combined to afford 0.961 g (76% yield) of methyl 1-(4-fluorobenzyl)-3-{[2-(2-oxopyrrolidin-1-yl)ethoxy]methyl}-1H-pyrrolo[2,3-c]pyridine-5-carboxylate as an off white solid. $^1$H NMR (300 MHz, CHLOROFORM-D) δ ppm 1.90-2.01 (m, 2H) 2.32 (t, J=8.10 Hz, 2H) 3.42-3.51 (m, 4H) 3.64 (t, J=5.27 Hz, 2H) 4.00 (s, 3H) 4.69 (s, 2H) 5.36 (s, 2H) 7.01 (t, J=8.57 Hz, 2H) 7.11-7.18 (m, 2H) 7.28 (s, 1H) 8.51 (s, 1H) 8.73 (s, 1H).

Step 2: 1-(4-Fluorobenzyl)-3-{[2-(2-oxopyrrolidin-1-yl)ethoxy]methyl}-1H-pyrrolo[2,3-c]pyridine-5-carboxylic acid

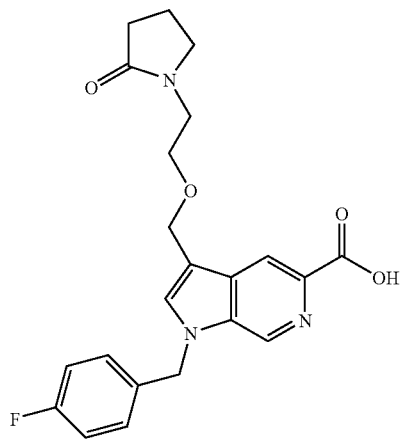

To a stirring solution of methyl 1-(4-fluorobenzyl)-3-{[2-(2-oxopyrrolidin-1-yl)ethoxy]methyl}-1H-pyrrolo[2,3-c]pyridine-5-carboxylate (0.915 g, 2.15 mmol) in methanol (25 mL) was added 3M LiOH$_{(aq)}$ (2.15 mL, 6.45 mmol). The clear reaction was warmed to 50° C. for 16 hours. After 16 hours a 50° C. the reaction was acidified to pH 4 by the addition of 1M HCl$_{(aq)}$. The solvent was evaporated in vacuo and the white residue stirred in water (50 mL) for 1 hour. The solid was filtered, washed with water, and dried under heat and vacuum to yield 1-(4-fluorobenzyl)-3-{[2-(2oxopyrrolidin-1-yl)ethoxy]methyl}-1H-pyrrolo[2,3-c]pyridine-5-carboxylic acid as a white solid (0.829 g, 94% yield). $^1$H NMR (400 MHz, DMSO-D6) δ ppm 1.76-1.85 (m, 2H) 2.13 (t, J=8.08 Hz, 2H) 3.31 (ddd, J=13.77, 6.69, 6.32 Hz, 4H) 3.52 (t, J=5.43 Hz, 2H) 4.66 (s, 2H) 5.57 (s, 2H) 7.16 (t, J=8.84 Hz, 2H) 7.35 (dd, J=8.46, 5.68 Hz, 2H) 7.86 (s, 1H) 8.33 (s, 1H) 8.95 (s, 1H).

Step 3: 1-(4-Fluorobenzyl)-N-hydroxy-N-methyl-3-{[2-(2-oxopyrrolidin-1-yl)ethoxy]methyl}-1H-pyrrolo[2,3-c]pyridine-5-carboxamide

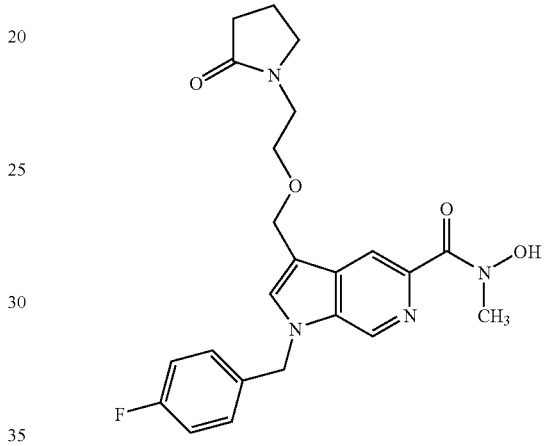

To a stirring solution of 1-(4-fluorobenzyl)-3-{[2-(2-oxopyrrolidin-1-yl)ethoxy]methyl}-1H-pyrrolo[2,3-c]pyridine-5-carboxylic acid (0.817 g, 1.99 mmol) and 2-chloro-4,6-dimethoxy-1,3,5-triazine (0.418 g, 2.38 mmol) in DMF (20 mL) was added N-methyl morpholine (0.2409, 2.38 mmol). After stirring at room temperature for 2 hours, N-methyl hydroxylamine hydrochloride (1.66 g, 19.9 mmol) was added. The reaction stirred for 16 hours at room temperature. After stirring for 16 hours, the reaction was concentrated in vacuo yielding a yellow oil. The oily residue was partitioned between a saturated sodium bicarbonate solution and ethyl acetate (50:50, 50 mL: 50 mL). The organic phase was separated and the aqueous phase extracted with ethyl acetate (2×100 mL). The organic phases were combined, washed with brine (100 mL), and dried over Na$_2$SO$_4$. The solution was filtered, concentrated, and triturated with diethyl ether to yield a pale yellow solid. The solid was recrystalized from isopropyl alcohol to give 1-(4-fluorobenzyl)-N-hydroxy-N-methyl-3-{[2-(2-oxopyrrolidin-1-yl)ethoxy]methyl}-1H-pyrrolo[2,3-c]pyridine-5-carboxamide as clear needles (0.425 g, 49% yield). $^1$H NMR (400 MHz, DMSO-D6) δ ppm 1.76-1.85 (m, 2H) 2.13 (t, J=8.08 Hz, 2H) 3.26-3.35 (m, 8H) 3.51 (t, J=5.43 Hz, 2H) 4.65 (s, 2H) 5.54 (s, 2H) 7.16 (t, J=8.84 Hz, 2H) 7.36 (dd, J=8.59, 5.56 Hz, 2H) 7.86 (s, 1H) 8.01 (s, 1H) 8.89 (s, 1H)

Example 118

1-(4-Fluorobenzyl)-N-hydroxy-N-methyl-3-[(tetrahydro-2H-pyran-4-yloxy)methyl]-1H-pyrrolo[2,3-c]pyridine-5-carboxamide

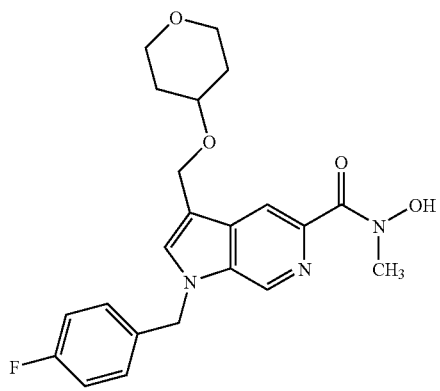

Step 1: Methyl 1-(4-fluorobenzyl)-3-[(tetrahydro-2H-pyran-4-yloxy)methyl]-1H-pyrrolo[2,3-c]pyridine-5-carboxylate

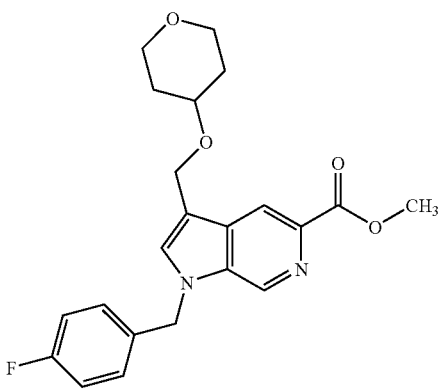

The title compound was prepared as in example 116, step 1, using methyl 3-[(dimethylamino) methyl]-1-(4-fluorobenzyl)-1H-pyrrolo[2,3-c]pyridine-5-carboxylate and tetrahydro-2H-pyran-4-ol.

$^1$H NMR (300 MHz, DMSO-D6) δ ppm 1.36-1.50 (m, 2H) 1.81-1.94 (m, 2H) 3.25-3.39 (m, 2H) 3.59 (ddd, J=8.85, 4.71, 4.52 Hz, 1H) 3.80 (dt, J=11.59, 4.38 Hz, 2H) 3.85 (s, 3H) 4.71 (s, 2H) 5.56 (s, 2H) 7.16 (t, J=8.85 Hz, 2H) 7.35 (dd, J=8.57, 5.56 Hz, 2H) 7.84 (s, 1H) 8.35 (s, 1H) 8.96 (s, 1H)

Step 2: 1-(4-fluorobenzyl)-3-[(tetrahydro-2H-pyran-4-yloxy)methyl]-1H-pyrrolo[2,3-c]pyridine-5-carboxylic acid

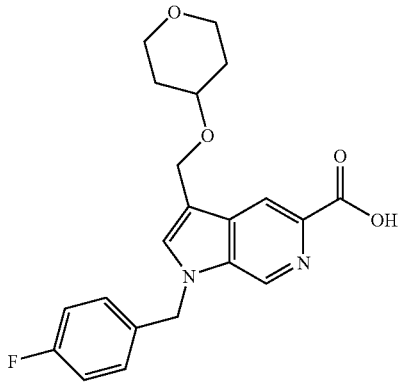

The title compound was prepared as in example 116, step 2, using methyl 1-(4-fluorobenzyl)-3-[(tetrahydro-2H-pyran-4-yloxy)methyl]-1H-pyrrolo[2,3-c]pyridine-5-carboxylate. $^1$H NMR (400 MHz, DMSO-D6) δ ppm 1.38-1.48 (m, J=13.20, 9.38, 9.38, 4.17 Hz, 2H) 1.88 (ddd, J=8.72, 4.17, 3.79 Hz, 2H) 3.28-3.37 (m, 2H) 3.56-3.65 (m, J=8.91, 8.91, 4.42, 4.04 Hz, 1H) 3.80 (ddd, J=11.49, 4.17, 4.04 Hz, 2H) 4.72 (s, 2H) 5.57 (s, 2H) 7.17 (t, J=8.84 Hz, 2H) 7.36 (dd, J=8.59, 5.56 Hz, 2H) 7.90 (s, 1H) 8.36 (s, 1H) 8.98 (s, 1H)

Step 3: 1-(4-Fluorobenzyl)-N-hydroxy-N-methyl-3-[(tetrahydro-2H-pyran-4-yloxy)methyl]-1H-pyrrolo[2,3-c]pyridine-5-carboxamide

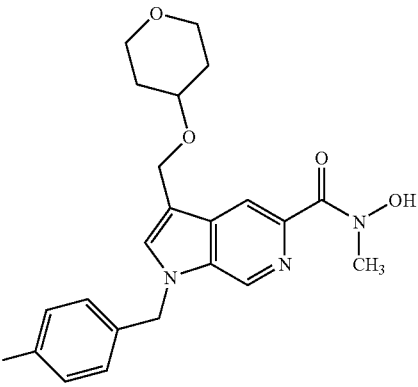

The title compound was prepared as in example 116, step 3, using 1-(4-fluorobenzyl)-3-[(tetrahydro-2H-pyran-4-yloxy)methyl]-1H-pyrrolo[2,3-c]pyridine-5-carboxylic acid, 2-chloro-4,6-dimethoxy-1,3,5-triazine, N-methyl morpholine, and N-methyl hydroxylamine hydrochloride. $^1$H NMR (400 MHz, DMSO-D6) δ ppm 1.38-1.48 (m, 2H) 1.84-1.91 (m, 2H) 3.28-3.37 (m, J=10.74, 10.74, 2.78 Hz, 5H) 3.60 (ddd, J=8.84, 4.80, 4.55 Hz, 1H) 3.80 (ddd, J=11.49, 4.29, 4.17 Hz, 2H) 4.69 (s, 2H) 5.54 (s, 2H) 7.16 (t, J=8.97 Hz, 2H) 7.36 (dd, J=8.72, 5.43 Hz, 2H) 7.86 (s, 1H) 8.03 (s, 1H) 8.89 (s, 1H)

Example 119

1-(4-Fluorobenzyl)-N-hydroxy-N-methyl-3-{[(1R)-1-phenylethoxy]methyl}-1H-pyrrolo[2,3-c]pyridine-5-carboxamide

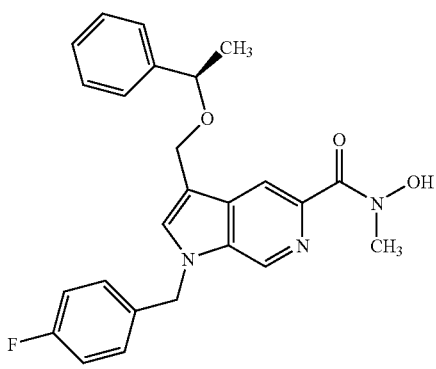

Step 1: Methyl 1-(4-fluorobenzyl)-3-{[(1R)-1-phenylethoxy]methyl}-1H-pyrrolo[2,3-c]pyridine-5-carboxylate

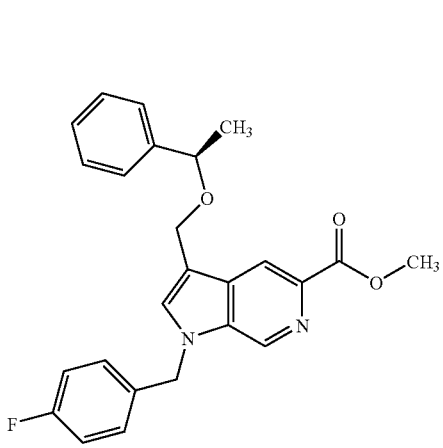

The title compound was prepared as in example 116, step 1, using methyl 3-[(dimethylamino)methyl]-1-(4-fluorobenzyl)-1H-pyrrolo[2,3-c]pyridine-5-carboxylate and (1R)-1-phenylethanol. $^1$H NMR (300 MHz, CHLOROFORM-D) δ ppm 1.48 (d, J=6.41 Hz, 3H) 4.01 (s, 3H) 4.48-4.59 (m, 3H) 5.34 (s, 2H) 6.97-7.05 (m, 2H) 7.10-7.17 (m, 2H) 7.23 (s, 1H) 7.29-7.42 (m, 5H) 8.47 (s, 1H) 8.72 (s, 1H)

Step 2: 1-(4-Fluorobenzyl)-3-([(1R)-1-phenylethoxy]methyl}-1H-pyrrolo[2,3-c]pyridine-5-carboxylic acid

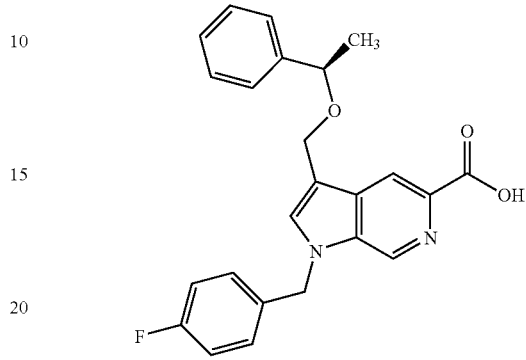

The title compound was prepared as in example 116, step 2, using methyl 1-(4-fluorobenzyl)-3-{[(1R)-1-phenylethoxy]methyl}-1H-pyrrolo[2,3-c]pyridine-5-carboxylate. $^1$H NMR (300 MHz, DMSO-D6) δ ppm 1.36 (d, J=6.41 Hz, 3H) 4.53 (d, J=1.88 Hz, 2H) 4.57 (d, J=6.41 Hz, 1H) 5.59 (s, 2H) δ 7.17 (t, J=8.85 Hz, 2H) 7.28-7.40 (m, 7H) 7.92 (s, 1H) 8.35 (s, 1H) 9.02 (s, 1H)

Step 3: 1-(4-Fluorobenzyl)-N-hydroxy-N-methyl-3-{[(1R)-1-phenylethoxy]methyl}-1H-pyrrolo[2,3-c]pyridine-5-carboxamide

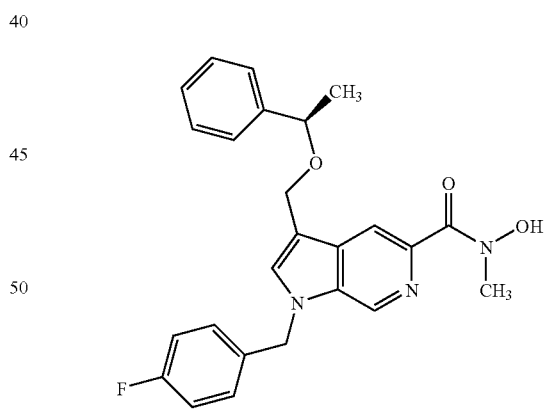

The title compound was prepared as in example 116, step 3, using 1-(4-fluorobenzyl)-3-{[(1R)-1-phenylethoxy]methyl}-1H-pyrrolo[2,3-c]pyridine-5-carboxylic acid, 2-chloro-4,6-dimethoxy-1,3,5-triazine, N-methyl morpholine, and N-methyl hydroxylamine hydrochloride. $^1$H NMR (400 MHz, DMSO-D6) δ ppm 1.35 (d, J=6.32 Hz, 3H) 3.33 (s, 3H) 4.50 (s, 2H) 4.55 (q, J=6.57 Hz, 1H) 5.53 (s, 2H) 7.16 (t, J=8.84 Hz, 2H) 7.29 (td, J=5.49, 3.16 Hz, 1H) 7.34-7.39 (m, 6H) 7.82 (s, 1H) 7.98 (s, 1H) 8.89 (s, 1H)

Example 120

3-[(2-ethoxyethoxy)methyl]-1-(4-fluorobenzyl)-N-hydroxy-N-methyl-1H-pyrrolo[2,3-c]pyridine-5-carboxamide

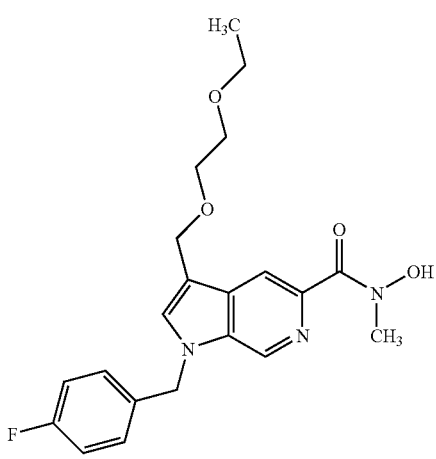

Step 1: Methyl 3-[(2-ethoxyethoxy)methyl]-1-(4-fluorobenzyl)-1 pyrrolo[2,3-c]pyridine-5-carboxylate Step 2: 3-[(2-Ethoxyethoxy)methyl]-1-(4-fluorobenzyl)-1H-pyrrolo[2,3-c]pyridine-5-carboxylic acid

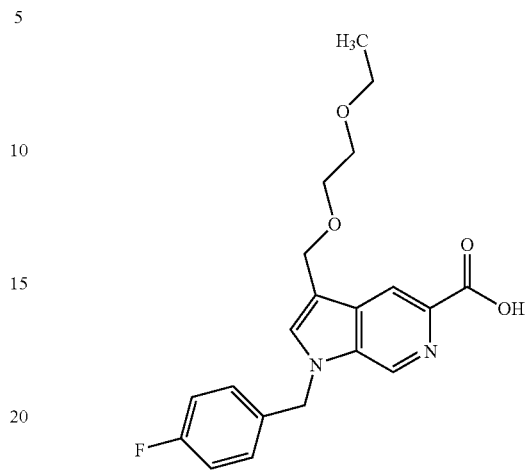

The title compound was prepared as in example 116, step 2, using methyl 3-[(2-ethoxyethoxy)methyl]-1-(4-fluorobenzyl)-1H-pyrrolo[2,3-c]pyridine-5-carboxylate. $^1$H NMR (400 MHz, DMSO-D6) δ ppm 1.06 (t, J=7.07 Hz, 3H) 3.40 (q, J=7.07 Hz, 2H) 3.46-3.51 (m, 2H) 3.53-3.57 (m, 2H) 4.67 (s, 2H) 5.57 (s, 2H) 7.16 (t, J=8.84 Hz, 2H) 7.36 (dd, J=8.34, 5.56 Hz, 2H) 7.87 (s, 1H) 8.37 (s, 1H) 8.95 (s, 1H)

Step 3: 3-[(2-Ethoxyethoxy)methyl]-1-(4-fluorobenzyl)-N-hydroxy-N-methyl-1 pyrrolo[2,3-c]pyridine-5-carboxamide

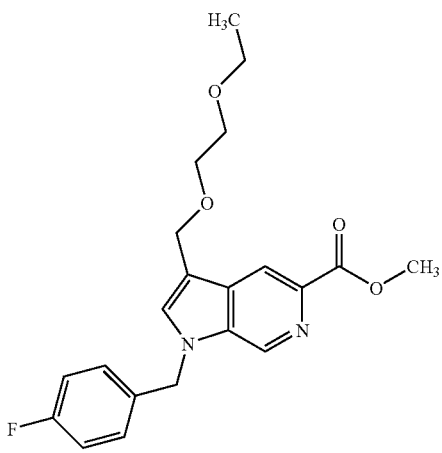

The title compound was prepared as in example 116, step 1, using methyl 3-[(dimethylamino)methyl]-1-(4-fluorobenzyl)-1H-pyrrolo[2,3-c]pyridine-5-carboxylate and 2-ethoxyethanol. $^1$H NMR (400 MHz, CHLOROFORM-D) δ ppm 1.20 (t, J=7.07 Hz, 3H) 3.52 (q, J=7.07 Hz, 2H) 3.59-3.63 (m, 2H) 3.65-3.69 (m, 2H) 4.00 (s, 3H) 4.76 (s, 2H) 5.36 (s, 2H) 6.98-7.04 (m, 2H) 7.14 (dd, J=8.46, 5.18 Hz, 2H) 7.31 (s, 1H) 8.55 (s, 1H) 8.73 (s, 1H)

The title compound was prepared as in example 116, step 3, using 3-[(2-ethoxyethoxy)methyl]-1-(4-fluorobenzyl)-1H-pyrrolo[2,3-c]pyridine-5-carboxylic acid, 2-chloro-4,6-dimethoxy-1,3,5-triazine, N-methyl morpholine, and N-methyl hydroxylamine hydrochloride. $^1$H NMR (400 MHz, DMSO-D6) δ ppm 1.06 (t, J=7.07 Hz, 3H) 3.32 (s, 3H) 3.40 (q, J=6.91 Hz, 2H) 3.46-3.50 (m, 2H) 3.53-3.56 (m, 2H) 4.66 (s, 2H) 5.54 (s, 2H) 7.16 (t, J=8.84 Hz, 2H) 7.36 (dd, J=8.59, 5.56 Hz, 2H) 7.87 (s, 1H) 8.04 (s, 1H) 8.89 (s, 1H).

Example 121

3-[(2-Ethoxyethoxy)methyl]-1-(4-fluorobenzyl)-N-methoxy-1H-pyrrolo[2,3-c]pyridine-5-carboxamide

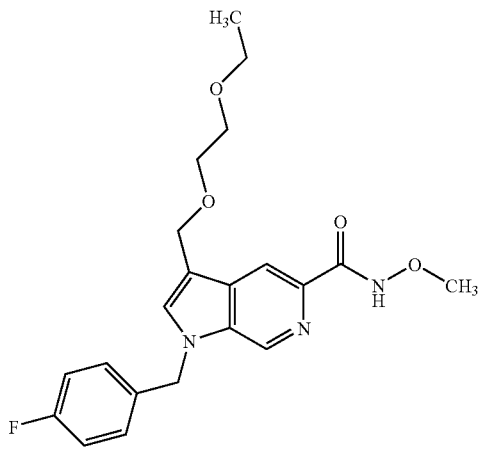

The title compound was prepared as in example 116, step 3, using 3-[(2-ethoxyethoxy)methyl]-1-(4-fluorobenzyl)-1H-pyrrolo[2,3-c]pyridine-5-carboxylic acid, 2-chloro-4,6-dimethoxy-1,3,5-triazine, N-methyl morpholine, and O-methyl hydroxylamine hydrochloride. $^1$H NMR (400 MHz, DMSO-D6) δ ppm 1.07 (t, J=6.95 Hz, 3H) 3.40 (q, J=6.99 Hz, 2H) 3.47-3.51 (m, 2H) 3.53-3.57 (m, 2H) 3.68 (s, 3H) 4.67 (s, 2H) 5.56 (s, 2H) 7.16 (t, J=8.97 Hz, 2H) 7.31-7.40 (m, 2H) 7.83 (s, 1H) 8.26 (s, 1H) 8.84 (s, 1H) 11.73 (s, 1H)

Example 122

1-(4-Fluorobenzyl)-AN-hydroxy-3-(methoxymethyl)-N-methyl-1H-pyrrolo[2,3-c]pyridine-5-carboxamide

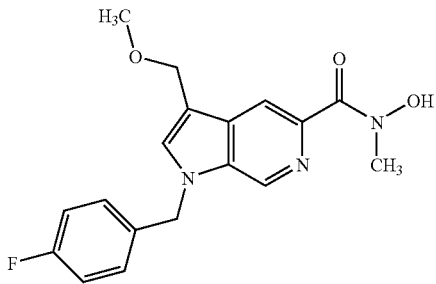

Step 1: Methyl 1-(4-fluorobenzyl)-3-(methoxymethyl)-1H-pyrrolo[2,3-c]pyridine-5-carboxylate

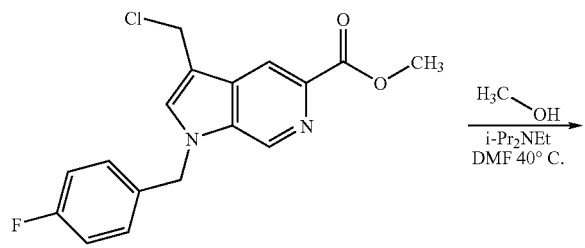

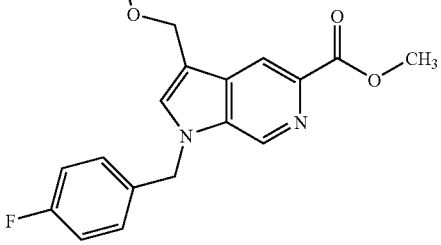

To a solution of methyl 3-(chloromethyl)-1-(4-fluorobenzyl)-1H-pyrrolo[2,3-c]pyridine-5-carboxylate (15 mL, 0.197M in CH$_2$Cl$_2$, 2.93 mmol)) [prepared as described in step 2 of example 40] was added methanol (4.0 mL) followed by i-Pr$_2$NEt (14.64 mmol, 2.55 mL, 5 eq.). The mixture, under nitrogen, was placed in an oil bath and the bath was warmed to 40° C. After stirring for 24 hours (40° C.) the reaction was judged to be complete by HPLC-MS analysis and the volatiles were removed in vacuo (ca. 2 torr) to give a golden yellow oil. The crude material was diluted with EtOAc (40 mL) and washed with water (4×20 mL) and brine (20 mL). The organic phase was separated, dried (Na$_2$SO$_4$), and concentrated in vacuo to afford 1048 mg of a brown oil. The crude material was purified by chromatography on a column of silica gel (40 mm OD, 100 g, 230-400 mesh, packed with CH$_2$Cl$_2$, eluted with CH$_2$Cl$_2$-MeOH 99:1 v/v, 1.0 L, 1.0 L, 25 mL fractions) using the flash technique. Fractions were combined to afford 0.960 g (100%) of methyl 1-(4-fluorobenzyl)-3-(methoxymethyl)-1H-pyrrolo[2,3-c]pyridine-5-carboxylate. LC-MS (Eclipse XDB-C8, 0.8 mL/min, gradient 80:20 to 5:95H$_2$O (+0.1% HOAc):CH$_3$CN—3 minutes, ESI, +mode): RT—1.122 min, m/e=329.2 (M+H$^+$, base).

$^1$H-NMR (300 MHz, CDCl$_3$): δ=3.46 (s, 3H), 4.02 (s, 3H), 4.64 (s, 2H), 5.37 (s, 2H), 7.00 (t, 2H), 7.16 (m, 2H), 7.32 (s, 1H), 8.54 (s, 1H), 8.74 (s, 1H).

Step 2: 1-(4-Fluorobenzyl)-3-(methoxymethyl)-1H-pyrrolo[2,3-c]pyridine-5-carboxylic acid

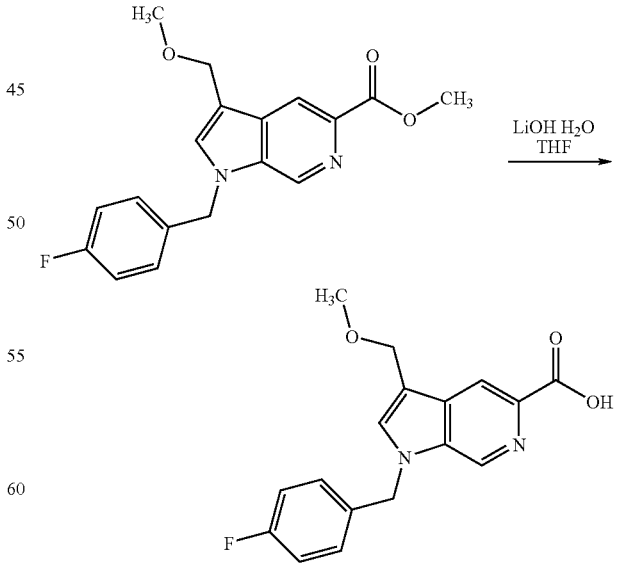

To a solution of methyl 1-(4-fluorobenzyl)-3-(methoxymethyl)-1H-pyrrolo[2,3-c]pyridine-5-carboxylate. (960 mg 1.2.924 mmol) in methanol (10 mL) was added lithium hydroxide monohydrate (246 mg 5.847 mmol, 2 eq.) and water (5 mL), and the clear solution was warmed to 40° C. for 15 hours. Methanol was removed under vacuum and 1 M HCl added (5.8 mL 5.847 mmol, 2 eq.). The crude product precipitated and was filtered under vacuum, washed with ether (40 ml) and dried in vacuo at 75° C. to give the title product as a white powder 664 mg (72%). LC-MS (Eclipse XDB-C8, 0.8 mL/min, gradient 80:20 to 5:95H$_2$O (+0.1% HOAc):CH$_3$CN—3 minutes, ESI, +mode): RT-0.828 min, m/e=315.2 (M+H$^+$, base). $^1$H-NMR (300 MHz, DMSO): δ=3.28 (s, 3H), 4.64 (s, 2H), 5.62 (s, 2H), 7.20 (t, 2H), 7.38 (m, 2H), 7.94 (s, 1H), 8.36 (s, 1H), 8.97 (s, 1H).

Step 3: 1-(4-Fluorobenzyl)-N-hydroxy-3-(methoxymethyl)-N-methyl-1H-pyrrolo[2,3-c]pyridine-5-carboxamide.

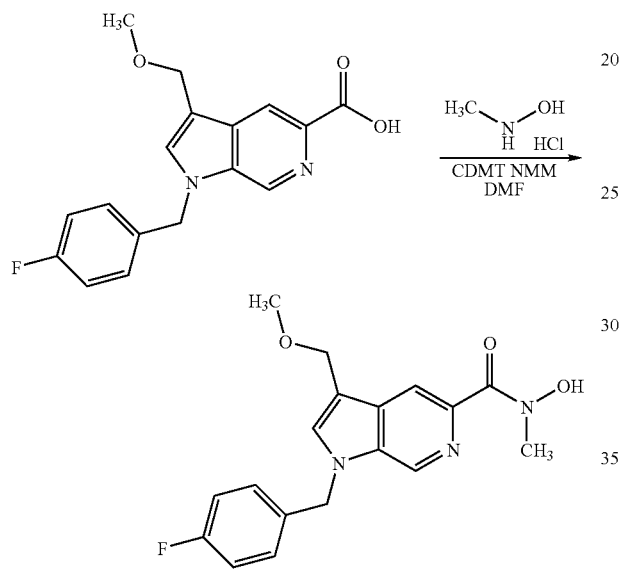

To a solution of 1-(4-fluorobenzyl)-3-(methoxymethyl)-1H-pyrrolo[2,3-c]pyridine-5-carboxylic acid 332 mg 0.9467 mmol) in anhydrous DMF (8.0 mL) was added CDMT (200 mg 1.136 mmol 1.2 eq.) and NMM (N-methyl morpholine) (0.13 mL 1.136 mmol 1.2 eq.). The mixture, under nitrogen, was stirred for 2.0 hours, during which it slowly darkened to a deep orange. N-Methylhydroxylamine hydrochloride (395 mg 4.734 mmol 5.0 eq) was added and stirring continued for 10 hours. The reaction was judged to be complete by HPLC-MS analysis and the volatiles were removed in vacuo (ca. 2 torr) to give a golden yellow oil. This oil was dissolved in EtOAc (30 mL) and washed with water (3×20 mL) and brine (20 mL). The organic phase was separated, dried (Na$_2$SO$_4$), and concentrated in vacuo to afford the crude product which was purified by recrystallisation in hot IPA (20 ml) with cooling at 4° C. overnight to give 194 mg (60%) of 1-(4-fluorobenzyl)-N-hydroxy-3-(methoxymethyl)-N-methyl-1H-pyrrolo[2,3-c]pyridine-5-carboxamide as a white solid. LC-MS (Eclipse XDB-C8, 0.8 mL/min, gradient 80:20 to 5:95H$_2$O (+0.1% HOAc):CH$_3$CN—3 minutes, APCI, +mode): RT—1.028 min, m/e=344.2 (M+H$^+$, base). $^1$H-NMR (300 MHz, DMSO): δ =3.26 (s, 3H), 3.34 (s, 3H), 4.57 (s, 2H), 5.54 (s, 2H), 7.14 (t, 2H), 7.36 (m, 2H), 7.87 (s, 1H), 8.02 (s, 1H), 8.92 (s, 1H). Found: C, 62.72; H, 5.20; N, 12.17%. C$_{18}$H$_{18}$FN$_3$O$_3$, requires C, 62.97; H, 5.28; N, 12.24%.

Example 123

1 (2,4-Difluorobenzyl)-N-hydroxy-3-[(2-methoxyethoxy)methyl]-N-methyl-1H-pyrrolo[2,3-c]pyridine-5-carboxamide

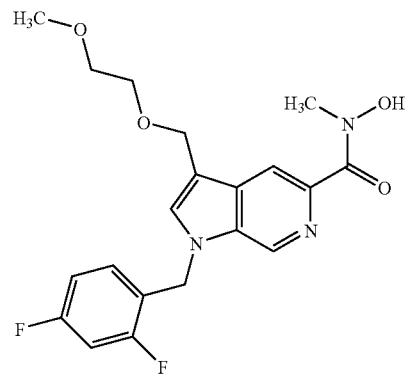

Step 1: Methyl 1-(2,4-difluorobenzyl)-3-[(2-methoxyethoxy)methyl]-1H-pyrrolo[2,3-c]pyridine -5-carboxylate

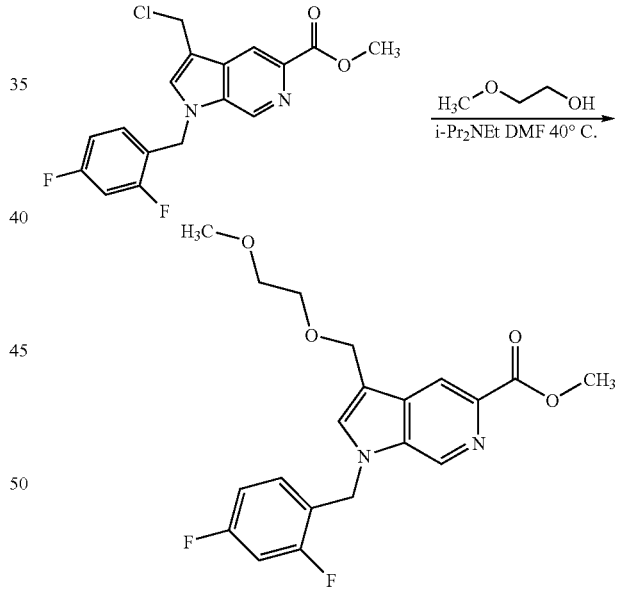

To a solution of methyl 3-(chloromethyl)-1-(2,4-difluorobenzyl)-1H-pyrrolo[2,3-c]pyridine-5-carboxylate (28.0 mL, 0.197M in CH$_2$Cl$_2$, 5.565 mmol)) [prepared as described in step 2 of example 40] in anhydrous DMF (20 mL) was added 2-(methoxyethoxy)-ethanol (27.83 mmol, 2.20 mL, 5 eq.) followed by i-Pr$_2$NEt (27.83 mmol, 4.84 mL, 5 eq.). The mixture, under nitrogen, was placed in an oil bath and the bath was warmed to 40° C. After stirring for 24 hours (40° C.) the reaction was judged to be complete by HPLC-MS analysis and the volatiles were removed in vacuo (ca. 2 torr) to give a golden yellow oil. The crude material was diluted with EtOAc (40 mL) and washed with water (4×20 mL) and brine (20 mL). The organic phase was separated, dried (Na$_2$SO$_4$), and concentrated in vacuo to afford 2000 mg (92%) of the target compound as a pale brown solid. LC-MS (Eclipse XDB-C8, 0.8 mL/min, gradient 80:20 to 5:95H$_2$O (+0.1% HOAc):CH$_3$CN—3 minutes, ESI, +mode): RT-1.22 min, m/e=391.2 (M+H$^+$, base). $^1$H-NMR (300 MHz, CDCl$_3$): δ=3.38 (s, 3H), 3.56 (m, 2H), 3.67 (m, 2H), 4.04 (s, 3H), 4.76 (s, 2H), 5.42 (s, 2H), 6.84 (m, 2H), 7.06 (q, 1H), 7.34 (s, 1H), 8.54 (s, 1H), 8.84 (s, 1H).

Step 2: 1-(2,4-Difluorobenzyl)-3-[(2-methoxyethoxy)methyl]-1H-pyrrolo[2,3-c]pyridine-5-carboxylic acid.

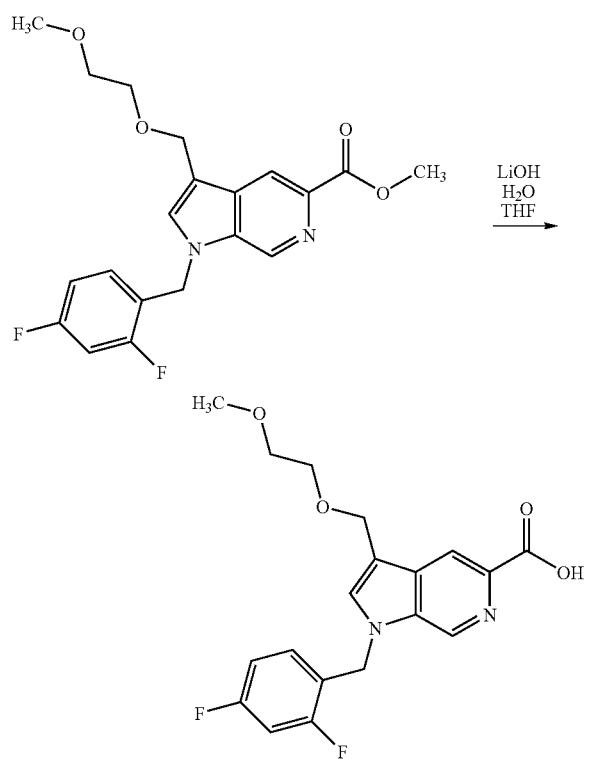

To a solution of methyl 1-(2,4-difluorobenzyl)-3-[(2-methoxyethoxy)methyl]-1H-pyrrolo[2,3-c]pyridine-5-carboxylate (2000 mg 5.123 mmol) in methanol (10 mL) was added lithium hydroxide monohydrate (430 mg 10.246 mmol, 2 eq.) and water (10 mL) and the clear solution was warmed to 40° C. for 3 hours. THF was removed under vacuum and 1 M HCl added (10.3 mL 10.3 mmol, 2 eq.). The crude product was extracted into EtOAc (3×30 mL), then DCM:MeOH 100:5 (3×30 mL). The organics were dried (Na$_2$SO$_4$), volatiles were removed in vacuo to give the title product as a cream colored powder 1563 mg (82%). LC-MS (Eclipse XDB-C8, 0.8 mL/min, gradient 80:20 to 5:95H$_2$O (+0.1% HOAc):CH$_3$CN—3 minutes, ESI, +mode): RT—0.91 min, m/e=377.2 (M+H$^+$, base). $^1$H-NMR (300 MHz, DMSO): δ=3.42 (s, 3H), 3.46 (m, 2H), 3.60 (m, 2H), 4.69 (s, 2H), 5.66 (s, 2H), 7.07 (m, 1H), 7.36 (m, 2H), 7.82 (s, 1H), 8.36 (s, 1H), 8.98 (s, 1H).

Step 3: 1-(2,4-Difluorobenzyl)-N-hydroxy-3-[(2-methoxyethoxy)methyl]-N-methyl-1H pyrrolo[2,3-c]pyridine-5-carboxamide.

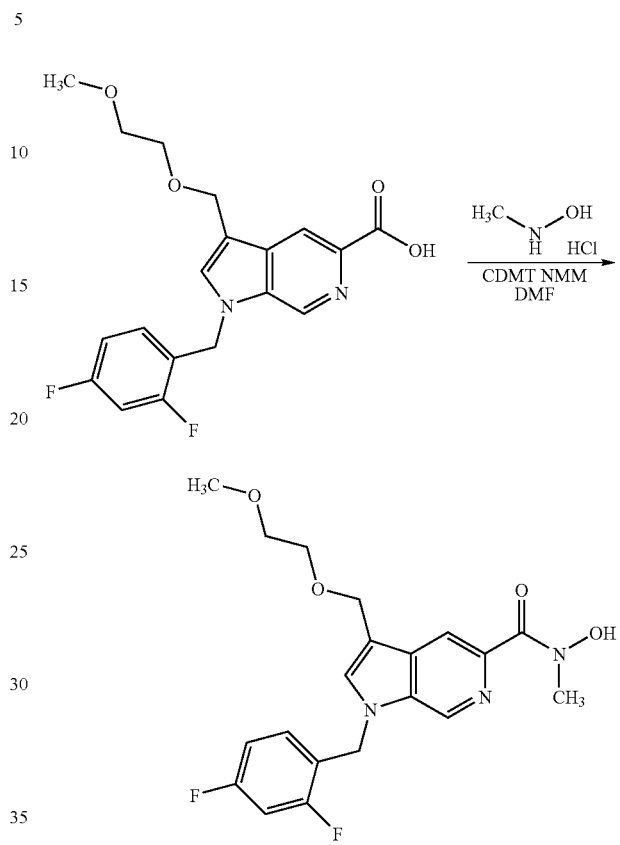

To a solution of 1-(2,4-difluorobenzyl)-3-[(2-methoxyethoxy)methyl]-1H-pyrrolo[2,3-c]pyridine-5-carboxylic acid 782 mg 2.078 mmol) in anhydrous DMF (10 ml) was added CDMT (438 mg 2.439 mmol 1.2 eq.) and NMM (N-methyl morpholine) (0.28 ml 2.493 mmol 1.2 eq.). The mixture, under nitrogen, was stirred for 2.0 hours, during which it slowly darkened to a deep orange. N-Methylhydroxylamine hydrochloride (868 mg 10.389 mmol 5.0 eq) was added and stirring continued for 10 hours. The reaction was judged to be complete by HPLC-MS analysis and the volatiles were removed in vacuo (ca. 2 torr) to give a golden yellow oil. This oil was dissolved in EtOAc (30 mL) and washed with water (3×20 mL) and brine (20 mL). The organic phase was separated, dried (Na$_2$SO$_4$), and concentrated in vacuo to afford the crude product which was purified by recrystallisation in hot IPA (20 ml) with cooling at 4° C. overnight to give 556 mg (66%) of 1-(2,4-difluorobenzyl)-N-hydroxy-3-[(2-methoxyethoxy)methyl]-N-methyl-1H-pyrrolo[2,3-c]pyridine-5-carboxamide as a pale tan powder. LC-MS (Eclipse XDB-C8, 0.8 mL/min, gradient 80:20 to 5:95H$_2$O (+0.1% HOAc):CH$_3$CN—3 minutes, APCI, +mode): RT—1.08 min, m/e=344.2 (M+H$^+$, base).

$^1$H-NMR (300 MHz, DMSO): δ=3.26 (s, 3H), 3.46 (m, 2H), 3.56 (m, 2H), 4.70 (s, 2H), 5.64 (s, 2H), 7.10 (m, 1H), 7.32 (m, 2H), 7.80 (s, 1H), 8.06 (s, 1H), 8.94 (s, 1H). Found: C, 59.10; H, 5.11; N, 10.34. C$_{20}$H$_{21}$N$_3$O$_4$; requires C, 59.26; H, 5.22; N, 10.36%.

Example 124

Integrase Strand-Transfer Scintillation Proximity Assay Oligonucleotides

Oligonucleotide #1-5'-(biotin)CCCCTTTTAGTCAGT-GTGGAAAATCTCTAGCA-3' (SEQ ID NO: 1) and oligonucleotide #2-5'-ACTGCTAGAGATTTTCCACACTGAC-TAAAAG-3' (SEQ ID NO: 2), were synthesized by TriLink BioTechnologies, Inc. (San Diego, Calif.). The annealed product represents preprocessed viral ds-DNA derived from the LTR U5 sequence of the viral genome. A ds-DNA control to test for non-specific interactions was made using a 3' dideoxy derivative of oligonucleotide #1 annealed to oligonucleotide #2. The CA overhang at the 5' end of the non-biotinylated strand of the ds-DNA was created artificially by using a complimentary DNA oligonucleotide shortened by 2 base pairs. This configuration eliminates the requisite 3' processing step of the integrase enzyme prior to the strand-transfer mechanism. Host ds-DNA was prepared as an unlabeled and [$^3$H]-thymidine labeled product from annealed oligonucleotide #3-5-AAAAAATGACCMGGGCTMT-TCACT-3' (SEQ ID NO: 3), and oligonucleotide #4-5'-AAAAAAGTGAATTAGCCCTTGGTCA-3' (SEQ ID NO: 4), both synthesized by TriLink BioTechnologies, Inc. (San Diego, Calif.). The annealed product had overhanging 3' ends of poly(dA). Host DNA was custom radiolabeled by PerkinElmer Life Sciences Inc. (Boston, Mass.) using an enzymatic method with a 12/1 ratio of [methyl-3H]dTTP/cold ds-DNA to yield 5'-blunt end ds-DNA with a specific activity of >900 Ci/mmol. The radiolabeled product was purified using a NENSORB cartridge and stored in stabilized aqueous solution (PerkinElmer). The final radiolabeled product had six [$^3$H]-thymidine nucleotides at both 5' ends of the host ds-DNA. Reagents: Streptavidin-coated polyvinyltoluene (PVT) SPA beads were purchased from Amersham Biosciences (Piscataway, N.J.). Cesium chloride was purchased from Shelton Scientific, Inc. (Shelton, Conn.). White, polystyrene, flat-bottom, non-binding surface, 96-well plates were purchased from Corning. All other buffer components were purchased from Sigma (St. Louis, Mo.) unless otherwise indicated.

Enzyme Construction: Full-length wild type HIV-1 integrase (SF1) sequence (amino acids 1-288) was constructed in a pET24a vector (Novagen, Madison, Wis.). The construct was confirmed through DNA sequencing. Enzyme Purification: Full length wild-type HIV Integrase was expressed in E. coli BL21 (DE3) cells and induced with 1 mM isopropyl-1 thio-β-D-galactopyranoside (IPTG) when cells reached an optical density between 0.8-1.0 at 600 nm. Cells were lysed by microfluidation in 50 mM HEPES pH 7.0, 75 mM NaCl, 5 mM DTT, 1 mM 4-(2-Aminoethyl)benzenesulfonylfluoride HCl (AEBSF). Lysate was then centrifuged 20 minutes at 11 k rpm in GSA rotor in Sorvall RC-5B at 4° C. Supernant was discarded and pellet resuspended in 50 mM HEPES pH 7.0, 750 mM NaCl, 5 mM DTT, 1 mM AEBSF and homogenized in a 40 mL Dounce homogenizer for 20 minutes on ice. Homogenate was then centrifuged 20 minutes at 11 k rpm in SS34 rotor in Sorvall RC-5B at 4° C. Supernant was discarded and pellet resuspended in 50 mM HEPES pH 7.0, 750 mM NaCl, 25 mM CHAPS, 5 mM DTT, 1 mM AEBSF. Preparation was then centrifuged 20 minutes at 11 k rpm in SS34 rotor in Sorvall RC-5B at 4° C. Supernant was then diluted 1:1 with 50 mM HEPES pH 7.0, 25 mM CHAPS, 1 mM DTT, 1 mM AEBSF and loaded onto a Q-Sepharose column pre-equilibrated with 50 mM HEPES, pH 7.0, 375 mM NaCl, 25 mM CHAPS, 1 mM DTT, 1 mM AEBSF. The flow through peak was collected and NaCl diluted to 0.1 M with 50 mM HEPES pH 7.0, 25 mM CHAPS, 1 mM DTT, 0.5 mM AEBSF and loaded onto a SP-Sepharose column pre-equilibrated with 50 mM HEPES pH 7.0, 100 mM NaCl, 25 mM CHAPS, 1 mM DTT, 0.5 mM AEBSF. After washing the column with the equilibration buffer, a 100 to 400 mM NaCl gradient was run. The eluted integrase was concentrated and run on a S-300 gel diffusion column using 50 mM HEPES pH 7.0, 500 mM NaCl, 25 mM CHAPS, 1 mM DTT, 0.5 mM AEBSF. The peak from this column was concentrated to 0.76 mg/mL and stored at −70° C. and later used for strand transfer assays. All columns were run in a 4° C. cold room. Viral DNA Bead Preparation: Streptavidin-coated SPA beads were suspended to 20 mg/mL in 25 mM 3-morpholinopropanesulfonic acid (MOPS) (pH 7.2) and 1.0% NaN$_3$. Biotinylated viral DNA was bound to the hydrated SPA beads in a batch process by combining 25 μmoles of ds-DNA to 1 mg of suspended SPA beads (10 μL of 50 μM viral DNA to 1 mL of 20 mg/mL SPA beads). The mixture was incubated at 22° C. for a minimum of 20 min. with occasional mixing followed by centrifugation at 2500 rpm for 10 min. However, the centrifugation speed and time may vary depending upon the particular centrifuge and conditions. The supernatant was removed and the beads suspended to 20 mg/mL in 25 mM MOPS (pH 7.2) and 1.0% NaN$_3$. The viral DNA beads were stable for several weeks when stored at 4° C. Di-deoxy viral DNA was prepared in an identical manner to yield control di-deoxy viral DNA beads. Preparation of Integrase-DNA Complex: Assay buffer was made as a 10× stock of 250 mM MOPS (pH 7.2), 500 mM NaCl, 50 mM 3-[(3-cholamidopropyl)dimethylammonio]-1propanesulfonate (CHAPS), 0.5% (octylphenoxy)polyethoxyethanol (NP40) (IGEPAL-CA) and 0.05% NaN$_3$. Viral DNA beads were diluted to 2.67 mg/mL in 1× assay buffer plus 3 mM MgCl$_2$, 1% DMSO, and 10 mM fresh DTT. Integrase (IN) was pre-complexed to viral DNA beads in a batch process (IN/viral DNA/bead complex) by combining diluted viral DNA beads with integrase at a concentration of 385 nM followed by a minimum incubation time of 20 min. at 22° C. with gentle agitation. The sample was kept at 22° C. until transferred to the assay wells. Preparation of Host DNA: Host DNA was prepared to 200 nM as a mixture of unlabeled and [$^3$H]T-labeled host DNA diluted in 1× assay buffer plus 8.5 mM MgCl$_2$ and 15 mM DTT. Concentrations used were 4 nM [$^3$H]T-labeled host DNA and 196 nM unlabeled host DNA. This ratio generates a SPA signal of 2000-3000 CPM in the absence of modulators such as inhibitors. Strand-transfer Scintillation Proximity Assay: The strand-transfer reaction was carried out in 96-well microtiter plates, with a final enzymatic reaction volume of 100 μL. Ten microliters of compounds or test reagents diluted in 10% DMSO were added to the assay wells followed by the addition of 65 μL of the IN/viral-DNA/bead complex and mixed on a plate shaker. Then 25 μL of host DNA was added to the assay wells and mixed on a plate shaker. The strand-transfer reaction was initiated by transferring the assay plates to 37° C. dry block heaters. An incubation time of 50 min., which was shown to be within the linear range of the enzymatic reaction, was used. The final concentrations of integrase and host DNA in the assay wells were 246 nM and 50 nM, respectively. The integrase strand-transfer reaction was terminated by adding 70 μL of stop buffer (150 mM EDTA, 90 mM NaOH, and 6 M CsCl) to the wells. Components of the stop buffer function to terminate enzymatic activity (EDTA), dissociate integrase/DNA complexes in addition to separating non-integrated DNA strands (NaOH), and float the SPA beads to the surface of the wells to be in closer range to the PMT detectors of the TopCount® plate-based scintillation counter (PerkinElmer Life Sciences Inc. (Boston, Mass.)). After the addition of stop buffer, the plates were mixed on a plate shaker, sealed with transparent tape, and allowed to incubate a minimum of 60 min. at 22° C. The assay signal was measured using a TopCount® plate-based scintillation counter with settings optimal for [$^3$H]-PVT SPA beads. The TopCount® program incorporated a quench standardization curve to normalize data for color absorption of the compounds. Data values for quench-corrected counts per minute (QCPM) were used to quantify integrase activity. Counting time was 2 min./well. The di-deoxy viral DNA beads were used to optimize the integrase strand-transfer reaction. The di-deoxy termination of the viral ds-DNA sequence prevented productive integration of viral DNA into the host DNA by integrase. Thus, the assay signal in the presence of di-deoxy viral DNA was a measure of non-specific interactions. Assay parameters were optimized to where reactions with di-deoxy viral DNA beads gave an assay signal closely matched to the true background of the assay. The true background of the assay was defined as a reaction with all assay components (viral DNA and [$^3$H]-host DNA) in the absence of integrase.

Determination of Compound Activity: The percent inhibition of the compound was calculated using the equation (1-((QCPM sample−QCPM min)/(QCPM max−QCPM min)))*100. The min value is the assay signal in the presence of a known inhibitor at a concentration 100-fold higher than the $IC_{50}$ for that compound. The min signal approximates the true background for the assay. The max value is the assay signal obtained for the integrase-mediated activity in the absence of compound (i.e. with DMSO instead of compound in DMSO). Compounds were prepared in 100% DMSO at 100-fold higher concentrations than desired for testing in assays (generally 5 mM), followed by dilution of the compounds in 100% DMSO to generate an 11-point titration curve with ½-log dilution intervals. The compound sample was further diluted 10-fold with water and transferred to the assay wells. The percentage inhibition for an inhibitory compound was determined as above with values applied to a nonlinear regression, sigmoidal dose response equation (variable slope) using GraphPad Prism curve fitting software (GraphPad Software, Inc., San Diego, Calif.). Concentration curves were assayed in duplicate and then repeated in an independent experiment.

Example 125

HIV-1 Cell Protection Assay

The antiviral activities of potential modulator compounds (test compounds) were determined in HIV-1 cell protection assays using the RF strain of HIV-1, CEM-SS cells, and the XTT dye reduction method (Weislow, O. S. et al., *J. Natl. Cancer Inst.* 81: 577-586 (1989)). Subject cells were infected with HIV-1 RF virus at an moi of 0.025 to 0.819 or mock infected with medium only and added at $2 \times 10^4$ cells per well into 96 well plates containing half-log dilutions of test compounds. Six days later, 50 µl of XTT solution (1 mg/ml XTT tetrazolium and 0.02 nM phenazine methosulfate) were added to the wells and the plates were reincubated for four hours. Viability, as determined by the amount of XTT formazan produced, was quantified spectrophotometrically by absorbance at 450 nm. Data from CPE assays were expressed as the percent of formazan produced in compound-treated cells compared to formazan produced in wells of uninfected, compound-free cells. The fifty percent effective concentration ($EC_{50}$) was calculated as the concentration of compound that affected an increase in the percentage of formazan production in infected, compound-treated cells to 50% of that produced by uninfected, compound-free cells. The 50% cytotoxicity concentration ($CC_{50}$) was calculated as the concentration of compound that decreased the percentage of formazan produced in uninfected, compound-treated cells to 50% of that produced in uninfected, compound-free cells. The therapeutic index was calculated by dividing the cytotoxicity ($CC_{50}$) by the antiviral activity ($EC_{50}$).

Example 126

Antiviral Data

| Example No. | EC50 (µM) | IC50 (µM) |
|---|---|---|
| 1 | 0.00795 | 0.084 |
| 2 | 0.068 | 0.0523 |
| 3 | 0.16 | 0.195 |
| 4 | 0.085 | 0.343 |
| 5 | 0.013 | 0.153 |
| 6 | 0.0052 | 0.108 |
| 7 | 0.021 | 0.14 |
| 8 | 0.052 | 0.045 |
| 9 | 0.0074 | 0.02 |
| 10 | 0.018 | 0.084 |
| 11 | 0.015 | 0.037 |
| 12 | 0.019 | 0.036 |
| 13 | 0.22 | 0.695 |
| 14 | 0.14 | 0.54 |
| 15 | 0.011 | 0.041 |
| 16 | 0.012 | 0.1085 |
| 17 | 0.025 | 0.2995 |
| 18 | 0.049 | 0.47 |
| 19 | 0.048 | 0.218 |
| 20 | 0.082 | 1.54 |
| 21 | 0.084 | 0.517 |
| 22 | 0.19 | 1.3 |
| 23 | 0.78 | 1.3 |
| 24 | 0.11 | 1.04 |
| 25 | 0.23 | 1.72 |
| 26 | 3.7 | 0.77 |
| 27 | 3.5 | 8 |
| 28 | 0.35 | 0.628 |
| 29 | 1.4 | 1.7 |
| 30 | 0.3 | 0.804 |
| 31 | 0.014 | 0.186 |
| 32 | 0.025 | 0.215 |
| 33 | 0.21 | 0.463 |
| 34 | 0.17 | 0.49 |
| 35 |  | 0.446 |
| 36 | 0.39 | 0.811 |
| 37 | 0.046 | 0.528 |
| 38 | 0.012 | 0.145 |
| 39 | 0.00305 |  |
| 42 | 0.001 | 0.027 |
| 43 | 0.42 | 0.371 |
| 44 | 1.2 | 2.25 |
| 45 | 0.051 | 0.295 |
| 46 | 0.13 | 0.912 |
| 51 | 0.23 | 0.752 |
| 52 | 0.26 | 0.781 |
| 53 | 0.011 | 0.359 |
| 54 | 0.038 | 0.746 |
| 55 | 0.02 | 0.216 |
| 56 | 0.011 | 0.278 |
| 57 | 0.024 | 0.542 |
| 58 | 0.1 | 0.585 |
| 59 | 0.018 | 0.221 |
| 60 | 0.012 | 0.521 |
| 61 | 0.035 | 0.916 |
| 62 | 0.017 | 0.671 |
| 63 | 0.016 | 0.424 |
| 64 | 0.017 | 0.328 |
| 65 | 0.014 | 0.625 |
| 66 | 0.011 | 0.357 |
| 67 | 0.015 | 0.283 |

| Example No. | EC50 (μM) | IC50 (μM) |
|---|---|---|
| 68 | 0.1 | 0.549 |
| 69 | 0.028 | 0.755 |
| 70 | 0.022 | 0.332 |
| 71 | 0.044 | 0.409 |
| 72 | 0.029 | 0.658 |
| 73 | 0.035 | 0.658 |
| 74 | 0.032 | 0.357 |
| 75 | 0.014 | 0.382 |
| 76 | 0.091 | 0.402 |
| 77 | 0.36 | 0.483 |
| 78 | 0.083 | 0.571 |
| 79 | 0.02 | 0.243 |
| 80 | 0.01 | 0.53 |
| 81 | 0.04 | 0.499 |
| 82 | 0.023 | 0.634 |
| 83 | 0.06 | 0.952 |
| 84 | 0.051 | 0.316 |
| 85 | 0.033 | 0.224 |
| 86 | 0.011 | 0.314 |
| 87 | 0.067 | 0.814 |
| 88 | 0.016 | 0.238 |
| 89 | 0.052 | 0.708 |
| 90 | 0.018 | 0.212 |
| 91 | 0.028 | 0.519 |
| 92 | 0.07 | 0.425 |
| 93 | 0.071 | 0.187 |
| 94 | 0.026 | 0.288 |
| 95 | 0.017 | 0.127 |
| 96 | 0.03 | 0.511 |
| 97 | 0.02 | 0.311 |
| 98 | 0.1 | 0.256 |
| 99 | 0.031 | 0.277 |
| 100 | 10 | 0.27 |
| 101 | 0.073 | 0.472 |
| 102 | 0.033 | 0.81 |
| 103 | 0.13 | 0.702 |
| 104 | 0.00445 | 0.182 |
| 106 | 0.0663 | 0.0120 |
| 107 | 0.0322 | 0.00340 |
| 108 | 0.334 | 0.0212 |
| 109 | 0.313 | 0.0630 |
| 110 | 0.341 | 0.0140 |
| 111 | 0.0774 | 0.0200 |
| 112 | 0.597 | 0.0620 |
| 113 | 0.437 | 0.0400 |
| 114 | 0.351 | 0.150 |
| 115 | 3.70 | N/D |
| 116 | 3.90 | N/D |
| 117 | 0.401 | 0.200 |
| 118 | 0.313 | 0.0570 |
| 119 | 0.505 | 0.0390 |
| 120 | 0.307 | 0.0570 |
| 121 | 0.512 | N/D |
| 122 | 0.242 | N/D/ |
| 123 | 0.519 | 0.0510 |

We claim:

1. A compound of formula (I),

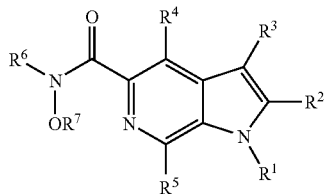

wherein:

$R^1$ is hydrogen, $C_1$-$C_8$ alkyl, $C_2$-$C_8$ alkenyl, or $C_1$-$C_8$ heteroalkyl, wherein said $C_1$-$C_8$ alkyl, $C_2$-$C_8$ alkenyl, or $C_1$-$C_8$ heteroalkyl groups may be optionally substituted with at least one substituent independently selected from:

halo, —$OR^{12a}$, —$N(R^{12a}R^{12b})$, —$C(O)N(R^{12a})_2$, —$NR^{12a}C(O)N(R^{12a}R^{12b})$, —$NR^{12a}C(O)R^{12a}$, —$NR^{12a}C(NR^{12a})N(R^{12a}R^{12b})$, —$SR^{12a}$, —$S(O)R^{12a}$, —$S(O)_2R^{12a}$, —$S(O)_2N(R^{12a}R^{12b})_2$, $C_1$-$C_8$ alkyl, $C_6$-$C_{14}$ aryl, $C_3$-$C_8$ cycloalkyl, and $C_2$-$C_9$ heteroaryl, wherein said $C_1$-$C_8$ alkyl, $C_6$-$C_{14}$ aryl, $C_3$-$C_8$ cycloalkyl, and $C_2$-$C_9$ heteroaryl groups are optionally substituted with at least one substituent independently selected from halo, —$C(R^{12a}R^{12b}R^{12c})$, —OH, and $C_1$-$C_8$ alkoxy;

$R^2$ is hydrogen;

$R^3$ is —$(CR^8R^9)_tNR^{10}R^{11}$ or $C_1$-$C_8$ heteroalkyl, wherein said $C_1$-$C_8$ heteroalkyl is substituted with $R^{24}$;

$R^4$ is hydrogen, halo, $C_1$-$C_8$ alkyl, —$OR^{12a}$, —$NR^{12}R^{12b}$, $C_1$-$C_8$ heteroalkyl, $C_2$-$C_8$ alkenyl, or $C_2$-$C_8$ alkynyl, wherein said $C_2$-$C_8$ alkenyl or $C_2$-$C_8$ alkynyl are optionally substituted with at least one $R^{26}$;

$R^5$ is hydrogen;

$R^6$ is hydrogen, $C_1$-$C_8$ alkyl, $C_1$-$C_8$ heteroalkyl, or $C_2$-$C_8$ alkenyl, wherein said $C_2$-$C_8$ alkenyl is optionally substituted with at least one —$OR^{12a}$ group;

$R^7$ is hydrogen, $C_1$-$C_8$ heteroalkyl, $C_6$-$C_{14}$ aryl, $C_2$-$C_8$ alkenyl, or $C_1$-$C_8$ alkyl, wherein said $C_1$-$C_8$ alkyl is optionally substituted with at least one $C_3$-$C_8$ cycloalkyl or $C_6$-$C_{14}$ aryl group;

each $R^8$ and $R^9$, which may be the same or different, are independently selected from hydrogen and $C_1$-$C_8$ alkyl;

$R^{10}$ and $R^{11}$, together with the nitrogen atom to which they are attached, form a $C_2$-$C_9$ cycloheteroalkyl group optionally substituted with at least one $C_1$-$C_8$ alkyl;

each $R^{12a}$, $R^{12b}$, and $R^{12c}$, which may be the same or different, is independently selected from hydrogen and $C_1$-$C_8$ alkyl;

$R^{24}$ is $C_3$-$C_8$ cycloalkyl, $C_2$-$C_9$ cycloheteroalkyl, or $C_2$-$C_9$ heteroaryl, each of which is optionally substituted with at least one substituent independently selected from $C_1$-$C_8$ alkyl, $C_6$-$C_{14}$ aryl, $C_2$-$C_9$ heteroaryl, —$CF_3$, and —$OR^{12a}$;

each $R^{26}$ is independently selected from —$OR^{12a}$, halo, $C_6$-$C_{14}$ aryl, $C_2$-$C_9$ heteroaryl, $C_1$-$C_8$ heteroalkyl, $C_3$-$C_8$ cycloalkyl, $C_2$-$C_9$ cycloheteroalkyl, and —$C(R^{12a}R^{12b}R^{12c})$; and t is an integer from 1 to 3; or a pharmaceutically acceptable salt or solvate thereof.

2. A compound according to claim 1, wherein $R^3$ is —$(CR^8R^9)_tNR^{10}R^{11}$.

3. A compound according to claim 2, wherein:

$R^1$ is $C_1$-$C_8$ alkyl substituted with $C_6$-$C_{14}$ aryl, $C_3$-$C_8$ cycloalkyl, or $C_2$-$C_9$ heteroaryl, wherein said $C_6$-$C_{14}$ aryl, $C_3$-$C_8$ cycloalkyl, and $C_2$-$C_9$ heteroaryl groups are optionally substituted with at least one substituent independently selected from halo, —$C(R^{12a}R^{12b}R^{12c})$, —OH, and $C_1$-$C_8$ alkoxy; and $R^8$ and $R^9$ are hydrogen.

4. A compound according to claim 3, wherein:

$R^1$ is $C_1$-$C_8$ alkyl substituted with $C_6$-$C_{14}$ aryl, wherein said $C_6$-$C_{14}$ aryl is optionally substituted with at least one substituent independently selected from halo, —$C(R^{12a}R^{12b}R^{12c})$, —OH, and $C_1$-$C_8$ alkoxy;

$R^4$ is hydrogen or $C_2$-$C_8$ alkenyl, wherein said $C_2$-$C_8$ alkenyl is optionally substituted with at least one $R^{26}$; and $R^6$ is hydrogen or $C_1$-$C_8$ alkyl.

5. A compound according to claim 4, wherein:

$R^1$ is $C_1$-$C_8$ alkyl substituted with $C_6$-$C_{14}$ aryl, wherein said $C_6$-$C_{14}$ aryl is optionally substituted with at least one halo; and $R^6$ is hydrogen or —$CH_3$.

6. A compound according to claim 5, wherein:

$R^1$ is $C_1$-$C_8$ alkyl substituted with $C_6$-$C_{14}$ aryl, wherein said $C_6$-$C_{14}$ aryl is substituted with at least one fluorine;

$R^4$ is hydrogen; and $R^7$ is hydrogen, —$CH_3$, phenyl, allyl, or benzyl.

7. A compound according to claim 6, wherein $R^1$ is benzyl substituted with at least one fluorine.

8. A compound according to claim 7, wherein $R^1$ is 2-fluorobenzyl, 3-fluorobenzyl, 4-fluorobenzyl, 2,3-difluorobenzyl, 2,4-difluorobenzyl, or 3,4-difluorobenzyl.

9. A compound according to claim 1, wherein $R^{10}$ and $R^{11}$, together with the nitrogen atom to which they are attached, form a $C_2$-$C_9$ cycloheteroalkyl group selected from:

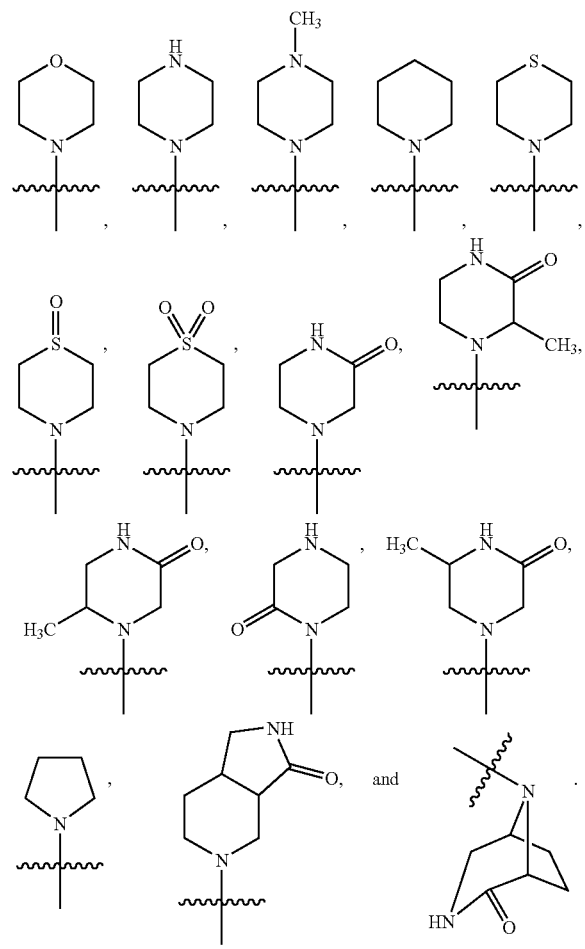

10. A compound according to claim 1, selected from 1-(2,4-difluorobenzyl)-N-hydroxy-3-(morpholin-4-ylmethyl)-1H-pyrrolo[2,3-c]pyridine-5-carboxamide; 1-(2,4-difluorobenzyl)-N-hydroxy-3-[(4-methylpiperazin-1-yl)methyl]-1H-pyrrolo[2,3-c]pyridine-5-carboxamide; 1-(2,4-difluorobenzyl)-N-hydroxy-3-(piperidin-1-ylmethyl)-1H-pyrrolo[2,3-c]pyridine-5-carboxamide; 1-(2,4-difluorobenzyl)-N-hydroxy-N-methyl-3-(morpholin-4-ylmethyl)-1H-pyrrolo[2,3-c]pyridine-5-carboxamide; 1-(2,4-difluorobenzyl)-3-[(1,1-dioxidothiomorpholin-4-yl)methyl]-N-hydroxy-1H-pyrrolo[2,3-c]pyridine-5-carboxamide; 1-(4-fluorobenzyl)-N-hydroxy-N-methyl-3-[(4-methylpiperazin-1-yl)methyl]-1H-pyrrolo[2,3-c]pyridine-5-carboxamide; 1-(4-fluorobenzyl)-N-hydroxy-3-[(3-oxopiperazin-1-yl)methyl]-1H-pyrrolo[2,3-c]pyridine-5-carboxamide; 1-(2,4-difluorobenzyl)-N-hydroxy-N-methyl-3-[(4-methylpiperazin-1-yl)methyl]-1H-pyrrolo[2,3-c]pyridine-5-carboxamide; 1-(4-fluorobenzyl)-N-hydroxy-N-methyl-3-[(2-methyl-3-oxopiperazin-1-yl)methyl]-1H-pyrrolo[2,3-c]pyridine-5-carboxamide; 1-(4-fluorobenzyl)-N-hydroxy-N-methyl-3-{[(1R,5S)-2-oxo-3,8-diazabicyclo[3.2.1]oct-8-yl]methyl}-1H-pyrrolo[2,3-c]pyridine-5-carboxamide; rac 1-(2,4-difluorobenzyl)-N-hydroxy-3-{[(3aR*,7aS*)-3-oxooctahydro-5H-pyrrolo[3,4-c]pyridin-5-yl]methyl}-1H-pyrrolo[2,3-c]pyridine-5-carboxamide; 1-(2,4-difluorobenzyl)-N-methoxy-3-[(4-methylpiperazin-1-yl)methyl]-1H-pyrrolo[2,3-c]pyridine-5-carboxamide; rac 1-(2,4-difluorobenzyl)-N-methoxy-3-{[(3aR*,7aS*)-3-oxooctahydro-5H-pyrrolo[3,4-c]pyridin-5-yl]methyl}-1H-pyrrolo[2,3-c]pyridine-5-carboxamide; rac 1-(2,4-difluorobenzyl)-N-hydroxy-N-methyl-3-{[(3aR*,7aS*)-3-oxooctahydro-5H-pyrrolo[3,4-c]pyridin-5-yl]methyl}-1H-pyrrolo[2,3-c]pyridine-5-carboxamide; N-(benzyloxy)-1-(4-fluorobenzyl)-3-[(3-oxopiperazin-1-yl)methyl]-1H-pyrrolo[2,3-c]pyridine-5-carboxamide; N-(allyloxy)-1-(4-fluorobenzyl)-3-[(3-oxopiperazin-1-yl)methyl]-1H-pyrrolo[2,3-c]pyridine-5-carboxamide; and 1-(4-fluorobenzyl)-3-[(3-oxopiperazin-1-yl)methyl]-N-phenoxy-1H-pyrrolo[2,3-c]pyridine-5-carboxamide; 1-(2,4-difluorobenzyl)-N-hydroxy-3-[(2-methylpyrrolidin-1-yl)methyl]-1H-pyrrolo[2,3-c]pyridine-5-carboxamide; 1-(2,4-Difluorobenzyl)-N-hydroxy-3-(4-methylpiperazin-1-yl)-1H-pyrrolo[2,3-c]pyridine-5-carboxamide; 1-(2,4-difluorobenzyl)-N-hydroxy-3-{[(3aR*,7aS*)-1-oxooctahydro-5H-pyrrolo[3,4-c]pyridin-5-yl]methyl}-1H-pyrrolo[2,3-c]pyridine-5-carboxamide; 1-(2,4-Difluorobenzyl)-N-methoxy-3-{[(3aR*,7aS*)-1-oxooctahydro-5H-pyrrolo[3,4-c]pyridin-5-yl]methyl}-1H-pyrrolo[2,3-c]pyridine-5-carboxamide; 1-(2,4-difluorobenzyl)-N-hydroxy-N-methyl-3-{[(3aR*,7aS*)-1-oxooctahydro-5H-pyrrolo[3,4-c]pyridin-5-yl]methyl}-1H-pyrrolo[2,3-c]pyridine-5-carboxamide; 1-(2,4-Difluorobenzyl)-N-hydroxy-N-methyl-3-{[(3aS,7aS*)-1-oxooctahydro-5H-pyrrolo[3,4-c]pyridin-5-yl]methyl}-1H-pyrrolo[2,3-c]pyridine-5-carboxamide; 1-(2,4-Difluorobenzyl)-N-hydroxy-N-methyl-3-{[(3aR,7aR*)-1-oxooctahydro-5H-pyrrolo[3,4-c]pyridin-5-yl]methyl}-1H-pyrrolo[2,3-c]pyridine-5-carboxamide; and 1-(4-fluorobenzyl)-N-hydroxy-N-methyl-3-[(3-oxopiperazin-1-yl)methyl]-1H-pyrrolo[2,3-c]pyridine-5-carboxamide; or a pharmaceutically acceptable salt or solvate thereof.

11. A compound according to claim 1, wherein $R^3$ is $C_1$-$C_8$ heteroalkyl substituted with $R^{24}$.

12. A compound according to claim 11, wherein $R^1$ is $C_1$-$C_8$ alkyl with substituted $C_6$-$C_{14}$ aryl, wherein said $C_6$-$C_{14}$ aryl is optionally substituted with at least one halo.

13. A compound according to claim 11, selected from 1-(2,4-difluorobenzyl)-N-hydroxy-3-{[methyl(pyridin-3-ylmethyl)amino]methyl}-1H-pyrrolo[2,3-c]pyridine-5-carboxamide; 1-(2,4-difluorobenzyl)-N-hydroxy-3-[(pyridin-3-ylamino)methyl]-1H-pyrrolo[2,3-c]pyridine-5-carboxamide; 1-(2,4-difluorobenzyl)-N-hydroxy-3-{[(2-pyridin-2-ylethyl)amino]methyl}-1H-pyrrolo[2,3-c]pyridine-5-carboxamide; 1-(2,4-difluorobenzyl)-N-hydroxy-3-[methyl(2-pyridin-2-ylethyl)amino]methyl]-1H-pyrrolo[2,3-c]pyridine-5-carboxamide; 1-(2,4-difluorobenzyl)-N-hydroxy-3-({[(5-methylpyrazin-2-yl)methyl]amino}methyl)-1H-pyrrolo[2,3-c]pyridine-5-carboxamide; 1-(2,4-difluorobenzyl)-N-hydroxy-3-({[2-(1H-indol-3-yl)ethyl]amino}methyl)-1H-pyrrolo[2,3-c]pyridine-5-carboxamide; 1-(2,4-difluorobenzyl)-N-hydroxy-3-({[(1S)-2-hydroxy-1-(1H-indol-3-ylmethyl)ethyl]amino}methyl)-1H-pyrrolo[2,3-c]pyridine-5-carboxamide; 1-(2,4-difluorobenzyl)-N-hydroxy-3-[({[6-(trifluoromethyl)pyridin-3-yl]methyl}amino)methyl]-1H-pyrrolo[2,3-c]pyridine-5-carboxamide; 1-(2,4-difluorobenzyl)-N-hydroxy-3-{[(2-methoxypyridin-3-yl)amino]methyl}-1H-pyrrolo[2,3-c]pyridine-5-carboxamide; 1-(2,4-difluorobenzyl)-N-hydroxy-3-({methyl[(1-phenyl- 1H-pyrazol-4-yl)methyl]amino}methyl)-1H-pyrrolo[2,3-c]pyridine-5-carboxamide; 1-(2,4-difluorobenzyl)-N-hydroxy-3-({[2-(5-methyl-4H-1,2,4-triazol-3-yl)ethyl]amino}methyl)-1H-pyrrolo[2,3-c]pyridine-5-carboxamide; 1-(2,4-difluorobenzyl)-3-{[(1,1-dioxidotetrahydrothien-3-yl)amino]methyl}-N-hydroxy-1H-pyrrolo[2,3-c]pyridine-5-carboxamide; 3-{[(cyclopropylmethyl)(propyl)amino]methyl}-1-(2,4-difluorobenzyl)-N-hydroxy-1H-pyrrolo[2,3-c]pyridine-5-carboxamide; 3-{[(1R,2R,4S)-bicyclo[2.2.1]hept-2-ylamino]methyl}-1-(2,4-difluorobenzyl)-N-hydroxy-1H-pyrrolo[2,3-c]pyridine-5-carboxamide; rac 1-(2,4-difluorobenzyl)-N-hydroxy-3-({[(1 S*,2R*)-2-phenylcyclopropyl]amino}methyl)-1H-pyrrolo[2,3-c]pyridine-5-carboxamide; 3-({[(1R)-1-cyclohexylethyl]amino}methyl)-1-(2,4-difluorobenzyl)-N-hydroxy-1H-pyrrolo[2,3-c]pyridine-5-carboxamide; 3-({[1-cyclopropyl-3-(cyclopropylamino)-3-oxopropyl]amino}methyl)-1-(2,4-difluorobenzyl)-N-hydroxy-1H-pyrrolo[2,3-c]pyridine-5-carboxamide; 1-(2,4-difluorobenzyl)-N-hydroxy-3-({[2-(1-methylpyrrolidin-2-yl)ethyl]amino}methyl)-1H-pyrrolo[2,3-c]pyridine-5-carboxamide; 1-(2,4-difluorobenzyl)-N-hydroxy-3-({[3-(4-methylpiperazin-1-yl)propyl]amino}methyl)-1H-pyrrolo[2,3-c]pyridine-5-carboxamide; 1-(2, 4-difluorobenzyl)-N-hydroxy-3-{[(2-morpholin-4-yl-ethyl)amino]methyl}-1H-pyrrolo[2,3-c]pyridine-5-carboxamide; 1-(2,4-difluorobenzyl)-N-hydroxy-3-{[(2-pyrrolidin-1-ylethyl)amino]methyl}-1H-pyrrolo[2,3-c]pyridine-5-carboxamide; 1-(2,4-difluorobenzyl)-N-hydroxy-3-{[(tetrahydrofuran-2-ylmethyl)amino]methyl}-1H-pyrrolo[2,3-c]pyridine-5-carboxamide; 1-(2,4-difluorobenzyl)-3-({[(1-ethylpyrrolidin-2-yl)methyl]amino}methyl)-N-hydroxy-1H-pyrrolo[2,3-c]pyridine-5-carboxamide; 1-(2, 4-difluorobenzyl)-N-hydroxy-3-({[3-(2-oxopyrrolidin-1-yl)propyl]amino}methyl)-1H-pyrrolo[2,3-c]pyridine-5-carboxamide; 1-(2,4-difluorobenzyl)-N-hydroxy-3-{[(1-methylpiperidin-4-yl)amino]methyl}-1H-pyrrolo[2, 3-c]pyridine-5-carboxamide; 1-(2,4-difluorobenzyl)-N-hydroxy-3-[(tetrahydro-2H-pyran-4-ylamino)methyl]-1H-pyrrolo[2,3-c]pyridine-5-carboxamide; 1-(2,4-difluorobenzyl)-N-hydroxy-3-{[(tetrahydro-1H-pyrrolizin-7a(5H)-ylmethyl)amino]methyl}-1H-pyrrolo[2,3-c]pyridine-5-carboxamide; 1-(2, 4-difluorobenzyl)-3-({[4-(difluoromethoxy)benzyl]amino}methyl)-N-hydroxy-1H-pyrrolo[2,3-c]pyridine-5-carboxamide; 1-(2,4-difluorobenzyl)-N-hydroxy-3-({[2-(tetrahydro-2H-pyran-4-yl)ethyl]amino}methyl)-1H-pyrrolo[2,3-c]pyridine-5-carboxamide; 1-(2,4-difluorobenzyl)-N-hydroxy-3-{([(6-methyl-3,4-dihydro-2H-chromen-4-yl)amino]methyl}-1H-pyrrolo[2,3-c]pyridine-5-carboxamide; 1-(2,4-difluorobenzyl)-N-hydroxy-3-{[(1,4,5,6-tetrahydrocyclopenta[c]pyrazol-3-ylmethyl)amino]methyl}-1H-pyrrolo[2,3-c]pyridine-5-carboxamide; 1-(2,4-difluorobenzyl)-3-({[(1-ethylpyrrolidin-2-yl)methyl]amino}methyl)-N-methoxy-1H-pyrrolo[2,3-c]pyridine-5-carboxamide; 1-(4-fluorobenzyl)-N,4-dihydroxy-1H-pyrrolo[2,3c]pyridine-5-carboxamide; 1-(4-fluorobenzyl)-4-hydroxy-N-methoxy-1H-pyrrolo[2,3-c]pyridine-5-carboxamide; 1-(4-fluorobenzyl)-N-hydroxy-4-methoxy-N-methyl-1H-pyrrolo[2,3-c]pyridine-5-carboxamide; 1-(4-fluorobenzyl)-N-hydroxy-N-propyl-1H-pyrrolo[2,3-c]pyridine-5-carboxamide; 1-(2,4-Difluorobenzyl)-N-hydroxy-3-[(2-methoxyethoxy)methyl]-1H-pyrrolo[2,3-c]pyridine-5-carboxamide; 1-(2,4-Difluorobenzyl)-N-hydroxy-3-{[2-(2-methoxyethoxy)ethoxy]methyl}-1H-pyrrolo[2,3-c]pyridine-5-carboxamide; 1-(2,4-Difluorobenzyl)-3-({[(4R)-2,2-dimethyl-1,3-dioxolan-4-yl]methoxy}methyl)-N-hydroxy-1H-pyrrolo[2,3-c]pyridine-5-carboxamide; 1-(4-Fluorobenzyl)-N-hydroxy-4-(3-hydroxypropyl)-1H-pyrrolo[2,3-c]pyridine-5-carboxamide; 4-Ethyl-1-(4-fluoro-benzyl)-1H-pyrrolo[2,3-c]pyridine-5-carboxylic acid hydroxyamide; 1-(2,4 -Difluorobenzyl)-N-hydroxy-3-{[(pyridin-2-ylmethyl)amino]methyl}-1H-pyrrolo[2,3-c]pyridine-5-carboxamide; 1-(2,4-Difluorobenzyl)-N-hydroxy-3-({[(1S,2R)-2-phenylcyclopropyl]amino}methyl)-1H-pyrrolo[2,3-c]pyridine-5-carboxamidel; and 3-({[(4S)-2,2-dimethyl-1,3 -dioxolan-4-yl]methoxy}methyl)-1-(4-fluorobenzyl)-N-hydroxy-1H-pyrrolo[2,3-c]pyridine-5-carboxamide; or a pharmaceutically acceptable salt or solvate thereof.

14. A compound selected from 1-(2,4-difluorobenzyl)-N-hydroxy-3-{[(2-hydroxyethyl)amino]methyl}-1H-pyrrolo[2,3-c]pyridine-5-carboxamide; 1-(2,4-difluorobenzyl)-3-({[3-(dimethylamino)propyl]amino}methyl)-N-hydroxy-1H-pyrrolo[2,3-c]pyridine-5-carboxamide; 3-{[(2-amino-2-oxoethyl)amino]methyl}-1-(2,4-difluorobenzyl)-N-hydroxy-1H-pyrrolo[2,3-c]pyridine-5-carboxamide; 1-(2,4-difluorobenzyl)-N-methoxy-4-(methoxymethyl)-1H-pyrrolo[2,3-c]pyridine-5-carboxamide; 3-(4-fluorobenzyl)-N-hydroxy-3H-imidazo[4,5-c]pyridine-6-carboxamide; 3-(4-fluorobenzyl)-N-hydroxy-N-methyl-3H-imidazo[4,5-c]pyridine-6-carboxamide; 3-(2,3-difluorobenzyl)-N-hydroxy-3H-imidazo[4,5-c]pyridine-6-carboxamide; 3-(2 -cyclohexylethyl)-N-hydroxy-3H-imidazo[4,5-c]pyridine-6-carboxamide; 1-(2-cyclohexylethyl)-N-hydroxy-1H-pyrrolo[2,3-c]pyridine-5-carboxamide; 1-(4-fluorobenzyl)-N-hydroxy-N-isopropyl-1H-pyrrolo[2, 3-c]pyridine-5-carboxamide; 1-(4-fluorobenzyl)-N-hydroxy-N-isobutyl-1H-pyrrolo[2,3-c]pyridine-5-carboxamide; 1-(4-fluorobenzyl)-N-hydroxy-N-(3-hydroxypropyl)-1H-pyrrolo[2,3-c]pyridine-5-carboxamide; 1-(4-fluorobenzyl)-3-[(4-fluorophenyl)(hydroxy)methyl]-N-hydroxy-1H-pyrrolo[3, 2-c]pyridine-6-carboxamide; 1,3-bis(4-fluorobenzyl)-N-hydroxy-1H-pyrrolo[3,2-c]pyridine-6-carboxamide; 1-(2,4-difluorobenzyl)-N-hydroxy-3-{[(2-hydroxy-1-methylethyl)amino]methyl}-1H-pyrrolo[2,3-c]pyridine-5-carboxamide; 1-(2,4-difluorobenzyl)-N-hydroxy-3-({[2-(2 -hydroxyethoxy)ethyl]amino}methyl)-1H-pyrrolo[2,3-c]pyridine-5-carboxamide; 1-(2,4-difluorobenzyl)-N-hydroxy-3 -({[(1R)-2-hydroxy-1-phenylethyl]amino}methyl)-1H-pyrrolo[2,3-c]pyridine-5-carboxamide; 1-(2,4-difluorobenzyl)-3-({[3-(dimethylamino)-2,2-dimethylpropyl]amino}methyl)-N-hydroxy-1H-pyrrolo[2,3-c]pyridine-5-carboxamide; 1-(2,4-difluorobenzyl)-N-hydroxy-3-{[(2 -hydroxypropyl)amino]methyl}-1H-pyrrolo[2,3-c]pyridine-5-carboxamide; 1-(2,4-difluorobenzyl)-3-{[ethyl(2-hydroxyethyl)amino]methyl}-N-hydroxy-1-H-pyrrolo[2,3-c]pyridine-5-carboxamide; 1-(2, 4-difluorobenzyl)-3-{[(4-fluorobenzyl)amino]methyl}-N-hydroxy-1H-pyrrolo[2,3-c]pyridine-5-carboxamide; 1-(2, 4-difluorobenzyl)-N-hydroxy-3-{[(1-phenylethyl)amino]methyl}-1H-pyrrolo[2,3-c]pyridine-5-carboxamide; 1-(2,4-difluorobenzyl)-3-({[2-(dimethylamino)ethyl]amino}methyl)-N-hydroxy-1H-pyrrolo[2,3-c]pyridine-5-carboxamide; 1-(2,4-difluorobenzyl)-N-hydroxy-3-({[1-(hydroxymethyl)-2-methylpropyl]amino}methyl)-1H-pyrrolo[2,3-c]pyridine-5-carboxamide; 1-(2,4-difluorobenzyl)-N-hydroxy-3-{[(3-methylbenzyl)amino]methyl}-1H-pyrrolo[2,3-c]pyridine-5-carboxamide; 1-(2,4-difluorobenzyl)-3-{[(1-ethylpropyl)amino]methyl}-N-hydroxy-1H-pyrrolo[2,3-c]pyridine-5-carboxamide; 1-(2, 4-difluorobenzyl)-N-hydroxy-3-{[(3-isopropoxypropyl)amino]methyl}-1H-pyrrolo[2,3-c]pyridine-5 -carboxamide; 1-(2,4-difluorobenzyl)-N-hydroxy-3-{[(2-hydroxy-2-phenylethyl)amino]methyl}-1H-pyrrolo[2, 3-c]pyridine-5-carboxamide; 1-5-carboxamide; 1-(2,4-difluorobenzyl)-N-hydroxy-3-{[(2-hydroxy-1-methyl-2-phenylethyl)amino]methyl}-1H-pyrrolo[2,3-c]pyridine-5-carboxamide; 1-(2,4-difluorobenzyl)-N-hydroxy-3-({[(1S)-1-(hydroxymethyl)-2,2-dimethylpropyl]amino}methyl)-1H-pyrrolo[2,3-c]pyridine-5-1H-pyrrolo[2,3-c]pyridine-5-carboxamide; 1-(2,4-difluorobenzyl)-N-hydroxy-3-[(phenylthio)methyl]-1H-pyrrolo[2,3-c]pyridine-5-carboxamide; 3-[(benzylthio)methyl]-1-(2,4-difluorobenzyl)-N-hydroxy-1H-pyrrolo[2,3-c]pyridine-5-carboxamide; 1-(2, 4-difluorobenzyl)-N-hydroxy-3-[(phenylsulfonyl)methyl]-1H-pyrrolo[2,3-c]pyridine-5-carboxamide; 1-(2,4-difluorobenzyl)-N-hydroxy-3-[(phenylsulfinyl) methyl]-1H-pyrrolo[2,3-c]pyridine-5-carboxamide; 1,3-Bis(4-fluorobenzyl)-N-hydroxy-1H-pyrrolo[3,2-c]pyridine-6-carboxamide; 4-[(E)-2-Ethoxyvinyl]-1-(4-fluorobenzyl)-N-hydroxy-1H-pyrrolo[2,3-c]pyridine-5-carboxamide; 1-(4-Fluorobenzyl)-N-hydroxy-4-vinyl-1H-pyrrolo[2,3-c]pyridine-5-carboxamide; 3-({[(1S)-1-Benzyl-2-hydroxyethyl]amino}methyl)-1-(2,4-difluorobenzyl)-N-hydroxy-1 H-pyrrolo[2,3-c]pyridine-5-carboxamide; Ethyl (1R,5S)-3-[({1-(2,4-difluorobenzyl)-5-[(hydroxyamino)carbonyl]-1H-pyrrolo[2,3-c]pyridin-3-yl}methyl)amino]-8-azabicyclo[3.2.1]octane-8-carboxylate; 1-(2, 4-Difluorobenzyl)-N-methoxyl-4-(methoxymethyl)-1H-pyrrolo[2,3-c]pyridine-5-carboxamide; 1-(2,4-Difluorobenzyl)-3-({[(2R)-2,3-dihydroxypropyl]oxy}methyl)-N-hydroxy-1H-pyrrolo[2,3-c]pyridine-5-carboxamide; 1-(2,4-Difluorobenzyl)-3-({[(2S)-2,3-dihydroxypropyl]oxy}methyl)-N-hydroxy-1H-pyrrolo[2,3-c]pyridine-5-carboxamide; 1-(4-Fluorobenzyl)-N-hydroxy-3-[(2-methoxyethoxy)methyl]-N-methyl-1H-pyrrolo[2,3-c]pyridine-5-carboxamide; 1-(4-Fluorobenzyl)-N-methoxy-3-[(2-methoxyethoxy)methyl]-1H-pyrrolo[2,3-c]pyridine-5-carboxamide; 3-({[(4R)-2,2-Dimethyl-1,3-dioxolan-4-yl]methoxy}methyl)-1-(4-fluorobenzyl)-N-hydroxy-N-methyl-1H-pyrrolo[2,3-c]pyridine-5-carboxamide; N-ethoxy-1-(4-fluorobenzyl)-3-{[(2-hydroxyethyl)(propyl)amino]methyl}-1H-pyrrolo[2,3-c]pyrid ire-5-carboxamide; 3-{[[3-(Dimethylamino)propyl](methyl)amino]methyl}-N-ethoxy-1-(4-fluorobenzyl)-1H-pyrrolo[2,3-c]pyridine-5-carboxamide; 1-(4-Fluorobenzyl)-N-hydroxy-N-methyl-3-{[2-(2-oxopyrrolidin-1yl)ethoxy]methyl}-1H-pyrrolo[2,3-c]pyridine-5-carboxamide; 1-(4-Fluorobenzyl)-N-hydroxy-N-methyl-3-[(tetrahydro-2H-pyran-4-yloxy)methyl]-1H-pyrrolo[2,3-c]pyridine-5-carboxamide; 1-(4-Fluorobenzyl)-N-hydroxy-N-methyl-3-{[(1R)-1-phenylethoxy]methyl}-1H-pyrrolo[2,3-c]pyridine-5-carboxamide; 3-[(2-ethoxyethoxy)methyl]-1-(4-fluorobenzyl)-N-hydroxy-N-methyl-1H-pyrrolo[2,3-c]pyridine-5-carboxamide; 3-[(2-Ethoxyethoxy)methyl]-1-(4-fluorobenzyl)-N-methoxy-1H-pyrrolo[2,3-c]pyridine-5-carboxamide; 1-(4-Fluorobenzyl)-N-hydroxy-3-(methoxymethyl)-N-methyl-1H-pyrrolo[2,3-c]pyridine-5-carboxamide; and 1-(2,4 -Difluorobenzyl)-N-hydroxy-3-[(2-methoxyethoxy)methyl]-N-methyl-1H-pyrrolo[2,3-c]pyridine-5-carboxamide; or a pharmaceutically acceptable salt or solvate thereof.

15. A pharmaceutical composition, comprising a therapeutically effective amount of a compound according to claim 1 and a pharmaceutically acceptable carrier or diluent.

16. A pharmaceutical composition, comprising a therapeutically effective amount of a compound according to claim 14 and a pharmaceutically acceptable carrier or diluent.

17. A method of inhibiting HIV replication in a mammal, comprising administering to said mammal an HIV-inhibiting amount of at least one compound according to claim 1.

18. A method of inhibiting HIV replication in a mammal, comprising administering to said mammal an HIV-inhibiting amount of at least one compound according to claim 17.

19. A method of inhibiting HIV integrase enzyme activity, comprising contacting said integrase enzyme with an HIV integrase-inhibiting amount of at least one compound according to claim 1.

20. A method of inhibiting HIV integrase enzyme activity, comprising contacting said integrase enzyme with an HIV integrase-inhibiting amount of at least one compound according to claim 14.

* * * * *

SEQUENCE LISTING

<160> NUMBER OF SEQ ID NOS: 4

<210> SEQ ID NO 1
<211> LENGTH: 32
<212> TYPE: PRT
<213> ORGANISM: HIV integrase enzyme

<400> SEQUENCE: 1

Cys Cys Cys Cys Thr Thr Thr Thr Ala Gly Thr Cys Ala Gly Thr Gly
1               5                   10                  15

Thr Gly Gly Ala Ala Ala Ala Thr Cys Thr Cys Thr Ala Gly Cys Ala
            20                  25                  30

<210> SEQ ID NO 2
<211> LENGTH: 31
<212> TYPE: PRT
<213> ORGANISM: HIV integrase enzyme

<400> SEQUENCE: 2

Ala Cys Thr Gly Cys Thr Ala Gly Ala Gly Ala Thr Thr Thr Thr Cys
1               5                   10                  15

Cys Ala Cys Ala Cys Thr Gly Ala Cys Thr Ala Ala Ala Ala Gly
            20                  25                  30

<210> SEQ ID NO 3
<211> LENGTH: 26
<212> TYPE: PRT

<400> SEQUENCE: 3

Ala Ala Ala Ala Ala Ala Thr Gly Ala Cys Cys Ala Ala Gly Gly Gly
1               5                   10                  15

```
Cys Thr Ala Ala Thr Thr Cys Ala Cys Thr
             20                  25

<210> SEQ ID NO 4
<211> LENGTH: 26
<212> TYPE: PRT
<213> ORGANISM: HIV integrase enzyme

<400> SEQUENCE: 4

Ala Ala Ala Ala Ala Ala Ala Gly Thr Gly Ala Ala Thr Thr Ala Gly
1               5                   10                  15

Cys Cys Cys Thr Thr Gly Gly Thr Cys Ala
             20                  25
```